(12) United States Patent
De Goeij et al.

(10) Patent No.: US 11,046,771 B2
(45) Date of Patent: Jun. 29, 2021

(54) MONOCLONAL ANTIBODIES AGAINST HER2

(71) Applicant: GENMAB A/S, Copenhagen V (DK)

(72) Inventors: Bart De Goeij, Maarssen (NL); Simone De Haij, Weesp (NL); Thilo Riedl, Arnhem (NL); Rene Hoet, Boxmeer (NL); Ole Baadsgaard, Hellerup (DK); Jan Van De Winkel, Zeist (NL); David Satijn, Utrecht (NL); Paul Parren, Utrecht (NL); Aran Frank Labrijn, Utrecht (NL); Joyce Meesters, Utrecht (NL); Janine Schuurman, Utrecht (NL); Edward N. Van Den Brink, Halfweg (NL)

(73) Assignee: GENMAB A/S, Copenhagen V (DK)

( * ) Notice: Subject to any disclaimer, the term of this patent is extended or adjusted under 35 U.S.C. 154(b) by 308 days.

(21) Appl. No.: 15/832,366

(22) Filed: Dec. 5, 2017

(65) Prior Publication Data
US 2018/0194845 A1 Jul. 12, 2018

Related U.S. Application Data

(62) Division of application No. 13/700,341, filed as application No. PCT/EP2011/058779 on May 27, 2011, now Pat. No. 9,862,769.

(60) Provisional application No. 61/349,180, filed on May 27, 2010.

(30) Foreign Application Priority Data

May 27, 2010 (DK) .................................. 2010 00467
Apr. 20, 2011 (DK) .................................. 2011 00312
Apr. 20, 2011 (WO) .................. PCT/EP2011/056388

(51) Int. Cl.
*C07K 16/28* (2006.01)
*C07K 16/32* (2006.01)
*A61K 39/00* (2006.01)

(52) U.S. Cl.
CPC ...... *C07K 16/2863* (2013.01); *C07K 16/2809* (2013.01); *C07K 16/32* (2013.01); *A61K 2039/505* (2013.01); *C07K 2317/31* (2013.01); *C07K 2317/52* (2013.01); *C07K 2317/526* (2013.01); *C07K 2317/528* (2013.01); *C07K 2317/56* (2013.01); *C07K 2317/565* (2013.01); *C07K 2317/732* (2013.01); *C07K 2317/77* (2013.01); *C07K 2317/92* (2013.01)

(58) Field of Classification Search
CPC ................ C07K 16/2863; C07K 16/32; C07K 16/2809; C07K 2317/31; C07K 2317/56; C07K 2317/565; C07K 2317/732; A61K 2039/505
See application file for complete search history.

(56) References Cited

U.S. PATENT DOCUMENTS

| 5,705,157 | A | 1/1998 | Greene |
|---|---|---|---|
| 5,731,168 | A | 3/1998 | Carter et al. |
| 5,807,706 | A | 9/1998 | Carter et al. |
| 6,123,939 | A | 9/2000 | Shawver et al. |
| 6,270,765 | B1 | 8/2001 | Deo et al. |
| 6,737,056 | B1 | 5/2004 | Presta |
| 7,309,486 | B1 | 12/2007 | Zamoyski |
| 9,212,230 | B2 | 12/2015 | Schuurman et al. |
| 9,714,294 | B2 | 7/2017 | De Goeij et al. |
| 9,862,769 | B2 | 1/2018 | De Goeij et al. |
| 2003/0118583 | A1 | 6/2003 | Emery et al. |
| 2004/0038894 | A1 | 2/2004 | Daeron et al. |
| 2006/0121604 | A1 | 6/2006 | Handa et al. |
| 2008/0051469 | A1 | 2/2008 | Brahmbhatt et al. |
| 2009/0202532 | A1 | 8/2009 | Kumagai et al. |
| 2009/0317869 | A1 | 12/2009 | Alley et al. |
| 2010/0015133 | A1 | 1/2010 | Igawa et al. |
| 2010/0015157 | A1 | 1/2010 | Andya et al. |
| 2010/0286374 | A1 | 11/2010 | Kannan et al. |
| 2011/0158988 | A1* | 6/2011 | Uhlen .................... C07K 16/32 424/133.1 |
| 2012/0149876 | A1 | 6/2012 | Von Kreudenstein et al. |
| 2013/0039913 | A1 | 2/2013 | Labrijn et al. |
| 2013/0171148 | A1 | 7/2013 | De Goeij et al. |
| 2013/0189271 | A1 | 7/2013 | De Goeij et al. |
| 2014/0141000 | A1 | 5/2014 | Chiu et al. |
| 2014/0170148 | A1 | 6/2014 | De Goeij et al. |
| 2014/0170149 | A1 | 6/2014 | Neijssen et al. |

(Continued)

FOREIGN PATENT DOCUMENTS

| CN | 101633695 A | 1/2010 |
|---|---|---|
| CN | 101721700 A | 6/2010 |

(Continued)

OTHER PUBLICATIONS

Almagro & Fransson, Frontiers in Bioscience 2008; 13:1619-33.*

(Continued)

*Primary Examiner* — Julie Wu
*Assistant Examiner* — Cheom-Gil Cheong
(74) *Attorney, Agent, or Firm* — Nelson Mullins Riley & Scarborough LLP; Jane E. Remillard, Esq.; Christopher L. Frank

(57) ABSTRACT

Isolated monoclonal antibodies which bind to human epidermal growth factor receptor 2 (HER2), and related antibody-based compositions and molecules, are disclosed. Pharmaceutical compositions comprising the antibodies and therapeutic and diagnostic methods for using the antibodies are also disclosed.

23 Claims, 24 Drawing Sheets
Specification includes a Sequence Listing.

(56) References Cited

U.S. PATENT DOCUMENTS

| | | |
|---|---|---|
| 2014/0303356 A1 | 10/2014 | Gramer et al. |
| 2016/0046727 A1 | 2/2016 | Labrijn et al. |
| 2017/0233497 A1 | 8/2017 | Labrijn et al. |
| 2017/0369590 A1 | 12/2017 | De Goeij et al. |
| 2017/0369594 A1 | 12/2017 | Neijssen et al. |
| 2018/0022816 A1 | 1/2018 | De Goeij et al. |
| 2018/0179286 A1 | 6/2018 | De Goeij et al. |
| 2018/0215827 A1 | 8/2018 | De Goeij et al. |

FOREIGN PATENT DOCUMENTS

| | | |
|---|---|---|
| CN | 101633695 B | 12/2012 |
| EP | 1980626 A1 | 10/2008 |
| EP | 2078732 A1 | 7/2009 |
| WO | 89/06692 A1 | 7/1989 |
| WO | 97/35885 A1 | 10/1997 |
| WO | 98/17797 A1 | 4/1998 |
| WO | 99/31140 A1 | 6/1999 |
| WO | 99/44645 A1 | 9/1999 |
| WO | 1999/048527 A1 | 9/1999 |
| WO | 99/55367 A1 | 11/1999 |
| WO | 00/69460 A1 | 11/2000 |
| WO | 01/000238 A1 | 1/2001 |
| WO | 01/00244 A2 | 1/2001 |
| WO | 01/00245 A2 | 1/2001 |
| WO | 2001/009187 A2 | 2/2001 |
| WO | 01/89566 A1 | 11/2001 |
| WO | 02/082041 A2 | 10/2002 |
| WO | 02/100348 A2 | 12/2002 |
| WO | 03/101491 A1 | 12/2003 |
| WO | 2004/032960 A1 | 4/2004 |
| WO | 2004/035607 A1 | 4/2004 |
| WO | 2005/034733 A2 | 4/2005 |
| WO | 2005/117973 A2 | 12/2005 |
| WO | 2005/118635 A2 | 12/2005 |
| WO | 2006/033386 A1 | 3/2006 |
| WO | 2006/033700 A2 | 3/2006 |
| WO | 2006/063042 A2 | 6/2006 |
| WO | 2006/091693 A2 | 8/2006 |
| WO | 2006/113643 A2 | 10/2006 |
| WO | 2006/116107 A2 | 11/2006 |
| WO | 2007/059782 A1 | 5/2007 |
| WO | 2007059782 A1 | 5/2007 |
| WO | 2007/084181 A2 | 7/2007 |
| WO | 2008/007648 A1 | 1/2008 |
| WO | 2008/019290 A2 | 2/2008 |
| WO | 2008/22746 A1 | 2/2008 |
| WO | 2008/031531 A1 | 3/2008 |
| WO | 2008/088861 A2 | 7/2008 |
| WO | 2008/097229 A1 | 8/2008 |
| WO | 2008/109440 A2 | 9/2008 |
| WO | 2008/119353 A1 | 10/2008 |
| WO | 2008/119493 A1 | 10/2008 |
| WO | 2008/127710 A2 | 10/2008 |
| WO | 2008/130910 A1 | 10/2008 |
| WO | 2008/145142 A1 | 12/2008 |
| WO | 2008/148546 A2 | 12/2008 |
| WO | 2008/150485 A2 | 12/2008 |
| WO | 2008/154249 A2 | 12/2008 |
| WO | 2009/030239 A1 | 3/2009 |
| WO | 2009026681 A1 | 3/2009 |
| WO | 09/055074 A2 | 4/2009 |
| WO | 2009/068625 A2 | 6/2009 |
| WO | 2009/073524 A2 | 6/2009 |
| WO | 2009/099829 A1 | 8/2009 |
| WO | 2009/100110 A1 | 8/2009 |
| WO | 2009/105230 A2 | 8/2009 |
| WO | 2009/106096 A1 | 9/2009 |
| WO | 2009/151356 A1 | 12/2009 |
| WO | 2009/154651 A1 | 12/2009 |
| WO | 2010/001251 A2 | 1/2010 |
| WO | 2010/002862 A2 | 1/2010 |
| WO | 2010/027981 A1 | 3/2010 |
| WO | 2010/070117 A1 | 6/2010 |
| WO | 2010066803 A2 | 6/2010 |
| WO | 2011/147986 A1 | 12/2011 |

OTHER PUBLICATIONS

De Genst et al., Developmental and Comparative Immunology, 2006, 30:187-98.*
Barthelemy et al., Journal of Biological Chemistry, 2008, 283:3639-3654.*
Choi et al., 2011, Molecular BioSystems, 2011, 7:3327-334.*
Griffiths et al., The EMBO Journal, 1993, 12:725-734.*
Klimka et al., British Journal of Cancer, 2000, 83:252-260.*
Beiboer et al., Journal of Molecular Biology, 2000, 296:833-849.*
Ward et al., Nature, 1989, 341:544-546.*
U.S. Appl. No. 13/700,341, filed Mar. 14, 2013, Bart De Goeij.
U.S. Appl. No. 15/832,337, filed Dec. 5, 2017, Bart De Goeij.
U.S. Appl. No. 15/832,421, filed Dec. 5, 2017, Bart De Goeij.
U.S. Appl. No. 13/700,341, Office Action dated Sep. 6, 2017.
U.S. Appl. No. 13/700,341, Office Action dated Aug. 24, 2017.
U.S. Appl. No. 13/700,341, Office Action dated Mar. 6, 2017.
U.S. Appl. No. 13/700,341, Office Action dated Oct. 14, 2016.
U.S. Appl. No. 13/700,341, Office Action dated Mar. 21, 2016.
U.S. Appl. No. 13/700,341, Office Action dated Oct. 7, 2015.
U.S. Appl. No. 13/700,341, Office Action dated Mar. 19, 2015.
U.S. Appl. No. 13/700,341, Office Action dated Sep. 18, 2014.
U.S. Appl. No. 15/832,337, Office Action dated Nov. 12, 2019.
U.S. Appl. No. 15/832,421, Office Action dated Nov. 12, 2019.
Agus DB., et al., "Targeting ligand-activated ErbB2 signaling inhibits breast and prostate tumor growth," Cancer Cell, vol. 2: pp. 127-137 (2002).
Andrechek E. et al., "Amplification of the neuy erbB-2 oncogene in a mouse model of mammary tumorigenesis," Proc Natl Acad Sci USA, vol. 97(7), pp. 3444-3449 (2000).
Baeuerle, P. et al., "Bispecific T-Cell Engaging Antibodies for Cancer Therapy," Cancer Research, vol. 69 (12), 5 pages, (2009).
Baeuerle, P. et al., BiTE Teaching antibodies to engage T-cells for Cancer Therapy, Current Opinion in Molecular Therapeutics, vol. 11, pp. 22-30 (2009).
Bargou, R. et al., "Tumor Regression in Cancer Patients by Very Low Doses of a T Cell-Engaging Antibody," Science, vol. 321, pp. 974-977, (2008).
Baselga, J. et al., "Phase II Trial of Pertuzumab and Trastuzumab in Patients With Human Epidermal Growth Factor Receptor 2-Positive Metastatic Breast Cancer That Progressed During Prior Trastuzumab Therapy," J Clin Oncol, vol. 28(7), pp. 1138-1144 (2010).
Baulida, J. et al., "All ErbB receptors other than the epidermal growth factor receptor are endocytosis impaired," J Biol Chem, vol. 271(9), pp. 5251-5257 (1996).
Ben-Kasus, T. et al., "Persistent elimination of ErbB-2/HER2-overexpressing tumors using combinations of monoclonal antibodies: relevance of receptor endocytosis," Proc Natl Acad Sci USA, vol. 106, pp. 3294-3299 (2009).
Bolt, S. et al., "The generation of a humanized, non-mitogenic CD3 monoclonal antibody which retains in vitro immunosuppressive properties," Eur J Immunol, vol. 23(2), pp. 403-411 (1993).
Boyer, CM. et al., "Relative cytotoxic activity of immunotoxins reactive with different epitopes on the extracellular domain of the c-erbB-2 (HER-2/neu) gene product p185," Int J Cancer vol. 82, pp. 525-531 (1999).
Burris, H. et al, Phase II study of the antibody drug conjugate trastuzumab-DM1 for the treatment of human epidermal growth factor receptor 2 (HER2)-positive breast cancer after prior HER2-directed therapy, J Clin Oncol, vol. 29(4), pp. 398-405 (2011).
Casset, F. et al., "A peptide mimetic of an anti-CD4 monoclonal antibody by rational design," (Biochemical and Biophysical Research Communications, vol. 307(1):198-205 (2003).
Chames, P. et al., "Bispecific antibodies for cancer therapy," Current Opinion in Drug Discovery & Development, vol. 12 (2), pp. 276-283 (2009).

(56) References Cited

OTHER PUBLICATIONS

Chen, Y. et al., "Selection and analysis of an optimized anti-VEGF antibody: crystal structure of an affinity-matured Fab in complex with antigen," Journal of Molecular Biology, vol. 293:865-881 (1999).
Cho, HS et al., "Structure of the extracellular region of HER2 alone and in complex with the Herceptin Fab," Nature, 421(6924), pp. 756-760 (2003).
Database Geneseq [online], Jan. 11, 2007, "Human anti-IL8 monoclonal antibody mAb 809 Vk".
Database Geneseq [online], Aug. 6, 2009, Human anti-RG-1 Monoclonal antibody 34E1 VL, Seq ID No. 16.
Database Geneseq [online], Mar. 20, 2008, Human HER2 specific antibody VL Seq ID No. 639.
Database Geneseq [online], Feb. 23, 2006, Antibody 28F10 light chain variable region Seq ID No. 8.
De Pascalis, R. et al., "Grafting of "abbreviated" complementarity-determining regions containing specificity-determining residues essential for ligand contact to engineer a less immunogenic humanized monoclonal antibody," Journal of Immunology, vol. 169(6):3076-3084 (2002).
Dinh, P. et al., "Trastuzumab for early breast cancer: current status and future directions," Clin Adv Hematol Oncol, vol. 5(9), pp. 707-717 (2007).
Emde, A. et al., "Combining Epitope-distinct antibodies to HER2, Cooperative inhibitory effects on invasive growth," Oncogene, vol. 30, pp. 1631-1642 (2011).
Franklin, M. et al., "Insights into ErbB signaling from the structure of the ErbB2-pertuzumab complex," Cancer Cell, vol. 5 (4), pp. 317-328 (2004).
Friedman, M. et al., "Engineering and characterization of a bispecific HER2 x EGFR-binding affibody molecule," Biotechnol. Appl. Biochem., vol. 54(2), pp. 121-131 (2009).
Garcia de Palazzo, I. et al.,"Immunohistochemical detection of c-erbB-2 expression by neoplastic human tissue using monospecific and bispecific monoclonal antibodies.," Int J Biol Markers, vol. 8(4), pp. 233-239; (1993).
Graus-Porta, D. et al.,"ErbB-2, the preferred heterodimerization partner of all ErbB receptors, is a mediator of lateral signaling," Embo J, vol. 16, pp. 1647-1655 (1997).
Guillemard, V. et al., "HER2-mediated internalization of a targeted prodrug cytotoxic conjugate is dependent on the valency of the targeting ligand, DNA Cell Biol., vol. 24(6), pp. 350-358 (2005).
Harwerth, IM, et al., "Monoclonal antibodies directed to the erbB-2 receptor inhibit in vivo tumour cell growth," Br J Cancer, vol. 68, pp. 1140-1145 (1993).
Heynes, et al., PI3K Inhibition Overcomes Trastuzumab Resistance: Blockade of ErbB2/ErbB3 Is Not Always Enough, Cancer Cell, 2009;15(5):353-355.
Holm, P. et al., "Functional mapping and single chain construction of the anti-cytokeratin 8 monoclonal antibody TS1," Molecular Immunology, vol. 44(6)1075-1084 (2007).
Hu, S , et al: "Epitope mapping and structural analysis of an anti-ErbB2 antibody A21: Molecular basis for tumor inhibitory mechanism", Proteins: Structure, Function and Bioinformatics, vol. 70 (3), pp. 938-949 (2008).
Huang, Z. et al., "A pan-HER approach for cancer therapy: background, current status and future development," Expert Opin Biol Ther., vol. 9(1), pp. 97-110 (2009).
Hudis, C., et al., "Drug therapy: Trastuzumab—Mechanism of action and use in clinical practice," New England Journal of Medicine, vol. 357(1), pp. 39-51 (2007).
Hughes, JB et al., "Pertuzumab increases epidermal growth factor receptor down-regulation by counteracting epidermal growth factor receptor-ErbB2 heterodimerization," Mol Cancer Ther., vol. 8 (7), pp. 1885-1892 (2009).
Hynes, NE, et al., "PI3K inhibition overcomes trastuzumab resistance: blockade of ErbB2/ErbB3 is not always enough," Cancer Cell, vol. 15(5), pp. 353-355 (2009).

Jasinska, J. et al: "Inhibition of tumor cell growth by antibodies induced after vaccination with peptides derived from the extracellular domain of Her-2/neu," International Journal of Cancer, vol. 107(6), pp. 976-983 (2003).
Jones, KL. et al., "Evolving novel anti-HER2 strategies," Lancet Oncol., vol. 10 (12), pp. 1179-1187 (2009).
Junttila TT., et al., "Ligand-independent HER2/HER3/PI3K complex is disrupted by trastuzumab and is effectively inhibited by the PI3K inhibitor GDC-0941," Cancer Cell, vol. 15 (5), pp. 429-440 (2009).
Kapitanovic, S. et al, "The expression of p185(HER-2/neu) correlates with the stage of disease and survival in colorectal cancer," Gastroenterology , vol. 112 (4), pp. 1103-1113 (1997).
Kiewe, P. et al., "Phase I trial of the trifunctional anti-HER2 x anti-CD3 antibody ertumaxomab in metastatic breast cancer," Clin Cancer Res., vol. 12(10), pp. 3085-3091 (2006).
Klapper LN, et al., "A subclass of tumor-inhibitory monoclonal antibodies to ErbB-2/HER2 blocks crosstalk with growth factor receptors," Oncogene, vol. 14, pp. 2099-2109 (1997).
Klein, C. et al., "Epitope Interactions of monoclonal antibodies targeting CD2+ and their relationship to functional properties," mAbs vol. 5(1), pp. 22-33 (2013).
Krop, I., et al., "Phase I Study of Trastuzumab-DM1, an HER2 Antibody-Drug Conjugate, Given Every 3 Weeks to Patients With HER2-Positive Metastatic Breast Cancer," J Clin Oncol., vol. 28 (16), pp. 2698-2704 (2010).
Langdon S P et al: "Pertuzumab—Humanized anti-HER2 monoclonal antibody HER dimerization inhibitor oncolytic," Drugs of the Future, Prous Science, vol. 33(2), pp. 123-130 (2008).
Larsen, SS., et al., "Acquired antiestrogen resistance in MCF-7 human breast cancer sublines is not accomplished by altered expression of receptors in the ErbB-family.," Breast Cancer Res Treat., vol. 58(1), pp. 41-56 (1999).
Lewis, P. et al., "Targeting HER2-positive breast cancer with trastuzumab-DM1, an antibody-cytotoxic drug conjugate," Cancer Res., vol. 68(22), pp. 9280-9290 (2008).
Li, J. et al., "A Biparatopic HER2-Targeting Antibody-Drug Conjugate Induces Tumor Regression in Primary Models Refractory to or Ineligible for HER2-Targeted Therapy," Cancer Cell, vol. 29, pp. 117-129 (2016).
Maccallum RM., et al: "Antibody-antigen interactions: Contact analysis and binding site topography," Journal of Molecular Biology, vol. 262(5), pp. 732-745 (1996).
Montgomery, RB. et al: "Endogenous anti-HER2 antibodies block HER2 phosphorylation and signaling throught extracellular signal-regulated kinase," Cancer Research, American Association for Cancer Research, vol. 65(2), pp. 650-656 (2005).
Moore, PA et al., "Application of dual affinity retargeting molecules to achieve optimal redirected T-cell killing of B-cell lymphoma," Blood, vol. 117(17), pp. 4542-4551 (2011).
Muller and Kontermann, "Cloning and sequencing of the cDNA encoding the human homologue of the murine immunoglobulin-associated protein B29," BioDrugs 2010;24:89-98.
Muller, D. et al., "Bispecific antibodies for cancer immunotherapy: Current perspectives," BioDrugs, vol. 24(2), pp. 89-98 (2010).
Nahta, R. et al., "Mechanisms of Disease: Understanding Resistance to HER2-targeted; therapy in human breast cancer," Nature Clinical Practice Oncology, vol. 3(5), pp. 269-280 (2006).
Nahta, R. et al., "Trastuzumab: triumphs and tribulations," Oncogene, vol. 26(25) pp. 3637-3643 (2007).
Natsume, A., et al., "Engineered anti-CD20 antibodies with enhanced complement-activating capacity mediate potent anti-lymphoma activity," Cancer Science, vol. 100 (12), pp. 2411-2418 (2009).
Oral Presentations, Experimental Hematology, Elsevier, Inc.; vol. 33(7), 34 pages, (2005).
Oshima, CT., et al., "C-erbB-2 oncoprotein in gastric carcinoma: correlation with clinical stage and prognosis," Int J Biol Markers, vol. 16(4) pp. 250-254 (2001).
Osman, I., et al., "Serum levels of shed Her2/neu protein in men with prostate cancer correlate with disease progression," J Urol., vol. 174(6), pp. 2174-2177 (2005).

(56) References Cited

OTHER PUBLICATIONS

Parren, PW., et al., "Induction of T-cell proliferation by recombinant mouse and chimeric mouse/human anti-CD3 monoclonal antibodies," Res Immunol., vol. 142 (9), pp. 749-763 (1991).

Pedersen, NM., et al., "Expression of epidermal growth factor receptor or ErbB3 facilitates geldanamycin-induced down-regulation of ErbB2," Mol Cancer Res., 7(2), pp. 275-284 (2009).

Perez, E.A., et al., "Efficacy and Safety of Trastuzumab-DM1 versus Trastuzumab Plus Docetaxel in Her2-Positive Metastatic Breast Cancer Patients with No Prior Chemotherapy for Metastatic Disease: Preliminary Results of a Randomized, Multicenter, Open-Label Phase 2 Study (TDM4450G)," Abstract BA3, European Society for Medical Oncology Meeting 2010, Annals of Oncology, vol. 21(Supp. 8), 12 pages (2010).

Reese, DM. et al., "HER-2/neu signal transduction in human breast and ovarian cancer.," Stem Cells, vol. 15(1), pp. 1-8 (1997).

Riese, DJ., et al, "Specificity within the EGF family/ErbB receptor family signaling network," Bioessays, vol. 20 (1), pp. 41-48 (1998).

Robinson, MK. et al., "Targeting ErbB2 and ErbB3 with a bispecific single-chain Fv enhances targeting selectivity and induces a therapeutic effect in vitro," British Journal of Cancer, vol. 99(9), pp. 1415-1425 (2008).

Rockberg J. et al.,"Discovery of epitopes for targeting the human epidermal growth factor receptor 2 (HER2) with antibodies," Molecular Oncology, vol. 3(3), pp. 238-247 (2009).

Ross, JS., et al., "The Her-2/neu gene and protein in breast cancer 2003: biomarker and target of therapy," Oncologist, vol. 8(4), pp. 307-325 (2003).

Routledge, EG. et al., "A humanized monovalent CD3 antibody which can activate homologous complement," Eur J Immunol., vol. 21(11), pp. 2717-2725 (1991).

Rudikoff S. et al, "Single amino acid substitution altering antigen-binding specificity," PNAS, vol. 79, pp. 1979-1983 (1982).

Scheuer, W. et al., "Strongly enhanced antitumor activity of Trastuzumab and Pertuzumab combination treatment on HER2 positive human xenograft tumor models," Cancer Research, vol. 69 (24), pp. 9330-9336 (2009).

Schmitz, KR. et al., "Interaction of antibodies with ErbB receptor extracellular regions," Exp Cell Res., vol. 315(4), pp. 659-670 (2009).

Slamon, DJ., et al., "Human breast cancer: correlation of relapse and survival with amplification of the HER-2/neu oncogene," Science, vol. 235 (4785), pp. 177-182 (1987).

Spiridon, C. et al., "Targeting Multiple Her-2 Epitopes with Monoclonal Antibodies Results in Improved Antigrowth Activity of a Human Breast Cancer Cell Line In Vitro and In Vivo," Clinical Cancer Research, vol. 8, pp. 1720-1730 (2002).

Staerz, U. et al., "Hybrid Antibodies can Target Sites for Attack by T Cells," Nature, vol. 314, pp. 628-631 (1985).

Tao, R.H. et al., "All EGF(ErbB) receptors have preformed homo- and heterodimeric structures in living cells," J Cell Sci., vol. 121, pp. 3207-3217 (2008).

Turken, O. et al., "Prevalence and prognostic value of c-erbB2 expression in non-small cell lung cancer (NSCLC)," Neoplasma, vol. 50 (4), pp. 257-261 (2003).

Vajdos, F. et al., "Comprehensive functional maps of the antigen-binding site of an anti-ErbB2 antibody obtained with shotgun scanning mutagenesis," Journal of Molecular Biology, vol. 320:415-428 (2002).

Van Berkel, PH. et al, "Rapid production of recombinant human IgG With improved ADCC effector function in a transient expression system," Biotechnology and Bioengineering, vol. 105(2), pp. 350-357 (2010).

Van der Neut Kolfschoten, M. et al., "Anti-inflammatory activity of human IgG4 antibodies by dynamic Fab arm exchange," Science, vol. 317(5844), pp. 1554-1557 (2007).

Van Spriel, A.B.et al., "Immunotherapeutic perspectives for bispecific antibodies," Immunology Today, vol. 21(8), pp. 391-397 (2000).

Wehrman, TS., et al., "A system for quantifying dynamic protein interactions defines a role for Herceptin in modulating ErbB2 interactions," PNAS USA, vol. 103(50), pp. 19063-19068 (2006).

Wu, H., et al. , "Humanization of a murine monoclonal antibody by simultaneous optimization of framework and CDR residues," Journal of Molecular Biology, vol. 294:151-162 (1999).

Zhu, Z. et al., "Engineering High Affinity Humanized Anti-P185HER2/Anti-CD3 Bispecific F(AB')2 for Efficient Lysis of P185HER2 Overexpressing Tumor Cells," International Journal of Cancer, vol. 62(3), pp. 319-324 (1995).

Hudis, C. et al., "Trastuzumab—Mechanism of Action and Use in Clinical Practice," The New England Journal of Medicine, vol. 357:39-51 (2007).

\* cited by examiner

FIG. 1A

<u>IgHV3-23-01 / IGHJ4-02 – VH alignment (Group 1)</u>

```
IgHV1-23-01  EVQLLESGGGLVQPGGSLRLSCAASGFTFSSYAMSWVRQAPGKGLEWVSAISGSGGSTYYADSVKG
TH1014-050   EVQLLESGGGLVQPGGSLRLSCAASGFTFSSYAMSWVRQAPGKGLEWVSAISGSGGSTYYADSVKG
VH1014-049   EVQLLESGGGLVQPGGSLRLSCAASGFTFSSYAMSWVRQAPGKGLEWVSAISGSGGSTYYADSVKG
VH1014-051   EVQLLESGGGLVQPGGSLRLSCAASGFTFSSYAMSWVRQAPGKGLEWVSAISGSGGSTYYADSVKG
VH1014-055   EVQLLESGGGLVQPGGSLRLSCAASGFTFSSYAMSWVRQAPGKGLEWVSAISGSGGSTYYADSVKG
Consensus    EVQLLESGGGLVQPGGSLRLSCAASGFTFSSYAMSWVRQAPGKGLEWVSAISGSGGSTYYADSVKG IgHV1-23-01  RFTISRDNSKNTLYLQMNSLRAEDTAVYYCAK------YFDYWGQGTLVTVSS
TH1014-050   RFTISRDNSKNTLYLQMSSLRAEDTAVYYCAKARANWDYFDYWGQGTLVTVSS
VH1014-049   RFTISRDNSKSTLSLQMNSLRAEDTAVYYCAKARANWDYFDYWGQGTLVTVSS
VH1014-051   RFTISRDNSKSTLSLQMNSLRAEDTAVYYCAKARANWDYFDYWGQGTLVTVSS
VH1014-055   RFTISRDNSKSTLSLQMNSLRAEDTAVYYCAKARANWDYFDYWGQGTLVTVSS
Consensus    RFTISRDNSKSTLSLQMSSLRAEDTAVYYCAKARANWDYFDYWGQGTLVTVSS
```

FIG. 1B

<u>IgHV1-69-04 / IGHJ6-02 – VH alignment (Group 1)</u>

```
IgHV1-69-04  QVQLVQSGAEVKKPGSSVKVSCKASGGTFSSYAISWVRQAPGQGLEWMGRIIPILGIANYAQKFQG
TH1014-084   QVQLVQSGAEVKKPGSSVKVSCKASGGTFSSYAISWVRQAPGQGLEWMGRISSLGINSAQKFQG
Consensus    QVQLVQSGAEVKKPGSSVKVSCKASGGTFSSYAISWVRQAPGQGLEWMGRISSLGINSAQKFQG IgHV1-69-04  RVTITADKSTSTAYMELSSLRSEDTAVYYCAR--------GMDVWGQGTTVTVSS
TH1014-084   RVTITADKSTSTAYMELSSLRSEDTAVYYCAREKGVDYYYGSVWGQGTTVTVSS
Consensus    RVTITADKSTSTAYMELSSLRSEDTAVYYCAREKGVDYYYGSVWGQGTTVTVSS
```

FIG. 1C

IgHV1-18-01 / IGHJ4-02 – VH alignment (Group 1)

```
IgHV1-18-01   QVQLVQSGAEVKKPGASVKVSCKASGYTFTSYGISWVRQAPGQGLEWMGWISAYNGNTNYAQKLQG
TH1014-169    QVQLVQSGAEVKKPGASVKVSCKASGYTFTXYGISWVRQAPGQGLEWMGWXSAYXGNTXYAQKLQG
VH1014-123    QVQLVQSGAEVKKPGASVKVSCKAAGYTFTXYGISWVRQAPGQXLEWMGWIXXYXSNTXYAQKLQG
VH1014-161    QVQLVQSGAEVKKPGASVKVSCKASGYTFTXYGISWVRQAPGQGLEWMGWLSAYXGNTXYAQKLQG
VH1014-124    QVQLVQSGAEVKKPGASVKVSCKAAGYTFTXYGISWVRQAPGQGLEWMGWIXXYNGNTXYAQXXQD
Consensus     QVQLVQSGAEVKKPGASVKVSCKASGYTFTXYGISWVRQAPGQXLEWMGWIXXYXGNTXYAQXXQG IgHV1-18-01   RVTMTTDTSTSTAYMELRSLRSDDTAVYYCAR--------YFDYWGQGTLVTVSS
TH1014-169    RVTMTTDTSTXTAYMELRSLRSDDTAVYYCARDRXXVRPDYFDYWGQGTLVTVSS
VH1014-123    RVTMTTDTSTSTAYMELRSLRSDDTAVYYCARDRXXVRPDYFDYWGQGTLVTVSS
VH1014-161    RVTMTTDTSTXTAYMELRSLRSDDTAVYYCARDRXXVRPDYFDYWGQGTLVTVSS
VH1014-124    RVTMTTDTSTSTAYMELRSLRSDDTAVYYCARDRXXVRPDYFDYWGQGTLVTVSS
Consensus     RVTMTTDTSTXTAYMELRSLRSDDTAVYYCARDRXXVRPDYFDYWGQGTLVTVSS
```

FIG. 1D

IgHV4-34-01 / IGHJ4-02 – VH alignment (Group 2, No. 1)

```
IgHV4-34-01   QVQLQQWGAGLLKPSETLSLTCAVYGGSFSGYYWSWIRQPPGKGLEWIGEINHSGSTNYNPSLKSR
TH1014-025    QVQLQQWGAGLLKPSETLSLTCAVYGGSFSXYYWXWIRQPPGKGLEWIGEIXHSGSTNYNPSLKSR
VH1014-001    QVQLQQWGAGLLKPSETLSLTCAVYGGSFSGYYWXWIRQPPGKGLEWIGEINHSGSTNYNPSLKSR
VH1014-143    QVQLQQWGAGLLKPSETLSLTCAVYGGSFSGYYWXWIRQPPGKGLEWIGEIXHSGSXNYNPSLXSR
VH1014-019    QVQLQQWGAGLLKPSETLSLTCAVYGGSFSXYYWXWIRQPPGKGLEWIGEIXHXGSTNYNPSLKSR
VH1014-021    QVQLQQWGAGLLKPSETLSLTCAVYGGSFSXYYWXWIRQPPGKGLEWIGEIXHSGSTNYNPSLKSR
VH1014-027    QVQLQQWGAGLLKPSETLSLTCAVYGGSFSXYXWXWIRQPPGKGLEWIGEIXHSGSTNYNPSLKSR
Consensus     QVQLQQWGAGLLKPSETLSLTCAVYGGSFSXYXWXWIRQPPGKGLEWIGEIXHXGSXNYNPSLXSR IgHV4-34-01   VTISVDTSKNQFSLKLSSVTAADTAVYYCAR--------YFDYWGQGTLVTVSS
TH1014-025    VTISVDTSKNQFSLKLSSVTAADTAVYYCARGXXXSGXYYFDXWXQGTLVTVSS
VH1014-001    VTISVDTSKNQFSLKLSSVTAADTAVYYCARGXXXSGXYYFDXWGXGTXVTVSS
VH1014-143    VTISVDTSKNQFSLXLSSVTAADTAVYYCARGXXXSGXYYFDXWGQGTLVTVSS
VH1014-019    VTISVDTSKXQFSLKLSSVTAADTAVYYCARGXXXSGXYYFDXWXQGTLVTVSS
VH1014-021    VTISVDTSKNQFSLKLSSVTAADTAVYYCARGXXXSGXYYFDXWGQGTLVTVSS
VH1014-027    VTISVDTSKNQFSLXLSSVTAADTAVYYCARGXXXSGXYYFDXWXQGTLVTVSS
Consensus     VTISVDTSKXQFSLXLSSVTAADTAVYYCARGXXXSGXYYFDXWXXGTXVTVSS
```

FIG. 1E

IgHV4-34-01 / IGHJ4-02 – VH alignment (Group 2, No. 2)

```
IgHV4-34-01   QVQLQQWGAGLLKPSETLSLTCAVYGGSFSGYYWSWIRQPPGKGLEWIGEINHSGSTNYNPSLKSR
TH1014-091    QVQLQQWGAGLLKPSETLSLTCAVGGSFSGYYWWIRQPPGKGLEWIGEIHSGTNYNPSLSR
VH1014-032    QVQLQQWGAGLLKPSETLSLTCAVYGGSFSGYYWSWIRQPPGKGLEWIGEINHSGTNYNPSLSR
VH1014-035    QVQLQQWGAGLLKPSETLSLTCAYGGSFSGYYWSWIRQPPGKGLEWIGEINHSGTNYNPSLSR
VH1014-036    QVQLQQWGAGLLKPSETLSLTCAVYGGSFSYYWSWIRQPPGKGLEWIGEINHSGSTNYNPSLKSR
VH1014-054    QVQLQQWGAGLLKPSETLSLTCAVYGGSFSGYYWSWIRQPPGKGLEWIGEIHSGSTNYNPSLKSR
VH1014-094    QVQLQQWGAGLLKPSETLSLTCAVGGSFSGYYWWIRQPPGKGLEWIGEIHSGTNYNPSLKSR
Consensus     QVQLQQWGAGLLKPSETLSLTCAGGSFSYYWWIRQPPGKGLEWIGEIHSGTNYNPSLSR IgHV4-34-01   VTISVDTSKNQFSLKLSSVTAADTAVYYCAR--------YFDYWGQGTLVTVSS
TH1014-091    VTISVDTSKNQFSLKLSVTAADTAVYYCARLGSGYYDYWGQGTLVTVSS
VH1014-032    VTISVDTSKNQFSLKLSSVTAADTAVYYCARLGSGYYFDYWGQGTLVTVSS
VH1014-035    VTISVDTSKNQFSLKLSSVTAADTAVYYCARLGSGYYFDYWGQGTLVTVSS
VH1014-036    VTISVDTSKNQFSLKLSSVTAADTAVYYCARLGSGYYFDYWGQGTLVTVSS
VH1014-054    VTISVDTSKNQFSLKLSSVTAADTAVYYCARLGSGYYFDYWGQGTLVTVSS
VH1014-094    VTISVDTSKNQFSLKLSVTAADTAVYYCARLGSGYYDYWGQGTLVTVSS
Consensus     VTISVDTSKNQFSLKLSVTAADTAVYYCARLGSGYYDYWGQGTLVTVSS
```

FIG. 1F

IgHV3-30-3-01 / IGHJ4-02 – VH alignment (Group 2)

```
IgV1-30-...   QVQLVESGGGVVQPGRSLRLSCAASGFTFSSYAMHWVRQAPGKGLEWVAVISYDGSNKYYADSVKGR
TH1014-129    QVQLVESGGGVVQPGRSLRLSCAASGFTFSAHWVRQAPGKGLEWVAVISYDGKYADSVKGR
Consensus     QVQLVESGGGVVQPGRSLRLSCAASGFTFSAHWVRQAPGKGLEWVAVISYDGKYADSVKGR IgHV3-30-...  FTISRDNSKNTLYLQMNSLRAEDTAVYYCAR------YFDYWGQGTLVTVSS
TH1014-129    FTISRDNSKNTLYLQMNSLRAEDTAYYCARGLGVWGFDYWGQGTLVTVSS
Consensus     FTISRDNSKNTLYLQMNSLRAEDTAYYCARGLGVWGFDYWGQGTLVTVSS
```

FIG. 1G

IgHV3-23-1 / IGHJ4-02 – VH alignment (Group 3a)

```
IgHV3-23-1   EVQLLESGGGLVQPGGSLRLSCAASGFTFSSYAMSWVRQAPGKGLEWVSAISGSGGSTYYADSVKG
TH1014-098   EVQLLESGGGLVQPGGSLRLSCAASGFTFSNYGMSWVRQAPGKGLEWVSAISGSXXSTYYADSVKG
VH1014-105   EVQLLESGGGLVQPGGSLRLSCAASGFTFSNYGMSWVRQAPGKGLEWVSAISGSXXSTYYADSVKG
VH1014-100   EVQLLESGGGLVQPGGSLRLSCAASGFTFXXYGMXWVRQAPGKGLEWVSAISGXGXSTYYADSVKG
VH1014-125   EVQLLESGGGLVQPGGSLRLSCAASGFTFXXYAMXWVRQAPGKGLEWVSXISGSGXTYYADSVKG
VH1014-162   EVQLXESGGGXVQPGGSLRLSCAASGFTFSSYGMSWVRQAPGKGLEWVSXISGSGXSTYYADSVKG
Consensus    EVQLXESGGGXVQPGGSLRLSCAASGFTFXXYXMXWVRQAPGKGLEWVSXISGXXXTYYADSVKG IgHV3-23-1   RFTISRDNSKNTLYLQMNSLRAEDTAVYYCAK----------YFDYWGQGTLVTVSS
TH1014-098   RFTISRDNSKNTLXLQMNSLRAEDTAVYYCAKXHYXGSGSYYTXFDYWGQGTLVTVSS
VH1014-105   RFTISRDNSKNTLXLQMNSLRAEDTAVYYCAKXHYXGSGSYYTXFDYWGQGTLVTVSS
VH1014-100   RFTISRDNSKNTLYLQMNSLRAEDTAVYYCAKXHYXGSGSYYTXFDYWGQGTLVTVSS
VH1014-125   RFTISRDNSKXTLYLQMNSLRAEDTAVYYCAKGHXXGSGSYYTXFDYWGQGTLVTVSS
VH1014-162   RFTISRDNSKNTLYLQMNSLRAEDTAVYYCAKGYXXGSGSYYTXFDYWGQGTLVTVSS
Consensus    RFTISRDNSKXTLXLQMNSLRAEDTAVYYCAKXXXXGSGSYYTXFDYWGQGTLVTVSS
```

FIG. 1H

IgHV5-51-01 / IGHJ2-01 – VH alignment (Group 3a, No. 1)

```
IgHV5-51-01  EVQLVQSGAEVKKPGESLKISCKGSGYSFTSYWIGWVRQMPGKGLEWMGIIYPGDSDTRYSPSFQG
TH1014-127   EVQLVQSGAEVKKPGESLXISCKGSGYSFXXYWIGWVRQMPGKGLEWMGIIXPGDSDXRYSPSFQG
Consensus    EVQLVQSGAEVKKPGESLXISCKGSGYSFXXYWIGWVRQMPGKGLEWMGIIXPGDSDXRYSPSFQG IgHV5-51-01  QVTISADKSISTAYLQWSSLKASDTAMYYCAR----------YFDLWGRGTLVTVSS
TH1014-127   QVTISADKSISTAYLQWSSLKASDTAMYYCARQPGDWSPRHWYFDLWGRGTLVTVSS
Consensus    QVTISADKSISTAYLQWSSLKASDTAMYYCARQPGDWSPRHWYFDLWGRGTLVTVSS
```

FIG. 1I

IgHV5-51-01-01 / IGHJ5-02 – VH alignment (Group 3a, No. 2)

```
IgHV5-51-01  EVQLVQSGAEVKKPGESLKISCKGSGYSFTSYWIGWVRQMPGKGLEWMGIIYPGDSDTRYSPSFQG
TH1014-159   EVQLVQSGAEVKKPGESLKISCKGSGYXFTSYWIGWVRQMPGKGLEWMGIIYPGDSDTRYSPSFQG
Consensus    EVQLVQSGAEVKKPGESLKISCKGSGYXFTSYWIGWVRQMPGKGLEWMGIIYPGDSDTRYSPSFQG IgHV5-51-01  QVTISADKSISTAYLQWSSLKASDTAMYYCAR------------NWFDPWGQGTLVTVSS
TH1014-159   QVTISADKSISTAYLQWSSLKASDTAMYYCARWGTYYDILTGYFNWFDPWGQGTLVTVSS
Consensus    QVTISADKSISTAYLQWSSLKASDTAMYYCARWGTYYDILTGYFNWFDPWGQGTLVTVSS
```

FIG. 1J

IgHV1-18-01 / IGHJ6-02  – VH alignment (Group 3b)

```
IgHV1-18-01   QVQLVQSGAEVKKPGASVKVSCKASGYTFTSYGISWVRQAPGQGLEWMGWISAYNGNTNYAQKLQG
TH1014-132    QVQLVQSGAEVKKPGASVKVSCKASGYTFTSYGISWVRQAPGQGLEWMGWISAYNGNXNYXQKXQG
Consensus     QVQLVQSGAEVKKPGASVKVSCKASGYTFTSYGISWVRQAPGQGLEWMGWISAYNGNXNYXQKXQG IgHV1-18-01   RVTMTTDTSTSTAYMELRSLRSDDTAVYYCAR-----------GMDVWGQGTTVTVSS
TH1014-132    RVTMTTDTXTSTAYMELRSLXSDDTAVYYCAREYSYDSGTYFYYGMDVWGQGTTVTVSS
Consensus     RVTMTTDTSTSTAYMELRSLRSDDTAVYYCAREYSYDSGTYFYYGMDVWGQGTTVTVSS
```

FIG. 1K

IgHV3-30-3-01 / IGHJ4-02  – VH alignment (Group 3b)

```
IgHV3-30...   QVQLVESGGGVVQPGRSLRLSCAASGFTFSSYAMHWVRQAPGKGLEWVAVISYDGSNKYYADSVKG
TH1014-153    QVQLVESGGGVVQPGRSLRLSCAASGFTFSXYXHWVRQAPGKGLEWVXVISYDGSNKYYADSVKG
VH1014-033    QVQLVESGGGVVQXGRSLRLSCAASGFTFSSXAMHWVRQAPGKGLEWVAXISYDGSNKYYADSVKG
VH1014-160    QVQLVESGGGVVQPGRSLRLSCAASGFTFSSXAMHWVRQAPGKGLEWVAXISYDGSNKYYADSVKG
VH1014-166    QVQLVESGGGVVQPGRSLRLSCAASGFTFSSYAMHWVRQAPGKGLEWVAVISYDGSNXYYADSVKG
VH1014-152    QVQVVESGGGVVQPGRSLRLSCAASGFTFSSYAMHWVRQAPGKGLEWVAVISYDGSXKYYADSVKG
VH1014-167    QVQLVESGGGVVQPGRSLRLSCAASGFTFSSYAXHWVRQAPGKGLEWVAVISYDGSNKYYADSVKG
Consensus     QVQLVESGGGVVQXGRSLRLSCAASGFTFSXXXXHWVRQAPGKGLEWVXXISYDGSXXYYADSVKG IgHV3-30...   RFTISRDNSKNTLYLQMNSLRAEDTAVYYCAR--------XFDYWGQGTLVTVSS
TH1014-153    RFTISRDNSKNTLYLQMNSLXAEDTAXYYCARGXXXXXXGVFDYWGQGTLVTVSS
VH1014-033    RFTISRDNSKNTLYLQMNSLRAEDTAVYYCARGXXXXXXGVFDYWGQGTLVTVSS
VH1014-160    RFTISRDNSKNTXYLQMNSLRAEDTAXYYCARGXXXXXXGVFDYWGQGTLVTVSS
VH1014-166    RFTISRDNSKNTLYLQMNSLRAEDTAVYYCARGXXXXXXGVFDYWGQGTLVTVSS
VH1014-152    RFTISRDNSKNTLYLQMNSLRAEDTAVYYCARGXXXXXXGVFDYWGQGTLVTVSS
VH1014-167    RFTISRDNSKNTLYLQMNSLRAEDTAVYYCARGXXXXXXGVFDYWGQGTLVTVSS
Consensus     RFTISRDNSKNTXYLQMNSLXAEDTAXYYCARGXXXXXXGXFDYWGQGTLVTVSS
```

FIG. 2A

IgKV1-12-01 / IGKJ5-01 – VL alignment (Group 1)

```
IgKV1-12-01  DIQMTQSPSSVSASVGDRVTITCRASQGISSWLAWYQQKPGKAPKLLIYAASSLQSGVPSRFSGSG
VL1014-050   DIQMTQSPSSVSASVGDRVTITCRASQGISSWLAWYQ KPGKAPKLLIYAAS LQSGVPSRFSGSG
VL1014-084   DIQMTQSPSSVSASVGDRVTITCRASQGISSWLAWYQ KPGKAPKLLIY AS LQSGVPSRFSGSG
VL1014-049   DIQMTQSPSSVSASVGDRVTITCRASQGISSWLAWYQ KPGKAPKLLIYAAS LQSGVPSRFSGSG
VL1014-051   DIQMTQSPSSVSASVGDRVTITCRASQGISSWLAWYQ KPGKAPKLLIYAAS LQSGVPSRFSGSG
VL1014-055   DIQMTQSPSSVSASVGDRVTITCRASQGISSWLAWYQ KPGKAPKLLIYAAS LQSGVPSRFSGSG
Consensus    DIQMTQSPSSVSASVGDRVTITCRASQGISSWLAWYQ KPGKAPKLLIY AS LQSGVPSRFSGSG IgKV1-12-01  SGTDFTLTISSLQPEDFATYYCQQANSFPITFGQGTRLEIK
VL1014-050   SGTDFTLTISSLQPEDFATYYCQQANSFPITFGQGTRLEIK
VL1014-084   SGTDFTLTISSLQPEDFATYYCQQANSFP TFG GTK EIK
VL1014-049   SGTDFTLTISSL PEDFATYYCQQANSFPITFGQGTRLEIK
VL1014-051   SGTDFTLTISSL PEDFATYYCQQANSFPITFGQGTRLEIK
VL1014-055   SGTDFTLTISSL PEDFATYYCQQANSFPITFGQGTRLEIK
Consensus    SGTDFTLTISSL PEDFATYYCQQANSFP TFG GTR EIK
```

FIG. 2B

IgKV3-11-01 / IGKJ1-01 – VL alignment (Group 1)

```
IgKV3-11-01  EIVLTQSPATLSLSPGERATLSCRASQSVSSYLAWYQQKPGQAPRLLIYDASNRATGIPARFSGSG
VL1014-169   EIVLTQSPATLSLSPGERATLSCRASQSVSSYLAWYQQKPGQAPRLLIYDASNRATGIPARFSGSG
VL1014-124   EIVLTQSPATLSLSPGERATLSCRASQSVSSYLAWYQQKPGQAPRLLIYDASNRATGIPARFSGSG
VL1014-161   EIVLTQSPATLSLSPGERATLSCRASQSVSSYLAWYQQKPGQAPRLLIYDASNRATGIPARFSGSG
VL1014-123   EIVLTQSPATLSLSPGERATLSCRASQSVSSYLAWYQQKPGQAPRLLIYD SNRATGIPARFSGSG
Consensus    EIVLTQSPATLSLSPGERATLSCRASQSVSSYLAWYQQKPGQAPRLLIYD SNRATGIPARFSGSG IgKV3-11-01  SGTDFTLTISSLEPEDFAVYYCQQRSNWPWTFGQGTKVEIK
VL1014-169   SGTDFTLTISSLEPEDFAVYYCQQRSNWPRTFGQGTKVEIK
VL1014-124   SGTDFTLTISSLEPEDFAVYYCQQRSNWPRTFGQGTKVEIK
VL1014-161   SGTDFTLTISSLEPEDFAVYYCQQRSNWPRTFGQGTKVEIK
VL1014-123   SGTDFTLTISSLEPEDFAVYYCQQRS WPRTFGQGTKVEIK
Consensus    SGTDFTLTISSLEPEDFAVYYCQQRS WPRTFGQGTKVEIK
```

FIG. 2C

IgKV1D-16-01 / IGKJ5-01– VL alignment (Group 2, No. 1)

```
IgKV1D-16 …  DIQMTQSPSSLSASVGDRVTITCRASQGISSWLAWYQQKPEKAPKSLIYAASSLQSGVPSRFSGSG
VL1014-025   DIQMTQSPSSLSASVGDRVTITCRASQGISSWLAWYQQKPEKAPKSLIYAASSLSSGVPSRFSGSG
VL1014-001   DIQMTQSPSSLSASVGDRVTITCRASQGISSWLAWYQQKPEKAPKSLIAASSLQSGVPSRFSGSG
VL1014-019   DIQMTQSPSSLSASVGDRVTITCRASQGISSWLAWYQQKPEKAPKSLIYAASSLSSGVPSRFSGSG
VL1014-143   DIQMTQSPSSLSASVGDRVTITCRASQGISSWLAWYQQKPEKAPKSLIYAASSLQSGVPSRFSGSG
VL1014-021   DIQMTQSPSSLSASVGDRVTITCRASQGISSWLAWYQQKPEKAPKSLIYAASSLQSGVPSRFSGSG
VL1014-027   DIQMTQSPSSLSASVGDRVTITCRASQGISSWLAWYQQKPEKAPKSLIYAASSLQSGVPSRFSGSG
Consensus    DIQMTQSPSSLSASVGDRVTITCRASQGISSWLAWYQQKPEKAPKSLIAASSLSSGVPSRFSGSG IgKV1D-16 …  SGTDFTLTISSLQPEDFATYYCQQYNSYPITFGQGTRLEIK
VL1014-025   SGTDFTLTISSLQPEDFATYYCQQYNSYPITFGQGTRLEIK
VL1014-001   SGTDFTLTISSLQPEDFATYYCQQYISSPITFGQGTRLEIK
VL1014-019   SGTDFTLTISSLQPEDFATYYCQQYNSYPITFGQGTRLEIK
VL1014-143   SGTDFTLTISSLQPEDFATYYCQQYNSYPITFGQGTRLEIK
VL1014-021   SGTDFTLTISSLQPEDFATYYCQQYNSYPITFGQGTRLEIK
VL1014-027   SGTDFTLTISSLQPEDFATYYCQQYNSYPITFGQGTRLEIK
Consensus    SGTDFTLTISSLQPEDFATYYCQQYNSSPITFGQGTRLEIK
```

FIG. 2D

IgKV1D-16-01 / IGKJ1-01– VL alignment (Group 2, No. 2)

```
IgKV1D-16 …  DIQMTQSPSSLSASVGDRVTITCRASQGISSWLAWYQQKPEKAPKSLIYAASSLQSGVPSRFSGSG
VL1014-091   DIQMTQSPSSLSASVGDRVTITCRASQGISSWLSWYQQKPEKAPKSLIYAASSLQSGVPSRFSGSG
VL1014-032   DIQMTQSPSSLSASVGDRVTITCRASQGISSWLAWYQQKPEKAPKSLIYASSSLQSGVPSRFSGSG
VL1014-035   DIQMTQSPSSLSASVGDRVTITCRASQGISSWLAWYQQKPEKAPKSLIYASSSLQSGVPSRFSGSG
VL1014-036   DIQMTQSPSSLSASVGDRVTITCRASQGISSWLSWYQQKPEKAPKSLIYAASSLQSGVPSRFSGSG
VL1014-054   DIQMTQSPSSLSASVGDRVTITCRASQGISSWLAWYQQKPEKAPKSLIYAASSLQSGVPSRFSGSG
VL1014-094   DIQMTQSPSSLSASVGDRVTITCRASQGISSWLSWYQQKPEKAPKSLIYAASSLQSGVPSRFSGSG
Consensus    DIQMTQSPSSLSASVGDRVTITCRASQGISSWLSWYQQKPEKAPKSLIYASSSLQSGVPSRFSGSG IgKV1D-16 …  SGTDFTLTISSLQPEDFATYYCQQYNSYPWTFGQGTKVEIK
VL1014-091   SGTDFTLTISSLQPEDFATYYCQQYNSFPPTFGQGTKVEIK
VL1014-032   SGTDFTLTISSLQPEDFATYYCQQYNSFPPTFGQGTKVEIK
VL1014-035   SGTDFTLTISSLQPEDFATYYCQQYNSFPPTFGQGTKVEIK
VL1014-036   SGTDFTLTISSLQPEDFATYYCQQYNSFPPTFGQGTKVEIK
VL1014-054   SGTDFTLTISSLQPEDFATYYCQQYNSFPPTFGSGTKVEIK
VL1014-094   SGTDFTLTISSLQPEDFATYYCQQYNSFPPTFGQGTKVEIK
Consensus    SGTDFTLTISSLQPEDFATYYCQQYNSFPPTFGSGTKVEIK
```

FIG. 2E

<u>IgKV1D-16-01 / IGKJ2-01 – VL alignment (Group 3a)</u>

```
IgKV1D-16  … DIQMTQSPSSLSASVGDRVTITCRASQGISSWLAWYQQKPEKAPKSLIYAASSLQSGVPSRFSGSG
VL1014-098   DIQMTQSPSSLSASVGDRVTITCRASQGISSWLAWYQQKPEKAPKSLIYAASSLQSGVPSRFSGSG
VL1014-100   DIQMTQSPSSLSASVGDRVTITCRASQGISSWLAWYQQKPEKAPKSLIYAASSLQSGVPSRFSGSG
VL1014-105   DIQMTQSPSSLSASVGDRVTITCRASQGISSWLAWYQQKPEKAPKSLIYAASSLQSGVPSRFSGSG
VL1014-125   DIQMTQSPSSLSASVGDRVTITCRASQGISSWLAWYQQKPEKAPKSLIYAASSLQSGVPSRFSGSG
VL1014-162   DIQMTQSPSSLSASVGDRVTITCRASQGISSWLAWYQQKPEKAPKSLIYAASSLQSGVPSRFSGSG
Consensus    DIQMTQSPSSLSASVGDRVTITCRASQGISSWLAWYQQKPEKAPKSLIYAASSLQSGVPSRFSGSG IgKV1D-16  … SGTDFTLTISSLQPEDFATYYCQQYNSYPYTFGQGTKLEIK
VL1014-098   SGTDFTLTISSLQPEDFATYYCQQYNSYPYTFGQGTKLEIK
VL1014-100   SGTDFTLTISSLQPEDFATYYCQQYNSYPYTFGQGTKLEIK
VL1014-105   SGTDFTLTISSLQPEDFATYYCQQYNSYPYTFGQGTKLEIK
VL1014-125   SGTDFTLTISSLQPEDFATYYCQQYNSYPYTFGQGTKLEIK
VL1014-162   SGTDFTLTISSLQPEDFATYYCQQYNSYPITFGQGTKLEIK
Consensus    SGTDFTLTISSLQPEDFATYYCQQYNSYPITFGQGTKLEIK
```

FIG. 2F

<u>IgKV1D-16-01 / IGKJ5-01 – VL alignment (Group 3b)</u>

```
IgKV1D-16  … DIQMTQSPSSLSASVGDRVTITCRASQGISSWLAWYQQKPEKAPKSLIYAASSLQSGVPSRFSGSG
VL1014-153   DIQMTQSPSSLSASVGDRVTITCRASQGISSWLAWYQQKPEKAPKSLIYAASSLQSGVPSRFSGSG
VL1014-152   DIQMTQSPSSLSASVGDRVTITCRASQGISSWLAWYQQKPEKAPKSLIYAASSLQSGVPSRFSGSG
VL1014-166   DIQMTQSPSSLSASVGDRVTITCRASQGISSWLAWYQQKPEKAPKSLIYAASSLQSGVPSRFSGSG
VL1014-167   DIQMTQSPSSLSASVGDRVTITCRASQGISSWLAWYQQKPEKAPKSLIYAASSLQSGVPSRFSGSG
VL1014-160   DIQMTQSPSSLSASVGDRVTITCRASQDISSWLAWYQQKPEKAPKSLIYAASSLQSGVPSRFSGSG
VL1014-033   DIQMTQSPSSLSASVGDRVTITCRASQGISSWLAWYQQKPEKAPKSLIYAASSLQSGVPSRFSGSG
Consensus    DIQMTQSPSSLSASVGDRVTITCRASQGISSWLAWYQQKPEKAPKSLIYAASSLQSGVPSRFSGSG IgKV1D-16  … SGTDFTLTISSLQPEDFATYYCQQYNSYPITFGQGTRLEIK
VL1014-153   SGTDFTLTISSLQPEDFATYYCQQYNSYPITFGQGTRLEIK
VL1014-152   SGTDFTLTISSLQPEDFATYYCQQYNSYPITFGQGTRLEIK
VL1014-166   SGTDFTLTISSLQPEDFATYYCQQYNSYPITFGQGTRLEIK
VL1014-167   SGTDFTLTISSLQPEDFATYYCQQYNSYPITFGQGTRLEIK
VL1014-160   SGTDFTLTISSLQPEDFATYYCQQYNSYPITFGQGTRLEIK
VL1014-033   SGTDFTLTISSLQPEDFATYYCQQYNSYPITFGQGTRLEIK
Consensus    SGTDFTLTISSLQPEDFATYYCQQYNSYPITFGQGTRLEIK
```

MONOCLONAL ANTIBODIES AGAINST HER2

RELATED APPLICATIONS

This application is a divisional of U.S. patent application Ser. No. 13/700,341, filed Mar. 14, 2013, which is a 35 U.S.C. 371 national stage filing of PCT/EP2011/058779, filed May 27, 2011, which claims priority to U.S. Provisional Application No. 61/349,180, filed May 27, 2010, International Patent Application No. PCT/EP2011/056388, filed Apr. 20, 2011, and Danish Patent Application Nos. PA201100312, filed Apr. 20, 2011, and PA201000467, filed May 27, 2010. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Dec. 5, 2017, is named GMI_131USDV2_Sequence_Listing.txt and is 149,702 bytes in size.

FIELD OF THE INVENTION

The present invention relates to monoclonal antibodies directed to human epidermal growth factor receptor 2 (HER2) and to uses of such antibodies, in particular their use in the treatment of cancer.

BACKGROUND OF THE INVENTION

HER2 is a 185-kDa cell surface receptor tyrosine kinase and member of the epidermal growth factor receptor (EGFR) family that comprises four distinct receptors: EGFR/ErbB-1, HER2/ErbB-2, HER3/ErbB-3, and HER4/ErbB-4. Both homo- and heterodimers are formed by the four members of the EGFR family, with HER2 being the preferred and most potent dimerization partner for other ErbB receptors (Graus-Porta et al., Embo J 1997; 16:1647-1655; Tao et al., J Cell Sci 2008; 121:3207-3217). HER2 can be activated by overexpression or by heterodimerization with other ErbBs that can be activated by ligand binding (Riese and Stern, Bioessays 1998; 20:41-48). For HER2, no ligand has been identified. HER2 activation leads to receptor phosphorylation, which triggers a cascade of downstream signals through multiple signaling pathways, such as MAPK, phosphoinositol 3-kinase/AKT, JAK/STAT and PKC, which ultimately results in the regulation of multiple cellular functions, such as growth, survival and differentiation (Huang et al., Expert Opin Biol Ther 2009; 9:97-110).

Much of the attention on HER2 in tumors has been focused on its role in breast cancer, in which HER2 overexpression is reported in approximately 20% of the cases and is correlated with poor prognosis (Reese et al., Stem Cells 1997; 15:1-8; Andrechek et al., Proc Natl Acad Sci USA 2000; 97:3444-3449; and Slamon et al., Science 1987; 235:177-182). Besides breast cancer, HER2 expression has also been associated with other human carcinoma types, including prostate cancer, non-small cell lung cancer, bladder cancer, ovarian cancer, gastric cancer, colon cancer, esophageal cancer and squamous cell carcinoma of the head & neck (Garcia de Palazzo et al., Int J Biol Markers 1993; 8:233-239; Ross et al., Oncologist 2003; 8:307-325; Osman et al., J Urol 2005; 174:2174-2177; Kapitanovic et al., Gastroenterology 1997; 112:1103-1113; Turken et al., Neoplasma 2003; 50:257-261; and Oshima et al., Int 3 Biol Markers 2001; 16:250-254).

Trastuzumab (Herceptin®) is a recombinant, humanized monoclonal antibody directed against domain IV of the HER2 protein, thereby blocking ligand-independent HER2 homodimerization, and to a lesser extend heterodimerization of HER2 with other family members in cells with high HER2 overexpression (Cho et al., Nature 2003; 421:756-760 and Wehrman et al., Proc Natl Acad Sci USA 2006; 103: 19063-19068). In cells with modest HER2 expressing levels, trastuzumab was found to inhibit the formation of HER2/EGFR heterodimers (Wehrman et al., (2006), supra; Schmitz et al., Exp Cell Res 2009; 315:659-670). Trastuzumab mediates antibody-dependent cellular cytotoxicity (ADCC) and prevents ectodomain shedding, which would otherwise result in the formation of a truncated constitutively active protein in HER2 overexpressing cells. Also inhibition of both in vitro and in vivo proliferation of tumor cells expressing high levels of HER2 has been reported for trastuzumab (reviewed in Nahta and Esteva, Oncogene 2007; 26:3637-3643). Herceptin® has been approved both for first-line and adjuvant treatment of HER2 overexpressing metastatic breast cancer, either in combination with chemotherapy, or as a single agent following one or more chemotherapy regimens. Trastuzumab has been found to be effective only in 20-50% of HER2 overexpressing breast tumor patients and many of the initial responders show relapse after a few months (Dinh et al., Clin Adv Hematol Oncol 2007; 5:707-717).

Pertuzumab (Omnitarg™) is another humanized monoclonal antibody. It is directed against domain II of the HER2 protein, resulting in inhibition of ligand-induced heterodimerization (i.e., HER2 dimerizing with another member of the ErbB family to which a ligand has bound); a mechanism reported to not strictly require high HER2 expression levels (Franklin et al., Cancer Cell 2004; 5:317-328.). Although pertuzumab also mediates ADCC, the main mechanism of action of pertuzumab relies on its dimerization blockade (Hughes et al., Mol Cancer Ther 2009; 8:1885-1892). Moreover, pertuzumab was found to enhance EGFR internalization and downregulation by inhibiting the formation of EGFR/HER2 heterodimers, which otherwise tethers EGFR at the plasma membrane (Hughes et al., 2009, supra). This correlates with the observation that EGFR homodimers internalize more efficient than EGFR/HER2 dimers (Pedersen et al., Mol Cancer Res 2009; 7:275-284. The complementary mechanisms of action of pertuzumab and trastuzumab reportedly results in enhanced anti-tumor effects and efficacy when combined in patients who progressed during prior trastuzumab therapy (Baselga et al., J Clin Oncol 2010; 28:1138-1144), and a phase III trial to evaluate this antibody combination together with Docetaxel in previously untreated HER2-positive metastatic breast cancer is underway.

An alternative approach to improve targeted antibody therapy is by delivering cytotoxic cells or drugs specifically to the antigen-expressing cancer cells. For example, the so-called trifunctional antibodies are bispecific antibodies, targeting with one arm the antigen on the tumor cell and with the other arm for instance CD3 on T cells. Upon binding, a complex of T cells, tumor cells and effector cells that bind Fc is formed, leading to killing of the tumor cells (Muller and Kontermann, BioDrugs 2010; 24:89-98.). Ertumaxomab is one such trifunctional antibody against HER2, which induces cytotoxicity in cell lines with low HER2 expression and which is in Phase II clinical development in metastatic breast cancer (Jones et al., Lancet Oncol 2009; 10:1179-1187 and Kiewe et al., Clin Cancer Res 2006; 12:3085-3091).

A HER2 antibody drug conjugate (ADC) is currently in clinical development. T-DM1 consists of trastuzumab conjugated to the fungal toxin maytansine. In Phase II trials, responses in a heavily pretreated patient cohort including prior trastuzumab and/or lapatinib therapy were reported Burris et al, 2011, J Clin Oncol 29: 398-405 and Lewis Phillips et al., Cancer Res 2008; 68:9280-9290). Preliminary data from a Phase II trial determining efficacy and safety of T-DM1 versus trastuzumab plus docetaxel in her2-positive metastatic breast cancer patients with no rior chemotherapy for metastatic disease were reported (Perez et al, Abstract BA3, European Society for Medical Oncology meeting 2010). A Phase III trial to evaluate T-DM1 efficacy and safety versus capecitabine+lapatinib in patients with HER2-positive locally advanced or metastatic breast cancer who received prior trastuzumab therapy is ongoing.

While many factors are involved in selecting a suitable antibody for HER2 targeted therapy, it is typically an advantage for an ADC approach if the HER2-antibody complex efficiently internalizes upon antibody binding. Studies on murine HER2 antibodies have shown that certain combinations of antibodies instigate HER2 endocytosis (Ben-Kasus et al., PNAS 2009; 106:3294-9). Human HER2 antibodies F5 and C1 have been reported to internalize relatively rapidly on their own and to bind the same epitope (WO 99/55367 and WO 2006/116107). As compared to EGFR, however, internalization of HER2 is impaired. Indeed, EGFR homodimers internalize much more efficiently than HER2 homodimers (Dinh et al., Clin Adv Hematol Oncol 2007; 5:707-717). EGFR, and also HER3, can increase endocytosis of HER2 by the formation of EGFR/HER2 and HER3/HER2 heterodimers, respectively (Baulida et al., J Biol Chem 1996; 271:5251-5257; Pedersen N M, et al., Mol Cancer Res 2009; 7:275-84).

The complex mechanisms regulating the function of HER2 warrant further research on new and optimized therapeutic strategies against this proto-oncogene. Accordingly, there remains a need for effective and safe products for treating HER2-related diseases, such as cancer.

SUMMARY OF THE INVENTION

It is an object of the present invention to provide novel highly specific and effective monoclonal HER2 antibodies for medical use. The antibodies of the invention exhibit HER2 binding characteristics that differ from antibodies described in the art. Particularly, although most of the antibodies apparently bind to HER2 segments overlapping with those bound by trastuzumab, pertuzumab or F5/C1 as shown in a cross-blocking HER2 binding assay, the novel antibodies are characterized by a higher efficiency in killing HER2-expressing tumor cells in an ADC assay, improved internalization and/or other advantages over the known antibodies.

In preferred embodiments, the antibodies of the invention are fully human, bind to novel epitopes, and/or have favorable properties for therapeutic use in human patients. Exemplary properties include, but are not limited to, favorable binding characteristics to cancer cells expressing human HER2 at high or low levels, specific binding rhesus epithelial cells expressing a HER2 ortholog, efficient internalization upon binding to HER2, high capacity for killing cancer cells expressing high- or low-levels of HER2 when administered as an ADC, promoting proliferation of HER2-expressing cells less than F5, a neutral or inhibitory effect on the proliferation of HER2-expressing cancer cells, and provide for effective ADCC-mediated killing of HER2-expressing cells, as well as any combination of the foregoing properties.

These and other aspects of the invention are described in further detail below.

BRIEF DESCRIPTION OF THE DRAWINGS

FIGS. 1A-1K: Alignment of HuMab heavy chain variable region (VH) sequences with germline (reference) sequences (FIGS. 1A-1K). In each VH sequence, the amino acids that differ from those of the germline (reference) at specific positions are highlighted. Consensus VH sequences are shown, where "X" indicates positions at which alternative amino acids (selected from those aligned at each position) are possible. The CDR1, CDR2, and CDR3 sequences are underlined in each VH sequence. The consensus CDR sequences are further defined in Table 4. Sequences in FIG. 1A are as follows: IgHV1-23-01 (SEQ ID NO: 175), TH1014-050 (SEQ ID NO: 8), VH1014-049 (SEQ ID NO: 77), VH1014-051 (SEQ ID NO: 79), VH1014-055 (SEQ ID NO: 81), consensus (SEQ ID NO: 176). Sequences in FIG. 1B are as follows: IgHV1-69-04 (SEQ ID NO: 177), TH1014-084 (SEQ ID NO: 15), consensus (SEQ ID NO: 178). Sequences in FIG. 1C are as follows: IgGV1-18-01 (SEQ ID NO: 179), TH1014-169 (SEQ ID NO: 1), VH1014-123 (SEQ ID NO: 83), VH1014-161 (SEQ ID NO: 85), VH1014-124 (SEQ ID NO: 87), consensus (SEQ ID NO: 180). Sequences in FIG. 1D are as follows: IgHV4-34-01 (SEQ ID NO: 181), TH1014-025 (SEQ ID NO: 22), VH1014-001 (SEQ ID NO: 89), VH1014-143 (SEQ ID NO: 91), VH1014-019 (SEQ ID NO: 93), VH1014-021 (SEQ ID NO: 95), VH1014-027 (SEQ ID NO: 97), consensus (SEQ ID NO: 182). Sequences in FIG. 1E are as follows: IgHV4-34-01 (SEQ ID NO: 183), TH1014-091 (SEQ ID NO: 29), VH1014-032 (SEQ ID NO: 99), VH1014-035 (SEQ ID NO: 101), VH1014-036 (SEQ ID NO: 103), VH1014-054 (SEQ ID NO: 105), VH1014-094 (SEQ ID NO: 107), consensus (SEQ ID NO: 184). Sequences in FIG. 1F are as follows: IgHV1-30- . . . (SEQ ID NO: 185), TH1014-129 (SEQ ID NO: 35), consensus (SEQ ID NO: 186). Sequences in FIG. 1G are as follows: IgHV2-23-1 (SEQ ID NO: 187), TH1014-098 (SEQ ID NO: 56), VH1014-105 (SEQ ID NO: 109), VH1014-100 (SEQ ID NO: 111), VH1014-125 (SEQ ID NO: 113), VH1014-162 (SEQ ID NO: 115), consensus (SEQ ID NO: 188). Sequences in FIG. 1H are as follows: IgHV5-51-01 (SEQ ID NO: 189), TH1014-127 (SEQ ID NO: 42), consensus (SEQ ID NO: 190). Sequences in FIG. 1I are as follows: IgHV5-51-01 (SEQ ID NO: 191), TH1014-159 (SEQ ID NO: 49), consensus (SEQ ID NO: 192). Sequences in FIG. 1J are as follows: IgHV1-18-01 (SEQ ID NO: 193), TH1014-132 (SEQ ID NO: 70), consensus (SEQ ID NO:194). Sequences in FIG. 1K are as follows: IgHV3-30 . . . (SEQ ID NO: 195), TH1014-153 (SEQ ID NO: 63), VH1014-033 (SEQ ID NO: 117), VH1014-160 (SEQ ID NO: 119), VH1014-166 (SEQ ID NO: 121), VH1014-152 (SEQ ID NO: 123), VH1014-167 (SEQ ID NO: 125), consensus (SEQ ID NO: 196).

FIGS. 2A-2F: Alignment of HuMab light chain variable region (VL) sequences with germline (reference) sequences (FIGS. 2A-2B). In each VL sequence, the amino acids that differ from those of the germline (reference) at specific positions are highlighted. In FIG. 2A, all VL sequences derived from the same V-segment (IgKV1-12-01), but the closest J-segment differed between antibodies. Consensus VL sequences are shown, where "X" indicates positions at which alternative amino acids (selected from those aligned at the indicated position) are possible. The CDR1, CDR2, and CDR3 sequences are underlined in each VL sequence. The consensus CDR sequences are further defined in Table 4. Sequences in FIG. 2A are as follows: IgKV1-12-01 (SEQ ID NO: 197), VL1014-050 (SEQ ID NO: 12), VL1014-084 (SEQ ID NO: 19), VL1014-049 (SEQ ID NO: 78), VL1014-051 (SEQ ID NO: 80), VL1014-055 (SEQ ID NO: 82), consensus (SEQ ID NO: 198). Sequences in FIG. 2B are as follows: IgKV3-11-01 (SEQ ID NO: 199), VL1014-169 (SEQ ID NO: 5), VL1014-124 (SEQ ID NO: 88), VL1014-161 (SEQ ID NO: 86), VL1014-123 (SEQ ID NO: 84), consensus (SEQ ID NO: 200). Sequences in FIG. 2C are as follows: IgKV1D-16 . . . (SEQ ID NO: 201), VL1014-025 (SEQ ID NO: 26), VL1014-001 (SEQ ID NO: 90), VL1014-019 (SEQ ID NO: 94), VL1014-143 (SEQ ID NO: 92), VL1014-021 (SEQ ID NO: 96), VL1014-027 (SEQ ID NO: 98), consensus (SEQ ID NO: 202). Sequences in FIG. 2D are as follows: IgKV1D-16 . . . (SEQ ID NO: 203), VL1014-091 (SEQ ID NO: 32), VL1014-032 (SEQ ID NO: 100), VL1014-035 (SEQ ID NO: 102), VL1014-036 (SEQ ID NO: 104), VL1014-054 (SEQ ID NO: 106), VL1014-094 (SEQ ID NO: 108), consensus (SEQ ID NO: 204). Sequences in FIG. 2E are as follows: IgKV1D-16 . . . (SEQ ID NO: 205), VL1014-098 (SEQ ID NO: 60), VL1014-100 (SEQ ID NO: 112), VL1014-105 (SEQ ID NO: 110), VL1014-125 (SEQ ID NO: 114), VL1014-162 (SEQ ID NO: 116), consensus (SEQ ID NO: 206). Sequences in FIG. 2F are as follows: IgKV1D-16 . . . (SEQ ID NO: 207), VL1014-153 (SEQ ID NO: 67), VL1014-152 (SEQ ID NO: 124), VL1014-166 (SEQ ID NO: 122), VL1014-167 (SEQ ID NO: 126), VL1014-160 (SEQ ID NO: 120), VL1014-033 (SEQ ID NO: 118), consensus (SEQ ID NO: 208).

(FIG. 8A, FIG. 8B) Data shown are fluorescence intensities (FI) of one representative experiment with AU565 cells treated with non-conjugated and anti-kappa-ETA'-conjugated HER2 antibodies. (FIG. 8C, FIG. 8D) Data shown are mean fluorescence intensities (MFI) of one representative experiment with A431 cells treated with non-conjugated and anti-kappa-ETA'-conjugated HER2 antibodies. See Example 18 for details.

FIG. 11B represents the mean value of FITC pixel intensity per LAMP1/Cy5 positive pixel calculated from the three different images. Together these results indicate that after internalization higher levels of bispecific antibodies, compared to monospecifics antibodies, localize to Lamp1/Cy5 positive vesicles.

DETAILED DESCRIPTION OF THE INVENTION

Definitions

Figure 3A:
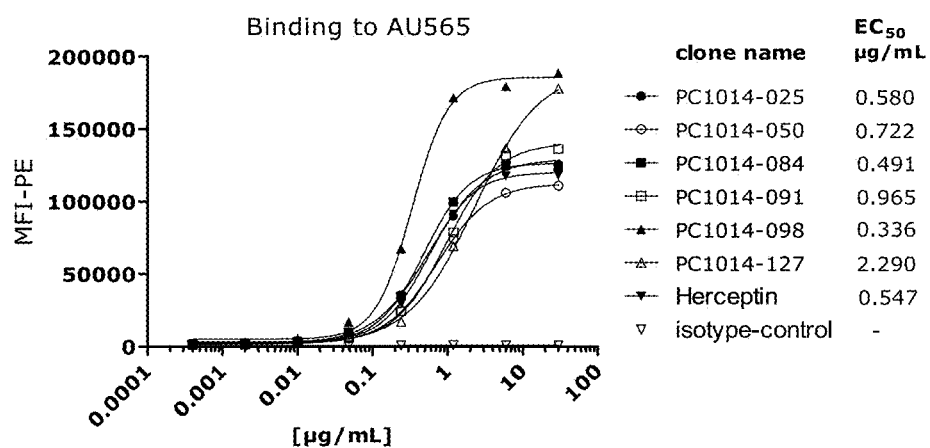
FIGS. 3A-3D: Binding curves of HER2 antibodies to (FIG. 3A, FIG. 3B) high (AU565) and (FIG. 3C, FIG. 3D) low (A431) HER2 expressing cell lines, determined as described in Example 12. Data shown are mean fluorescence intensities (MFI) of one representative experiment for each cell line. The $EC_{50}$ values indicate the apparent affinities.
Figure 3B:
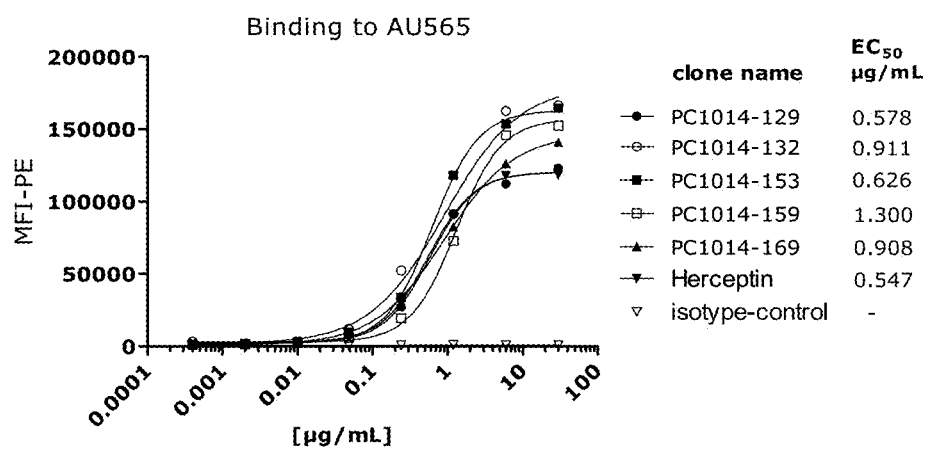
Figure 3C:
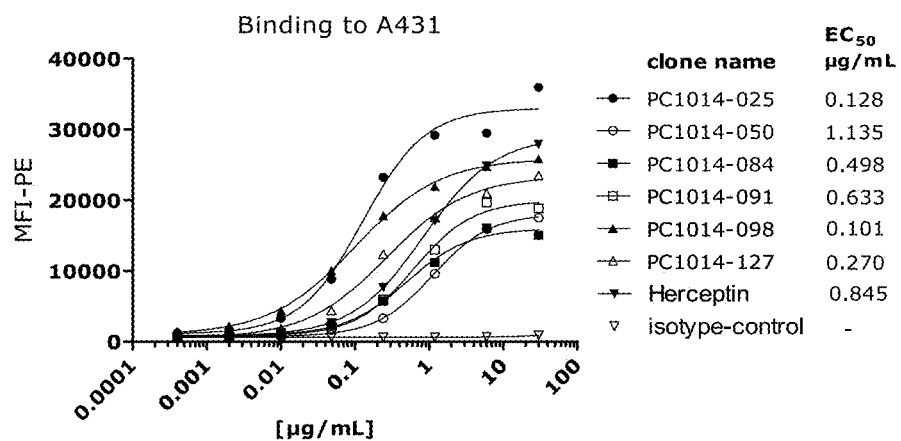
Figure 3D:
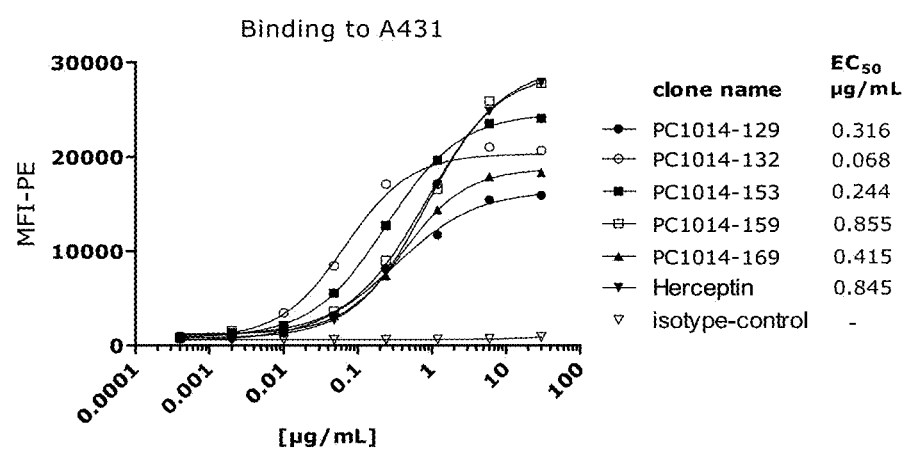

The term "HER2" (also known as ErbB-2, NEU, HER-2, and CD340), when used herein, refers to human epidermal growth factor receptor 2 (SwissProt P04626) and includes any variants, isoforms and species homologs of HER2 which are naturally expressed by cells, including tumor cells, or are expressed on cells transfected with the HER2 gene. Species homologs include rhesus monkey HER2 (macaca mulatta; Genbank accession No. GI:109114897).

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region. The heavy chain constant region typically is comprised of three domains, $C_H1$, $C_H2$, and $C_H3$. Each light chain typically is comprised of a light chain variable region (abbreviated herein as $V_L$ or VL) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Unless otherwise stated or contradicted by context, CDR sequences herein are identified according to IMGT rules (Brochet X., Nucl Acids Res. 2008; 36:W503-508 and Lefranc M P., Nucleic Acids Research 1999; 27:209-212; see also internet http address imgt.cines.fr/IMGT_vquest/ vquest?livret=0&Option=humanIg. However, the numbering of amino acid residues in an antibody sequence can also be performed by the method described in Kabat et al., Sequences of Proteins of Immunological Interest, 5th Ed. Public Health Service, National Institutes of Health, Bethesda, Md. (1991) (phrases such as "variable domain residue numbering as in Kabat", "Kabat position" or "according to Kabat" herein refer to this numbering system). Particularly, for numbering of amino acids in the constant region, the EU index numbering system according to Kabat et al, supra, can be used. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. A HER2 antibody may also be a bispecific antibody, diabody, or similar molecule (see for instance PNAS USA 90(14), 6444-8 (1993) for a description of diabodies). Indeed, bispecific antibodies, diabodies, and the like, provided by the present invention may bind any suitable target in addition to a portion of HER2. As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol. 2003 November; 21(11):484-90); (vi) camelid or nanobodies (Revets et al; Expert Opin Biol Ther. 2005

January; 5(1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

As used herein, "isotype" refers to the immunoglobulin class (for instance IgG1, IgG2, IgG3, IgG4, IgD, IgA, IgE, or IgM) that is encoded by heavy chain constant region genes.

The term "monovalent antibody" means in the context of the present invention that an antibody molecule is capable of binding a single molecule of the antigen, and thus is not able of antigen crosslinking.

An "antibody deficient in effector function" or an "effector-function-deficient antibody" refers to an antibody which has a significantly reduced or no ability to activate one or more effector mechanisms, such as complement activation or Fc receptor binding. Thus, effector-function deficient antibodies have significantly reduced or no ability to mediate antibody-dependent cell-mediated cytotoxicity (ADCC) and/or complement-dependent cytotoxicity (CDC). An example of such an antibody is IgG4.

A "HER2 antibody" or "anti-HER2 antibody" is an antibody as described above, which binds specifically to the antigen HER2.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 9, 8, 7, 6 or 5, for instance no more than 4, 3, 2, or 1 amino acid difference from the amino acid sequence encoded by the germline immunoglobulin gene.

In a preferred embodiment, the antibody of the invention is isolated. An "isolated antibody," as used herein, is intended to refer to an antibody which is substantially free of other antibodies having different antigenic specificities (for instance an isolated antibody that specifically binds to HER2 is substantially free of antibodies that specifically bind antigens other than HER2). An isolated antibody that specifically binds to an epitope, isoform or variant of HER2 may, however, have cross-reactivity to other related antigens, for instance from other species (such as HER2 species homologs). Moreover, an isolated antibody may be substantially free of other cellular material and/or chemicals. In one embodiment of the present invention, two or more "isolated" monoclonal antibodies having different antigen-binding specificities are combined in a well-defined composition.

When used herein in the context of two or more antibodies, the term "competes with" or "cross-competes with" indicates that the two or more antibodies compete for binding to HER2, e.g. compete for HER2 binding in the assay described in Example 14. An antibody "blocks" or "cross-blocks" one or more other antibodies from binding to HER2 if the antibody competes with the one or more other antibodies 25% or more, with 25%-74% representing "partial block" and 75%-100% representing "full block", preferably as determined using the assay of Example 14. For some pairs of antibodies, competition or blocking in the assay of the Examples is only observed when one antibody is coated on the plate and the other is used to compete, and not vice versa. Unless otherwise defined or negated by context, the terms "competes with", "cross-competes with", "blocks" or "cross-blocks" when used herein is also intended to cover such pairs of antibodies.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked or covered by the specifically antigen binding peptide (in other words, the amino acid residue is within the footprint of the specifically antigen binding peptide).

The term "monoclonal antibody" as used herein refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

As used herein, the term "binding" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_c$" (sec$^{-1}$), as used herein, refers to the dissociation rate constant of a particular antibody-antigen interaction. Said value is also referred to as the koff value.

The term "$k_a$" (M$^{-1}$×sec$^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" (M$^{-1}$), as used herein, refers to the association equilibrium constant of a particular antibody-antigen interaction and is obtained by dividing the $k_a$ by the $k_d$.

As used herein, the term "inhibits proliferation" (e.g. referring to cells, such as tumor cells) is intended to include any substantial decrease in the cell proliferation when contacted with a HER2 antibody as compared to the proliferation of the same cells not in contact with a HER2 antibody, e.g., the inhibition of proliferation of a cell culture by at least about 10%, at least about 20% or at least about 30%, or at least as much as a reference antibody such as trastuzumab, e.g., as determined by an assay in the Examples, e.g., example 16.

As used herein, the term "promotes proliferation" (e.g. referring to cells, such as tumor cells) is intended to include any substantial increase in the cell proliferation when contacted with a HER2 antibody as compared to the proliferation of the same cells not in contact with a HER2 antibody, e.g., the promotion of proliferation of a cell culture by at least about 10%, at least about 20% or at least about 30%, or at least as much as a reference antibody as F5, e.g., as determined by an assay in the Examples.

As used herein, the term "internalization", when used in the context of a HER2 antibody includes any mechanism by which the antibody is internalized into a HER2-expressing cell from the cell-surface and/or from surrounding medium, e.g., via endocytosis. The internalization of an antibody can be evaluated using a direct assay measuring the amount of internalized antibody (such as, e.g., the fab-CypHer5E assay described in Example 18), or an indirect assay where the effect of an internalized antibody-toxin conjugate is measured (such as, e.g., the anti-kappa-ETA' assay of Example 17).

The present invention also provides antibodies comprising functional variants of the $V_L$ region, $V_H$ region, or one or more CDRs of the antibodies of the examples. A functional variant of a $V_L$, $V_H$, or CDR used in the context of a HER2 antibody still allows the antibody to retain at least a substantial proportion (at least about 50%, 60%, 70%, 80%, 90%, 95% or more) of the affinity/avidity and/or the specificity/selectivity of the parent antibody and in some cases such a HER2 antibody may be associated with greater affinity, selectivity and/or specificity than the parent antibody.

Such functional variants typically retain significant sequence identity to the parent antibody. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

Exemplary variants include those which differ from a parent antibody VH and/or VL sequence shown in FIGS. 1 and 2 at one or more "variant" amino acid positions, denoted "X" in the corresponding consensus sequence. Preferred variants are those in which the new amino acid is selected from those at the corresponding position in one of the aligned sequences in FIG. 1 or 2 (for details on CDR sequence variants, see Table 4). Alternatively or additionally, the sequence of VH, VL or CDR variants may differ from the sequence of the VH, VL or CDR of the parent antibody sequences mainly by conservative substitutions; for instance at least 10, such as at least 9, 8, 7, 6, 5, 4, 3, 2 or 1 of the substitutions in the variant are conservative amino acid residue replacements.

In the context of the present invention, conservative substitutions may be defined by substitutions within the classes of amino acids reflected in the following table:

| Amino acid residue classes for conservative substitutions | |
| --- | --- |
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

The term "recombinant host cell" (or simply "host cell"), as used herein, is intended to refer to a cell into which an expression vector has been introduced, e.g. an expression vector encoding an antibody of the invention. Recombinant host cells include, for example, transfectomas, such as CHO cells, HEK293 cells, NS/0 cells, and lymphocytic cells.

The term "transgenic non-human animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human HER2 antibodies when immunized with HER2 antigen and/or cells expressing HER2. The human heavy chain transgene may be integrated into the chromosomal DNA of the mouse, as is the case for transgenic mice, for instance HuMAb mice, such as HCo7, HCo12, or HCo17 mice, or the human heavy chain transgene may be maintained extrachromosomally, as is the case for transchromosomal KM mice as described in WO02/43478. Similar mice, having a larger human Ab gene repertoire, include HCo7 and HCo20 (see e.g. WO2009097006). Such transgenic and transchromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching. Transgenic, nonhuman animal can also be used for production of antibodies against a specific antigen by introducing genes encoding such specific antibody, for example by operatively linking the genes to a gene which is expressed in the milk of the animal.

"Treatment" refers to the administration of an effective amount of a therapeutically active compound of the present invention with the purpose of easing, ameliorating, arresting or eradicating (curing) symptoms or disease states.

An "effective amount" or "therapeutically effective amount" refers to an amount effective, at dosages and for periods of time necessary, to achieve a desired therapeutic result. A therapeutically effective amount of a HER2 antibody may vary according to factors such as the disease state, age, sex, and weight of the individual, and the ability of the HER2 antibody to elicit a desired response in the individual. A therapeutically effective amount is also one in which any toxic or detrimental effects of the antibody or antibody portion are outweighed by the therapeutically beneficial effects.

An "anti-idiotypic" antibody is an antibody which recognizes unique determinants generally associated with the antigen-binding site of an antibody.

FURTHER ASPECTS AND EMBODIMENTS OF THE INVENTION

As described above, in a first aspect, the invention relates to a monoclonal antibody which binds HER2.

Monoclonal antibodies of the present invention may be produced, e.g., by the hybridoma method first described by Kohler et al., Nature 256, 495 (1975), or may be produced by recombinant DNA methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody of the invention is a human antibody. Human monoclonal antibodies directed against HER2 may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al., Nature 368, 856-859 (1994)). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (Lonberg, N. et al. (1994), supra; reviewed in Lonberg, N. Handbook of Experimental Pharmacology 113, 49-101 (1994), Lonberg, N. and Huszar, D., Intern. Rev. Immunol. Vol. 13 65-93 (1995) and Harding, F. and Lonberg, N. Ann. N.Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 821-830 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the Hco7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/C mice can be generated by crossing HCo12 to KCo5[J/K](Balb) as described in WO/2009/097006.

Splenocytes from these transgenic mice may be used to generate hybridomas that secrete human monoclonal antibodies according to well known techniques.

Further, human antibodies of the present invention or antibodies of the present invention from other species may be identified through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russel et al., Nucl. Acids Research 21, 1081-1085 (1993), Hogenboom et al., Immunol. Reviews 130, 43-68 (1992), Chiswell and McCafferty TIBTECH 10, 80-84 (1992), and U.S. Pat. No. 5,733,743). If display technologies are utilized to produce antibodies that are not human, such antibodies may be humanized.

Antibodies of Cross-Block Group 1

In one aspect of the antibody of the invention, the antibody binds the same epitope on HER2 as one or more of the novel human antibodies of cross-block group 1 described herein.

In one embodiment, the antibody cross-blocks the binding to soluble HER2 of trastuzumab, when determined as described in Example 14.

In one embodiment, the antibody binds the same epitope as a reference antibody comprising a VH region comprising the sequence of SEQ ID NO:1 and a VL region comprising the sequence of SEQ ID NO:5 (169).

In one embodiment, the antibody binds the same epitope as a reference antibody comprising a VH region comprising the sequence of SEQ ID NO:8 and a VL region comprising the sequence of SEQ ID NO:12 (050).

In one embodiment, the antibody binds the same epitope as a reference antibody comprising a VH region comprising the sequence of SEQ ID NO:15 and a V L region comprising the sequence of SEQ ID NO:84 (084).

In one embodiment, the antibody binds to the same epitope as a reference antibody comprising VH and VL regions selected from the group consisting of:
a) a VH region comprising the sequence of SEQ ID NO:77 and a VL region comprising the sequence of SEQ ID NO:78 (049);
b) a VH region comprising the sequence of SEQ ID NO:79 and a VL region comprising the sequence of SEQ ID NO:80 (051);
c) a VH region comprising the sequence of SEQ ID NO:81 and a VL region comprising the sequence of SEQ ID NO:82 (055);
d) a VH region comprising the sequence of SEQ ID NO:83 and a VL region comprising the sequence of SEQ ID NO:84 (123);
e) a VH region comprising the sequence of SEQ ID NO:85 and a VL region comprising the sequence of SEQ ID NO:86 (161); and
f) a VH region comprising the sequence of SEQ ID NO:87 and a VL region comprising the sequence of SEQ ID NO:88 (124).

In another additional or alternative aspect of the antibody of the invention, the antibody binds to HER2 and comprises a VH CDR3, VH region and/or VL region sequence similar or identical to a sequence of the novel antibodies described herein.

In one embodiment, the antibody comprises a VH CDR3 region having a sequence selected from the group consisting of
SEQ ID NO:11 (050, 049, 051, 055), optionally wherein the VH region is derived from the IgHV3-21-1 germline sequence;
SEQ ID No:130, such as the sequence of SEQ ID NO:18 (084), optionally wherein the VH region is derived from the IgHV1-69-04 germline sequence;
SEQ ID NO:133 (169, 123, 161, 124), such as the sequence of SEQ ID NO:4 (169), optionally wherein the VH region is derived from the IgHV1-18-1 germline sequence; or In one embodiment, the antibody comprises a VH CDR3 region of one of antibodies 123, 161, or 124, as shown in FIG. 1, optionally wherein the VH region is derived from an IgHV1-18-1 germline.

In one embodiment, the antibody comprises a VH region selected from the group consisting of
a) a VH region comprising the CDR1, CDR2 and CDR3 sequences of SEQ ID NOs:9, 127 and 11, such as the CDR1, CDR2 and CDR3 sequences of SEQ ID NOS: 9, 10 and 11 (050); optionally where the VH region is derived from an IgHV3-23-1 germline;
b) a VH region comprising the CDR1, CDR2 and CDR3 sequences of SEQ ID NOs:128, 129 and 130, such the CDR1, CDR2 and CDR3 sequences of SEQ ID NOs: 16, 17 and 18, respectively (084), optionally where the VH region is derived from an IgHV1-69-04 germline; and
c) a VH region comprising the CDR1, CDR2, and CDR3 sequences of SEQ ID NOs:131, 132, and 133, such as the CRD1, CDR2, and CDR3 sequences of SEQ ID NOs: 2, 3 and 4 (169), respectively, optionally where the VH region is derived from an IgHV1-18-1 germline.

In one embodiment, the antibody comprises a VH region selected from the preceding embodiments (a) or (b) and a VL region comprising the CDR1, CDR2, and CDR3 sequences of SEQ ID NO:13, XAS (wherein X is A or V), and SEQ ID No:155, respectively, such as a CDR1 sequence selected from SEQ ID Nos: 13 or 20, a CDR2 which is AAS or VAS, and a CDR3 sequence selected from SEQ ID NOs:14 and 21 (050, 084); respectively, optionally where the VL region is derived from an IgKV1-12-01 germline.

In one embodiment, the antibody comprises a VH region which is the preceding embodiment (c) and a VL region comprising the CDR1, CDR2, and CDR3 sequences of SEQ ID NO:6, DXS (wherein X=A or T), and SEQ ID NO:156 (169), respectively, optionally wherein the VL region is derived from IgKV3-11-01.

In one embodiment, the antibody comprises a VH region comprising the CDR1, CDR2 and CDR3 sequences of SEQ ID NOs:2, 3 and 4, respectively; and a VL region comprising the CDR1, CDR2 and CDR3 sequences of SEQ ID NOs:6, DAS, and SEQ ID NO:7, respectively (169).

In one embodiment, the antibody comprises a VH region comprising the CDR1, CDR2 and CDR3 sequences of SEQ ID NOs:9, 10 and 11, respectively; and a VL region comprising the CDR1, CDR2 and CDR3 sequences of SEQ ID NOs:13, AAS, and SEQ ID NO:14, respectively (050).

In one embodiment, the antibody comprises a VH region comprising the CDR1, CDR2 and CDR3 sequences of SEQ ID NOs:16, 17 and 18, respectively; and a VL region comprising the CDR1, CDR2 and CDR3 sequences of SEQ ID NOs:20, VAS, and SEQ ID NO:21, respectively (084).

In separate embodiments, the antibody comprises:
a) a VH region comprising the sequence of SEQ ID NO:1 and, preferably, a VL region comprising the sequence of SEQ ID NO:5 (169);
b) a VH region comprising the sequence of SEQ ID NO:8 and, preferably, a VL region comprising the sequence of SEQ ID NO:12 (050);
c) a VH region comprising the sequence of SEQ ID NO:15 and, preferably, a VL region comprising the sequence of SEQ ID NO:19 (084);
d) a VH region comprising the sequence of SEQ ID NO:77 and, preferably, a VL region comprising the sequence of SEQ ID NO:78 (049);
e) a VH region comprising the sequence of SEQ ID NO:79 and, preferably, a VL region comprising the sequence of SEQ ID NO:80 (051);
f) a VH region comprising the sequence of SEQ ID NO:81 and, preferably, a VL region comprising the sequence of SEQ ID NO:82 (055);
g) a VH region comprising the sequence of SEQ ID NO:83 and, preferably, a VL region comprising the sequence of SEQ ID NO:84 (123);
h) a VH region comprising the sequence of SEQ ID NO:85 and, preferably, a VL region comprising the sequence of SEQ ID NO:86 (161);
i) a VH region comprising the sequence of SEQ ID NO:87 and, preferably, a VL region comprising the sequence of SEQ ID NO:88 (124); and/or
j) a variant of any of said antibodies, wherein said variant preferably has at most 1, 2 or 3 amino-acid modifications, more preferably amino-acid substitutions, such as conservative amino acid substitutions and substitutions where the new amino acid is one at the same position in an aligned sequence in FIG. 1 or 2, particularly at positions indicated by "X" in the corresponding consensus sequence.

Antibodies of Cross-Block Group 2

In one aspect of the antibody of the invention, the antibody binds the same epitope on HER2 as one or more of the novel human antibodies of cross-block group 2 described herein.

In one embodiment, the antibody cross-blocks the binding to soluble HER2 of pertuzumab, when determined as described in Example 14.

In one embodiment, the antibody binds the same epitope as a reference antibody comprising a VH region comprising the sequence of SEQ ID NO:22 and a VL region comprising the sequence of SEQ ID NO:26 (025).

In one embodiment, the antibody binds the same epitope as a reference antibody comprising a VH region comprising the sequence of SEQ ID NO:29 and a VL region comprising the sequence of SEQ ID NO:32 (091).

In one embodiment, the antibody binds the same epitope as a reference antibody comprising a VH region comprising the sequence of SEQ ID NO:35 and a VL region comprising the sequence of SEQ ID NO:39 (129).

In one embodiment, the antibody binds to the same epitope as a reference antibody comprising VH and VL regions selected from the group consisting of:
a) a VH region comprising the sequence of SEQ ID NO:89 and a VL region comprising the sequence of SEQ ID NO:90 (001);
b) a VH region comprising the sequence of SEQ ID NO:91 and a VL region comprising the sequence of SEQ ID NO:92 (143);
c) a VH region comprising the sequence of SEQ ID NO:93 and a VL region comprising the sequence of SEQ ID NO:94 (019);
d) a VH region comprising the sequence of SEQ ID NO:95 and a VL region comprising the sequence of SEQ ID NO:96 (021);
e) a VH region comprising the sequence of SEQ ID NO:97 and a VL region comprising the sequence of SEQ ID NO:98 (027);
f) a VH region comprising the sequence of SEQ ID NO:99 and a VL region comprising the sequence of SEQ ID NO:100 (032)
g) a VH region comprising the sequence of SEQ ID NO:101 and a VL region comprising the sequence of SEQ ID NO:102 (035);
h) a VH region comprising the sequence of SEQ ID NO:103 and a VL region comprising the sequence of SEQ ID NO:104 (036);
i) a VH region comprising the sequence of SEQ ID NO:105 and a VL region comprising the sequence of SEQ ID NO:106 (054); and
j) a VH region comprising the sequence of SEQ ID NO:107 and a VL region comprising the sequence of SEQ ID NO:108 (094).

In another additional or alternative aspect of the antibody of the invention, the antibody binds to HER2 and comprises a VH CDR3, VH region and/or VL region sequence similar or identical to a sequence of the novel antibodies described herein.

In one embodiment, the antibody comprises a VH CDR3 region having a sequence selected from the group consisting of
SEQ ID NO:136, such as the sequence of SEQ ID NO:25 (025), optionally wherein the VH region is derived from the IgHV4-34-1 germline sequence;
SEQ ID NO:139, such as the sequence of SEQ ID NO:31 (091), optionally wherein the VH region is derived from the IgHV4-34-01 germline sequence; and
SEQ ID NO:142, such as the sequence of SEQ ID NO:38 (129), optionally wherein the VH region is derived from the IgHV3-30-01 germline sequence.

In one embodiment, the antibody comprises a VH CDR3 region of one of antibodies 001, 143, 019, 021, 027, 032, 035, 036, 054 or 094 as shown in FIG. 1, optionally wherein the VH region is derived from an IgHV4-34-1 germline.

In one embodiment, the antibody comprises a VH region selected from the group consisting of
a) a VH region comprising the CDR1, CDR2 and CDR3 sequences of SEQ ID NOs:134, 135 and 136, such as the CDR1, CDR2 and CDR3 sequences of SEQ ID NOS: 23, 24 and 25 (025); optionally where the VH region is derived from an IgHV4-34-1 germline;
b) a VH region comprising the CDR1, CDR2 and CDR3 sequences of SEQ ID NOs:137, 138 and 139, such the CDR1, CDR2 and CDR3 sequences of SEQ ID NOs: 30, 163, and 31, respectively (091), optionally where the VH region is derived from an IgHV4-34-01 germline; and
c) a VH region comprising the CDR1, CDR2, and CDR3 sequences of SEQ ID NOs:140, 141 and 142, such as the CRD1, CDR2, and CDR3 sequences of SEQ ID NOs: 36, 37 and 38 (129), respectively, optionally where the VH region is derived from an IgHV3-30-01 germline.

In one embodiment, the antibody comprises a VH region selected from the preceding embodiment (a) and a VL region comprising the CDR1, CDR2, and CDR3 sequences of SEQ ID NO:157, AAS, and SEQ ID No:164, respectively, such as the CDR1, CDR2, and CDR3 sequences of SEQ ID Nos:27, AAS, and SEQ ID NO:28 (025); respectively, optionally where the VL region is derived from an IgKV1D-16-01 germline.

In one embodiment, the antibody comprises a VH region selected from the preceding embodiment (b) and a VL region comprising the CDR1, CDR2, and CDR3 sequences of SEQ ID NO:33, $AX_1X_2$ (wherein $X_1$ is A or T, preferably A; and $X_2$ is S or F, preferably S), and SEQ ID No:158, respectively, such as the CDR1, CDR2 and CDR3 sequences of SEQ ID Nos:33, AAS, and SEQ ID NO:34 (091); respectively, optionally where the VL region is derived from an IgKV1D-16-01 germline.

In one embodiment, the antibody comprises a VH region which is the preceding embodiment (c) and a VL region comprising the CDR1, CDR2, and CDR3 sequences of SEQ ID NO:40, DAS and SEQ ID NO:41 (129), respectively, optionally wherein the VL region is derived from IgKV3-11-01.

In one embodiment, the antibody comprises a VH region comprising the CDR1, CDR2 and CDR3 sequences of SEQ ID NOs:23, 24 and 25, respectively; and a VL region comprising the CDR1, CDR2 and CDR3 sequences of SEQ ID NOs:27, AAS, and SEQ ID NO:28, respectively (025).

In one embodiment, the antibody comprises a VH region comprising the CDR1, CDR2 and CDR3 sequences of SEQ ID NOs:30, 163 and 31, respectively; and a VL region comprising the CDR1, CDR2 and CDR3 sequences of SEQ ID NOs:33, AAS, and SEQ ID NO:34, respectively (091).

In one embodiment, the antibody comprises a VH region comprising the CDR1, CDR2 and CDR3 sequences of SEQ ID NOs:36, 37 and 38, respectively; and a VL region comprising the CDR1, CDR2 and CDR3 sequences of SEQ ID NOs:40, DAS, and SEQ ID NO:41, respectively (129).

In separate embodiments, the antibody comprises:
- a) a VH region comprising the sequence of SEQ ID NO:22 and, preferably, a VL region comprising the sequence of SEQ ID NO:26 (025);
- b) a VH region comprising the sequence of SEQ ID NO:29 and, preferably, a VL region comprising the sequence of SEQ ID NO:32 (091);
- c) a VH region comprising the sequence of SEQ ID NO:35 and, preferably, a VL region comprising the sequence of SEQ ID NO:39 (129);
- d) a VH region comprising the sequence of SEQ ID NO:89 and, preferably, a VL region comprising the sequence of SEQ ID NO:90 (001);
- e) a VH region comprising the sequence of SEQ ID NO:91 and, preferably, a VL region comprising the sequence of SEQ ID NO:92 (143);
- f) a VH region comprising the sequence of SEQ ID NO:93 and, preferably, a VL region comprising the sequence of SEQ ID NO:94 (019);
- g) a VH region comprising the sequence of SEQ ID NO:95 and, preferably, a VL region comprising the sequence of SEQ ID NO:96 (021);
- h) a VH region comprising the sequence of SEQ ID NO:97 and, preferably, a VL region comprising the sequence of SEQ ID NO:98 (027);
- i) a VH region comprising the sequence of SEQ ID NO:99 and, preferably, a VL region comprising the sequence of SEQ ID NO:100 (032);
- j) a VH region comprising the sequence of SEQ ID NO:101 and, preferably, a VL region comprising the sequence of SEQ ID NO:102 (035);
- k) a VH region comprising the sequence of SEQ ID NO:103 and, preferably, a VL region comprising the sequence of SEQ ID NO:104 (036);
- l) a VH region comprising the sequence of SEQ ID NO:105 and, preferably, a VL region comprising the sequence of SEQ ID NO:106 (054);
- m) a VH region comprising the sequence of SEQ ID NO:106 and, preferably, a VL region comprising the sequence of SEQ ID NO:108 (094); and/or
- n) a variant of any of said antibodies, wherein said variant preferably has at most 1, 2 or 3 amino-acid modifications, more preferably amino-acid substitutions, such as conservative amino acid substitutions and substitutions where the new amino acid is one at the same position in an aligned sequence in FIG. 1 or 2, particularly at positions indicated by "X" in the corresponding consensus sequence.

Antibodies of Cross-Block Group 3

In one aspect of the antibody of the invention, the antibody binds the same epitope on HER2 as one or more of the novel human antibodies of cross-block group 3 described herein.

In one embodiment, the antibody cross-blocks the binding to soluble HER2 of F5 and/or C5, when determined as described in Example 14.

In one embodiment, the antibody binds the same epitope as a reference antibody comprising a VH region comprising the sequence of SEQ ID NO:46 and a VL region comprising the sequence of SEQ ID NO:49 (127).

In one embodiment, the antibody binds the same epitope as a reference antibody comprising a VH region comprising the sequence of SEQ ID NO:49 and a VL region comprising the sequence of SEQ ID NO:53 (159).

In one embodiment, the antibody binds the same epitope as a reference antibody comprising a VH region comprising the sequence of SEQ ID NO:56 and a VL region comprising the sequence of SEQ ID NO:60 (098).

In one embodiment, the antibody binds the same epitope as a reference antibody comprising a VH region comprising the sequence of SEQ ID NO:63 and a VL region comprising the sequence of SEQ ID NO:67 (153).

In one embodiment, the antibody binds the same epitope as a reference antibody comprising a VH region comprising the sequence of SEQ ID NO:70 and a VL region comprising the sequence of SEQ ID NO:74 (132).

In one embodiment, the antibody binds to the same epitope as a reference antibody comprising VH and VL regions selected from the group consisting of:
- k) a VH region comprising the sequence of SEQ ID NO:109 and a VL region comprising the sequence of SEQ ID NO:110 (105);
- l) a VH region comprising the sequence of SEQ ID NO:111 and a VL region comprising the sequence of SEQ ID NO:112 (100);
- m) a VH region comprising the sequence of SEQ ID NO:113 and a VL region comprising the sequence of SEQ ID NO:114 (125);
- n) a VH region comprising the sequence of SEQ ID NO:115 and a VL region comprising the sequence of SEQ ID NO:116 (162);
- o) a VH region comprising the sequence of SEQ ID NO:117 and a VL region comprising the sequence of SEQ ID NO:118 (033);
- p) a VH region comprising the sequence of SEQ ID NO:119 and a VL region comprising the sequence of SEQ ID NO:120 (160)
- q) a VH region comprising the sequence of SEQ ID NO:121 and a VL region comprising the sequence of SEQ ID NO:122 (166);

r) a VH region comprising the sequence of SEQ ID NO:123 and a VL region comprising the sequence of SEQ ID NO:124 (152); and s) a VH region comprising the sequence of SEQ ID NO:125 and a VL region comprising the sequence of SEQ ID NO:126 (167).

In another additional or alternative aspect of the antibody of the invention, the antibody binds to HER2 and comprises a VH CDR3, VH region and/or VL region sequence similar or identical to a sequence of the novel antibodies described herein.

In one embodiment, the antibody comprises a VH CDR3 region having a sequence selected from the group consisting of SEQ ID NO:148, such as the sequence of SEQ ID NO:48 (127), optionally wherein the VH region is derived from the IgHV5-51-01 germline sequence;

SEQ ID NO:52 (159), optionally wherein the VH region is derived from the IgHV5-51-01 germline sequence;

SEQ ID NO:145, such as the sequence of SEQ ID NO:59 (098), optionally wherein the VH region is derived from the IgHV3-23-01 germline sequence;

SEQ ID NO:154, such as the sequence of SEQ ID NO:66 (153), optionally wherein the VH region is derived from the IgHV3-30-03-01 germline sequence; and SEQ ID NO:151, such as the sequence of SEQ ID NO:73 (132), optionally wherein the VH region is derived from the IgHV1-18-01 germline sequence.

In one embodiment, the antibody comprises a VH CDR3 region of one of antibodies 105, 100, 125 or 162 as shown in FIG. 1, optionally wherein the VH region is derived from an IgHV3-23-1 germline.

In one embodiment, the antibody comprises a VH CDR3 region of one of antibodies 033, 160, 166, 152 or 167 as shown in FIG. 1, optionally wherein the VH region is derived from an IgHV3-30-3-01 germline.

In one embodiment, the antibody comprises a VH region selected from the group consisting of a) a VH region comprising the CDR1, CDR2 and CDR3 sequences of SEQ ID NOs:146, 147 and 148, such as the CDR1, CDR2 and CDR3 sequences of SEQ ID NOS: 43, 44 and 45 (127); optionally where the VH region is derived from an IgHV5-51-01 germline;

b) a VH region comprising the CDR1, CDR2 and CDR3 sequences of SEQ ID NOs:149, 51 and 52, such as the CDR1, CDR2 and CDR3 sequences of SEQ ID NOs: 50, 51 and 52, respectively (159), optionally where the VH region is derived from an IgHV5-51-01 germline;

c) a VH region comprising the CDR1, CDR2 and CDR3 sequences of SEQ ID NOs:143, 144 and 145, such as the CRD1, CDR2, and CDR3 sequences of SEQ ID NOs: 57, 58 and 59 (098), respectively, optionally where the VH region is derived from an IgHV3-23-01 germline;

d) a VH region comprising the CDR1, CDR2 and CDR3 sequences of SEQ ID NOs:152, 153 and 154, such as the CDR1, CDR2 and CDR3 sequences of SEQ ID NOs:64, 65 and 66, respectively (153), optionally where the VH region is derived from an IgHV3-30-03-01 germline; and e) a VH region comprising the CDR1, CDR2, and CDR3 sequences of SEQ ID NOs:71, 150 and 151, such as the CRD1, CDR2, and CDR3 sequences of SEQ ID NOs: 71, 72 and 73 (132), respectively, optionally where the VH region is derived from an IgHV1-18-01 germline.

In one embodiment, the antibody comprises a VH region selected from the preceding embodiment (a) and a VL region comprising the CDR1, CDR2, and CDR3 sequences of SEQ ID NO:47, AAS and SEQ ID NO:48, respectively (127); respectively, optionally where the VL region is derived from an IgKV1D-8-01 germline.

In one embodiment, the antibody comprises a VH region selected from the preceding embodiment (b) and a VL region comprising the CDR1, CDR2, and CDR3 sequences of SEQ ID NO:54, AAS, and SEQ ID No:55 (159); respectively, optionally where the VL region is derived from an IgKV1D-16-01 germline.

In one embodiment, the antibody comprises a VH region which is the preceding embodiment (c) and a VL region comprising the CDR1, CDR2, and CDR3 sequences of SEQ ID NO:159, AAS and SEQ ID NO:160, respectively, such as the VL CDR1, CDR2 and CDR3 sequences of SEQ ID NOS: 61, AAS and SEQ ID NO:62 (098), optionally wherein the VL region is derived from IgKV1D-16-01.

In one embodiment, the antibody comprises a VH region which is the preceding embodiment (d) and a VL region comprising the CDR1, CDR2, and CDR3 sequences of SEQ ID NO:161, XAS (wherein X=D or A, preferably D), and SEQ ID NO:162 (153), respectively, such as the VL CDR sequences of SEQ ID NO:68, DAS, and 69, optionally wherein the VL region is derived from IgKV1D-16-01.

In one embodiment, the antibody comprises a VH region which is the preceding embodiment (e) and a VL region comprising the CDR1, CDR2, and CDR3 sequences of SEQ ID NO:75, DAS and SEQ ID NO:76 (132), respectively, optionally wherein the VL region is derived from IgKV3-11-01.

In one embodiment, the antibody comprises a VH region comprising the CDR1, CDR2 and CDR3 sequences of SEQ ID NOs:43, 44 and 45, respectively; and a VL region comprising the CDR1, CDR2 and CDR3 sequences of SEQ ID NOs:47, AAS, and SEQ ID NO:48, respectively (127).

In one embodiment, the antibody comprises a VH region comprising the CDR1, CDR2 and CDR3 sequences of SEQ ID NOs:50, 51 and 52, respectively; and a VL region comprising the CDR1, CDR2 and CDR3 sequences of SEQ ID NOs:54, AAS, and SEQ ID NO:55, respectively (159).

In one embodiment, the antibody comprises a VH region comprising the CDR1, CDR2 and CDR3 sequences of SEQ ID NOs:57, 58 and 59, respectively; and a VL region comprising the CDR1, CDR2 and CDR3 sequences of SEQ ID NOs:60, AAS, and SEQ ID NO:61, respectively (098).

In one embodiment, the antibody comprises a VH region comprising the CDR1, CDR2 and CDR3 sequences of SEQ ID NOs:64, 65 and 66, respectively; and a VL region comprising the CDR1, CDR2 and CDR3 sequences of SEQ ID NOs:68, DAS, and SEQ ID NO:69, respectively (153).

In one embodiment, the antibody comprises a VH region comprising the CDR1, CDR2 and CDR3 sequences of SEQ ID NOs:71, 72 and 73, respectively; and a VL region comprising the CDR1, CDR2 and CDR3 sequences of SEQ ID NOs:75, DAS, and SEQ ID NO:76, respectively (132).

In separate embodiments, the antibody comprises:

a) a VH region comprising the sequence of SEQ ID NO:46 and, preferably, a VL region comprising the sequence of SEQ ID NO:49 (127);

b) a VH region comprising the sequence of SEQ ID NO:49 and, preferably, a VL region comprising the sequence of SEQ ID NO:53 (159);

c) a VH region comprising the sequence of SEQ ID NO:56 and, preferably, a VL region comprising the sequence of SEQ ID NO:60 (098);

d) a VH region comprising the sequence of SEQ ID NO:63 an, preferably, a VL region comprising the sequence of SEQ ID NO:67 (153);
e) a VH region comprising the sequence of SEQ ID NO:70 and, preferably, a VL region comprising the sequence of SEQ ID NO:74 (132);
f) a VH region comprising the sequence of SEQ ID NO:109 and, preferably, a VL region comprising the sequence of SEQ ID NO:110 (105);
g) a VH region comprising the sequence of SEQ ID NO:111 and, preferably, a VL region comprising the sequence of SEQ ID NO:112 (100);
h) a VH region comprising the sequence of SEQ ID NO:113 and, preferably, a VL region comprising the sequence of SEQ ID NO:114 (125);
i) a VH region comprising the sequence of SEQ ID NO:115 and, preferably, a VL region comprising the sequence of SEQ ID NO:116 (162);
j) a VH region comprising the sequence of SEQ ID NO:117 and, preferably, a VL region comprising the sequence of SEQ ID NO:118 (033);
k) a VH region comprising the sequence of SEQ ID NO:119 and, preferably, a VL region comprising the sequence of SEQ ID NO:120 (160)
l) a VH region comprising the sequence of SEQ ID NO:121 and, preferably, a VL region comprising the sequence of SEQ ID NO:122 (166);
m) a VH region comprising the sequence of SEQ ID NO:123 and, preferably, a VL region comprising the sequence of SEQ ID NO:124 (152);
o) a VH region comprising the sequence of SEQ ID NO:125 and, preferably, a VL region comprising the sequence of SEQ ID NO:126 (167); and/or
p) a variant of any of said antibodies, wherein said variant preferably has at most 1, 2 or 3 amino-acid modifications, more preferably amino-acid substitutions, such as conservative amino acid substitutions and substitutions where the new amino acid is one at the same position in an aligned sequence in FIG. 1 or 2, particularly at positions indicated by "X" in the corresponding consensus sequence.

Bispecific Antibodies

In one embodiment, the antibody is a bispecific antibody, comprising (i) a first antibody comprising antigen-binding region of an antibody as defined herein, e.g. an antibody of cross-block 1, 2 or 3, or the VH and VL region comprising the sequences of (005), and (ii) a second antibody comprising an antigen-binding region of an antibody which binds to CD3.

In one embodiment, the antibody is a bispecific antibody, comprising (i) a first antibody comprising an antigen-binding region of an antibody as defined herein or the VH and VL region comprising the sequences of (005), and (ii) a second antibody comprising antigen-binding region of an antibody as defined herein or the VH and VL region comprising sequences of (005), wherein the first antigen-binding region binds to a different epitope than the second antigen-binding region.

In one embodiment the first antibody comprises a VH region comprising a CDR3 sequence of an antibody of cross-block 1, 2 or 3 as defined herein, such as SEQ ID NO: 4, 25 or 66 (169, 025 or 153), or a CDR3 sequence of SEQ ID NO:168 (005).

In one embodiment the first antibody comprises a VH region comprising CDR1, CDR2 and CDR3 sequences of an antibody of cross-block 1, 2 or 3 as defined herein, such as CDR1, CDR2, and CDR3 sequences SEQ ID NOs: 2, 3 and 4 (169), or CDR1, CDR2 and CDR3 sequences of SEQ ID NOs:23, 24 and 25 (025), or CDR1, CDR2 and CDR3 sequences of SEQ ID NOs: 64, 65 and 66 (153), or CDR1, CDR2 CDR3 sequence of SEQ ID NOs: 166, 167 and 168 (005).

In a further or alternative embodiment the first antibody comprises a VH region comprising a CDR3 sequence of an antibody of cross-block 1, 2 or 3 as defined herein, such as CDR3 sequence an antibody of cross-block 1 of SEQ ID NO: 11 (050), or SEQ ID NO: 18 (084); or a CDR3 sequence of an antibody of cross-block 2 of SEQ ID NO: 31 (091), or SEQ ID NO: 38 (129), or a CDR3 sequence of an antibody of cross-block 3 of SEQ ID NO: 45 (127), or SEQ ID NO:52 (159), or SEQ ID NO:59 (098), or SEQ ID NO:73 (132).

In one embodiment the first antibody comprises a VH region comprising CDR1, CDR2 and CDR3 sequences of an antibody of cross-block 1, 2 or 3 as defined herein, such as CDR1, CDR2, and CDR3 sequences SEQ ID NOs: 2, 3 and 4 (169), or CDR1, CDR2 and CDR3 sequences of SEQ ID NOs:23, 24 and 25 (025), or CDR1, CDR2 and CDR3 sequences of SEQ ID NOs: 64, 65 and 66 (153), or CDR1, CDR2 CDR3 sequence of SEQ ID NOs: 166, 167 and 168 (005).

In one embodiment the first antibody comprises a VH region comprising CDR1, CDR2 and CDR3 sequences of an antibody of cross-block 1, 2 or 3 as defined herein a VL region comprising CDR1, CDR2 and CDR3 sequences of an antibody of cross-block 1, 2 or 3 as defined herein.

In a further or alternative embodiment the first antibody comprises a VH region comprising CDR1, CDR2 and CDR3 sequences of an antibody of cross-block 1, 2 or 3 as defined herein, such as CDR1, CDR2, and CDR3 sequences of an antibody of cross-block 1 of SEQ ID NOs: 9, 10 and 11 (050), or SEQ ID NOs: 16, 17 and 18 (084); or CDR1, CDR2, and CDR3 sequences of an antibody of cross-block 2 of SEQ ID NOs: 30, 163 and 31 (091), or SEQ ID NOs: 36, 37 and 38 (129), or CDR1, CDR2, and CDR3 sequences of an antibody of cross-block 3 SEQ ID NOs: 43, 44 and 45 (127), or SEQ ID NOs:50, 51 and 52 (159), or SEQ ID NOs:57, 58 and 59 (098), or SEQ ID NOs:71, 72 and 73 (132).

In one embodiment the first antibody comprises a VH region and a VL region selected from the group consisting of:
 a) a VH region comprising the CDR1, CDR2, and CDR3 sequences of SEQ ID NOs: 2, 3 and 4; and a VL region comprising the CDR1, CDR2 and CDR3 sequences of SEQ ID: 6, GAS and SEQ ID NO:7, respectively (169);
 b) a VH region comprising the CDR1, CDR2, and CDR3 sequences of SEQ ID NOs: 23, 24 and 25; and a VL region comprising the CDR1, CDR2 and CDR3 sequences of SEQ ID NO: 27, AAS and SEQ ID NO:28, respectively (025);
 c) a VH region comprising the CDR1, CDR2 and CDR3 sequences of SEQ ID NOs:64, 65 and 66; and a VL region comprising the CDR1, CDR2 and CDR3 sequences of SEQ ID NO: 68, DAS and SEQ ID NO:69 (153); and
 d) a VH region comprising the CDR1, CDR2 and CDR3 sequences of SEQ ID NOs:166, 167 and 168; and a VL region comprising the CDR1, CDR2 and CDR3 sequences of SEQ ID NO: 169, GAS and SEQ ID NO:170 (005).

In a further or alternative embodiment the first antibody comprises a VH region and a VL region selected from the group consisting of:

a) a VH region comprising the CDR1, CDR2 and CDR3 sequences of SEQ ID NOs:9, 127 and 11, such as the CDR1, CDR2 and CDR3 sequences of SEQ ID NOS: 9, 10 and 11 (050); optionally where the VH region is derived from an IgHV3-23-1 germline;
b) a VH region comprising the CDR1, CDR2 and CDR3 sequences of SEQ ID NOs:128, 129 and 130, such the CDR1, CDR2 and CDR3 sequences of SEQ ID NOs: 16, 17 and 18, respectively (084), optionally where the VH region is derived from an IgHV1-69-04 germline; and
c) a VH region comprising the CDR1, CDR2 and CDR3 sequences of SEQ ID NOs:137, 138 and 139, such the CDR1, CDR2 and CDR3 sequences of SEQ ID NOs: 30, 163, and 31, respectively (091), optionally where the VH region is derived from an IgHV4-34-01 germline; and
d) a VH region comprising the CDR1, CDR2, and CDR3 sequences of SEQ ID NOs:140, 141 and 142, such as the CRD1, CDR2, and CDR3 sequences of SEQ ID NOs: 36, 37 and 38 (129), respectively, optionally where the VH region is derived from an IgHV3-30-01 germline.
e) a VH region comprising the CDR1, CDR2 and CDR3 sequences of SEQ ID NOs:146, 147 and 148, such as the CDR1, CDR2 and CDR3 sequences of SEQ ID NOS: 43, 44 and 45 (127); optionally where the VH region is derived from an IgHV5-51-01 germline;
f) a VH region comprising the CDR1, CDR2 and CDR3 sequences of SEQ ID NOs:149, 51 and 52, such as the CDR1, CDR2 and CDR3 sequences of SEQ ID NOs: 50, 51 and 52, respectively (159), optionally where the VH region is derived from an IgHV5-51-01 germline;
g) a VH region comprising the CDR1, CDR2 and CDR3 sequences of SEQ ID NOs:143, 144 and 145, such as the CRD1, CDR2, and CDR3 sequences of SEQ ID NOs: 57, 58 and 59 (098), respectively, optionally where the VH region is derived from an IgHV3-23-01 germline;
h) a VH region comprising the CDR1, CDR2, and CDR3 sequences of SEQ ID NOs:71, 150 and 151, such as the CRD1, CDR2, and CDR3 sequences of SEQ ID NOs: 71, 72 and 73 (132), respectively, optionally where the VH region is derived from an IgHV1-18-01 germline.

In one embodiment the second antibody is one of the previous embodiment described for the first antibody, but wherein the second antibody binds to a different epitope than the first antibody.

In one embodiment the second antibody is a CD3 antibody. In one embodiment a CD3 antibody may be an antibody comprising a VH region comprising the sequence of SEQ ID NO: 171 (YTH12.5) and VL region comprising the sequence of SEQ ID NO:172 (YTH12.5). Another example of a CD3 antibody is an antibody comprising a VH region comprising the sequence of SEQ ID NO: 173 (hu-CLB-T3/4) and VL region comprising the sequence of SEQ ID NO:174 (huCLB-T3/4).

In one embodiment, the antibody is a bispecific antibody, comprising (i) a first antibody having an Fc region and VH and VL sequences, which antibody comprises the VH and VL region sequences of (005), (025), (153) or (169), and which antibody comprises an IgG1 wildtype Fc region, wherein the CH3 region contains Ile at position 350, a Thr at position 370, and a Leu at position 405 and (ii) a second antibody having an Fc region and VH and VL sequences, which antibody comprising the VH and VL region sequences of (005), (025), (153) or (169), and which antibody comprises a IgG1 wildtype Fc region, wherein the CH3 region contains an Arg at position 409. Specific embodiments are disclosed in examples.

In one embodiment, the antibody is a bispecific antibody, comprising (i) a first antibody having an Fc region and VH and VL sequences, wherein the VH region comprises the amino acid sequence of SEQ ID NO: 164, and the VL region comprises the amino acid sequence of SEQ ID NO: 165 (005), optionally wherein the first antibody comprises an IgG1,κ Fc region, wherein the CH3 region contains Ile at position 350, a Thr at position 370, and a Leu at position 405; and (ii) a second antibody having an Fc region and VH and VL sequences, wherein the VH region comprises the amino acid sequence of SEQ ID NO:1 and the VL region comprises the amino acid sequence of SEQ ID NO:5 (169), optionally wherein the second antibody comprises an IgG1,κ Fc region having an Arg at position 409.

In one embodiment, the antibody is a bispecific antibody, comprising (i) a first antibody having an Fc region and VH and VL sequences, wherein the VH region comprises the amino acid sequence of SEQ ID NO:22, and the VL region comprises the amino acid sequence of SEQ ID NO:26 (025), optionally wherein the first antibody comprises an IgG1,κ Fc region, wherein the CH3 region contains Ile at position 350, a Thr at position 370, and a Leu at position 405; and (ii) a second antibody having an Fc region and VH and VL sequences, wherein the VH region comprises the amino acid sequence of SEQ ID NO:164 and the VL region comprises the amino acid sequence of SEQ ID NO:165 (005), optionally wherein the second antibody comprises an IgG1,κ Fc region having an Arg at position 409.

In one embodiment, the antibody is a bispecific antibody, comprising (i) a first antibody having an Fc region and VH and VL sequences, wherein the VH region comprises the amino acid sequence of SEQ ID NO:22, and the VL region comprises the amino acid sequence of SEQ ID NO:26 (025), optionally wherein the first antibody comprises an IgG1,κ Fc region, wherein the CH3 region contains Ile at position 350, a Thr at position 370, and a Leu at position 405; and (ii) a second antibody having an Fc region and VH and VL sequences, wherein the VH region comprises the amino acid sequence of SEQ ID NO:63 and the VL region comprises the amino acid sequence of SEQ ID NO:37 (153), optionally wherein the second antibody comprises an IgG1,κ Fc region having an Arg at position 409.

In one embodiment, the antibody is a bispecific antibody, comprising (i) a first antibody having an Fc region and VH and VL sequences, wherein the VH region comprises the amino acid sequence of SEQ ID NO:22, and the VL region comprises the amino acid sequence of SEQ ID NO:26 (025), optionally wherein the first antibody comprises an IgG1,κ Fc region, wherein the CH3 region contains Ile at position 350, a Thr at position 370, and a Leu at position 405; and (ii) a second antibody having an Fc region and VH and VL sequences, wherein the VH region comprises the amino acid sequence of SEQ ID NO:1 and the VL region comprises the amino acid sequence of SEQ ID NO:5 (169), optionally wherein the second antibody comprises an IgG1,κ Fc region having an Arg at position 409.

In one embodiment, the antibody is a bispecific antibody, comprising (i) a first antibody having an Fc region and VH and VL sequences, wherein the VH region comprises the amino acid sequence of SEQ ID NO:63, and the VL region comprises the amino acid sequence of SEQ ID NO:67 (153), optionally wherein the first antibody comprises an IgG1,κ Fc region, wherein the CH3 region contains Ile at position 350, a Thr at position 370, and a Leu at position 405; and (ii) a second antibody having an Fc region and VH and VL sequences, wherein the VH region comprises the amino acid sequence of SEQ ID NO:164 and the VL region comprises the amino acid sequence of SEQ ID NO:165 (005), optionally wherein the second antibody comprises an IgG1,κ Fc region having an Arg at position 409.

In one embodiment, the antibody is a bispecific antibody, comprising (i) a first antibody having an Fc region and VH and VL sequences, wherein the VH region comprises the amino acid sequence of SEQ ID NO:63, and the VL region comprises the amino acid sequence of SEQ ID NO:67 (153), optionally wherein the first antibody comprises an IgG1,κ Fc region, wherein the CH3 region contains Ile at position 350, a Thr at position 370, and a Leu at position 405; and (ii) a second antibody having an Fc region and VH and VL sequences, wherein the VH region comprises the amino acid sequence of SEQ ID NO:1 and the VL region comprises the amino acid sequence of SEQ ID NO:5 (169), optionally wherein the second antibody comprises an IgG1,κ Fc region having an Arg at position 409.

In one embodiment, the antibody is a bispecific antibody, comprising (i) a first antibody having an Fc region and VH and VL sequences, wherein the VH region comprises the amino acid sequence of SEQ ID NO:63, and the VL region comprises the amino acid sequence of SEQ ID NO:67 (153), optionally wherein the first antibody comprises an IgG1,κ Fc region having Arg at position 409, or Gln at position 297, or Arg at position 409 and Gln at position 297; and (ii) a second antibody having an Fc region and VH and VL sequences, wherein the VH region comprises the amino acid sequence of SEQ ID NO:171 and the VL region comprises the amino acid sequence of SEQ ID NO:172 (YTH12.5), optionally wherein the second antibody comprises an IgG1,κ Fc region having an Gln at position 297, or Leu at position 405, or Gln at position 297 and Leu at position 405.

In one embodiment, the antibody is a bispecific antibody, comprising (i) a first antibody having an Fc region and VH and VL sequences, wherein the VH region comprises the amino acid sequence of SEQ ID NO:1, and the VL region comprises the amino acid sequence of SEQ ID NO:5 (169), optionally wherein the first antibody comprises an IgG1,κ Fc region having Arg at position 409; and (ii) a second antibody having an Fc region and VH and VL sequences, wherein the VH region comprises the amino acid sequence of SEQ ID NO:171 and the VL region comprises the amino acid sequence of SEQ ID NO:172 (YTH12.5), optionally wherein the second antibody comprises an IgG1,κ Fc region having an Gln at position 297, or Leu at position 405, or Gln at position 297 and Leu at position 405.

In one embodiment, the antibody is a bispecific antibody, comprising (i) a first antibody having an Fc region and VH and VL sequences, wherein the VH region comprises the amino acid sequence of SEQ ID NO:63, and the VL region comprises the amino acid sequence of SEQ ID NO:67 (153), optionally wherein the first antibody comprises an IgG1,κ Fc region having Arg at position 409, or Gln at position 297, or Arg at position 409 and Gln at position 297; and (ii) a second antibody having an Fc region and VH and VL sequences, wherein the VH region comprises the amino acid sequence of SEQ ID NO:173 and the VL region comprises the amino acid sequence of SEQ ID NO:174 (huCLB-T3/4), optionally wherein the second antibody comprises an IgG1,κ Fc region having an Gln at position 297, or Leu at position 405, or Gln at position 297 and Leu at position 405.

In one embodiment, the antibody is a bispecific antibody, comprising (i) a first antibody having an Fc region and VH and VL sequences, wherein the VH region comprises the amino acid sequence of SEQ ID NO:1, and the VL region comprises the amino acid sequence of SEQ ID NO:5 (169), optionally wherein the first antibody comprises an IgG1,κ Fc region having Arg at position 409; and (ii) a second antibody having an Fc region and VH and VL sequences, wherein the VH region comprises the amino acid sequence of SEQ ID NO:173 and the VL region comprises the amino acid sequence of SEQ ID NO:174 (huCLB-T3/4), optionally wherein the second antibody comprises an IgG1,κ Fc region having an Gln at position 297, or Leu at position 405, or Gln at position 297 and Leu at position 405.

A CD3 antibody is an antibody with a VH region comprising the sequence of SEQ ID NO: 171 (VH YTH12.5) and VL region comprising the sequence of SEQ ID NO:172 (VL YTH12.5). Another example is a CD3 antibody with a VH region comprising the sequence of SEQ ID NO: 173 (VH huCLB-T3/4) and VL region comprising the sequence of SEQ ID NO:174 (VL huCLB-T3/4).

In one embodiment a bispecific antibody of the present invention may be selected from the group consisting of: IgG1-005-ITL×IgG1-169-K409R, IgG1-025-ITL×IgG1-005-K409R, IgG1-025-ITL×IgG1-153-K409R, IgG1-025-ITL×IgG1-169-K409R, IgG1-153-ITL×IgG1-005-K409R; and IgG1-153-ITL×IgG1-169-K409R, wherein IgG1-005-ITL means 005 IgG1,κ having Ile at position 350, Thr at position 370, and Leu at position 405, IgG1-005-K409R means 005 IgG1,κ having an Arg at position 409, IgG1-025-ITL means 025 IgG1,κ having Ile at position 350, Thr at position 370, and Leu at position 405, IgG1-153-ITL means 153 IgG1,κ having contains Ile at position 350, Thr at position 370, and Leu at position 405, IgG1-153-K409R means 153 IgG1,κ having an Arg at position 409, IgG1-169-K409R means 169 IgG1,κ having an Arg at position 409, and wherein the bold numbers refer to antibodies described herein with the VH and VL regions comprising the sequences described in table 1 and for 005 in example 21; i.e. SEQ ID NOs:164 and 165.

In one embodiment the bispecific antibody may be selected from the group consisting of: IgG1-HER2-153-K409R×IgG1-YTH12.5-F405L, IgG1-HER2-153-K409R×IgG1-YTH12.5-N297Q-F405L, IgG1-HER2-153-K409R×IgG1-hu-CLB-T3/4-F405L, IgG1-HER2-153-K409R×IgG1-hu-CLB-T3/4-N297Q-F405L, IgG1-HER2-153-N297Q-K409R×IgG1-YTH12.5-F405L, IgG1-HER2-153-N297Q-K409R×IgG1-YTH12.5-N297Q-F405L, IgG1-HER2-153-N297Q-K409R×IgG1-hu-CLB-T3/4-F405L, IgG1-HER2-153-N297Q-K409R×IgG1-hu-CLB-T3/4-N297Q-F405L, IgG1-HER2-169-K409R×IgG1-hu-CLB-T3/4-F405L, IgG1-HER2-169-K409R×IgG1-hu-CLB-T3/4-N297Q-F405L, IgG1-HER2-169-K409R×IgG1-YTH12.5-F405L and IgG1-HER2-169-K409R×IgG1-YTH12.5-N297Q-F405L.

Functional Properties of Group 1, 2 and 3 Antibodies and Bispecific Antibodies

In another aspect of the antibody of the invention, the antibody binds to the same HER2 epitope as one or more of the novel Group 1, 2 or 3 antibodies described herein, preferably when determined as described in Example 14; and is further characterized by one or more properties determined as described in Examples 12, 13, 15, 16, 17, 18 and 19.

In one embodiment, the HER2 antibody has a lower $EC_{50}$ value (half maximal effective concentration) than trastuzumab in binding to A431 cells, preferably an $EC_{50}$ value lower than 0.80 µg/ml, 0.50 µg/ml, or 0.30 µg/ml, when determined as described in Example 12, and preferably binds the same epitope as at least one reference antibody comprising the VH and VL regions selected from the group consisting of
  a) a VH region comprising the sequence of SEQ ID NO:1 and a VL region comprising the sequence of SEQ ID NO:5 (169);
  b) a VH region comprising the sequence of SEQ ID NO:15 and a VL region comprising the sequence of SEQ ID NO:19 (084);
  c) a VH region comprising the sequence of SEQ ID NO:22 and a VL region comprising the sequence of SEQ ID NO:26 (025);
  d) a VH region comprising the sequence of SEQ ID NO:29 and a VL region comprising the sequence of SEQ ID NO:32 (091);
  e) a VH region comprising the sequence of SEQ ID NO:46 and a VL region comprising the sequence of SEQ ID NO:49 (127);
  f) a VH region comprising the sequence of SEQ ID NO:49 and a VL region comprising the sequence of SEQ ID NO:53 (159);
  g) a VH region comprising the sequence of SEQ ID NO:56 and a VL region comprising the sequence of SEQ ID NO:60 (098);
  h) a VH region comprising the sequence of SEQ ID NO:63 and a VL region comprising the sequence of SEQ ID NO:67 (153); and
  i) a VH region comprising the sequence of SEQ ID NO:70 and a VL region comprising the sequence of SEQ ID NO:74 (132).

In an additional or alternative embodiment, the anti-HER2 antibody specifically binds HER2-positive Rhesus epithelial cells, when determined as described in Example 13, and preferably binds the same epitope as at least one reference antibody comprising the VH and VL regions selected from the group consisting of the VH and VL regions of any of antibodies 169, 050, 084, 025, 091, 129, 127, 159, 098, 153 and 132.

In an additional or alternative embodiment, the anti-HER2 antibody efficiently induces ADCC (antibody-dependent cell-mediated cytotoxicity), preferably achieving a specific $^{51}$Cr-release of at least 30%, more preferably at least 40%, when determined as described in Example 15, and preferably binds the same epitope as at least one reference antibody comprising the VH and VL regions selected from the group consisting of:
  a) a VH region comprising the sequence of SEQ ID NO:1 and a VL region comprising the sequence of SEQ ID NO:5 (169);
  b) a VH region comprising the sequence of SEQ ID NO:8 and a VL region comprising the sequence of SEQ ID NO:12 (050);
  c) a VH region comprising the sequence of SEQ ID NO:15 and a VL region comprising the sequence of SEQ ID NO:19 (084);
  d) a VH region comprising the sequence of SEQ ID NO:22 and a VL region comprising the sequence of SEQ ID NO:26 (025);
  e) a VH region comprising the sequence of SEQ ID NO:29 and a VL region comprising the sequence of SEQ ID NO:32 (091);
  f) a VH region comprising the sequence of SEQ ID NO:35 and a VL region comprising the sequence of SEQ ID NO:39 (129); and
  g) a VH region comprising the sequence of SEQ ID NO:63 an, preferably, a VL region comprising the sequence of SEQ ID NO:67 (153).

In an additional or alternative embodiment, the HER2 antibody specifically binds HER2-expressing AU565 cells but promotes ligand-independent proliferation of the cells less than any of F5 and C1 when determined as described in Example 16, and preferably binds the same epitope as at least one reference antibody comprising the VH and VL regions selected from the group consisting of
  a) a VH region comprising the sequence of SEQ ID NO:1 and a VL region comprising the sequence of SEQ ID NO:5 (169);
  b) a VH region comprising the sequence of SEQ ID NO:8 and a VL region comprising the sequence of SEQ ID NO:12 (050);
  c) a VH region comprising the sequence of SEQ ID NO:15 and a VL region comprising the sequence of SEQ ID NO:19 (084);
  d) a VH region comprising the sequence of SEQ ID NO:22 and a VL region comprising the sequence of SEQ ID NO:26 (025);
  e) a VH region comprising the sequence of SEQ ID NO:29 and a VL region comprising the sequence of SEQ ID NO:32 (091);
  f) a VH region comprising the sequence of SEQ ID NO:35 and a VL region comprising the sequence of SEQ ID NO:39 (129);
  g) a VH region comprising the sequence of SEQ ID NO:46 and a VL region comprising the sequence of SEQ ID NO:49 (127);
  h) a VH region comprising the sequence of SEQ ID NO:49 and a VL region comprising the sequence of SEQ ID NO:53 (159);
  i) a VH region comprising the sequence of SEQ ID NO:56 and a VL region comprising the sequence of SEQ ID NO:60 (098);
  j) a VH region comprising the sequence of SEQ ID NO:63 and a VL region comprising the sequence of SEQ ID NO:67 (153); and
  k) a VH region comprising the sequence of SEQ ID NO:70 and a VL region comprising the sequence of SEQ ID NO:74 (132).

In an additional or alternative embodiment, the HER2 antibody specifically binds HER2-expressing AU565 cells and inhibits ligand-independent proliferation of the cells, preferably inhibiting proliferation by at least 20%, more preferably at least 25%, when determined as described in Example 16, and preferably binds the same epitope as at least one reference antibody comprising the VH and VL regions selected from the group consisting of:
  a) a VH region comprising the sequence of SEQ ID NO:1 and a VL region comprising the sequence of SEQ ID NO:5 (169); and
  b) a VH region comprising the sequence of SEQ ID NO:8 and a VL region comprising the sequence of SEQ ID NO:12 (050).

In an additional or alternative embodiment, the HER2 antibody specifically binds HER2-expressing AU565 cells but has no significant effect on, or does not promote, ligand-induced proliferation of the cells, preferably inhibiting proliferation by no more than 25%, more preferably by no more than 15%, when determined as described in Example 17, and binds the same epitope as at least one reference antibody comprising the VH and VL regions selected from the group consisting of:
  a) a VH region comprising the sequence of SEQ ID NO:1 and a VL region comprising the sequence of SEQ ID NO:5 (169);

b) a VH region comprising the sequence of SEQ ID NO:8 and a VL region comprising the sequence of SEQ ID NO:12 (050);

c) a VH region comprising the sequence of SEQ ID NO:15 and a VL region comprising the sequence of SEQ ID NO:19 (084); and d) a VH region comprising the sequence of SEQ ID NO:56 and a VL region comprising the sequence of SEQ ID NO:60 (098).

In an additional or alternative embodiment, the HER2 antibody specifically binds HER2-expressing MCF-7 cells and inhibits ligand-induced proliferation, e.g. it may completely inhibit the ligand-induced effect or inhibit the total proliferation by 50%, e.g. 60% or 70% or 80%, of the cells when determined as described in Example 17, and binds the same epitope as at least one reference antibody comprising the V H and VL regions selected from the group consisting of:

a) a VH region comprising the sequence of SEQ ID NO:22 and a VL region comprising the sequence of SEQ ID NO:26 (025);

b) a VH region comprising the sequence of SEQ ID NO:29 and a VL region comprising the sequence of SEQ ID NO:32 (091);

c) a VH region comprising the sequence of SEQ ID NO:35 and a VL region comprising the sequence of SEQ ID NO:39 (129); and d) a VH region comprising the sequence of SEQ ID NO:63 an, preferably, a VL region comprising the sequence of SEQ ID NO:67 (153).

In an additional or alternative embodiment, the antibody, when conjugated directly or indirectly to a therapeutic moiety such as a truncated form of the *pseudomonas*-exotoxin A, is more effective than trastuzumab in killing AU565 cells, A431 cells, or both AU565 and A431 cells, when determined as described in Example 18.

In one embodiment, the conjugated antibody has an $EC_{50}$ value of less than 70 ng/ml, less than 50 ng/ml, or less than 30 ng/ml in killing AU565 cells and/or A431 cells, when determined as described in Example 18, and binds the same epitope as at least one reference antibody comprising the VH and VL regions of an antibody selected from the group consisting of 169, 091, 050, 084, 098, 05, 153, 129, 132, 127 and 159; preferably selected from antibodies 153, 129, 098, 091 and 025.

In one embodiment, the conjugated antibody has or results in a higher percentage of killed AU565 cells than trastuzumab and pertuzumab when determined as described in Example 18, preferably killing at least 49%, more preferably at least 60% of the AU565 cells, and binds the same epitope as at least one reference antibody comprising the VH and VL regions of an antibody selected from the group consisting of 169, 091, 050, 084, 098, 025, 153, 129, 132, 127 and 159; preferably selected from antibodies 153, 132, 127, 129, 159 and 025.

In a preferred embodiment, the conjugated antibody binds to the same epitope as a reference antibody comprising a VH region comprising the sequence of SEQ ID NO:49 and a VL region comprising the sequence of SEQ ID NO:53 (159).

In one embodiment, the conjugated antibody has a higher percentage of killed AU431 cells than trastuzumab and pertuzumab when determined as described in Example 18, preferably killing at least 50%, more preferably at least 70%, and binds the same epitope as at least one reference antibody comprising the VH and VL regions of an antibody selected from the group consisting of 025, 084, 091, 098, 129 and 153; preferably selected from antibodies 025, 091, 098, 129 and 153.

In a preferred embodiment, the conjugated antibody binds to the same epitope as a reference antibody comprising a VH region comprising the sequence of SEQ ID NO:56 and a VL region comprising the sequence of SEQ ID NO:60 (098).

In an additional or alternative embodiment, the antibody is internalized by tumor cells expressing HER2, such as AU565 cells, to a higher degree than trastuzumab and pertuzumab, preferably more than twice or three times the amount of internalized trastuzumab, preferably when determined according to Example 18, and binds to the same epitope as an antibody comprising VH and VL regions selected from the group consisting of:

a) a VH region comprising the sequence of SEQ ID NO:46 and a VL region comprising the sequence of SEQ ID NO:49 (127);

b) a VH region comprising the sequence of SEQ ID NO:49 and a VL region comprising the sequence of SEQ ID NO:53 (159);

c) a VH region comprising the sequence of SEQ ID NO:56 and a VL region comprising the sequence of SEQ ID NO:60 (098); d) a VH region comprising the sequence of SEQ ID NO:63 and a VL region comprising the sequence of SEQ ID NO:67 (153); and e) a VH region comprising the sequence of SEQ ID NO:70 and a VL region comprising the sequence of SEQ ID NO:74 (132).

Preferably, the antibody binds to the same epitope as an antibody comprising VH and VL regions selected from a) a VH region comprising the sequence of SEQ ID NO:46 and a VL region comprising the sequence of SEQ ID NO:49 (127) and b) a VH region comprising the sequence of SEQ ID NO:56 and a VL region comprising the sequence of SEQ ID NO:60 (098).

In a further embodiment, the antibody binds to Domain II or IV of HER2, preferably wherein the antibody does not significantly promote proliferation of HER2 expressing cells, and is more efficiently internalized, or is internalized to a higher degree, than trastuzumab or pertuzumab into HER2-expressing tumor cells, preferably when determined as described in the Examples, e.g. examples 16 and 19, respectively.

In a further embodiment the antibody enhanced HER2 downmodulation more than trastuzumab, e.g. the antibody enhanced HER2 downmodulation by more 30%, such as more than 40% or more than 50% when determined as described in example 22, preferably wherein the antibody binds to the same epitope as an antibody of cross-block group 3 of the present invention, e.g. an antibody binding to the same epitope as an antibody comprising VH and VL regions selected from the group consisting of:

a) a VH region comprising the sequence of SEQ ID NO:56 and a VL region comprising the sequence of SEQ ID NO:60 (098);

b) a VH region comprising the sequence of SEQ ID NO:63 and a VL region comprising the sequence of SEQ ID NO:67 (153).

In another or alternative embodiment the antibody decreased tumour growth and improved survival in vivo more than trastuzumab, when determined as described in example 29, preferably wherein the antibody binds to the same epitope as an antibody of cross-block 1 or cross-block 2 of the present invention, e.g. an antibody binding to the same epitope as an antibody comprising VH and VL regions selected from the group consisting of:

a) a VH region comprising the sequence of SEQ ID NO:1 and a VL region comprising the sequence of SEQ ID NO:5 (169);
b) a VH region comprising the sequence of SEQ ID NO:15 and a VL region comprising the sequence of SEQ ID NO:19 (084); and
c) a VH region comprising the sequence of SEQ ID NO:29 and a VL region comprising the sequence of SEQ ID NO:32 (091).

In another or alternative embodiment the antibody decreased tumour growth and improved survival in vivo more than trastuzumab, when determined as described in example 30, preferably wherein the antibody binds to the same epitope as an antibody of cross-block 2 or cross-block 3 of the present invention, e.g. an antibody binding to the same epitope as an antibody comprising VH and VL regions selected from the group consisting of:
a) a VH region comprising the sequence of SEQ ID NO:22 and a VL region comprising the sequence of SEQ ID NO:26 (025);
b) a VH region comprising the sequence of SEQ ID NO:29 and a VL region comprising the sequence of SEQ ID NO:32 (091);
c) a VH region comprising the sequence of SEQ ID NO:35 and a VL region comprising the sequence of SEQ ID NO:39 (129); and
d) a VH region comprising the sequence of SEQ ID NO:63 and a VL region comprising the sequence of SEQ ID NO:67 (153).

More particularly, wherein the antibody binds to the same epitope as an antibody comprising VH and VL regions selected from the group consisting of:
a) a VH region comprising the sequence of SEQ ID NO:22 and a VL region comprising the sequence of SEQ ID NO:26 (025); and
b) a VH region comprising the sequence of SEQ ID NO:29 and a VL region comprising the sequence of SEQ ID NO:32 (091).

In one embodiment the antibody is a bispecific antibody.
In a further embodiment the antibody is a bispecific antibody which enhanced HER2 downmodulation, in particular more than their monospecific counterparts, e.g. the antibody enhanced HER2 downmodulation by more 20%, such as more than 30% or more than 40% when determined as described in example 22, preferably wherein the antibody binds to the same epitopes as bispecific antibody selected from the group consisting of IgG1-005-ITL×IgG1-169-K409R, IgG1-025-ITL×IgG1-005-K409R, IgG1-025-ITL×IgG1-153-K409R, IgG1-025-ITL×IgG1-169-K409R, IgG1-153-ITL×IgG1-005-K409R; and IgG1-153-ITL×IgG1-169-K409R.

In an additional or alternative embodiment, the bispecific antibody specifically binds HER2-expressing AU565 cells and inhibits ligand-induced proliferation of the cells when determined as described in Example 24, and binds the same epitopes as at least one bispecific antibody selected from the group consisting of: IgG1-005-ITL×IgG1-169-K409R, IgG1-025-ITL×IgG1-005-K409R, IgG1-025-ITL×IgG1-153-K409R, IgG1-025-ITL×IgG1-169-K409R, IgG1-153-ITL×IgG1-005-K409R; and IgG1-153-ITL×IgG1-169-K409R. In particular the bispecific antibody inhibits proliferation of the AU565 cells more than their monospecific counterparts and is selected from the group consisting of IgG1-005-ITL×IgG1-169-K409R and IgG1-025-ITL×IgG1-005-K409R.

In an additional or alternative embodiment the bispecific antibody is a HER2×CD3 bispecific antibody induce T cell mediated cytotoxicity of AU565 as described in example 25, and binds the same epitopes as at least one of the bispecific antibodies selected from the group consisting of: Duo huCLB-Q/153-Q, Duo huCLB-Q/B12-Q, Duo YTH12.5/153-Q and Duo YTH12.5/B12-Q (Duo indicating bispecific antibody).

Antibody Formats

The present invention provides HER2 antibodies which efficiently bind to and internalize into HER2-expressing tumor cells, typically without significantly promoting ligand-independent proliferation of the cells. Depending on the desired functional properties for a particular use, particular antibodies can be selected from the set of antibodies provided in the present invention and/or their format can be adapted to change these properties, as described below.

The antibody of the invention can be of any isotype. The choice of isotype typically will be guided by the desired effector functions, such as ADCC induction. Exemplary isotypes are IgG1, IgG2, IgG3, and IgG4. Either of the human light chain constant regions, kappa or lambda, may be used. If desired, the class of a HER2 antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1,κ.

In a further embodiment, the antibody of the invention is glyco-engineered to reduce fucose and thus enhance ADCC, e.g. by addition of compounds to the culture media during antibody production as described in US2009317869 or as described in van Berkel et al. (2010) Biotechnol. Bioeng. 105:350 or by using FUT8 knockout cells, e.g. as described in Yamane-Ohnuki et al (2004) Biotechnol. Bioeng 87:614. ADCC may alternatively be optimized using the method described by Umaña et al. (1999) Nature Biotech 17:176.

In a further embodiment, the antibody of the invention has been engineered to enhance complement activation, e.g. as described in Natsume et al. (2009) Cancer Sci. 100:2411.

In one embodiment, the antibody of the invention is a full-length antibody, preferably an IgG1 antibody, in particular an IgG1,κ antibody. In another embodiment, the antibody of the invention is an antibody fragment or a single-chain antibody.

Antibody fragments may e.g. be obtained by fragmentation using conventional techniques, and the fragments screened for utility in the same manner as described herein for whole antibodies. For example, F(ab')$_2$ fragments may be generated by treating an antibody with pepsin. The resulting F(ab')$_2$ fragment may be treated to reduce disulfide bridges with a reducing agent, such as dithiothreitol, to produce Fab' fragments. Fab fragments may be obtained by treating an antibody with papain. A F(ab')$_2$ fragment may also be produced by binding Fab' fragments via a thioether bond or a disulfide bond. Antibody fragments may also be generated by expression of nucleic acids encoding such fragments in recombinant cells (see for instance Evans et al., J. Immunol. Meth. 184, 123-38 (1995)). For example, a chimeric gene encoding a portion of an F(ab')$_2$ fragment could include DNA sequences encoding the $C_H1$ domain and hinge region of the H chain, followed by a translational stop codon to yield such a truncated antibody fragment molecule.

As explained above, in one embodiment, the HER2 antibody of the invention is a bivalent antibody, i.e. an antibody capable of binding two antigens or epitopes on the same antigen.

In another embodiment, the HER2 antibody of the invention is a monovalent antibody.

In one embodiment, the antibody of the invention is a Fab fragment or a one-armed antibody, such as described in US20080063641 (Genentech) or other monovalent antibody, e.g. such as described in WO2007048037 (Amgen).

In a preferred embodiment, a monovalent antibody has a structure as described in WO2007059782 (Genmab) (incorporated herein by reference) having a deletion of the hinge region. Accordingly, in one embodiment, the antibody is a monovalent antibody, wherein said HER2 antibody is constructed by a method comprising:

i) providing a nucleic acid construct encoding the light chain of said monovalent antibody, said construct comprising a nucleotide sequence encoding the VL region of a selected antigen specific HER2 antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being;

ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together;

iii) providing a cell expression system for producing said monovalent antibody;

iv) producing said monovalent antibody by co-expressing the nucleic acid constructs of (i) and (ii) in cells of the cell expression system of (iii).

Similarly, in one embodiment, the HER2 antibody is a monovalent antibody, which comprises (i) a variable region of an antibody of the invention as described herein or an antigen binding part of the said region, and (ii) a $C_H$ region of an immunoglobulin or a fragment thereof comprising the $C_H2$ and $C_H3$ regions, wherein the $C_H$ region or fragment thereof has been modified such that the region corresponding to the hinge region and, if the immunoglobulin is not an IgG4 subtype, other regions of the $C_H$ region, such as the $C_H3$ region, do not comprise any amino acid residues, which are capable of forming disulfide bonds with an identical $C_H$ region or other covalent or stable non-covalent inter-heavy chain bonds with an identical $C_H$ region in the presence of polyclonal human IgG.

In a further embodiment hereof, the heavy chain of the monovalent HER2 antibody has been modified such that the entire hinge has been deleted.

In another further embodiment, the immunoglobulin referred to in step ii) above is of the IgG4 subtype.

In another further embodiment, said monovalent antibody is of the IgG4 subtype, but the $C_H3$ region has been modified so that one or more of the following amino acid substitutions have been made:

| | Numbering of CH3 mutations | |
|---|---|---|
| KABAT* | EU index G4* | Mutations |
| E378 | E357 | E357A or E357T or E357V or E357I |
| S387 | S364 | S364R or S364K |
| T389 | T366 | T366A or T366R or T366K or T366N |
| L391 | L368 | L368A or L368V or L368E or L368G or L368S or L368T |
| D427 | D399 | D399A or D399T or D399S |
| F436 | F405 | F405A or F405L or F405T or F405D or F405R or F405Q or F405K or F405Y |
| Y438 | Y407 | Y407A or Y407E or Y407Q or Y407K or Y407F |
| F436 and Y438 | F405 and Y407 | (F405T and Y407E) or (F405D and Y407E) |
| D427 and Y438 | D399 and Y407 | (D399S and Y407Q) or (D399S and Y407K) or (D399S and Y407E) |

*KABAT indicates amino acid numbering according to Kabat (Kabat et al., Sequences of Proteins of Immunological Interest, 5th Ed. Public Health Service, National Institutes of Health, Bethesda, MD. (1991). EU index indicates amino acid numbering according to EU index as outlined in Kabat et al., (supra).

In another further embodiment, the sequence of said monovalent antibody has been modified so that it does not comprise any acceptor sites for N-linked glycosylation. HER2 antibodies of the invention also include single chain antibodies. Single chain antibodies are peptides in which the heavy and light chain Fv regions are connected. In one embodiment, the present invention provides a single-chain Fv (scFv) wherein the heavy and light chains in the Fv of a HER2 antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single $V_H$ and $V_L$ are used, bivalent, if two $V_H$ and $V_L$ are used, or polyvalent, if more than two $V_H$ and $V_L$ are used.

In one embodiment, the HER2 antibody of the invention is an effector-function-deficient antibody. In one embodiment, the effector-function-deficient HER2 antibody is a human stabilized IgG4 antibody, which has been modified to prevent Fab-arm exchange (van der Neut Kolfschoten et al. (2007) Science 317(5844):1554-7). Examples of suitable human stabilized IgG4 antibodies are antibodies, wherein arginine at position 409 in a heavy chain constant region of human IgG4, which is indicated in the EU index as in Kabat et al., is substituted with lysine, threonine, methionine, or leucine, preferably lysine (described in WO2006033386

(Kirin)) and/or wherein the hinge region has been modified to comprise a Cys-Pro-Pro-Cys sequence.

In one embodiment, the stabilized IgG4 HER2 antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions, but does not comprise a Cys-Pro-Pro-Cys sequence in the hinge region. Preferably, said antibody comprises a Lys or Ala residue at the position corresponding to 409 or the CH3 region of the antibody has been replaced by the CH3 region of human IgG1, of human IgG2 or of human IgG3. See also WO2008145142 (Genmab).

In an even further embodiment, the stabilized IgG4 HER2 antibody is an IgG4 antibody comprising a heavy chain and a light chain, wherein said heavy chain comprises a human IgG4 constant region having a residue selected from the group consisting of: Lys, Ala, Thr, Met and Leu at the position corresponding to 409 and/or a residue selected from the group consisting of: Ala, Val, Gly, Ile and Leu at the position corresponding to 405, and wherein said antibody optionally comprises one or more further substitutions, deletions and/or insertions and wherein said antibody comprises a Cys-Pro-Pro-Cys sequence in the hinge region. Preferably, said antibody comprises a Lys or Ala residue at the position corresponding to 409 or the CH3 region of the antibody has been replaced by the CH3 region of human IgG1, of human IgG2 or of human IgG3.

In a further embodiment, the effector-function-deficient HER2 antibody is an antibody of a non-IgG4 type, e.g. IgG1, IgG2 or IgG3 which has been mutated such that the ability to mediate effector functions, such as ADCC, has been reduced or even eliminated. Such mutations have e.g. been described in Dall'Acqua W F et al., J Immunol. 177(2): 1129-1138 (2006) and Hezareh M, J Virol.; 75(24):12161-12168 (2001).

Conjugates

In a further embodiment, the present invention provides a HER2 antibody or an HER2 bispecific antibody linked or conjugated to a therapeutic moiety, such as a cytotoxin, a chemotherapeutic drug, a cytokine, an immunosuppressant, or a radioisotope. Such conjugates are referred to herein as "immunoconjugates". Immunoconjugates which include one or more cytotoxins are referred to as "immunotoxins".

A cytotoxin or cytotoxic agent includes any agent that is detrimental to (e.g., kills) cells. Suitable therapeutic agents for forming immunoconjugates of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, maytansine or an analog or derivative thereof, mitoxantrone, mithramycin, actinomycin D, 1-dehydrotestosterone, glucocorticoids, procaine, tetracaine, lidocaine, propranolol, and puromycin; calicheamicin or analogs or derivatives thereof; antimetabolites (such as methotrexate, 6-mercaptopurine, 6-thioguanine, cytarabine, fludarabin, 5-fluorouracil, decarbazine, hydroxyurea, asparaginase, gemcitabine, cladribine), alkylating agents (such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin; as well as duocarmycin A, duocarmycin SA, CC-1065 (a.k.a. rachelmycin), or analogs or derivatives of CC-1065), antibiotics (such as dactinomycin (formerly actinomycin), bleomycin, daunorubicin (formerly daunomycin), doxorubicin, idarubicin, mithramycin, mitomycin, mitoxantrone, plicamycin, anthramycin (AMC)), anti-mitotic agents (e.g., tubulin-inhibitors) such as monomethyl auristatin E, monomethyl auristatin F, or other analogs or derivatives of dolastatin 10; diphtheria toxin and related molecules (such as diphtheria A chain and active fragments thereof and hybrid molecules); ricin toxin (such as ricin A or a deglycosylated ricin A chain toxin), cholera toxin, a Shiga-like toxin (SLT-I, SLT-II, SLT-IIV), LT toxin, C3 toxin, Shiga toxin, pertussis toxin, tetanus toxin, soybean Bowman-Birk protease inhibitor, *Pseudomonas* exotoxin, alorin, saporin, modeccin, gelanin, abrin A chain, modeccin A chain, alphasarcin, Aleurites fordii proteins, dianthin proteins, Phytolacca americana proteins (PAPI, PAPII, and PAP-S), *Momordica charantia* inhibitor, curcin, crotin, *Sapaonaria officinalis* inhibitor, gelonin, mitogellin, restrictocin, phenomycin, and enomycin toxins. Other suitable conjugated molecules include antimicrobial/lytic peptides such as CLIP, Magainin 2, mellitin, Cecropin, and P18; ribonuclease (RNase), DNase I, Staphylococcal enterotoxin-A, pokeweed antiviral protein, diphtherin toxin, and *Pseudomonas* endotoxin. See, for example, Pastan et al., Cell 47, 641 (1986) and Goldenberg, Calif. A Cancer Journal for Clinicians 44, 43 (1994). Therapeutic agents that may be administered in combination with a HER2 antibody of the present invention as described elsewhere herein, such as, e.g., anti-cancer cytokines or chemokines, are also candidates for therapeutic moieties useful for conjugation to an antibody of the present invention.

In one embodiment, a HER2 antibody of the invention comprises a conjugated nucleic acid or nucleic acid-associated molecule. In one such embodiment, the conjugated nucleic acid is a cytotoxic ribonuclease, an antisense nucleic acid, an inhibitory RNA molecule (e.g., a siRNA molecule) or an immunostimulatory nucleic acid (e.g., an immunostimulatory CpG motif-containing DNA molecule). In another embodiment, a HER2 antibody of the invention is conjugated to an aptamer or a ribozyme.

In one embodiment, HER2 antibodies comprising one or more radiolabeled amino acids are provided. A radiolabeled HER2 antibody may be used for both diagnostic and therapeutic purposes (conjugation to radiolabeled molecules is another possible feature). Non-limiting examples of labels for polypeptides include 3H, 14C, 15N, 35S, 90Y, 99Tc, and 125I, 131I, and 186Re.

In one embodiment, the antibody is conjugated to a radioisotope or to a radioisotope-containing chelate. For example, the antibody can be conjugated to a chelator linker, e.g. DOTA, DTPA or tiuxetan, which allows for the antibody to be complexed with a radioisotope. The antibody may also or alternatively comprise or be conjugated to one or more radiolabeled amino acids or other radiolabeled molecule. A radiolabeled CD74 Ab may be used for both diagnostic and therapeutic purposes. Non-limiting examples of radioisotopes include $^{3}$H, $^{14}$C, $^{15}$N, $^{35}$S, $^{90}$Y, $^{99}$Tc, $^{125}$I, $^{111}$In, $^{131}$I, $^{186}$Re, $^{213}$Bs, $^{225}$Ac and $^{227}$Th.

HER2 antibodies may also be chemically modified by covalent conjugation to a polymer to for instance increase their circulating half-life. Exemplary polymers, and methods to attach them to peptides, are illustrated for instance U.S. Pat. Nos. 4,766,106, 4,179,337, 4,495,285 and 4,609,546. Additional polymers include polyoxyethylated polyols and polyethylene glycol (PEG) (e.g., a PEG with a molecular weight of between about 1,000 and about 40,000, such as between about 2,000 and about 20,000).

Any method known in the art for conjugating the HER2 antibody to the conjugated molecule(s), such as those described above, may be employed, including the methods described by Hunter et al., Nature 144, 945 (1962), David et al., Biochemistry 13, 1014 (1974), Pain et al., J. Immunol. Meth. 40, 219 (1981) and Nygren, J. Histochem. and Cytochem. 30, 407 (1982). Such antibodies may be produced by chemically conjugating the other moiety to the N-terminal side or C-terminal side of the HER2 antibody or fragment thereof (e.g., a HER2 antibody H or L chain) (see, e.g., Antibody Engineering Handbook, edited by Osamu Kanemitsu, published by Chijin Shokan (1994)). Such conjugated antibody derivatives may also be generated by conjugation at internal residues or sugars, where appropriate.

The agents may be coupled either directly or indirectly to a HER2 antibody of the present invention. One example of indirect coupling of a second agent is coupling via a spacer moiety to cysteine or lysine residues in the antibody. In one embodiment, a HER2 antibody is conjugated to a prodrug molecule that can be activated in vivo to a therapeutic drug via a spacer or linker. After administration, the spacers or linkers are cleaved by tumor-cell associated enzymes or other tumor-specific conditions, by which the active drug is formed. Examples of such prodrug techologies and linkers are described in WO02083180, WO2004043493, WO2007018431, WO2007089149, and WO2009017394 by Syntarga BV, et al. Suitable antibody-prodrug technology and duocarmycin analogs can also be found in U.S. Pat. No. 6,989,452 (Medarex).

In one embodiment, the HER2 antibody of the present invention is attached to a chelator linker, e.g. tiuxetan, which allows for the antibody to be conjugated to a radioisotope.

Bispecific Antibodies

In a further aspect, the invention relates to a bispecific molecule comprising a first antigen binding site from a HER2 antibody of the invention as described herein above and a second antigen binding site with a different binding specificity, such as a binding specificity for a human effector cell, a human Fc receptor, a T cell receptor, a B cell receptor or a binding specificity for a non-overlapping epitope of HER2, i.e. a bispecific antibody wherein the first and second antigen binding sites do not cross-block each other for binding to HER2, e.g. when tested as described in Example 14.

Exemplary bispecific antibody molecules of the invention comprise (i) two antibodies, one with a specificity to HER2 and another to a second target that are conjugated together, (ii) a single antibody that has one chain or arm specific to HER2 and a second chain or arm specific to a second molecule, (iii) a single chain antibody that has specificity to HER2 and a second molecule, e.g., via two scFvs linked in tandem by an extra peptide linker; (iv) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (v) a chemically-linked bispecific (Fab')$_2$ fragment; (vi) a Tandab, which is a fusion of two single chain diabodies resulting in a tetravalent bispecific antibody that has two binding sites for each of the target antigens; (vii) a flexibody, which is a combination of scFvs with a diabody resulting in a multivalent molecule; (viii) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (ix) a so-called Scorpion molecule, comprising, e.g., two scFvs fused to both termini of a human Fc-region; and (x) a diabody. In one embodiment, the bispecific antibody of the present invention is a diabody, a cross-body, or a bispecific obtained via a controlled Fab arm exchange as those described in the present invention. Examples of platforms useful for preparing bispecific antibodies include but are not limited to BITE (Micromet), DART (MacroGenics), Fcab and Mab$^2$ (F-star), Fc-engineered IgG1 (Xencor) or DuoBody (based on Fab arm exchange, Genmab, this application). Examples of different classes of bispecific antibodies include but are not limited to asymmetric IgG-like molecules, wherein the one side of the molecule contains the Fab region or part of the Fab region of at least one antibody, and the other side of the molecule contains the Fab region or parts of the Fab region of at least one other antibody; in this class, asymmetry in the Fc region could also be present, and be used for specific linkage of the two parts of the molecule;

symmetric IgG-like molecules, wherein the two sides of the molecule each contain the Fab region or part of the Fab region of at least two different antibodies;

IgG fusion molecules, wherein full length IgG antibodies are fused to extra Fab regions or parts of Fab regions;

Fc fusion molecules, wherein single chain Fv molecules or stabilized diabodies are fused to Fcγ regions or parts thereof;

Fab fusion molecules, wherein different Fab-fragments are fused together;

ScFv- and diabody-based molecules wherein different single chain Fv molecules or different diabodies are fused to each other or to another protein or carrier molecule.

Examples of asymmetric IgG-like molecules include but are not limited to the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (EMD Serono), the Biclonic (Merus) and the DuoBody (Genmab A/S).

Example of symmetric IgG-like molecules include but are not limited to Dual Targeting (DT)-Ig (GSK/Domantis), Two-in-one Antibody (Genentech), Cross-linked Mabs (Karmanos Cancer Center), mAb$^2$ (F-Star) and CovX-body (CovX/Pfizer).

Examples of IgG fusion molecules include but are not limited to Dual Variable Domain (DVD)-Ig (Abbott), IgG-like Bispecific (ImClone/Eli Lilly), Ts2Ab (MedImmune/AZ) and BsAb (Zymogenetics), HERCULES (Biogen Idec) and TvAb (Roche).

Examples of Fc fusion molecules include but are not limited to ScFv/Fc Fusions (Academic Institution), SCORPION (Emergent BioSolutions/Trubion, Zymogenetics/BMS), Dual Affinity Retargeting Technology (Fc-DART) (MacroGenics) and Dual(ScFv)$_2$-Fab (National Research Center for Antibody Medicine-China).

Examples of class V bispecific antibodies include but are not limited to F(ab)$_2$ (Medarex/AMGEN), Dual-Action or Bis-Fab (Genentech), Dock-and-Lock (DNL) (ImmunoMedics), Bivalent Bispecific (Biotecnol) and Fab-Fv (UCB-Celltech).

Examples of ScFv- and diabody-based molecules include but are not limited to Bispecific T Cell Engager (BITE)

(Micromet9, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COM BODY (Epigen Biotech).

In one embodiment, the second molecule is a cancer antigen/tumor-associated antigen such as carcinoembryonic antigen (CEA), prostate specific antigen (PSA), RAGE (renal antigen), α-fetoprotein, CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), ganglioside antigens, tyrosinase, gp75, c-Met, C-myc, Marti., MelanA, MUM-1, MUM-2, MUM-3, HLA-B7, Ep-CAM or a cancer-associated integrin, such as α5β3 integrin. In another embodiment, the second molecule is a T cell and/or NK cell antigen, such as CD3 or CD16. In another embodiment, the second molecule is an angiogenic factor or other cancer-associated growth factor, such as a vascular endothelial growth factor, a fibroblast growth factor, epidermal growth factor, angiogenin or a receptor of any of these, particularly receptors associated with cancer progression (for instance another one of the HER receptors; HER1, HER3, or HER4). In one embodiment, the second antigen-binding site binds a different, preferably non-blocking, site on HER2 than the one bound by the antibody of the invention. For example, the second molecule may be derived from, or cross-block HER2-binding of, trastuzumab, pertuzumab, F5, or C1.

Methods of preparing bispecific antibodies include those described in WO 2008119353 (Genmab) and reported van der Neut-Kolfschoten et al. (Science. 2007 Sep. 14; 317 (5844):1554-7) and it may for example be performed as described in example 20 of the present invention.

Nucleic Acid Sequences, Vectors and Host Cells

In a further aspect, the invention relates to nucleic acid sequences, such as DNA sequences, encoding heavy and light chains of an antibody of the invention.

In one embodiment, the nucleic acid sequence encodes an amino acid sequence selected from the group consisting of: SEQ ID NO: 1, 5, 8, 12, 15, 19, 22, 26, 29, 32, 35, 39, 42, 46, 49, 53, 56, 60, 63, 67, 70, 74, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125 and 126.

In another particular embodiment, the nucleic acid sequence encodes a VH amino acid sequence selected from the group consisting of: SEQ ID NO: 1, 8, 15, 22, 29, 35, 42, 49, 56, 63, 70, 77, 79, 81, 83, 85, 87, 89, 91, 93, 95, 97, 99, 101, 103, 105, 107, 109, 111, 113, 115, 117, 119, 121, 123, and 125.

In another particular embodiment, the nucleic acid sequence encodes a VL amino acid sequence selected from the group consisting of: SEQ ID NO: 5, 12, 19, 26, 32, 39, 46, 53, 60, 67, 74, 78, 80, 82, 84, 86, 88, 90, 92, 94, 96, 98, 100, 102, 104, 106, 108, 110, 112, 114, 116, 118, 120, 122, 124, and 126.

In an even further aspect, the invention relates to an expression vector, or a set of expression vectors, encoding an antibody of the invention. The heavy and light chain of the antibody may be encoded by the same vector or by different vector.

Such expression vectors may be used for recombinant production of antibodies of the invention.

In one embodiment, the expression vector of the invention comprises a nucleotide sequence encoding one or more of the amino acid sequences selected from the group consisting of: SEQ ID NO: 1, 5, 8, 12, 15, 19, 22, 26, 29, 32, 35, 39, 42, 46, 49, 53, 56, 60, 63, 67, 70, 74, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125 and 126.

In another particular embodiment, the expression vector of the invention comprises a nucleotide sequence encoding one or more of the VH amino acid sequences selected from the group consisting of: SEQ ID NO: 1, 8, 15, 22, 29, 35, 42, 49, 56, 63, 70, 77, 79, 81, 83, 85, 87, 89, 91, 93, 95, 97, 99, 101, 103, 105, 107, 109, 111, 113, 115, 117, 119, 121, 123, and 125.

In another particular embodiment, the expression vector of the invention comprises a nucleotide sequence encoding one or more of the VL amino acid sequences selected from the group consisting of: SEQ ID NO: 5, 12, 19, 26, 32, 39, 46, 53, 60, 67, 74, 78, 80, 82, 84, 86, 88, 90, 92, 94, 96, 98, 100, 102, 104, 106, 108, 110, 112, 114, 116, 118, 120, 122, 124, and 126.

In a further embodiment, the expression vector further comprises a nucleotide sequence encoding the constant region of a light chain, a heavy chain or both light and heavy chains of an antibody, e.g. a human antibody.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a HER2 antibody-encoding nucleic acid is comprised in a naked DNA or RNA vector, including, for example, a linear expression element (as described in for instance Sykes and Johnston, Nat Biotech 17, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793-800 (2001)), or as a precipitated nucleic acid vector construct, such as a CaPO4-precipitated construct (as described in for instance WO 00/46147, Benvenisty and Reshef, PNAS USA 83, 9551-55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

Exemplary expression vectors for the antibodies of the invention are also described in Examples 2 and 3.

In one embodiment, the vector is suitable for expression of the HER2 antibody in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516-544 (1987)).

An expression vector may also or alternatively be a vector suitable for expression in mammalian cells, e.g. a vector comprising glutamine synthetase as a selectable marker, such as the vectors described in Bebbington (1992) Biotechnology (NY) 10:169-175.

A nucleic acid and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides.

In an expression vector of the invention, HER2 antibody-encoding nucleic acids may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the HER2 antibody-encoding expression vector may be positioned in and/or delivered to the host cell or host animal via a viral vector.

In an even further aspect, the invention relates to a recombinant eukaryotic or prokaryotic host cell, such as a transfectoma, which produces an antibody of the invention as defined herein. Examples of host cells include yeast, bacterial, and mammalian cells, such as CHO or HEK cells. For example, in one embodiment, the present invention provides a cell comprising a nucleic acid stably integrated into the cellular genome that comprises a sequence coding for expression of a HER2 antibody of the present invention. In another embodiment, the present invention provides a cell comprising a non-integrated nucleic acid, such as a plasmid, cosmid, phagemid, or linear expression element, which comprises a sequence coding for expression of a HER2 antibody of the invention.

In a further aspect, the invention relates to a hybridoma which produces an antibody of the invention as defined herein. In an even further aspect, the invention relates to a transgenic non-human animal or plant comprising nucleic acids encoding a human heavy chain and a human light chain, wherein the animal or plant produces an antibody of the invention of the invention.

In a further aspect, the invention relates to a method for producing a HER2 antibody of the invention, said method comprising the steps of
a) culturing a hybridoma or a host cell of the invention as described herein above, and
b) purifying the antibody of the invention from the culture media.

Compositions

In a further main aspect, the invention relates to a pharmaceutical composition comprising:
  a HER2 antibody as defined herein, and
  a pharmaceutically-acceptable carrier.

The pharmaceutical composition of the present invention may contain one antibody of the present invention or a combination of different antibodies of the present invention.

The pharmaceutical compositions may be formulated in accordance with conventional techniques such as those disclosed in Remington: The Science and Practice of Pharmacy, 19th Edition, Gennaro, Ed., Mack Publishing Co., Easton, Pa., 1995. A pharmaceutical composition of the present invention may e.g. include diluents, fillers, salts, buffers, detergents (e. g., a nonionic detergent, such as Tween-20 or Tween-80), stabilizers (e. g., sugars or protein-free amino acids), preservatives, tissue fixatives, solubilizers, and/or other materials suitable for inclusion in a pharmaceutical composition.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

The actual dosage levels of the active ingredients in the pharmaceutical compositions may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode. In one embodiment, a pharmaceutical composition of the present invention is administered parenterally. "Administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion.

In one embodiment that pharmaceutical composition is administered by intravenous or subcutaneous injection or infusion.

Uses

In a further main aspect, the invention relates to a HER2 antibody of the invention for use as a medicament.

The HER2 antibodies of the invention may be used for a number of purposes. In particular, the antibodies of the invention may be used for the treatment of various forms of cancer, including metastatic cancer and refractory cancer.

In one embodiment, the HER2 antibodies of the invention are used for the treatment of breast cancer, including primary, metastatic, and refractory breast cancer.

In one embodiment, the HER2 antibodies of the invention are used for the treatment of a form of cancer selected from the group consisting of prostate cancer, non-small cell lung cancer, bladder cancer, ovarian cancer, gastric cancer, colorectal cancer, esophageal cancer, squamous cell carcinoma of the head & neck, cervical cancer, pancreatic cancer, testis cancer, malignant melanoma and a soft-tissue cancer (e.g. synovial sarcoma).

Similarly, the invention relates to a method for killing a tumor cell expressing HER2, comprising administration, to an individual in need thereof, of an effective amount of an antibody of the invention, such as an antibody drug-conjugate (ADC).

In one embodiment, said tumor cell is involved in a form of cancer selected from the group consisting of: breast cancer, prostate cancer, non-small cell lung cancer, bladder cancer, ovarian cancer, gastric cancer, colorectal cancer, esophageal cancer and squamous cell carcinoma of the head & neck, cervical cancer, pancreatic cancer, testis cancer, malignant melanoma, and a soft-tissue cancer (e.g., synovial sarcoma).

In one embodiment, the tumor cell is one that co-expresses HER2 and at least one other member of the EGFR family, preferably EGFR, HER3, or both of EGFR and HER3, and is a tumor cell involved in breast cancer, colorectal cancer, endometrial/cervical cancer, lung cancer, malignant melanoma, ovarian cancer, pancreatic cancer, prostate cancer, testis cancer, a soft-tissue tumor (e.g., synovial sarcoma), or bladder cancer.

In one aspect, the invention relates to a method for treating cancer in a subject, comprising selecting a subject suffering from a cancer comprising tumor cells co-expressing HER2 and EGFR and/or HER3, and administering to the subject an antibody of the invention, optionally in the form of an antibody conjugated to a cytotoxic agent or drug. In one embodiment, the subject suffers from a cancer selected from the group consisting of breast cancer, colorectal cancer, endometrial/cervical cancer, lung cancer, malignant melanoma, ovarian cancer, pancreatic cancer, prostate cancer, testis cancer, a soft-tissue tumor (e.g., synovial sarcoma), or bladder cancer.

Also, the invention relates to the use of a monoclonal antibody that binds to human HER2 for the preparation of a medicament for the treatment of cancer, such as one of the specific cancer indications mentioned above.

The invention further relates to a monoclonal antibody for use in the treatment of cancer, such as one of the cancer indications mentioned above.

In a further embodiment of the methods of treatment of the present invention, the efficacy of the treatment is being monitored during the therapy, e.g. at predefined points in time, by determining tumor burden or HER2 expression levels on the relevant tumor cells.

Dosage regimens in the above methods of treatment and uses are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage.

The efficient dosages and the dosage regimens for the HER2 antibodies depend on the disease or condition to be treated and may be determined by the persons skilled in the art. An exemplary, non-limiting range for a therapeutically effective amount of a compound of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3, about 5, or about 8 mg/kg.

A physician or veterinarian having ordinary skill in the art may readily determine and prescribe the effective amount of the pharmaceutical composition required. For example, the physician or veterinarian could start doses of the HER2 antibody employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Administration may e.g. be parenteral, such as intravenous, intramuscular or subcutaneous. In one embodiment, the HER2 antibodies may be administered by infusion in a weekly dosage of from 10 to 500 mg/m$^2$, such as of from 200 to 400 mg/m$^2$. Such administration may be repeated, e.g., 1 to 8 times, such as 3 to 5 times. The administration may be performed by continuous infusion over a period of from 2 to 24 hours, such as of from 2 to 12 hours. In one embodiment, the HER2 antibodies may be administered by slow continuous infusion over a long period, such as more than 24 hours, in order to reduce toxic side effects.

In one embodiment the HER2 antibodies may be administered in a weekly dosage of from 250 mg to 2000 mg, such as for example 300 mg, 500 mg, 700 mg, 1000 mg, 1500 mg or 2000 mg, for up to 8 times, such as from 4 to 6 times when given once a week. Such regimen may be repeated one or more times as necessary, for example, after 6 months or 12 months. The dosage may be determined or adjusted by measuring the amount of compound of the present invention in the blood upon administration by for instance taking out a biological sample and using anti-idiotypic antibodies which target the antigen binding region of the HER2 antibodies of the present invention.

The efficient dosages and the dosage regimens for the bispecific antibodies depend on the disease or condition to be treated and may be determined by the persons skilled in the art. An exemplary, non-limiting range for a therapeutically effective amount of a bispecific antibody of the present invention is about 0.1-100 mg/kg, such as about 0.1-50 mg/kg, for example about 0.1-20 mg/kg, such as about 0.1-10 mg/kg, for instance about 0.5, about such as 0.3, about 1, about 3, about 5, or about 8 mg/kg.

In one embodiment, the HER2 antibodies may be administered by maintenance therapy, such as, e.g., once a week for a period of 6 months or more.

A HER2 antibody may also be administered prophylactically in order to reduce the risk of developing cancer, delay the onset of the occurrence of an event in cancer progression, and/or reduce the risk of recurrence when a cancer is in remission. HER2 antibodies may also be administered in combination therapy, i.e., combined with other therapeutic agents relevant for the disease or condition to be treated. Accordingly, in one embodiment, the antibody-containing medicament is for combination with one or more further therapeutic agent, such as a cytotoxic, chemotherapeutic or anti-angiogenic agent.

Such combined administration may be simultaneous, separate or sequential. For simultaneous administration the agents may be administered as one composition or as separate compositions, as appropriate. The present invention thus also provides methods for treating a disorder involving cells expressing HER2 as described above, which methods comprise administration of a HER2 antibody of the present invention combined with one or more additional therapeutic agents as described below.

In one embodiment, the present invention provides a method for treating a disorder involving cells expressing HER2 in a subject, which method comprises administration of a therapeutically effective amount of a HER2 antibody of the present invention, and optionally at least one additional therapeutic agent, or an antibody binding to a different epitope than said HER2 antibody, to a subject in need thereof.

In one embodiment, the present invention provides a method for treating or preventing cancer, which method comprises administration of a therapeutically effective amount of a HER2 antibody of the present invention and at least one additional therapeutic agent to a subject in need thereof.

In one embodiment, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In another embodiment, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In another embodiment, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In another embodiment, such an additional therapeutic agent may be selected from a topoisomerase inhibitor, such as topotecan or irinotecan, or a cytostatic drug, such as etoposide and teniposide.

In another embodiment, such an additional therapeutic agent may be selected from a growth factor inhibitor, such as an inhibitor of ErbB1 (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM1 or pertuzumab) or an inhibitor of both EGFR and HER2, such as lapatinib).

In another embodiment, such an additional therapeutic agent may be selected from a tyrosine kinase inhibitor, such as imatinib (Glivec, Gleevec STI571) or lapatinib, PTK787/ZK222584.

In another embodiment, the present invention provides a method for treating a disorder involving cells expressing HER2 in a subject, which method comprises administration of a therapeutically effective amount of an HER2 antibody of the present invention and at least one inhibitor of angiogenesis, neovascularization, and/or other vascularization to a subject in need thereof.

Examples of such angiogenesis inhibitors are urokinase inhibitors, matrix metalloprotease inhibitors (such as marimastat, neovastat, BAY 12-9566, AG 3340, BMS-275291 and similar agents), inhibitors of endothelial cell migration and proliferation (such as TNP-470, squalamine, 2-methoxyestradiol, combretastatins, endostatin, angiostatin, penicillamine, SCH66336 (Schering-Plough Corp, Madison, N.J.), R115777 (Janssen Pharmaceutica, Inc, Titusville, N.J.) and similar agents), antagonists of angiogenic growth factors (such as such as ZD6474, SU6668, antibodies against angiogenic agents and/or their receptors (such as VEGF (e.g. bevacizumab), bFGF, and angiopoietin-1), thalidomide, thalidomide analogs (such as CC-5013), Sugen 5416, SU5402, antiangiogenic ribozyme (such as angiozyme), interferon α (such as interferon α2a), suramin and similar agents), VEGF-R kinase inhibitors and other anti-angiogenic tyrosine kinase inhibitors (such as SU011248), inhibitors of endothelial-specific integrin/survival signaling (such as vitaxin and similar agents), copper antagonists/chelators (such as tetrathiomolybdate, captopril and similar agents), carboxyamido-triazole (CAI), ABT-627, CM101, interleukin-12 (IL-12), IM862, PNU145156E as well as nucleotide molecules inhibiting angiogenesis (such as antisense-VEGF-cDNA, cDNA coding for angiostatin, cDNA coding for p53 and cDNA coding for deficient VEGF receptor-2).

Other examples of such inhibitors of angiogenesis, neovascularization, and/or other vascularization are anti-angiogenic heparin derivatives (e.g., heperinase III), temozolomide, NK4, macrophage migration inhibitory factor, cyclooxygenase-2 inhibitors, inhibitors of hypoxia-inducible factor 1, anti-angiogenic soy isoflavones, oltipraz, fumagillin and analogs thereof, somatostatin analogues, pentosan polysulfate, tecogalan sodium, dalteparin, tumstatin, thrombospondin, NM-3, combrestatin, canstatin, avastatin, antibodies against other targets, such as anti-alpha-v/beta-3 integrin and anti-kininostatin antibodies.

In one embodiment, a therapeutic agent for use in combination with a HER2 antibody for treating the disorders as described above may be an anti-cancer immunogen, such as a cancer antigen/tumor-associated antigen (e.g., epithelial cell adhesion molecule (EpCAM/TACSTD1), mucin 1 (MUC1), carcinoembryonic antigen (CEA), tumor-associated glycoprotein 72 (TAG-72), gp100, Melan-A, MART-1, KDR, RCAS1, MDA7, cancer-associated viral vaccines (e.g., human papillomavirus vaccines) or tumor-derived heat shock proteins, In one embodiment, a therapeutic agent for use in combination with a HER2 antibody for treating the disorders as described above may be an anti-cancer cytokine, chemokine, or combination thereof. Examples of suitable cytokines and growth factors include IFNγ, IL-2, IL-4, IL-6, IL-7, IL-10, IL-12, IL-13, IL-15, IL-18, IL-23, IL-24, IL-27, IL-28a, IL-28b, IL-29, KGF, IFNα (e.g., INFα2b), IFNβ, GM-CSF, CD40L, Flt3 ligand, stem cell factor, ancestim, and TNFα. Suitable chemokines may include Glu-Leu-Arg (ELR)-negative chemokines such as IP-10, MCP-3, MIG, and SDF-1a from the human CXC and C—C chemokine families. Suitable cytokines include cytokine derivatives, cytokine variants, cytokine fragments, and cytokine fusion proteins.

In one embodiment, a therapeutic agent for use in combination with a HER2 antibody for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, □ and anti-sense Bcl-2.

In one embodiment, a therapeutic agent for use in combination with a HER2 antibody for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In one embodiment, a therapeutic agent for use in combination with a HER2 antibody for treating the disorders as described above may be an anti-anergic agent, such as compounds are molecules that block the activity of CTLA-4, e.g. ipilimumab.

In one embodiment, a therapeutic agent for use in combination with a HER2 antibody for treating the disorders as described above may be an anti-cancer nucleic acid or an anti-cancer inhibitory RNA molecule.

Examples of other anti-cancer agents, which may be relevant as therapeutic agents for use in combination with a HER2 antibody for treating the disorders as described above are differentiation inducing agents, retinoic acid analogues (such as all trans retinoic acid, 13-cis retinoic acid and similar agents), vitamin D analogues (such as seocalcitol and similar agents), inhibitors of ErbB3, ErbB4, IGF-IR, insulin receptor, PDGFRa, PDGFRbeta, Flk2, Flt4, FGFR1, FGFR2, FGFR3, FGFR4, TRKA, TRKC, RON (such as an anti-RON antibody), Sea, Tie, Tie2, Eph, Ret, Ros, Alk, LTK, PTK7 and similar agents.

Examples of other anti-cancer agents, which may be relevant as therapeutic agents for use in combination with a HER2 antibody for treating the disorders as described above are estramustine and epirubicin.

Examples of other anti-cancer agents, which may be relevant as therapeutic agents for use in combination with a HER2 antibody for treating the disorders as described above are a HSP90 inhibitor like 17-allyl amino geld-anamycin, antibodies directed against a tumor antigen such as PSA, CA125, KSA, integrins, e.g. integrin β1, or inhibitors of VCAM.

Examples of other anti-cancer agents, which may be relevant as therapeutic agents for use in combination with a HER2 antibody for treating the disorders as described above are calcineurin-inhibitors (such as valspodar, PSC 833 and other MDR-1 or p-glycoprotein inhibitors), TOR-inhibitors (such as sirolimus, everolimus and rapamcyin). and inhibitors of "lymphocyte homing" mechanisms (such as FTY720), and agents with effects on cell signaling such as adhesion molecule inhibitors (for instance anti-LFA).

In one embodiment, the HER2 antibody of the invention is for use in combination with one or more other therapeutic antibodies, such as ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva) and/or rituximab.

In another embodiment, two or more different antibodies of the invention as described herein are used in combination for the treatment of disease. Particularly interesting combinations include two or more non-blocking antibodies. Such combination therapy may lead to binding of an increased number of antibody molecules per cell, which may give increase efficacy, e.g. via activation of complement-mediated lysis.

In addition to the above, other embodiments of combination therapies of the invention include the following:

For the treatment of breast cancer, a HER2 antibody or a therapeutic conjugate thereof, in combination with methotrexate, paclitaxel, doxorubicin, carboplatin, cyclophosphamide, daunorubicin, epirubicin, 5-fluorouracil, gemcitabine, ixabepilone, mutamycin, mitoxantrone, vinorelbine, docetaxel, thiotepa, vincristine, capecitabine, an EGFR antibody (e.g. zalutumumab, cetuximab, panitumumab or nimotuzumab) or other EGFR inhibitor (such as gefitinib or erlotinib), another HER2 antibody or -conjugate (such as, e.g., trastuzumab, trastuzumab-DM1 or pertuzumab), an inhibitor of both EGFR and HER2 (such as lapatinib), and/or in combination with a HER3 inhibitor.

For the treatment of non-small-cell lung cancer, a HER2 antibody in combination with EGFR inhibitors, such as an EGFR antibody, e.g. zalutumumab, cetuximab, panitumumab or nimotuzumab or other EGFR inhibitors (such as gefitinib or erlotinib), or in combination with an another HER2 agent (such as a HER2 antibody, e.g. trastuzumab, trastuzumab-DM1 or pertuzumab) or in combination with an inhibitor of both EGFR and HER2, such as lapatinib, or in combination with a HER3 inhibitor.

For the treatment of colorectal cancer a HER2 antibody in combination with one or more compounds selected from: gemcitabine, bevacizumab, FOLFOX, FOLFIRI, XELOX, IFL, oxaliplatin, irinotecan, 5-FU/LV, Capecitabine, UFT, EGFR targeting agents, such as cetuximab, panitumumab, zalutumumab; VEGF inhibitors, or tyrosine kinase inhibitors such as sunitinib.

For the treatment of prostate cancer a HER2 antibody in combination with one or more compounds selected from: hormonal/antihormonal therapies; such as antiandrogens, Luteinizing hormone releasing hormone (LHRH) agonists, and chemotherapeutics such as taxanes, mitoxantrone, estramustine, 5FU, vinblastine, and ixabepilone.

Radiotherapy-Surgery

In one embodiment, the present invention provides a method for treating a disorder involving cells expressing HER2 in a subject, which method comprises administration of a therapeutically effective amount of a HER2 antibody, such as a HER2 antibody of the present invention, and radiotherapy to a subject in need thereof.

In one embodiment, the present invention provides a method for treating or preventing cancer, which method comprises administration of a therapeutically effective amount of a HER2 antibody, such as a HER2 antibody of the present invention, and radiotherapy to a subject in need thereof.

In one embodiment, the present invention provides the use of a HER2 antibody, such as a HER2 antibody of the present invention, for the preparation of a pharmaceutical composition for treating cancer to be administered in combination with radiotherapy.

Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In a further embodiment, the present invention provides a method for treating or preventing cancer, which method comprises administration to a subject in need thereof of a therapeutically effective amount of a HER2 antibody, such as a HER2 antibody of the present invention, in combination with surgery.

Diagnostic Uses

The HER2 antibodies of the invention may also be used for diagnostic purposes. Thus, in a further aspect, the invention relates to a diagnostic composition comprising a HER2 antibody as defined herein.

In one embodiment, the HER2 antibodies of the present invention may be used in vivo or in vitro for diagnosing diseases wherein activated cells expressing HER2 play an active role in the pathogenesis, by detecting levels of HER2, or levels of cells which contain HER2 on their membrane surface. This may be achieved, for example, by contacting a sample to be tested, optionally along with a control sample, with the HER2 antibody under conditions that allow for formation of a complex between the antibody and HER2.

Thus, in a further aspect, the invention relates to a method for detecting the presence of HER2 antigen, or a cell expressing HER2, in a sample comprising:

contacting the sample with a HER2 antibody of the invention under conditions that allow for formation of a complex between the antibody and HER2; and analyzing whether a complex has been formed.

In one embodiment, the method is performed in vitro.

More specifically, the present invention provides methods for the identification of, and diagnosis of invasive cells and tissues, and other cells targeted by HER2 antibodies of the present invention, and for the monitoring of the progress of therapeutic treatments, status after treatment, risk of developing cancer, cancer progression, and the like.

Suitable labels for the HER2 antibody and/or secondary antibodies used in such techniques are well-known in the art.

In a further aspect, the invention relates to a kit for detecting the presence of HER2 antigen, or a cell expressing HER2, in a sample comprising a HER2 antibody of the invention or a bispecific molecule of the invention; and instructions for use of the kit.

In one embodiment, the present invention provides a kit for diagnosis of cancer comprising a container comprising a HER2 antibody, and one or more reagents for detecting binding of the HER2 antibody to HER2. Reagents may include, for example, fluorescent tags, enzymatic tags, or other detectable tags. The reagents may also include secondary or tertiary antibodies or reagents for enzymatic reactions, wherein the enzymatic reactions produce a product that may be visualized.

Anti-Idiotypic Antibodies

In a further aspect, the invention relates to an anti-idiotypic antibody which binds to a HER2 antibody of the invention as described herein.

An anti-idiotypic (Id) antibody is an antibody which recognizes unique determinants generally associated with the antigen-binding site of an antibody. An Id antibody may be prepared by immunizing an animal of the same species and genetic type as the source of a HER2 mAb with the mAb to which an anti-Id is being prepared. The immunized animal typically can recognize and respond to the idiotypic determinants of the immunizing antibody by producing an antibody to these idiotypic determinants (the anti-Id antibody).

An anti-Id antibody may also be used as an "immunogen" to induce an immune response in yet another animal, producing a so-called anti-anti-Id antibody. An anti-anti-Id may be epitopically identical to the original mAb, which induced the anti-Id. Thus, by using antibodies to the idiotypic determinants of a mAb, it is possible to identify other clones expressing antibodies of identical specificity.

The present invention is further illustrated by the following examples, which should not be construed as limiting the scope of the invention.

The present invention is further illustrated by the following examples, which should not be construed as limiting the scope of the invention.

EXAMPLES

Example 1

Expression Constructs for HER2 and HER2 Variants

Fully codon-optimized constructs for expression of full length HER2 (1255 aa, Swissprot P04626), the extracellular domain (ECD) of HER2 (Her2-ECDHis, aa 1-653 with a C-terminal His6 tag), the naturally occurring HER2 splice variant (Her2-delex16, resulting from exon 16 deletion and lacking aa 633-648) and a truncated form of the HER2 receptor (Her2-stumpy, aa 648-1256), were generated. The construct contained suitable restriction sites for cloning and an optimal Kozak sequence (Kozak, M., Gene 1999; 234 (2):187-208). The constructs were cloned in the mammalian expression vector pEE13.4 (Lonza Biologics; Bebbington, C. R., et al., Biotechnology (N Y) 1992; 10(2):169-75) and fully sequenced to confirm the correctness of the construct.

Example 2

Expression Constructs for Pertuzumab, C1 and F5

Fully codon-optimized constructs for expression of the heavy chain (HC) and the light chain (LC) of the IgG1 antibodies pertuzumab, C1 and F5 in HEK cells, were generated. The variable regions encoded by these constructs are identical to those described in U.S. Pat. No. 6,949,245 for pertuzumab heavy chain and light chain and U.S. Pat. No. 7,244,826 for C1 and F5 heavy and light chain. For C1 and F5, the mammalian expression vectors p33G1f and p33K or p33L (pcDNA3.3 (Invitrogen)) containing the fully codon optimized constant region for the human IgG1 heavy chain (allotype f), the human kappa light chain or the human lambda light chain, respectively, were used. For pertuzumab, the mammalian expression vectors pG1f (pEE12.4 (Lonza Biologics) and pKappa (pEE6.4 (Lonza Biologics), containing the fully codon-optimized constant region for the human IgG1 heavy chain (allotype f) and the human kappa light chain, respectively, were used.

Trastuzumab (Herceptin®) can be produced in the same manner, using the heavy and light chain sequences described in, e.g., U.S. Pat. No. 7,632,924.

Example 3

Transient Expression in HEK-293 or CHO Cells

Freestyle™ 293-F (a HEK-293 subclone adapted to suspension growth and chemically defined Freestyle medium, (HEK-293F)) cells were obtained from Invitrogen and transfected with the appropriate plasmid DNA, using 293fectin (Invitrogen) according to the manufacturer's instructions. In the case of antibody expression, the appropriate heavy chain and light chain expression vectors were co-expressed.

pEE13.4Her2, pEE13.4Her2-delex16 and pEE13.4Her2-stumpy were transiently transfected in the Freestyle™ CHO-S (Invitrogen) cell line using Freestyle MAX transfection reagent (Invitrogen). Expression of HER2 and Her2-delex16 was tested by means of FACS analysis as described below.

Example 4

Stable Polyclonal Pool Expression in NS0 pEE13.4Her2, pEE130.4Her2-delex16 and pEE13.4Her2-stumpy were stably transfected in NS0 cells by nucleofection (Amaxa). A pool of stably transfected cells was established after selection on glutamine dependent growth, based on the integrated glutamine synthetase selection marker (Barnes, L. M., et al., Cytotechnology 2000; 32(2):109-123).

Example 5

Purification of His-Tagged HER2

Her2ECDHis was expressed in HEK-293F cells. The His-tag in Her2ECDHis enabled purification with immobilized metal affinity chromatography, since the His-tagged protein binds strongly to the resin beads, while other proteins present in the culture supernatant do not bind strongly. In this process, a chelator fixed onto the chromatographic resin was charged with $Co^{2+}$ cations. Her2ECDHis containing supernatant was incubated with the resin in batch mode (i.e. solution). After incubation, the beads were retrieved from the supernatant and packed into a column. The column was washed in order to remove weakly bound proteins. The strongly bound Her2ECDHis proteins were then eluted with a buffer containing imidazole, which competes with the binding of His to $Co^{2\alpha}$. The eluent was removed from the protein by buffer exchange on a desalting column.

Example 6

Immunization Procedure of Transgenic Mice

Antibodies 001, 019, 021, 025, 027, 032, 033, 035, 036, 049, 050, 051, 054, 055, 084, 091, 094, 098, 100, 105, 123 and 124 were derived from the following immunization: three female HCo12 mice, one male and two female HCo12-Balb/C mice, one male HCo17 mouse and one male HCo20 mouse (Medarex, San Jose, Calif., USA) were immunized alternating with $5 \times 10^6$ NS0 cells transiently transfected with Her2ECD intraperitoneal (IP) and 20 μg Her2ECDHis protein coupled to the hapten Keyhole Limpet Hemocyanin (KLH) subcutaneous (SC) at the tail base, with an interval of fourteen days. A maximum of eight immunizations was performed per mouse (four IP and four SC immunizations). The first immunization with cells was done in complete Freunds' adjuvant (CFA; Difco Laboratories, Detroit, Mich., USA). For all other immunizations, cells were injected IP in PBS and KLH coupled Her2ECD was injected SC using incomplete Freunds' adjuvant (IFA; Difco Laboratories, Detroit, Mich., USA).

Antibodies 125, 127, 129, 132, 152, 153 and 159 were derived from the following immunization: one male and two female HCo12-Balb/C mice, one female HCo20 mouse, and one female HCo12 mouse (Medarex) were immunized alternating with $5 \times 10^6$ NS0 cells transiently transfected with Her2delex16 IP and 20 μg Her2ECDHis protein coupled to the hapten Keyhole Limpet Hemocyanin (KLH) SC at the tail base, with an interval of fourteen days. A maximum of eight immunizations was performed per mouse (four IP and four SC immunizations). The first immunization with cells was done in complete Freunds' adjuvant (CFA; Difco Laboratories, Detroit, Mich., USA). For all other immunizations, cells were injected IP in PBS and KLH coupled Her2ECD was injected SC using incomplete Freunds' adjuvant (IFA; Difco Laboratories, Detroit, Mich., USA).

Antibody 143, 160, 161, 162, 166 and 169 were derived from the following immunization: one female and one male Hco12 mouse, one female Hco12-Balb/C mouse, one male HCo17 mouse and one male HCo20 mouse (Medarex) were immunized alternating with 20 μg Her2ECDHis protein coupled to the hapten Keyhole Limpet Hemocyanin (KLH), alternating IP and SC at the tail base with an interval of fourteen days. A maximum of eight immunizations was performed per mouse (four IP and four SC immunizations). The first immunization was done IP in complete Freunds' adjuvant (CFA; Difco Laboratories, Detroit, Mich., USA). The other immunizations were injected using incomplete Freunds' adjuvant (IFA; Difco Laboratories, Detroit, Mich., USA).

Mice with at least two sequential titers against TC1014-Her2, TC1014-Her2delex16 or TC1014-Her2stumpy in the antigen specific FMAT screening assay (as described in example 7), were considered positive and fused.

Example 7

Homogeneous Antigen Specific Screening Assay

The presence of HER2 antibodies in sera of immunized mice or HuMab (human monoclonal antibody) hybridoma or transfectoma culture supernatant was determined by homogeneous antigen specific screening assays (four quadrant) using Fluorometric Micro volume Assay Technology (FMAT; Applied Biosystems, Foster City, Calif., USA). For this, a combination of 4 cell based assays was used. Binding to TC1014-Her2 (HEK-293F cells transiently expressing the HER2 receptor; produced as described above), TC1014-Her2delex16 (HEK-293F cells transiently expressing the extracellular domain of Her2-delex (a 16 amino acid deletion mutant of the HER2 receptor; produced as described above) and TC1014-Her2stumpy (HEK-293F cells transiently expressing the extracellular stumpy domain of the HER2 receptor; produced as described above) as well as HEK293 wild type cells (negative control cells which do not express HER2) was determined. Samples were added to the cells to allow binding to HER2. Subsequently, binding of HuMab was detected using a fluorescent conjugate (Goat anti-Human IgG-Cy5; Jackson ImmunoResearch). TH1014-Pertuzumab (produced in HEK-293F cells) was used as a positive control and HuMab-mouse pooled serum and HuMab-KLH were used as negative controls. The samples were scanned using an Applied Biosystems 8200 Cellular Detection System (8200 CDS) and 'counts×fluorescence' was used as read-out. Samples were stated positive when counts were higher than 50 and counts×fluorescence were at least three times higher than the negative control.

Example 8

HuMab Hybridoma Generation

HuMab mice with sufficient antigen-specific titer development (defined as above) were sacrificed and the spleen and lymph nodes flanking the abdominal aorta and vena cava were collected. Fusion of splenocytes and lymph node cells to a mouse myeloma cell line was done by electrofusion using a CEEF 50 Electrofusion System (Cyto Pulse Sciences, Glen Burnie, Md., USA), essentially according to the manufacturer's instructions. Next, the primary wells were sub cloned using the ClonePix system (Genetix, Hampshire, UK). To this end specific primary well hybridoma's were seeded in semisolid medium made from 40% CloneMedia (Genetix, Hampshire, UK) and 60% HyQ 2× complete media (Hyclone, Waltham, USA). The sub clones were retested in the antigen-specific binding assay as described in Example 7 and IgG levels were measured using an Octet (Fortebio, Menlo Park, USA) in order to select the most specific and best producing clone per primary well for further expansion. Further expansion and culturing of the resulting HuMab hybridomas were done based upon standard protocols (e.g. as described in Coligan J. E., Bierer, B. E., Margulies, D. H., Shevach, E. M. and Strober, W., eds. Current Protocols in Immunology, John Wiley & Sons, Inc., 2006). Clones derived by this process were designated PC1014.

Example 9

Mass Spectrometry of Purified Antibodies

Small aliquots of 0.8 mL antibody containing supernatant from 6-well or Hyperflask stage were purified using PhyTip columns containing Protein G resin (PhyNexus Inc., San Jose, USA) on a Sciclone ALH 3000 workstation (Caliper Lifesciences, Hopkinton, USA). The PhyTip columns were used according to manufacturer's instructions, although buffers were replaced by: Binding Buffer PBS (B. Braun, Medical B.V., Oss, Netherlands) and Elution Buffer 0.1M Glycine-HCl pH 2.7 (Fluka Riedel-de Haën, Buchs, Germany). After purification, samples were neutralized with 2M Tris-HCl, pH 9.0 (Sigma-Aldrich, Zwijndrecht, Netherlands). Alternatively, in some cases larger volumes of culture supernatant were purified using MabSelect SuRe.

After purification, the samples were placed in a 384-well plate (Waters, 100 µl square well plate, part #186002631). Samples were deglycosylated overnight at 37° C. with N-glycosidase F (Roche cat no 11365177001. DTT (15 mg/mL) was added (1 µL/well) and incubated for 1 h at 37° C. Samples (5 or 6 µL) were desalted on an Acquity UPLC™ (Waters, Milford, USA) with a BEH300 C18, 1.7 µm, 2.1×50 mm column at 60° C. MQ water and LC-MS grade acetonitrile (Biosolve, cat no 01204101, Valkenswaard, The Netherlands) with both 0.1% formic acid (Fluke, cat no 56302, Buchs, Germany), were used as Eluens A and B, respectively. Time-of-flight electrospray ionization mass spectra were recorded on-line on a micrOTOF™ mass spectrometer (Bruker, Bremen, Germany) operating in the positive ion mode. Prior to analysis, a 900-3000 m/z scale was calibrated with ES tuning mix (Agilent Technologies, Santa Clara, USA). Mass spectra were deconvoluted with DataAnalysis™ software v. 3.4 (Bruker) using the Maximal Entropy algorithm searching for molecular weights between 5 and 80 kDa.

After deconvolution, the resulting heavy and light chain masses for all samples were compared in order to find duplicate antibodies. This was sometimes due to the presence of an extra light chain, but in the comparison of the heavy chains, the possible presence of C-terminal lysine variants was also taken into account. This resulted in a list of unique antibodies, i.e., a unique combination of specific heavy and light chains. In case duplicate antibodies were found, one unique antibody was selected based on results from other tests.

Example 10

Sequence Analysis of the HER2 Antibody Variable Domains and Cloning in Expression Vectors Total RNA of the HER2 HuMabs was prepared from $5\times10^6$ hybridoma cells and 5'-RACE-Complementary DNA (cDNA) was prepared from 100 ng total RNA, using the SMART RACE cDNA Amplification kit (Clontech), according to the manufacturer's instructions. VH and VL coding regions were amplified by PCR and cloned directly, in frame, in the pG1f and pKappa expression vectors, by ligation independent cloning (Aslanidis, C. and P. J. de Jong, Nucleic Acids Res 1990; 18(20): 6069-74). Clones derived by this process were designated TH1014. For each antibody, 16 VL clones and 8 VH clones were sequenced. Clones which predicted heavy and light chain mass in agreement with the mass of the hybridoma derived material of the same antibody (as determined by mass spectrometry) were selected for further study and expression.

The resulting sequences are shown in FIGS. 1 and 2 and in the Sequence Listing. Selected sequences are also described in more detail below. CDR sequences were defined according to IMGT (Lefranc M P. et al., Nucleic Acids Research, 27, 209-212, 1999 and Brochet X. Nucl. Acids Res. 36, W503-508 (2008)). Table 1, Table 2 and Table 3 give an overview of antibody sequence information or germline sequences, and Table 4 shows consensus sequences.

TABLE 1

Heavy chain variable region (VH), light chain variable region (VL) and CDR sequences of HuMabs 169, 050, 084, 025, 091, 129, 127, 159, 098, 153, and 132.

| | | |
|---|---|---|
| SEQ ID No: 1 | VH 169 | QVQLVQSGAEVKKPGASVKVSCKASGYTFTNYGISW VRQAPGQGLEWMGWLSAYSGNTIYAQKLQGRVTMT TDTSTTTAYMELRSLRSDDTAVYYCARDRIVVRPDYF DYWGQGTLVTVSS |
| SEQ ID No: 2 | VH 169, CDR1 | GYTFTNYG |
| SEQ ID No: 3 | VH 169, CDR2 | LSAYSGNT |
| SEQ ID No: 4 | VH 169, CDR3 | ARDRIVVRPDYFDY |
| SEQ ID No: 5 | VL 169 | EIVLTQSPATLSLSPGERATLSCRASQSVSSYLAWYQ QKPGQAPRLLIYDASNRATGIPARFSGSGSGTDFTLTI SSLEPEDFAVYYCQQRSNWPRTFGQGTKVEIK |
| SEQ ID No: 6 | VL 169, CDR1 | QSVSSY |
| | VL 169, CDR2 | DAS |
| SEQ ID No: 7 | VL 169, CDR3 | QQRSNWPRT |
| SEQ ID No: 8 | VH 050 | EVQLLESGGGLVQPGGSLRLSCAASGFTFSSYAMNW VRQAPGKGLEWVSAISGRGGTTYYADSVKGRFTISR DNSKNTLYLQMSSLRAEDTAVYYCAKARANWDYFDY WGQGTLVTVSS |
| SEQ ID No: 9 | VH 050, CDR1 | GFTFSSYA |
| SEQ ID No: 10 | VH 050, CDR2 | ISGRGGTT |
| SEQ ID No: 11 | VH 050, CDR3 | AKARANWDYFDY |
| SEQ ID No: 12 | VL 050 | DIQMTQSPSSVSASVGDRVTITCRASQGISSWLAWY QHKPGKAPKLLIYAASILQSGVPSRFSGSGSGTDFTL TISSLQPEDFATYYCQQANSFPITFGQGTRLEIK |
| SEQ ID No: 13 | VL 050, CDR1 | QGISSW |
| | VL 050, CDR2 | AAS |
| SEQ ID No: 14 | VL 050, CDR3 | QQANSFPIT |
| SEQ ID No: 15 | VH 084 | QVQLVQSGAEVKKPGSSVKVSCKASGGTFRTYAINW VRQAPGQGLEWMGRINTVLGIVNHAQKFQGRVTITA DKSTNTAYMELNSLRSEDTAVYYCAREKGVDYYYGIE VWGQGTTVTVSS |
| SEQ ID No: 16 | VH 084, CDR1 | GGTFRTYA |
| SEQ ID No: 17 | VH 084, CDR2 | INTVLGIV |
| SEQ ID No: 18 | VH 084, CDR3 | AREKGVDYYYGIEV |
| SEQ ID No: 19 | VL 084 | DIQMTQSPSSVSASVGDRVTITCRASQGISSWLAWY QHKPGKAPKLLIYVASTLQSGVPSRFSGSGSGTDFTL TISSLQPEDFATYYCQQANSFPLTFGGGTKVEIK |
| SEQ ID No: 20 | VL 084, CDR1 | QGISSW |
| | VL 084, CDR2 | VAS |

TABLE 1-continued

Heavy chain variable region (VH), light chain variable region (VL) and CDR sequences of HuMabs 169, 050, 084, 025, 091, 129, 127, 159, 098, 153, and 132.

| | | |
|---|---|---|
| SEQ ID No: 21 | VL 084, CDR3 | QQANSFPLT |
| SEQ ID No: 22 | VH 025 | QVQLQQWGAGLLKPSETLSLTCAVYGGSFSDYYWN WIRQPPGKGLEWIGEIHHSGSTNYNPSLKSRVTISVD TSKNQFSLKLSSVTAADTAVYYCARGYYDSGVYYFDY WAQGTLVTVSS |
| SEQ ID No: 23 | VH 025, CDR1 | GGSFSDYY |
| SEQ ID No: 24 | VH 025, CDR2 | IHHSGST |
| SEQ ID No: 25 | VH 025, CDR3 | ARGYYDSGVYYFDY |
| SEQ ID No: 26 | VL 025 | DIQMTQSPSSLSASVGDRVTITCRASQGISRWLAWY QQKPEKAPKSLIYAASSLRSGVPSRFSGSGSGTDFTL TISSLQPEDFATYYCQQYNSYPITFGQGTRLEIK |
| SEQ ID No: 27 | VL 025, CDR1 | QGISRW |
| | VL 025, CDR2 | AAS |
| SEQ ID No: 28 | VL 025, CDR3 | QQYNSYPIT |
| SEQ ID No: 29 | VH 091 | QVQLQQWGAGLLKPSETLSLTCAVSGGSFSGYYWT WIRQPPGKGLEWIGEIYHSGDTNYNPSLKSRVTISVD TSKNQFSLKLYSVTAADTAVYYCARLYFGSGIYYLDY WGQGTLVTVSS |
| SEQ ID No: 30 | VH 091, CDR1 | GGSFSGYY |
| SEQ ID No: 163 | VH 091, CDR2 | IYHSGDT |
| SEQ ID No: 31 | VH 091, CDR3 | ARLYFGSGIYYLDY |
| SEQ ID No: 32 | VL 091 | DIQMTQSPSSLSASVGDRVTITCRASQGISSWLVWY QQKPEKAPKSLIYAASSLQSGVPSRFSGSGSGTDFTL TISSLQPEDFATYYCQQYNSFPPTFGQGTKVEIK |
| SEQ ID No: 33 | VL 091, CDR1 | QGISSW |
| | VL 091, CDR2 | AAS |
| SEQ ID No: 34 | VL 091, CDR3 | QQYNSFPPT |
| SEQ ID No: 35 | VH 129 | QVQLVESGGGVVQPGRSLRLSCAASGFTFSTFAIHW VRQAPGKGLEWVAVISYDGGHKFYADSVKGRFTISR DNSKNTLYLQMNSLRAEDTAMYYCARGLGVWGAFD YWGQGTLVTVSS |
| SEQ ID No: 36 | VH 129, CDR1 | GFTFSTFA |
| SEQ ID No: 37 | VH 129, CDR2 | ISYDGGHK |
| SEQ ID No: 38 | VH 129, CDR3 | ARGLGVWGAFDY |
| SEQ ID No: 39 | VL 129 | EIVLTQSPATLSLSPGERATLSCRASQSVSSYLAWYQ QKPGQAPRLLIYDASNRATGIPARFSGSGSGTDFTLTI SSLEPEDFAVYYCQQRSNWWTFGQGTKVEIK |
| SEQ ID No: 40 | VL 129, CDR1 | QSVSSY |
| | VL 129, CDR2 | DAS |
| SEQ ID No: 41 | VL 129, CDR3 | QQRSNWWT |
| SEQ ID No: 42 | VH 127 | EVQLVQSGAEVKKPGESLTISCKGSGYSFSIYWIGW VRQMPGKGLEWMGIIFPGDSDIRYSPSFQGQVTISA DKSISTAYLQWSSLKASDTAMYYCARQPGDWSPRH WYFDLWGRGTLVTVSS |
| SEQ ID No: 43 | VH 127, CDR1 | GYSFSIYW |
| SEQ ID No: 44 | VH 127, CDR2 | IFPGDSDI |
| SEQ ID No: 45 | VH 127, CDR3 | ARQPGDWSPRHWYFDL |

TABLE 1-continued

Heavy chain variable region (VH), light chain variable region (VL) and CDR sequences of HuMabs 169, 050, 084, 025, 091, 129, 127, 159, 098, 153, and 132.

| SEQ ID No: 46 | VL 127 | VIWMTQSPSLLSASTGDRVTISCRMSQGISSYLAWY<br>QQKPGKAPELLIYAASTLQSGVPSRFSGSGSGTDFTL<br>TISYLQSEDFATYYCQQYYSFPLTFGGGTKVEIK |
| --- | --- | --- |
| SEQ ID No: 47 | VL 127, CDR1 | QGISSY |
| | VL 127, CDR2 | AAS |
| SEQ ID No: 48 | VL 127, CDR3 | QQYYSFPLT |
| SEQ ID No: 49 | VH 159 | EVQLVQSGAEVKKPGESLKISCKGSGYNFTSYWIGW<br>VRQMPGKGLEWMGIIYPGDSDTRYSPSFQGQVTISA<br>DKSISTAYLQWSSLKASDTAMYYCARWGTYYDILTG<br>YFNWFDPWGQGTLVTVSS |
| SEQ ID No: 50 | VH 159, CDR1 | GYNFTSYW |
| SEQ ID No: 51 | VH 159, CDR2 | IYPGDSDT |
| SEQ ID No: 52 | VH 159, CDR3 | ARWGTYYDILTGYFN |
| SEQ ID No: 53 | VL 159 | DIQMTQSPSSLSASVGDRVTITCRASQGISSWLAWY<br>QQKPEKAPKSLIYAASSLQSGVPSRFSGSGSGTDFTL<br>TISSLQPEDFATYYCQQYYIYPWTFGQGTKVEIK |
| SEQ ID No: 54 | VL 159, CDR1 | QGISSW |
| | VL 159, CDR2 | AAS |
| SEQ ID No: 55 | VL 159, CDR3 | QQYYIYPWT |
| SEQ ID No: 56 | VH 098 | EVQLLESGGGLVQPGGSLRLSCAASGFTFSNYGMSW<br>VRQAPGKGLEWVSAISGSAYSTYYADSVKGRFTISR<br>DNSKNTLWLQMNSLRAEDTAVYYCAKAHYHGSGSYY<br>TLFDYWGQGTLVTVSS |
| SEQ ID No: 57 | VH 098, CDR1 | GFTFSNYG |
| SEQ ID No: 58 | VH 098, CDR2 | ISGSAYST |
| SEQ ID No: 59 | VH 098, CDR3 | AKAHYHGSGSYYTLFDY |
| SEQ ID No: 60 | VL 098 | DIQMTQSPSSLSASVGDRVTITCRASQGISSWLAWY<br>QQKPEKAPKSLIYAASSLQSGVPSRFSGSGSGTDFTL<br>TISSLQPEDFATYYCQQYNSYPYTFGQGTKLEIK |
| SEQ ID No: 61 | VL 098, CDR1 | QGISSW |
| | VL 098, CDR2 | AAS |
| SEQ ID No: 62 | VL 098, CDR3 | QQYNSYPYT |
| SEQ ID No: 63 | VH 153 | QVQLVESGGGVVQPGRSLRLSCAASGFTFSDYVIHW<br>VRQAPGKGLEWVTVISYDGSNKYYADSVKGRFTISR<br>DNSKNTLYLQMNSLSAEDTAMYYCARGGITGTTGVF<br>DYWGQGTLVTVSS |
| SEQ ID No: 64 | VH 153, CDR1 | GFTFSDYV |
| SEQ ID No: 65 | VH 153, CDR2 | ISYDGSNK |
| SEQ ID No: 66 | VH 153, CDR3 | ARGGITGTTGVFDY |
| SEQ ID No: 67 | VL 153 | DIQMTQSPSSLSASVGDRVTITCRASQGISSWLAWY<br>QQKPEKAPKSLIYDASSLQSGVPSRFSGSGYGTDFSL<br>TISSLQPEDFAIYYCQQYKSYPITFGQGTRLEIK |
| SEQ ID No: 68 | VL 153, CDR1 | QGISSW |
| | VL 153, CDR2 | DAS |
| SEQ ID No: 69 | VL 153, CDR3 | QQYKSYPIT |
| SEQ ID No: 70 | VH 132 | QVQLVQSGAEVKKPGASVKVSCKASGYTFTSYGISW<br>VRQAPGQGLEWMGWISAYNGNSNYVQKFQGRVTM |

TABLE 1-continued

Heavy chain variable region (VH), light chain variable region (VL) and CDR sequences of HuMabs 169, 050, 084, 025, 091, 129, 127, 159, 098, 153, and 132.

|  |  |  |
|---|---|---|
|  |  | TTDTTTSTAYMELRSLTSDDTAVYYCAREYSYDSGTYFYYGMDVWGQGTTVTVSS |
| SEQ ID No: 71 | VH 132, CDR1 | GYTFTSYG |
| SEQ ID No: 72 | VH 132, CDR2 | ISAYNGNS |
| SEQ ID No: 73 | VH 132, CDR3 | AREYSYDSGTYFYYGMDV |
| SEQ ID No: 74 | VL 132 | EIVLTQSPATLSLSPGERATLSCRASQSVSSYLAWYQQKPGQAPRLLIYDASNRATGIPARFSGSGSGTDFTLTISSLEPEDFAVYYCQQRSNWPMYTFGQGTKLEIK |
| SEQ ID No: 75 | VL 132, CDR1 | QSVSSY |
|  | VL 132, CDR2 | DAS |
| SEQ ID No: 76 | VL 132, CDR3 | QQRSNWPMYT |

TABLE 2

Mouse origin and heavy and light chain sequence homologies of selected HuMabs.

| HuMab: | Mouse: | Strain: | Germline VH: | Germline VL: |
|---|---|---|---|---|
| 169 | 361494 | HCo20 | IgHV1-18-01 | IgKV3-11-01 |
| 050 | 350633 | HCo12 | IgHV3-23-01 | IgKV1-12-01 |
| 084 | 350615 | HCo12-BalbC | IgHV1-69-04 | IgKV1-12-01 |
| 025 | 350631 | HCo12 | IgHV4-34-01 | IgKV1D-16-01 |
| 091 | 350630 | HCo12 | IgHV4-34-01 | IgKV1D-16-01 |
| 129 | 359783 | HCo12-BalbC | IgHV3-30-3-01 | IgKV3-11-01 |
| 127 | 359783 | HCo12-BalbC | IgHV5-51-01 | IgKV1D-8-01 |
| 159 | 363503 | HCo12 | IgHV5-51-01 | IgKV1D-16-01 |
| 098 | 350659 | HCo17 | IgHV3-23-01 | IgKV1D-16-01 |
| 153 | 359785 | HCo12-BalbC | IgHV3-30-3-01 | IgKV1D-16-01 |
| 132 | 361487 | HCo20 | IgHV1-18-01 | IgKV3-11-01 |

TABLE 3

Heavy chain variable region (VH), light chain variable region (VL) sequences of HuMabs 049, 051, 055, 123, 161, 124, 001, 143, 019, 021, 027, 032, 035, 036, 054, 094. The respective CDRs correspond to those underlined in FIGS. 1 and 2, for VH and VL sequences, respectively.

| SEQ ID No: 77 | VH 049 | EVQLLESGGDLVQPGGSLRLSCAASGFTFSSYAMSWVRQAPGKGLEWVSAISGRGGTTYYADSVKGRFTISRDNSKSTLCLQMNSLRAEDTAVYYCAKARANWDYFDYWGQGTLVTVSS |
| --- | --- | --- |
| SEQ ID No: 78 | VL 049 | DIQMTQSPSSVSASVGDRVTITCRASQGISSWLAWYQHKPGKAPKLLIYAASILQSGVPSRFSGSGSGTDFTLTISSLRPEDFATYYCQQANSFPITFGQGTRLEIK |
| SEQ ID No: 79 | VH 051 | EVQLLESGGDLVQPGGSLRLSCAASGFTFSSYAMSWVRQAPGKGLEWVSAISGRGGTTYYADSVKGRFTISRDNSKSTLCLQMNSLRAEDTAVYYCAKARANWDYFDYWGQGTLVTVSS |
| SEQ ID No: 80 | VL 051 | DIQMTQSPSSVSASVGDRVTITCRASQGISSWLAWYQHKPGKAPKLLIYAASILQSGVPSRFSGSGSGTDFTLTISSLRPEDFATYYCQQANSFPITFGQGTRLEIK |
| SEQ ID No: 81 | VH 055 | EVQLLESGGGLVQPGGSLRLSCAASGFTFSSYAMNWVRQAPGKGLEWVSAISGRGGTTYYADSVKGRFTISRDNSKSTLCLQMNSLRAEDTAVYYCAKARANWDYFDYWGQGTLVTVSS |
| SEQ ID No: 82 | VL 055 | DIQMTQSPSSVSASVGDRVTITCRASQGISSWLAWYQHKPGKAPKLLIYAASILQSGVPSRFSGSGSGTDFTLTISSLRPEDFATYYCQQANSFPITFGQGTRLEIK |
| SEQ ID No: 83 | VH 123 | QVQLVQSGAEVKKPGASVKVSCKAAGYTFTNYGISWVRQAPGQALEWMGWITTYSSNTIYAQKLQGRVTMTTDTSTSTAYMELRSLRSDDTAVYYCARDRVVVRPDYFDYWGQGTLVTVSS |
| SEQ ID No: 84 | VL 123 | EIVLTQSPATLSLSPGERATLSCRASQSVSSYLAWYQQKPGQAPRLLIYDTSNRATGIPARFSGSGSGTDFTLTISSLEPEDFAVYYCQQRSHWPRTFGQGTKVEIK |

TABLE 3-continued

Heavy chain variable region (VH), light chain variable region (VL) sequences of HuMabs 049, 051, 055, 123, 161, 124, 001, 143, 019, 021, 027, 032, 035, 036, 054, 094. The respective CDRs correspond to those underlined in FIGS. 1 and 2, for VH and VL sequences, respectively.

SEQ ID No: 85  VH 161  QVQLVQSGAEVKKPGASVKVSCKASGYTFTNYGISWVRQAPG
QGLEWMGWLSAYSGNTIYAQKLQGRVTMTTDTSTTAYMELR
SLRSDDTAVYYCARDRIVVRPDYFDYWGQGTLVTVSS

SEQ ID No: 86  VL 161  EIVLTQSPATLSLSPGERATLSCRASQSVSSYLAWYQQKPGQAP
RLLIYDASNRATGIPARFSGSGSGTDFTLTISSLEPEDFAVYYCQ
QRSNWPRTFGQGTKVEIK

SEQ ID No: 87  VH 124  QVQLVQSGAEVKKPGASVKVSCKAAGYTFTNYGISWVRQAPG
QGLEWMGWIITYNGNTIYAQRFQDRVTMTTDTSTSTAYMELRS
LRSDDTAVYYCARDRIIVRPDYFDYWGQGTLVTVSS

SEQ ID No: 88  VL 124  EIVLTQSPATLSLSPGERATLSCRASQSVSSYLAWYQQKPGQAP
RLLIYDASNRATGIPARFSGSGSGTDFTLTISSLEPEDFAVYYCQ
QRSNWPRTFGQGTKVEIK

SEQ ID No: 89  VH 001  QVQLQQWGAGLLKPSETLSLTCAVYGGSFSGYYWNWIRQPPG
KGLEWIGEINHSGSTNYNPSLKSRVTISVDTSKNQFSLKLSSVT
AADTAVYYCARGNYGSGYYYFDLWGRGTQVTVSS

SEQ ID No: 90  VL 001  DIQMTQSPSSLSASVGDRVTITCRASQGISSWLAWYQQKPEK
APKSLIFAASSLQSGVPSRFSGSGSGTDFTLTISSLQPEDFATYY
CQQYISFPITFGQGTRLEIK

SEQ ID No: 91  VH 143  QVQLQQWGAGLLKPSETLSLTCAVYGGSFSGYYWNWIRQPPG
KGLEWIGEIHHSGSANYNPSLMSRVTISVDTSKNQFSLQLSSV
TAADTAVYYCARGYYGSGYYYFDYWGQGTLVTVSS

SEQ ID No: 92  VL 143  DIQMTQSPSSLSASVGDRVTITCRASQGISSWLAWYQQKPEK
APKSLIYAASRLQSGVPSRFSGSGSGTDFTLTISSLQPEDFATYY
CQQYNSYPITFGQGTRLEIK

SEQ ID No: 93  VH 019  QVQLQQWGAGLLKPSETLSLTCAVYGGSFSDYYWNWIRQPPG
KGLEWIGEIHHVGSTNYNPSLKSRVTISVDTSKSQFSLKLSSVT
AADTAVYYCARGYYDSGVYYFDYWAQGTLVTVSS

SEQ ID No: 94  VL 019  DIQMTQSPSSLSASVGDRVTITCRASQGISRWLAWYQQKPEK
APKSLIYAASSLRSGVPSRFSGSGSGTDFTLTISSLQPEDFATYY
CQQYNSYPITFGQGTRLEIK

SEQ ID No: 95  VH 021  QVQLQQWGAGLLKPSETLSLTCAVYGGSFSDYYWNWIRQPPG
KGLEWIGEIHHSGSTNYNPSLKSRVTISVDTSKNQFSLKLSSVT
AADTAVYYCARGYYASGVYYFDYWGQGTLVTVSS

SEQ ID No: 96  VL 021  DIQMTQSPSSLSASVGDRVTITCRASQGISSWLAWYQQKPEK
APKSLIYAASSLQSGVPSRFSGSGSGTDFTLTISSLQPEDFATYY
CQQYNSYPITFGQGTRLEIK

SEQ ID No: 97  VH 027  QVQLQQWGAGLLKPSETLSLTCAVYGGSFSDYFWNWIRQPPG
KGLEWIGEIHHSGSTNYNPSLKSRVTISVDTSKNQFSLNLSSVT
AADTAVYYCARGLIGSGYYYFDYWDQGTLVTVSS

SEQ ID No: 98  VL 027  DIQMTQSPSSLSASVGDRVTITCRASQGISSWLAWYQQKPEK
APKSLIYAASSLQSGVPSRFSGSGSGTDFTLTISSLQPEDFATYY
CQQYNSYPITFGQGTRLEIK

SEQ ID No: 99  VH 032  QVQLQQWGAGLLKPSETLSLTCAVYGGSFSGYYWSWIRQPPG
KGLEWIGEINHSGDTNYNPSLTSRVTISVDTSKNQFSLKLSSVT
AADTAVYYCARLFYGSGIYYFDYWGQGTLVTVSS

SEQ ID No: 100 VL 032  DIQMTQSPSSLSASVGDRVTITCRASQGISSWLAWYQQKPEK
APKSLIYATFRLQSGVPSRFSGSGSGTDFTLTISSLQPEDFATYY
CQQYNSFPPTFGQGTKVEIK

SEQ ID No: 101 VH 035  QVQLQQWGAGLLKPSETLSLTCAIYGGSFSGYYWSWIRQPPG
KGLEWIGEINHSGDTNYNPSLTSRVTISVDTSKNQFSLKLSSVT
AADTAVYYCARLFYGSGIYYFDYWGQGTLVTVSS

SEQ ID No: 102 VL 035  DIQMTQSPSSLSASVGDRVTITCRASQGISSWLAWYQQKPEK
APKSLIYATFRLQSGVPSRFSGSGSGTDFTLTISSLQPEDFATYY
CQQYNSFPPTFGQGTKVEIK

TABLE 3-continued

Heavy chain variable region (VH), light chain variable region (VL) sequences of HuMabs 049, 051, 055, 123, 161, 124, 001, 143, 019, 021, 027, 032, 035, 036, 054, 094. The respective CDRs correspond to those underlined in FIGS. 1 and 2, for VH and VL sequences, respectively.

SEQ ID No: 103 VH 036 QVQLQQWGAGLLKPSETLSLTCAVYGGSFSDYYWSWIRQPPG
KGLEWIGEINHSGSTNYNPSLKSRVTISVDTSKNQFSLKLSSVT
AADTAVYYCARLYYGSGTYYFDYWGQGTLVTVSS

SEQ ID No: 104 VL 036 DIQMTQSPSSLSASVGDRVTITCRASQGISSWLTWYQQKPEKA
PKSLIYAASRLQSGVPSRFSGSGSGTDFTLTISSLQPEDFATYYC
QQYNSFPPTFGQGTKVEIK

SEQ ID No: 105 VH 054 QVQLQQWGAGLLKPSETLSLTCAVYGGSFSGYYWSWIRQPPG
KGLEWIGEIHHSGSTNYNPSLKSRVTISVDTSKNQFSLKLSSVT
AADTAVYYCARLWYGSGSYYFDYWGQGTLVTVSS

SEQ ID No: 106 VL 054 DIQMTQSPSSLSASVGDRVTITCRASQGISSWLAWYQQKPEK
APKSLIYAASSLQSGVPSRFSGSGSGTDFTLTISSLQPEDFATYY
CQQYNSFPPTFGGGTKVEIK

SEQ ID No: 107 VH 094 QVQLQQWGAGLLKPSETLSLTCAVSGGSFSGYYWTWIRQPPG
KGLEWIGEIYHSGDTNYNPSLKSRVTISVDTSKNQFSLKLYSVT
AADTAVYYCARLYFGSGIYYLDYWGQGTLVTVSS

SEQ ID No: 108 VL 094 DIQMTQSPSSLSASVGDRVTITCRASQGISSWLVWYQQKPEK
APKSLIYAASSLQSGVPSRFSGSGSGTDFTLTISSLQPEDFATYY
CQQYNSFPPTFGQGTKVEIK

SEQ ID No: 109 VH 105 EVQLLESGGGLVQPGGSLRLSCAASGFTFSNYGMSWVRQAPG
KGLEWVSAISGSAYSTYYADSVKGRFTISRDNSKNTLWLQMNS
LRAEDTAVYYCAKAHYHGSGSYYTLFDYWGQGTLVTVSS

SEQ ID No: 110 VL 105 DIQMTQSPSSLSASVGDRVTITCRASQGISSWLAWYQQKPEK
APKSLIYAASSLQSGVPSRFSGSGSGTDFTLTISSLQPEDFATYY
CQQYNSYPYTFGQGTKLEIK

SEQ ID No: 111 VH 100 EVQLLESGGGLVQPGGSLRLSCAASGFTFNNYGMNWVRQAPG
KGLEWVSAISGTGYSTYYADSVKGRFTISRDNSKNTLYLQMNS
LRAEDTAVYYCAKAHYFGSGSYYTLFDYWGQGTLVTVSS

SEQ ID No: 112 VL 100 DIQMTQSPSSLSASVGDRVTITCRASQGISSWLAWYQQKPEK
APKSLIYAASSLQSGVPSRFSGSGSGTDFTLTISSLQPEDFATYY
CQQYNSYPYTFGQGTKLEIK

SEQ ID No: 113 VH 125 EVQLLESGGGLVQPGGSLRLSCAASGFTFTDYAMNWVRQAPG
KGLEWVSTISGSGYATYYADSVKGRFTISRDNSKTTLYLQMNS
LRAEDTAVYYCAKGHTLGSGSYYTLFDYWGQGTLVTVSS

SEQ ID No: 114 VL 125 DIQMTQSPSSLSASVGDRVTITCRASQGINSWLAWYQQKPEK
APKSLIYAASSLQSGVPSRFSGSGSGTDFTLTISSLQPEDFATYY
CQQYNSYPYTFGQGTKLEIK

SEQ ID No: 115 VH 162 EVQLWESGGGSVQPGGSLRLSCAASGFTFSSYGMSWVRQAP
GKGLEWVSGISGSGYSTYYADSVKGRFTISRDNSKNTLYLQMN
SLRAEDTAVYYCAKGYYHGSGSYYTSFDYWGQGTLVTVSS

SEQ ID No: 116 VL 162 DIQMTQSPSSLSASVGDRVTITCRASQGISSWLAWYQQKPEK
APKSLIYAASSLQSGVPSRFSGSGSGTDFTLTISSLQPEDFATYY
CQQYNSYPLTFGGGTKVEIK

SEQ ID No: 117 VH 033 QVQLVESGGGVVQTGRSLRLSCAASGFTFSSHAMHWVRQAPG
KGLEWVAAISYDGSNKYYADSVKGRFTISRDNSKNTLYLQMNS
LRAEDTAVYYCARGDYISSSGVFDYWGQGTLVTVSS

SEQ ID No: 118 VL 033 DIQMTQSPSSLSASVGDRVTITCRASQGISSWLAWYQQKPEK
APKSLIYAASSLQSGVPSRFSGSGSGTDFTLTISSLQPEDFATYY
CQQYNSYPITFGQGTRLEIK

SEQ ID No: 119 VH 160 QVQLVESGGGVVQPGRSLRLSCAASGFTFSSHAMHWVRQAPG
KGLEWVAAISYDGSNKYYADSVKGRFTISRDNSKNTMYLQMN
SLRAEDTAMCYCARGSITGSTGVFDYWGQGTLVTVSS

SEQ ID No: 120 VL 160 DIQMTQSPSSLSASVGDRVTITCRASQDISSWLAWYQQKPEK
APKSLIYAASSLQSGVPSRFSGSGSGTDFTLTISSLQPEDFATYY
CQQYNSYPITFGQGTRLEIK

TABLE 3-continued

Heavy chain variable region (VH), light chain variable region (VL) sequences of HuMabs 049, 051, 055, 123, 161, 124, 001, 143, 019, 021, 027, 032, 035, 036, 054, 094. The respective CDRs correspond to those underlined in FIGS. 1 and 2, for VH and VL sequences, respectively.

SEQ ID No: 121 VH 166  QVQLVESGGGVVQPGRSLRLSCAASGFTFSSYAMHWVRQAPG
KGLEWVAVISYDGSNEYYADSVKGRFTISRDNSKNTLYLQMNS
LRAEDTAVYYCARGSIIGSTGVFDYWGQGTLVTVSS

SEQ ID No: 122 VL 166  DIQMTQSPSSLSASVGDRVTITCRASQGISNWLAWYQQKPEK
APKSLIYDASSLQSGVPSRFSGSGSGTDFTLTISSLQPEDFATYY
CQQYNSYPITFGQGTRLEIK

SEQ ID No: 123 VH 152  QVQVVESGGGVVQPGRSLRLSCAASGFTFSSYAMHWVRQAPG
KGLEWVAVISYDGSYKYYADSVKGRFTISRDNSKNTLYLQMNS
LRAEDTAVYYCARGSITGSTGVFDYWGQGTLVTVSS

SEQ ID No: 124 VL 152  DIQMTQSPSSLSASVGDRVTITCRASQGINSWLAWYQQKPEK
APKSLIYDASSLQSGVPSRFSGSGSGTDFTLTISSLQPENFATYY
CQQYNSYPITFGQGTRLEIK

SEQ ID No: 125 VH 167  QVQLVESGGGVVQPGRSLRLSCAASGFTFSSYAIHWVRQAPG
KGLEWVAVISYDGSNKYYADSVKGRFTISRDNSKNTLYLQMNS
LRAEDTAVYYCARGSITGSTGVFDYWGQGTLVTVSS

SEQ ID No: 126 VL 167  DIQMTQSPSSLSASVGDRVTITCRASQGISNWLAWYQQKPEK
APKSLIYDASSLQSGVPSRFSGSGSGTDFTLTISSLQPEDFATYY
CQQYNSYPITFGQGTRLEIK

TABLE 4

Consensus CDRs based on sequence alignments shown in FIGS. 1 and 2.

| SEQ ID No | Gene | Region | Sequence | Notes |
|---|---|---|---|---|
| SEQ ID No: 9 050-049-051-055 | IgHV3-23-1 | VH CDR1 | GFTFSSYA | |
| SEQ ID No: 127 050-049-051-055 | IgHV3-23-1 | VH CDR2 | ISGX1GGX2T | Wherein X1 = R or S, and X2 = T or S; preferably, wherein X1 = R and X2 = T |
| SEQ ID No: 11 050-049-051-055 | IgHV3-23-1 | VH CDR3 | AKARANWDYFDY | |
| SEQ ID No: 128 084 | IgHV1-69-04 | VH CDR1 | GGTFX1X2YA | Wherein X1 = R or S, and X2 = T or S; preferably, wherein X1 = R and X2 = T |
| SEQ ID No: 129 084 | IgHV1-69-04 | VH CDR2 | IX2X3X3LGIX4 | Wherein X1 = N or I, X2 = T or P, X3 = V or I, and X4 = V or A, preferably, wherein X1 = N, X2 = T, X3 = V, and X4 = V |
| SEQ ID No: 130 084 | IgHV1-69-04 | VH CDR3 | AREKGVDYYYGX1X2 | Wherein X1 = I or M, X2 = E or D; preferably, wherein X1 = I, X2 = E |
| SEQ ID No: 131 169-123-161-124 | IgHV1-18-1 | VH CDR1 | GYTFTXYG | Wherein X = N or S, preferably N |
| SEQ ID No: 132 169-123-161-124 | IgHV1-18-1 | VH CDR2 | IX1X2YX3GNT | Wherein X1 = S, T, or I; X2 = A or T; X3 = S or N; preferably, wherein X1 = S, X2 = A, and X3 = S |
| SEQ ID No: 133 169-123-161-124 | IgHV1-18-1 | VH CDR3 | ARDRX1X2VRPDYFDY | Wherein X1 = I or V, X2 = V or I; preferably, wherein X1 = I and X2 = V |
| SEQ ID No: 134 025-001-143-019-021-027 | IgHV4-34-01 | VH CDR1 | GGSFSX1YX2 | Wherein X1 = D or G and X2 = Y or F; preferably, wherein X1 = D and X2 = Y |

TABLE 4-continued

Consensus CDRs based on sequence alignments shown in FIGS. 1 and 2.

| SEQ ID No: 135 IgHV4-34-01 025-001-143-019-021-027 | VH CDR2 | IX1HX2GSX3 | Wherein X1 = H or N, X2 = S or V, and X3 = T or A; preferably, wherein X1 = H, X2 = S, and X3 = T |
|---|---|---|---|
| SEQ ID No: 136 IgHV4-34-01 025-001-143-019-021-027 | VH CDR3 | ARGX1X2X3SG X4YYFDX5 | Wherein X1 = Y, N or L; X2 = Y or I, X3 = D, G or A; X4 = V or Y; and X5 = Y or L; preferably, wherein X1 = Y, X2 = Y, X3 = D, X4 = V, and X5 = Y |
| SEQ ID No: 137 IgHV4-34-01 091-032-035-036-054-094 | VH CDR1 | GGSFSX1YY | Wherein X1 = G or D, preferably G |
| SEQ ID No: 138 IgHV4-34-01 091-032-035-036-054-094 | VH CDR2 | IX1HSGX2T | Wherein X1 = Y, N or H; and X2 = D or S; preferably, wherein X1 = Y and X2 = D |
| SEQ ID No: 139 IgHV4-34-01 091-032-035-036-054-094 | VH CDR3 | ARLX1X2GSGX 3YYX4DY | Wherein X1 = Y, F or W; X2 = F or Y; X3 = I, T or S; and X4 = L or F; preferably, wherein X1 = Y, X2 = F, X3 = I, and X4 = L |
| SEQ ID No: 140 IgHV3-30-01 129 | VH CDR1 | GFTFSX1X2A | Wherein X1 = T or F, X2 = F or Y; preferably, wherein X1 = T and X2 = F |
| SEQ ID No: 141 IgHV3-30-01 129 | VH CDR2 | ISYDGX1X2K | Wherein X1 = G or S, X2 = H or N; preferably, wherein X1 = G and X2 = H |
| SEQ ID No: 142 IgHV3-30-01 129 | VH CDR3 | ARGLGVWGX1F DY | Wherein X1 = A or Y, preferably A |
| SEQ ID No: 143 IgHV3-23-01 098-105-100-125-162 | VH CDR1 | GFTFX1X2YX3 | Wherein X1 = S, N or T; X2 = N, D or S; and X3 = G or A; preferably, wherein X1 = S, X2 = N and X3 = G |
| SEQ ID No: 144 IgHV3-23-01 098-105-100-125-162 | VH CDR2 | ISGX1X2X3X4T | Wherein X1 = S or T, X2 = A or G, X3 = Y or G, X4 = S or A; preferably, wherein X1 = S, X2 = A, X3 = Y, X4 = S |
| SEQ ID No: 145 IgHV3-23-01 098-105-100-125-162 | VH CDR3 | AKX1X2X3X4G SGSYYTX5FDY | Wherein X1 = A or G; X2 = H or Y; X3 = Y or T; X4 = H, F or L; X5 = L or S; preferably, wherein X1 = A; X2 = H; X3 = Y; X4 = H; X5 = L |
| SEQ ID No: 146 IgHV5-51-01 127 | VH CDR1 | GYSFX1X2YW | Wherein X1 = S or T, X2 = I or S; preferably, wherein X1 = S, X2 = I |
| SEQ ID No: 147 IgHV5-51-01 127 | VH CDR2 | IX1PGDSDX2 | Wherein X1 = F or Y, X2 = I or T; preferably, wherein X1 = F, X2 = I |
| SEQ ID No: 148 IgHV5-51-01 127 | VH CDR3 | ARQPGDWSPR HWYFDL | |
| SEQ ID No: 149 IgHV5-51-01 159 | VH CDR1 | GYXFTSYW | Wherein X = N or S, preferably N |
| SEQ ID No: 51 IgHV5-51-01 159 | VH CDR2 | IYPGDSDT | |
| SEQ ID No: 52 IgHV5-51-01 159 | VH CDR3 | ARWGTYYDILT GYFN | |
| SEQ ID No: 71 IgHV1-18-01 132 | VH CDR1 | GYTFTSYG | |
| SEQ ID No: 150 IgHV1-18-01 132 | VH CDR2 | ISAYNGNX | Wherein X = S or T, preferably S |

TABLE 4-continued

Consensus CDRs based on sequence alignments shown in FIGS. 1 and 2.

| SEQ ID No | Identifier | Chain | Region | Sequence | Notes |
|---|---|---|---|---|---|
| SEQ ID No: 151 132 | IgHV1-18-01 | VH | CDR3 | AREYSYDSGTY FYYGMDV | |
| SEQ ID No: 152 153-033-160-166-152-167 | IgHV3-30-03-01 | VH | CDR1 | GFTFSX1X2X3 | Wherein X1 = D or S, X2 = Y or H, X3 = V or A; preferably, wherein X1 = D, X2 = Y, X3 = V |
| SEQ ID No: 153 153-033-160-166-152-167 | IgHV3-30-03-01 | VH | CDR2 | ISYDGSX1X2 | Wherein X1 = N or Y, X2 = K or E, preferably wherein X1 = N and X2 = K |
| SEQ ID No: 154 153-033-160-166-152-167 | IgHV3-30-03-01 | VH | CDR3 | ARGX1X2X3X4 X5X6GX7FDY | Wherein X1 = G, D or S; X2 = I or Y; X3 = T or I; X4 = G or S; X5 = T or S; X6 = T or S; X7 = Y or V; preferably, wherein X1 = G; X2 = I; X3 = T; X4 = G; X5 = T; X6 = T; and X7 = V |
| SEQ ID No: 13 050-084-049-051-055 | IgKV1-12-01 | VL | CDR1 | QGISSW | |
| 050-084-049-051-055 | IgKV1-12-01 | VL | CDR2 | XAS | Wherein X = A or V |
| SEQ ID No: 155 050-084-049-051-055 | IgKV1-12-01 | VL | CDR3 | QQANSFPXT | Wherein X = I or L |
| SEQ ID No: 6 169-124-161-123 | IgKV3-11-01 | VL | CDR1 | QSVSSY | |
| 169-124-161-123 | IgKV3-11-01 | VL | CDR2 | DXS | Wherein X = A or T, preferably A |
| SEQ ID No: 156 169-124-161-123 | IgKV3-11-01 | VL | CDR3 | QQRSXWPRT | Wherein X = N or H, preferably N |
| SEQ ID No: 157 025-001-019-143-021-027 | IgKV1D-16-01 | VL | CDR1 | QGISXW | Wherein X = R or S, preferably R |
| 025-001-019-143-021-027 | IgKV1D-16-01 | VL | CDR2 | AAS | |
| SEQ ID No: 164 025-001-019-143-021-027 | IgKV1D-16-01 | VL | CDR3 | QQYNSXPIT | Wherein X = Y or F, preferably Y |
| SEQ ID No: 33 091-032-035-036-054-094 | IgKV1D-16-01 | VL | CDR1 | QGISSW | |
| 091-032-035-036-054-094 | IgKV1D-16-01 | VL | CDR2 | AX1X2 | Wherein X1 = A or T, and X2 = S or F; preferably, wherein X1 = A and X2 = S |
| SEQ ID No: 158 091-032-035-036-054-094 | IgKV1D-16-01 | VL | CDR3 | QQYNSFPPT | |
| SEQ ID No: 159 098-100-105-125-162 | IgKV1D-16-01 | VL | CDR1 | QGIXSW | Wherein X = S or N, preferably S |
| 098-100-105-125-162 | IgKV1D-16-01 | VL | CDR2 | AAS | |
| SEQ ID No: 160 098-100-105-125-162 | IgKV1D-16-01 | VL | CDR3 | QQYNSYPXT | Wherein X = Y or L, preferably Y |
| SEQ ID No: 161 153-152-166-167-160-033 | IgKV1D-16-01 | VL | CDR1 | QGIX1X2W | Wherein X1 = S or N; X2 = S or N; preferably, wherein X1 = X2 = S |

TABLE 4-continued

Consensus CDRs based on sequence alignments shown in FIGS. 1 and 2.

| | | | | |
|---|---|---|---|---|
| 153-152-166-<br>167-160-033 | IgKV1D-16-<br>01 | VL<br>CDR2 | XAS | Wherein X = D or A, preferably D |
| SEQ ID No: 162<br>153-152-166-<br>167-160-033 | IgKV1D-16-<br>01 | VL<br>CDR3 | QQYXSYPIT | Wherein X = K or N, preferably K |

Example 11

Purification of Antibodies

Culture supernatant was filtered over 0.2 μm dead-end filters, loaded on 5 ml MabSelect SuRe columns (GE Health Care) and eluted with 0.1 M sodium citrate-NaOH, pH 3. The eluate was immediately neutralized with 2M Tris-HCl, pH 9 and dialyzed overnight to 12.6 mM NaH2PO4, 140 mM NaCl, pH 7.4 (B. Braun). Alternatively, subsequent to purification, the eluate was loaded on a HiPrep Desalting column and the antibody was exchanged into 12.6 mM NaH2PO4, 140 mM NaCl, pH 7.4 (B. Braun) buffer. After dialysis or exchange of buffer, samples were sterile filtered over 0.2 μm dead-end filters. Purity was determined by SDS-PAGE and concentration was measured by nephelometry and absorbance at 280 nm. Purified antibodies were stored at 4° C. Mass spectrometry was performed to identify the molecular mass of the antibody heavy and light chains expressed by the hybridomas as described in Example 9.

Example 12

Binding of HER2 Clones to Tumor Cells Expressing Membrane-Bound HER2 Measured by Means of FACS Analysis The binding of HER2 antibodies to AU565 cells (purchased at ATCC, CRL-2351) and A431 cells (purchased at ATCC, CRL-1555), was tested using flow cytometry (FACS Canto II, BD Biosciences). Qifi analysis (Dako, Glostrup, Denmark) revealed that AU565 cells expressed on average 1,000,000 copies of HER2 protein per cell, whereas A431 cells expressed on average 15,000 copies per cell. Binding of HER2 antibodies was detected using a Phycoerythrin (PE)-conjugated goat-anti-human IgG antibody (Jackson). Trastuzumab (clinical-grade Herceptin®) was used as positive control antibody, and an isotype control antibody was used as negative control antibody. $EC_{50}$ values were determined by means of non-linear regression (sigmoidal dose-response with variable slope) using GraphPad Prism V4.03 software (GraphPad Software, San Diego, Calif., USA).

As shown in FIG. 3, all tested HER2 antibodies bound to HER2 expressed on both AU565 and A431 cells in a dose-dependent manner. The $EC_{50}$ values for binding varied between 0.336-2.290 μg/mL for AU565 cells and 0.068-1.135 μg/mL for A431 cells. Especially on A431 cells, large differences in $EC_{50}$ values were observed between the tested antibodies. However, antibody 098 had the best (i.e., lowest) $EC_{50}$ value on both types of cells. Also some differences in maximum binding levels were observed between different antibodies, on both AU565 and A431 cells. Of the tested antibodies, antibody 098 also had the highest maximum binding level on AU565 cells, whereas antibody 025 had the highest maximum binding level on A431 cells.

Example 13

Binding of HER2 Antibodies to Membrane-Bound HER2 Expressed on Rhesus Epithelial Cells Measured by Means of FACS Analysis To determine cross-reactivity with Rhesus HER2, the binding of HER2 antibodies to HER2-positive Rhesus epithelial cells (4MBr-5 purchased at ATCC) was tested using flow cytometry (FACS Canto II, BD Biosciences). A Phycoerythrin-conjugated goat-anti-human IgG antibody (Jackson) was used as a secondary conjugate. An isotype control antibody was used as negative control antibody.

Figure 4:
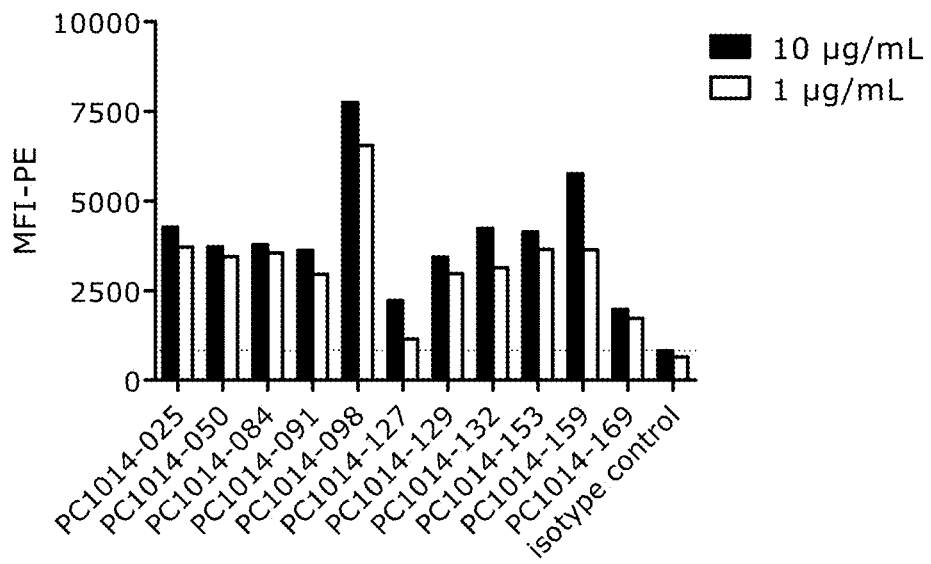
FIG. 4: Binding of HER2 antibodies to HER2 expressed on monkey Rhesus epithelial cells. Data shown are mean fluorescence intensities (MFI) of one experiment, described in Example 13.

As shown in FIG. 4, all tested HER2 antibodies were cross-reactive with Rhesus monkey HER2. At both tested concentrations (1 μg/mL and 10 μg/mL), the HER2 antibodies were able to bind specifically to Rhesus monkey HER2. Antibody 127 demonstrated poor binding at 1 μg/mL concentration, but showed good binding at 10 μg/mL concentration. Antibody 098 had the highest binding level at both antibody concentrations. No binding was observed with the isotype control antibody.

Example 14

Competition of HER2 Antibodies for Binding to Soluble Her2ECDHis Measured in Sandwich-ELISA The optimal coating concentrations of the tested HER2 antibodies and optimal Her2ECDHis concentration were determined in the following manner: ELISA wells were coated overnight at 4° C. with HER2 HuMabs serially diluted in PBS (0.125-8 μg/mL in 2-fold dilutions). Next, the ELISA wells were washed with PBST (PBS supplemented with 0.05% Tween-20 [Sigma-Aldrich, Zwijndrecht, The Netherlands]) and blocked for one hour at room temperature (RT) with PBSTC (PBST supplemented 2% [v/v] chicken serum [Gibco, Paisley, Scotland]). The ELISA wells were then washed with PBST and incubated for one hour at RT with Her2ECDHis serially diluted in PBSTC (0.25-2 μg/mL in 2-fold dilutions). Unbound Her2ECDHis was washed away with PBST, and bound Her2ECDHis was incubated for one hour at RT with 0.25 μg/mL biotinylated rabbit-anti-6× his-biot (Abcam, Cambridge, UK). The plate was thereafter washed with PBST and incubated for one hour with 0.1 μg/mL Streptavidin-poly-HRP (Sanquin, Amsterdam, The Netherlands) diluted in PBST. After washing, the reaction was visualized through a 15 minutes incubation with 2,2'-azino-bis (3-ethylbenzothiazoline-6-sulfonic acid (ABTS: one ABTS tablet diluted in 50 mL ABTS buffer (Roche Diagnostics, Almere, The Netherlands)) at RT protected from light. The colorization was stopped by adding an equal volume of oxalic acid (Sigma-Aldrich, Zwijndrecht, The Netherlands). Fluorescence at 405 nm was measured on a microtiter plate reader (Biotek Instruments, Winooski, USA). The antibody concentrations that resulted in suboptimal binding of each antibody were determined and used for the following cross-block experiments.

Each HER2 antibody was coated to the ELISA wells at the sub-optimal dose that was determined as described above. After blocking of the ELISA wells, the wells were incubated with the predetermined concentration of 1 µg/mL biotinylated Her2ECDHis in the presence or absence of an excess of a second (competitor) HER2 antibody. The ELISA was then performed as described above. Residual binding of Her2ECDHis to the coated antibody was expressed as a percentage relative to the binding observed in the absence of competitor antibody. Percentage competition was then determined as 100 minus the percentage of inhibition. 75% competition was considered as complete cross-block, whereas 25-74% competition was considered as partial cross-block, and 0-24% competition was considered non-blocking.

As shown in Table 5, all HER2 antibodies were found to be able to block binding to Her2ECDHis, at least partially, for themselves. After dividing the antibodies into 3 major cross-block groups, all antibodies were tested for competition with at least one representative antibody from each group.

The first group comprised trastuzumab and antibodies 169, 050 and 084, which blocked each other for binding to Her2ECDHis, but did not cross-block antibodies from other groups.

The second group comprised pertuzumab and antibodies 025, 091 and 129, which blocked each other for binding to Her2ECDHis, except for antibodies 129 and 091 which both cross-blocked pertuzumab and 025, but not each other. None of the antibodies of group 2 blocked antibodies from other groups.

A third group comprised antibodies C1, F5, 127, 098, 132, 153 and 159, which did not cross-block any antibody from the other groups. Within this group 3, some variation was observed. Antibody 127 was the only antibody that was able to cross-block all other antibodies in this group for binding to Her2ECDHis; antibody 159 cross-blocked all other antibodies within this group, except 132; clone 098 cross-blocked all antibodies of group 3, except 132 and 153; antibody 153 cross-blocked 127, 132 and 159 for binding to Her2ECDHis, but not 098, C1 or F5; clone 132 cross-blocked 127, 132 and 153. When added as competitor antibodies, F5 and C1 only demonstrated cross-blocking of each other. However, the reverse reaction also revealed competition with antibodies 127, 098 and 159, but not 153 and 132. Possibly, these differences may have resulted from lower affinities of antibodies C1 and F5 for Her2ECDHis.

Values higher than 100% can be explained by avidity effects and the formation of antibody-Her2ECDHis complexes containing two non-competing antibodies.

TABLE 5

Competition and cross-blocking of HER2 antibodies for binding to Her2ECDHis

| Immobilized mAb | Competing mAb | | | | | | | | | | | | | | |
|---|---|---|---|---|---|---|---|---|---|---|---|---|---|---|---|
| | tras | 169 | 050 | 084 | pert | 025 | 091 | 129 | C1 | F5 | 127 | 159 | 098 | 153 | 132 |
| Trastuzumab | 6 | 15 | 6 | 51 | 100 | 107 | 100 | 85 | 103 | 99 | 115 | 90 | 101 | 101 | 101 |
| TH1014-169 | 19 | 45 | 21 | 73 | 101 | 98 | 105 | 106 | ND | ND | ND | ND | 105 | 102 | ND |
| TH1014-050 | 13 | 30 | 12 | 74 | 95 | 104 | 98 | 110 | ND | ND | ND | ND | 102 | 104 | ND |
| TH1014-084 | 74 | 73 | 76 | 20 | 101 | 106 | 104 | 104 | ND | ND | ND | ND | 109 | 98 | ND |
| TH1014-pert | 104 | 100 | 94 | 95 | 9 | 20 | 19 | 39 | 106 | 125 | 116 | 81 | 103 | 100 | 109 |
| TH1014-025 | 98 | 98 | 100 | 104 | 8 | 18 | 21 | 15 | ND | ND | ND | ND | 102 | 99 | ND |
| TH1014-091 | 99 | 99 | 95 | 100 | 5 | 13 | 15 | 78 | ND | ND | ND | ND | 98 | 98 | ND |
| TH1014-129 | 93 | 99 | 97 | 92 | 22 | 55 | 76 | 12 | ND | ND | ND | ND | 106 | 98 | ND |
| TH1014-C1 | 89 | ND | ND | ND | ND | ND | ND | ND | 65 | 58 | 73 | 53 | 58 | 77 | 90 |
| TH1014-F5 | 197 | ND | ND | ND | ND | ND | ND | ND | 70 | 21 | 62 | 15 | 16 | 80 | 125 |
| TH1014-127 | 102 | ND | ND | ND | ND | ND | ND | ND | 112 | 88 | 11 | 8 | 58 | 21 | 44 |
| TH1014-159 | 111 | ND | ND | ND | 112 | ND | ND | ND | 96 | 86 | 15 | 6 | 11 | 40 | 79 |
| TH1014-098 | 107 | 102 | 100 | 103 | 104 | 108 | 104 | 107 | 125 | 96 | 21 | 9 | 17 | 110 | 142 |
| TH1014-153 | 134 | 111 | 103 | 107 | 121 | 97 | 102 | 106 | 257 | 96 | 27 | 23 | 115 | 28 | 33 |
| TH1014-132 | 353 | ND | ND | ND | 288 | ND | ND | ND | 422 | 379 | 30 | 131 | 309 | 41 | 32 |
| Cross-block group | 1 | 1 | 1 | 1 | 2 | 2 | 2 | 2b | 3a | 3a | 3a | 3a | 3a | 3b | 3b |

Depicted values are mean percentages of binding relative to the binding observed in the absence of competitor antibody, of two independent experiments. Competition experiments with HEK produced TH1014-C1 and TH1014-F5 were performed once. Trastuzumab (clinical grade Herceptin®) and HEK-produced pertuzumab (TH1014-pert) were also tested.

Example 15

Antibody-Dependent Cell-Mediated Cytotoxicity (ADCC)

SK-BR-3 cells (purchased at ATCC, HTB-30) were harvested ($5 \times 10^6$ cells), washed (twice in PBS, 1500 rpm, 5 min) and collected in 1 mL RPMI 1640 medium supplemented with 10% cosmic calf serum (CCS) (HyClone, Logan, Utah, USA), to which 200 µCi $^{51}$Cr (Chromium-51; Amersham Biosciences Europe GmbH, Roosendaal, The Netherlands) was added. The mixture was incubated in a shaking water bath for 1.5 hours at 37° C. After washing of the cells (twice in PBS, 1500 rpm, 5 min), the cells were resuspended in RPMI 1640 medium supplemented with 10% CCS, counted by trypan blue exclusion and diluted to a concentration of $1 \times 10^5$ cells/mL.

Meanwhile, peripheral blood mononuclear cells (PBMCs) were isolated from fresh buffy coats (Sanquin, Amsterdam, The Netherlands) using standard Ficoll density centrifugation according to the manufacturer's instructions (lymphocyte separation medium; Lonza, Verviers, France). After resuspension of cells in RPMI 1640 medium supplemented with 10% CCS, cells were counted by trypan blue exclusion and concentrated to $1 \times 10^7$ cells/mL.

Trastuzumab was produced in CHO cells resulting in an (increased) non-core fucosylation grade of 12.4%, whereas the other HER2 antibodies were produced in HEK cells, resulting on average in 4% non-core fucosylation.

For the ADCC experiment, 50 µL $^{51}$Cr-labeled SK-BR-3 cells (5.000 cells) were pre-incubated with 15 µg/mL HER2 antibody (IgG1,κ) in a total volume of 100 µL RPMI medium supplemented with 10% CCS in a 96-well microtiter plate. After 15 min at RT, 50 µL PBMCs (500,000 cells) were added, resulting in an effector to target ratio of 100:1. The maximum amount of cell lysis was determined by incubating 50 µL $^{51}$Cr-labeled SK-BR-3 cells (5000 cells) with 100 µL 5% Triton-X100. The amount of spontaneous lysis was determined by incubating 5000 $^{51}$Cr-labeled SK-BR-3 cells in 150 µL medium, without any antibody or effector cells. The level of antibody-independent cell lysis was determined by incubating 5000 SK-BR-3 cells with 500,000 PBMCs without antibody. Subsequently, the cells were incubated 4 hr at 37° C., 5% $CO_2$. To determine the amount of cell lysis, the cells were centrifuged (1200 rpm, 3 min) and 75 µL of supernatant was transferred to micronic tubes, after which the released $^{51}$Cr was counted using a gamma counter. The measured counts per minute (cpm) were used to calculate the percentage of antibody-mediated lysis as follows:

(cpm sample−cpm Ab−independent lysis)/(cpm max. lysis−cpm spontaneous lysis)×100%

Figure 5:
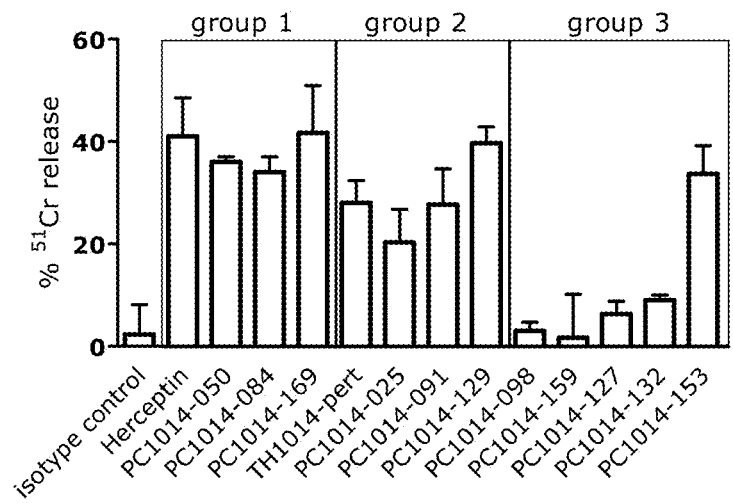
FIG. 5: Chromium-release (ADCC) assay of HER2 antibodies, showing PBMC-mediated lysis of $^{51}$Cr-labeled SK-BR-3 cells after incubation with HER2 antibody. Values depicted are the mean maximum percentages $^{51}$Cr-release±the standard deviation from one representative in vitro ADCC experiment with SK-BR-3 cells. See Example 15 for details.

As shown in FIG. 5, HER2 antibodies from cross-block groups 1 and 2 induced efficient lysis of SK-BR-3 cells through ADCC. From group 3, antibody 153 was the only antibody that induced efficient ADCC, antibody 132 induced about 10% ADCC, and clones 098, 159 and 127 did not induce ADCC.

Example 16

Inhibition of Ligand-Independent Proliferation of AU565 Cells

HER2 antibodies were tested for their ability to inhibit proliferation of AU565 cells in vitro. Due to the high HER2 expression levels on AU565 cells (1,000,000 copies per cell as described in Example 12), HER2 is constitutively active in these cells and thus not dependent on ligand-induced heterodimerization.

In a 96-well tissue culture plate (Greiner bio-one, Frickenhausen, Germany), 9000 AU565 cells were seeded per well in the presence of 10 µg/mL HER2 antibody in serum-free cell culture medium. As a control, cells were seeded in serum-free medium without antibody. After 3 days, the amount of viable cells was quantified with Alamarblue (BioSource International, San Francisco, US) according to the manufacturer's instructions. Fluorescence was monitored using the EnVision 2101 Multilabel reader (PerkinElmer, Turku, Finland) with standard Alamarblue settings. The Alamarblue signal of antibody-treated cells was plotted as a percentage relative to untreated cells. Dunnett's test was applied for statistical analysis.

Figure 6:
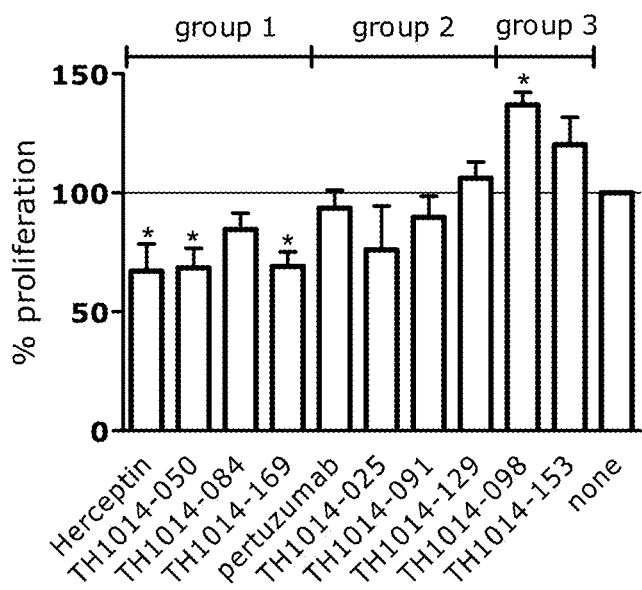
FIG. 6: Effect of HER2 antibodies on the proliferation of AU565 cells, as compared to untreated cells (set to 100%). Data shown are percentages proliferation of AU565 cells compared to untreated cells measured in three independent experiments±the standard deviation. * Significant (P<0.05). See Example 16 for details.

The results are shown in FIG. 6, depicting the percentage proliferation of AU565 cells after HER2 antibody treatment compared to untreated cells, which was set to 100%. Of the tested Group 1 antibodies, trastuzumab, 050 and 169 demonstrated significant inhibition of AU565 cell proliferation (P<0.05), whereas 084 had no effect. None of the tested antibodies from group 2 (Pertuzumab, 025, 092 and 129) was able to inhibit AU565 cell proliferation. The tested antibodies from group 3 (098 and 153) did not inhibit AU565 proliferation. In contrast, both antibodies induced enhanced proliferation of AU565 cells compared to untreated cells (098 more than 153). Enhancing proliferation can be an advantage in some therapeutic applications of ADC-conjugates, e.g., where the cytotoxic action of the drug relies on, or is enhanced by, cell proliferation. For trastuzumab and pertuzumab, this was in accordance with the results described by Juntilla et al. (Cancer Cell 2009; 15(5):353-355).

Example 17

Inhibition of Ligand-Induced Proliferation of MCF-7 Cells

Since HER2 is an orphan receptor, its signaling is mainly dependent on activation of other ErbB-family members such as EGFR and Her3. Upon ligand binding, these two receptors can bind to and activate the HER2 receptor, resulting in e.g. proliferation. Various publications describe that pertuzumab efficiently inhibits Heregulin-β1-induced proliferation (Franklin MC. Cancer Cell 2004/Landgraf R. BCR 2007). For trastuzumab, it has been described that it has little effect on Heregulin-β1-induced HER2/HER3 heterodimerization and proliferation (Larsen S S., et al., Breast Cancer Res Treat 2000; 58:41-56; Agus D B., et al., Cancer Cell 2002; 2:127-137; Wehrman et al. (2006), supra).

To investigate the ability of the present human HER2 antibodies to interfere with Heregulin-β1-induced HER2/HER3 heterodimers, a Heregulin-β1-induced proliferation assay was performed. Therefore, MCF7 cells (purchased at ATCC, HTB-22) expressing ~20.000 HER2 molecules per cell, were seeded in a 96-wells tissue culture plate (Greiner bio-one) (2.500 cells/well) in complete cell culture medium. After 4 hours, the cell culture medium was replaced with starvation medium containing 1% Cosmic Calf Serum (CCS) and 10 µg/mL HER2 antibody. Next, Heregulin-β1 (PeproTech, Princeton Business Park, US) diluted in 1% CCS containing starvation medium was added to the wells to a final concentration of 1.5 ng/ml. After 4 days incubation, the amount of viable cells was quantified with Alamarblue (BioSource International) according to the manufacturer's instructions. Fluorescence was monitored using the EnVision 2101 Multilabel reader (PerkinElmer) with standard Alamarblue settings. The Alamarblue signal of HER2 antibody-treated ligand-induced cells was plotted as a percentage signal compared to ligand-induced cells incubated without HER2 antibody. Dunnett's test was applied for statistical analysis.

Figure 7:
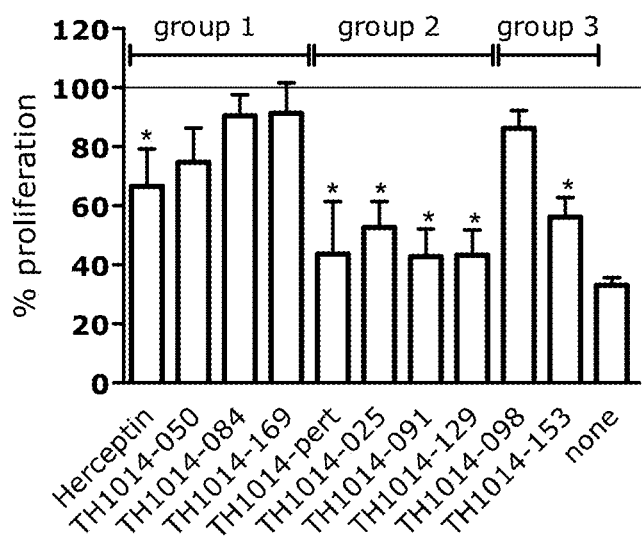
FIG. 7: Percentage of viable MCF7 cells stimulated with Heregulin-β1 and treated with the indicated HER2 antibodies, relative to cells stimulated with Heregulin-β1 only. As a control, the percentage proliferation of unstimulated cells is shown (none). Data was obtained from three independent experiments±the stdev. *Significant inhibition of Heregulin-β1-induced proliferation (P<0.05). See Example 17 for details.

FIG. 7 shows the percentage of viable MCF7 cells stimulated with Heregulin-β1 and treated with the indicated HER2 antibody, relative to the viable cells after stimulation with Heregulin-β1 in the absence of HER2 antibody, which was set to 100%. MCF-7 proliferation in absence of both Heregulin-β1 and antibody was also depicted (none). Antibodies 025, 091, 129, 153 and pertuzumab (TH1014-pert) demonstrated significant inhibition of Heregulin-β1-induced MCF-7 proliferation (P<0.05). Also trastuzumab showed some inhibition of Heregulin-β1-induced proliferation of MCF-7 cells, although not as efficient as the other tested HER2 antibodies. It has been reported that domain IV of HER2 is involved in the stabilization of EGFR/HER2 heterodimers, but without details on its contribution to HER2/HER3 heterodimers (Wehrman et al., supra). Antibodies 050, 084, 169 and 098 had no statistically significant effect on Heregulin-β1-induced proliferation of MCF-7 cells.

Without being limited to theory, this suggests that these antibodies do not inhibit ligand-induced HER2/HER3 heterodimerization.

Example 18

Anti-Kappa-ETA' Assay

To investigate the suitability of HER2 antibodies for an antibody-drug conjugate approach, a generic in vitro cell-based killing assay using kappa-directed pseudomonas-exotoxin A (anti-kappa-ETA') was developed. The assay makes use of a high affinity anti-kappa domain antibody conjugated to a truncated form of the pseudomonas-exotoxin A. Upon internalization, the anti-kappa-ETA' domain antibody undergoes proteolysis and disulfide-bond reduction, separating the catalytic from the binding domain. The catalytic domain is transported from the Golgi to the endoplasmic reticulum via the KDEL retention motif, and subsequently translocated to the cytosol where it inhibits protein synthesis and induces apoptosis (ref. Kreitman R J. BioDrugs 2009; 23(1):1-13). In this assay, to identify HER2 antibodies that enable internalization and killing through the toxin, HER2 antibodies are preconjugated with the anti-kappa-ETA' before incubation with HER2-positive cells.

First, the optimal concentration of anti-kappa-ETA' was determined for each cell line, i.e. the maximally tolerated dose that does not lead to induction of non-specific cell death. AU565 cells (7500 cells/well) and A431 cells (2500 cells/well) were seeded in normal cell culture medium in 96-wells tissue culture plate (Greiner bio-one) and allowed to adhere for at least 4 hours. Next, cells were incubated with 100, 10, 1, 0.1, 0.01, 0.001 and 0 µg/mL anti-kappa-ETA' dilutions in normal cell culture medium. After 3 days, the amount of viable cells was quantified with Alamarblue (BioSource International, San Francisco, US) according to the manufacturer's instruction. Fluorescence was monitored using the EnVision 2101 Multilabel reader (PerkinElmer, Turku, Finland) with standard Alamarblue settings. The highest concentration anti-kappa-ETA' that did not kill the cells by itself was used for following experiments (0.5 µg/mL for AU565 and 1 µg/mL for A431).

Next, antibody-mediated internalization and killing by the toxin was tested for different HER2 antibodies. Cells were seeded as described above. Dilution-series of HER2 antibodies were pre-incubated for 30 minutes with the predetermined concentration anti-kappa-ETA' before adding them to the cells. After 3 days of incubation, the amount of viable cells was quantified as described above. The Alamarblue signal of cells treated with anti-kappa-ETA' conjugated antibodies was plotted compared to cells treated with antibody alone. 23.4 µg/mL Staurosporin was used as positive control for cell killing. An isotype control antibody was used as negative control.

Figure 8A:
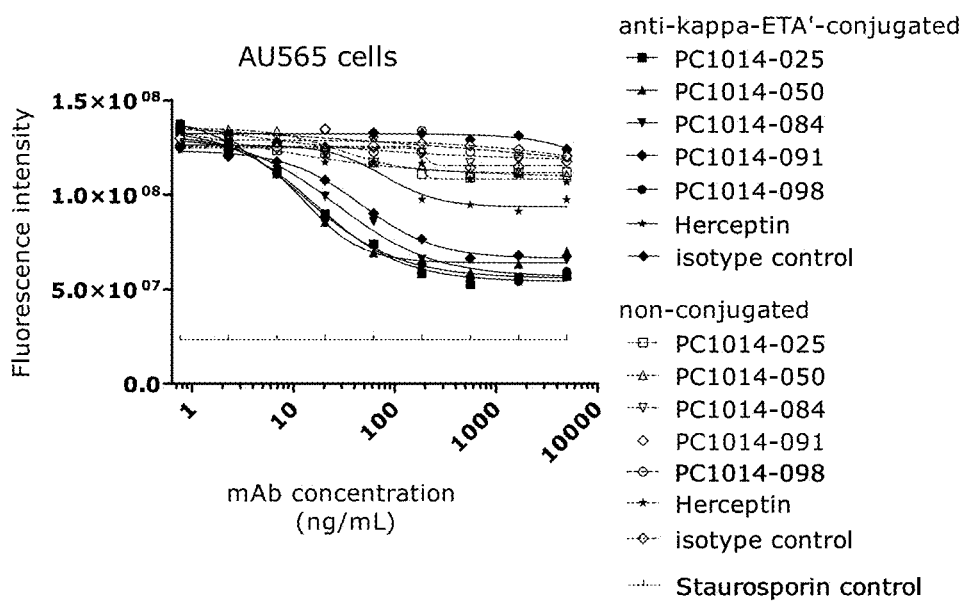
FIGS. 8A-8D: ADC assay, showing killing of AU565 cells (FIG. 8A, FIG. 8B) or A431 cells (FIG. 8C, FIG. 8D) via anti-kappa-ETA'-conjugated HER2 antibodies.
Figure 8B:
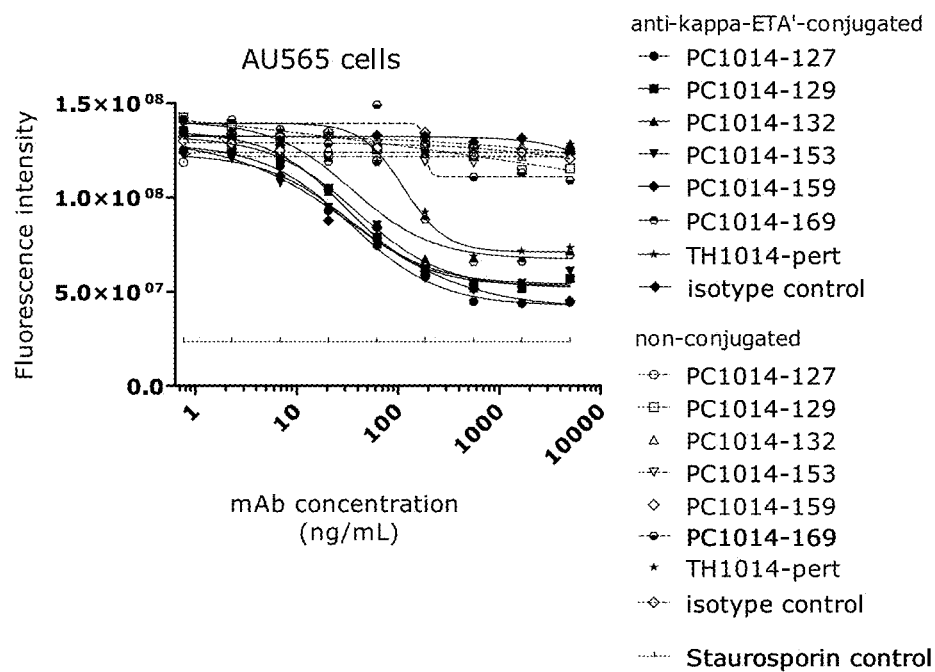

As shown in FIG. 8A,B and Table 6, all anti-kappa-ETA'-conjugated HER2 antibodies were able to kill AU565 cells in a dose-dependent manner. All tested anti-kappa-ETA'-conjugated HER2 antibodies demonstrated better killing of AU565 cells compared to both anti-kappa-ETA'-conjugated trastuzumab and anti-kappa-ETA'-conjugated pertuzumab (TH1014-pert). Moreover, the percentage of killed AU565 cells was higher for anti-kappa-ETA'-conjugated HER2 antibodies (70.3-49.9%), compared to anti-kappa-ETA'-conjugated trastuzumab (31.9%) and anti-kappa-ETA'-conjugated pertuzumab (47.51%), and the $EC_{50}$ values were increased. $EC_{50}$ values for anti-kappa-ETA'-conjugated HER2 antibodies ranged between 12.12 ng/mL and 46.49 ng/mL) compared to 78.49 ng/mL for anti-kappa-ETA'-conjugated trastuzumab and 117.8 ng/mL for anti-kappa-ETA'-conjugated pertuzumab. Antibody 159 had the highest percentage of cell-kill, and 098 the lowest $EC_{50}$.

TABLE 6

Data shown are $EC_{50}$ values and maximal percentage cell kill of AU565 cells treated with anti-kappa-ETA'-conjugated HER2 antibodies, measured in one representative experiment. Cell-kill induced by Staurosporin was set as 100% and MFI of untreated cells was set as 0%.

| antibody | % cells killed | EC50 ng/mL |
|---|---|---|
| PC1014-159 | 70.3 | 34.93 |
| PC1014-127 | 69.0 | 34.46 |
| PC1014-132 | 61.6 | 39.35 |
| PC1014-129 | 60.8 | 30.85 |
| PC1014-153 | 60.3 | 32.26 |
| PC1014-025 | 60.0 | 16.71 |
| PC1014-098 | 58.7 | 12.12 |
| PC1014-084 | 58.1 | 26.97 |
| PC1014-050 | 52.4 | 12.71 |
| PC1014-091 | 50.6 | 46.49 |
| PC1014-169 | 49.9 | 35.62 |
| TH1014-pert | 47.5 | 117.8 |
| trastuzumab | 31.9 | 78.49 |
| isotype control | Ndet | Ndet |

Ndet = not detected.

Figure 8C:
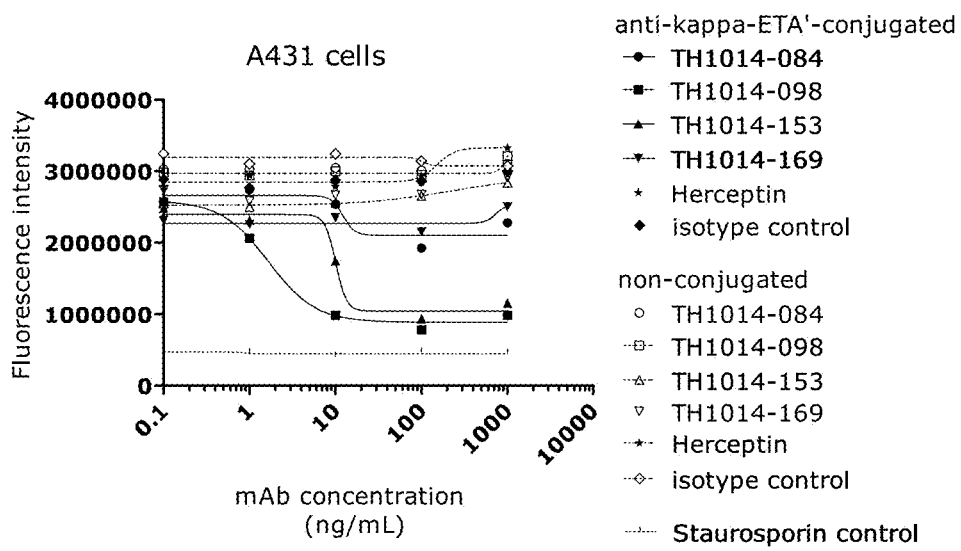
Figure 8D:
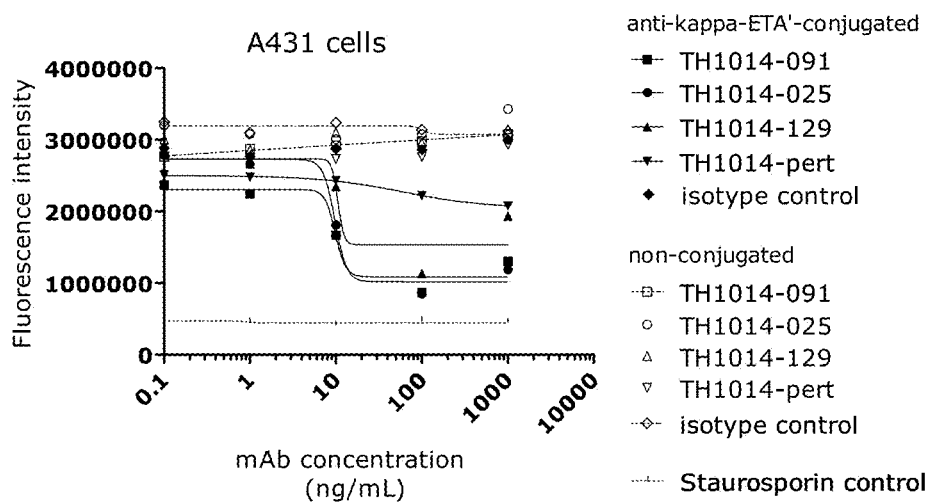

As shown in FIG. 8C,D and Table 7, antibodies 025, 091, 098, 129 and 153 were able to induce effective killing of A431 cells (75%). The highest percentage of cell-kill, and lowest $EC_{50}$ was shown by antibody 098. When conjugated to anti-kappa-ETA', trastuzumab and isotype control antibody did not induce killing of A431 cells. Antibodies 169, 084 and pertuzumab induced percentages of cell kill of no more than about 50%. No cell kill was observed with non-conjugated HER2 antibodies.

TABLE 7

Data shown are $EC_{50}$ values and maximal percentage cell kill of A431 cells treated with anti-kappa-ETA'-conjugated HER2 antibodies, measured in one representative experiment. Cell kill induced by Staurosporin was set as 100% and MFI of untreated cells was set as 0%.

| antibody | % cells killed | EC50 ng/mL |
|---|---|---|
| PC1014-025 | 86.7 | ~9.77 |
| PC1014-084 | 50.5 | ND |
| PC1014-091 | 83.3 | ~9.86 |
| PC1014-098 | 87.2 | 1.65 |
| PC1014-129 | 75.9 | ~10.60 |
| PC1014-153 | 82.4 | ~10.11 |
| PC1014-169 | 34.0 | ND |
| TH1014-pert | 37.0 | 61.58 |
| trastuzumab | Ndet | Ndet |
| isotype control | NDet | NDet |

"NDet" means not detected.

Example 19

Internalization of HER2 Antibodies Measured with an FMAT-Based Fab-CypHer5E Assay To investigate whether the enhanced killing of AU565 cells observed in the kappa-toxin-ETA' assay described in the previous Example correlated with enhanced internalization of HER2 antibodies, a fab-CypHer5E-based internalization assay was performed. CypHer5E is a pH sensitive dye which is non-fluorescent at basic pH (extracellular: culture medium) and fluorescent at acidic pH (intracellular: lysosomes), with an acid dissociation constant (pKa) of 7.3.

AU565 cells were seeded in 384-well tissue culture plates (Greiner bio-one), at a density of 3000 cells/well in normal cell culture medium supplemented with 240 ng/mL fab-CypHer5E (conjugation of Goat-fab-anti-Human IgG [Jackson] with CypHer5E [GE Healthcare, Eindhoven, The Netherlands] was made according to manufacturer's instructions). Next, HER2 antibodies were serially diluted in normal cell culture medium, added to the cells and left at room temperature for 9 hours. Mean fluorescent intensities (MFI) of intracellular CypHer5E were measured using the 8200 FMAT (Applied Biosystems, Nieuwerkerk A/D Ijssel, The Netherlands) and 'counts×fluorescence' was used as read-out. An isotype control antibody was used as negative control antibody. $EC_{50}$ values and maximal MFI were determined by means of non-linear regression (sigmoidal dose-response with variable slope) using GraphPad Prism V4.03 software (GraphPad Software, San Diego, Calif., USA).

The results are shown in Table 8, depicting the $EC_{50}$ and maximal MFI values for all tested HER2 antibodies in the CypHer5E internalization assay with AU565 cells. The maximal MFI values indicate how many HER2 receptors are internalized upon antibody binding. All HER2 antibodies showed higher maximal MFI values (137,904-38,801) compared to trastuzumab (35,000) and pertuzumab (TH1014-pert) (32,366), indicating that the tested HER2 antibodies induced enhanced receptor internalization. Notably, antibodies that did not compete with trastuzumab or TH1014-pert induced more receptor internalization compared to antibodies that did compete with trastuzumab and TH1014-pert, with the highest MFI achieved by antibodies 098 and 127. Without being limited to theory, this might be inherent to an inability to inhibit HER2 heterodimerization.

TABLE 8

Cypher-5-based internalization assay of HER2 antibodies. Data shown are MFI and $EC_{50}$ values of one representative experiment of two experiments with AU565 cells treated with fab-CypHer5E-labeled HER2 antibodies. Some $EC_{50}$ values could not be calculated (ND). mAbs that compete with Herceptin: PC1014-025, PC1014-091, PC-1014-129, TH1014-pert; mAbs that compete with TH1014-pert: PC1014-169, PC1014-084, trastuzumab; mAbs that compete with TH1014-F5: PC1014-098, PC1014-127, PC1014-159, TH1014-F5: Non-competing mAbs: PC1014-132, PC1104.153.

| Antibody | Cypher 5 | |
|---|---|---|
| | $EC_{50}$ ng/mL | Maximal MFI |
| PC1014-025 | 30.05 | 63428 |
| PC1014-091 | 32.99 | 50711 |
| PC1014-129 | 7.15 | 60302 |
| TH1014-pert | 530 | 32366 |
| PC1014-169 | ND | 38801 |
| PC1014-084 | 30.51 | 71059 |
| trastuzumab | 21.70 | 35000 |
| PC1014-098 | 13.77 | 134575 |
| PC1014-127 | ~9.68 | 137904 |
| PC1014-159 | ND | 92427 |
| TH1014-F5 | 22.65 | 113116 |
| PC1014-132 | 11.42 | 112270 |
| PC1014-153 | ~14.91 | 87531 |

Example 20

Generation of Bispecific Antibodies by 2-MEA-Induced Fab-Arm Exchange

An in vitro method for producing bispecific antibodies is described in WO 2008119353 (Genmab) and reported van der Neut-Kolfschoten et al. (Science. 2007 Sep. 14; 317 (5844):1554-7). Herein, a bispecific antibody is formed by "Fab-arm" or "half-molecule" exchange (swapping of a heavy chain and attached light chain) between two monospecific IgG4- or IgG4-like antibodies upon incubation under mildly reducing conditions. This Fab-arm exchange reaction is the result of a disulfide-bond isomerization reaction wherein the inter heavy-chain disulfide bonds in the hinge regions of monospecific antibodies are reduced and the resulting free cysteines form a new inter heavy-chain disulfide bond with cysteine residues of another antibody molecule with a different specificity. The resulting product is a bispecific antibody having two Fab arms with different sequences.

In a novel invention the knowledge of this natural IgG4 Fab-arm exchange is adapted to generate a method to produce stable IgG1-based bispecific antibodies. The bispecific antibody product generated by this method described below will no longer participate in IgG4 Fab-arm exchange. The basis for this method is the use of complimentary CH3 domains, which promote the formation of heterodimers under specific assay conditions. To enable the production of bispecific antibodies by this method, IgG1 molecules carrying certain mutations in the CH3 domain were generated: in one of the parental IgG1 antibody T350I, K370T and F405L mutations in the other parental IgG1 antibody the K409R mutation.

To generate bispecific antibodies, these two parental antibodies, each antibody at a final concentration of 0.5 mg/mL (equimolar concentration), were incubated with 25 mM 2-mercaptoethylamine-HCl (2-MEA) in a total volume of 100 μL TE at 37° C. for 90 min. The reduction reaction is stopped when the reducing agent 2-MEA is removed by using spin columns (Microcon centrifugal filters, 30 k, Millipore) according to the manufacturer's protocol.

Example 21

HER2×HER2 Bispecific Antibodies Tested in an In Vitro Kappa-Directed ETA' Killing Assay The example shows that HER2×HER2 bispecific antibodies can deliver a cytotoxic agent into tumor cells after internalization in a generic in vitro cell-based killing assay using kappa-directed pseudomonas-exotoxin A (anti-kappa-ETA'). This assay makes use of a high affinity anti-kappa domain antibody conjugated to a truncated form of the pseudomonas-exotoxin A. Similar fusion proteins of antibody binding proteins (IgG-binding motif from Streptococcal protein A or protein G) and diphtheria toxin or *Pseudomonas* exotoxin A have previously been (Mazor Y. et al., *J. Immunol. Methods* 2007; 321:41-59); Kuo S R. et al., 2009 *Bioconjugate Chem.* 2009; 20:1975-1982). These molecules in contrast to anti-kappa-ETA' bound the Fc part of complete antibodies. Upon internalization and endocytic sorting the anti-kappa-ETA' domain antibody undergoes proteolysis and disulfide-bond reduction, separating the catalytic from the binding domain. The catalytic domain is then transported from the Golgi to the endoplasmic reticulum via a KDEL retention motif, and subsequently translocated to the cytosol where it inhibits protein synthesis and induces apoptosis (Kreitman R I et. al., *BioDrugs* 2009; 23:1-13).

The anti-HER2 antibodies used in this example are 025, 153 and 169. In addition a fully human monoclonal IgG1,κ antibody 005 of the following sequence was used:
005:

| | | |
|---|---|---|
| SEQ ID NO: 164 | VH 005 | EVQLVQSGAEVKKPGESLKISCKASGYSFHFYWIGWVRQMPGKGLEWM GSIYPGDSDTRYRPSFQGQVTISADKSISTAYLQWTSLKASDTAIYYCAR QRGDYYYFYGMDVWGQGTTVTVSS |
| SEQ ID NO: 165 | VL 005 | EIVLTQSPGTLSLSPGERATLSCRASQSVSSSYLAWYQQKPGQVPRLLIY GASSRATGIPDRFSGSGSGTDFTLTISRLEPEDFAVYYCQQYGSSLTFGG GTKVEIK |
| SEQ ID NO: 166 | VH CDR1 | GYSFHFYW |
| SEQ ID NO: 167 | VH CDR2 | YPGDSDT |
| SEQ ID NO: 168 | VH CDR3 | ARQRGDYYYFYGMDV |
| SEQ ID NO: 169 | VL CDR1 | QSVSSSY |
| | VL CDR2 | GAS |
| SEQ ID NO: 170 | VL CDR3 | QQYGSSLT |

The following antibodies were used as starting materials:
IgG1-005-ITL=005 IgG1,κ having Ile at position 350, Thr at position 370, and Leu at position 405
IgG1-005-K409R=005 IgG1,κ having an Arg at position 409
IgG1-025-ITL=025 IgG1,κ having Ile at position 350, Thr at position 370, and Leu at position 405
IgG1-153-ITL=153 IgG1,κ having contains Ile at position 350, Thr at position 370, and Leu at position 405
IgG1-153-K409R=153 IgG1,κ having an Arg at position 409
IgG1-169-K409R=169 IgG1,κ having an Arg at position 409
The following bispecific antibodies were generated in analogy with the below procedure:
IgG1-005-ITLxIgG1-169-K409R
IgG1-025-ITLxIgG1-005-K409R
IgG1-025-ITLxIgG1-153-K409R
IgG1-025-ITLxIgG1-169-K409R
IgG1-153-ITLxIgG1-005-K409R
IgG1-153-ITLxIgG1-169-K409R
The bispecific antibodies were produced according to the procedure described in example 20.
The antibody mixtures, containing each antibody at a final concentration of 0.5 mg/mL, was incubated with 25 mM 2-mercaptoethylamine HCl (2-MEA) in a total volume of 100 μL TE at 37° C. for 90 min. To stop the reduction reaction, the reducing agent 2-MEA was removed by desalting the samples using spin columns (Microcon centrifugal filters, 30 k, Millipore) according to the manufacturer's recommendations.

The HER2×HER2 bispecific antibodies were pre-incubated with the anti-kappa-ETA' before incubation with A431 cells. A431 cells express ~15,000 HER2 antibodies per cell (determined via Qifi analysis) and are not sensitive to treatment with 'naked' HER2-antibodies.

First, the optimal concentration of anti-kappa-ETA' was determined for each cell line, i.e. the maximally tolerated dose that does not lead to induction of non-specific cell death. A431 cells (2500 cells/well) were seeded in normal cell culture medium in a 96-wells tissue culture plate (Greiner bio-one) and allowed to adhere for at least 4 hours. These cells were incubated with an anti-kappa-ETA' dilution series, 100, 10, 1, 0.1, 0.01, 0.001 and 0 μg/mL in normal cell culture medium. After 3 days, the amount of viable cells was quantified with Alamarblue (BioSource International, San Francisco, US) according to the manufacturer's instruction. Fluorescence was monitored using the EnVision 2101 Multilabel reader (PerkinElmer, Turku, Finland) with standard Alamarblue settings. The highest concentration anti-kappa-ETA' that did not kill the cells by itself (1 μg/mL for A431 cells) was used for following experiments.

Next, the effect of HER2×HER2 bispecific antibodies and HER2 monospecific antibodies pre-incubated with anti-kappa-ETA' was tested for their ability to induce cell kill. A431 cells were seeded as described above. A dilution series of the HER2 specific antibodies (monospecific and bispecific antibodies) was made and pre-incubated for 30 min with the predetermined concentration of anti-kappa-ETA' before adding them to the cells. After 3 days incubation at 37° C., the amount of viable cells was quantified as described above. The Alamarblue signal of cells treated with anti-kappa-ETA' pre-incubated with the antibodies was plotted compared to cells treated without antibody treatment. $EC_{50}$ values and maximal cell death were calculated using GraphPad Prism 5 software. Staurosporin (23.4 μg/mL) was used as positive control for cell killing. An isotype control antibody (IgG1/kappa; IgG1-3G8-QITL) was used as negative control.

Figure 9:
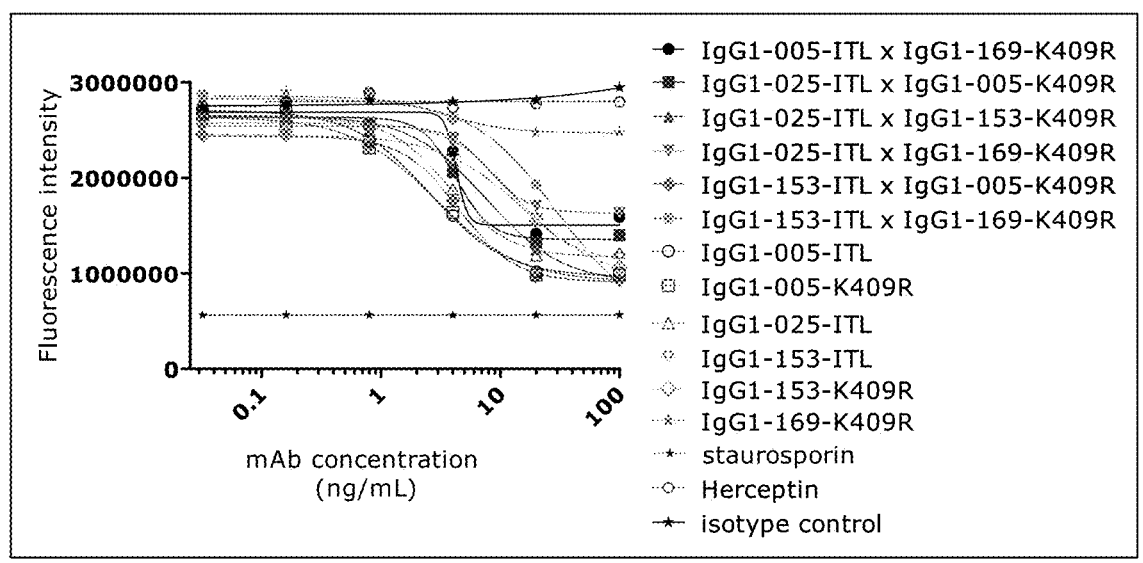
FIG. 9: Killing of A431 cells induced by anti-kappa-ETA' pre-incubated HER2×HER2 bispecific antibodies. The viability of A431 cells after 3 days incubation with HER2 antibodies, pre-incubated with anti-kappa-ETA'. Cell viability was quantified using Alamarblue. Data shown are fluorescence intensities (FI) of one experiment with A431 cells treated with anti-kappa-ETA'-conjugated HER2 antibodies and HER2×HER2 bispecific antibodies. Staurosporin was used as positive control, whereas an isotype control antibody was used as negative control.

FIG. 9 and table 9 shows that all anti-kappa-ETA' pre-incubated HER2 bispecific antibodies were able to kill A431 cells in a dose-dependent manner. These results demonstrate that most HER2 bispecific antibodies tested were more effective than the monospecific antibody present in the combination in this anti-kappa-ETA' assay. In addition, the efficacy of bispecific antibody 005X169, 025X169 and 153X169 showed that the efficacy of a monospecific antibody which lacks activity in this in vitro kappa-directed ETA' killing, HER2 specific antibody (169), can be increased through bispecific combination with another HER2 specific antibody.

TABLE 9

$EC_{50}$ values and maximal percentage cell kill of AU565 cells treated with anti-kappa-ETA'-conjugated HER2 × HER2 bispecific antibodies.

| antibody | percentage kill | EC50 [ng/mL] |
|---|---|---|
| Herceptin | 2.79 | Ndet |
| IgG1-005-ITL | 79.34 | 2.57 |
| IgG1-005-K409R | 79.83 | 2.87 |
| IgG1-025-ITL | 69.81 | 3.76 |
| IgG1-153-ITL | 70.66 | 12.45 |
| IgG1-153-K409R | 72.84 | 15.47 |
| IgG1-169-K409R | 16.45 | 3.45 |
| IgG1-005-ITL × IgG1-169-K409R | 59.94 | 4.28 |
| IgG1-025-ITL × IgG1-005-K409R | 63.45 | 4.27 |
| IgG1-025-ITL × IgG1-153-K409R | 80.82 | 7.66 |
| IgG1-025-ITL × IgG1-169-K409R | 45.88 | 7.97 |
| IgG1-153-ITL × IgG1-005-K409R | 80.05 | 4.51 |
| IgG1-153-ITL × IgG1-169-K409R | 84.68 | 29.14 |

"Ndet" means not detected.

Example 22

HER2 Receptor Downmodulation by Incubation with Bispecific Antibodies Targeting Different HER2 Epitopes HER2×HER2 bispecific antibodies may bind two different epitopes on two spatially different HER2 receptors. This may allow other HER2×HER2 bispecific antibodies to bind to the remaining epitopes on these receptors. This could result in multivalent receptor crosslinking (compared to dimerization induced by monovalent antibodies) and consequently enhance receptor downmodulation. To investigate whether HER2×HER2 bispecific antibodies induce enhanced downmodulation of HER2, AU565 cells were incubated with antibodies and bispecific antibodies for three days. Total levels of HER2 and levels of antibody bound HER2 were determined.

AU565 cells were seeded in a 24-well tissue culture plate (100.000 cells/well) in normal cell culture medium and cultured for three days at 37° C. in the presence of 10 μg/mL HER2 antibody with either the ITL or the K409R mutation or HER2×HER2 bispecific antibodies. As a control, the combination of two monospecific HER2 antibodies, with unmodified IgG1 backbones, was also tested (1:1), at a final concentration of 10 μg/mL. After washing with PBS, cells were lysed by incubating them for 30 min at room temperature with 25 μL Surefire Lysis buffer (Perkin Elmer, Turku, Finland). Total protein levels were quantified using bicinchoninic acid (BCA) protein assay reagent (Pierce) following manufacturer's protocol. HER2 protein levels in the lysates were analyzed using a HER2-specific sandwich ELISA. Rabbit-anti-human HER2 intracellular domain antibody (Cell Signaling) was used to capture HER2 and biotinylated goat-anti-human HER2 polyclonal antibody R&D systems, Minneapolis, USA), followed by streptavidin-poly-HRP, were used to detect bound HER2. The reaction was visualized using 2,2'-azino-bis 3-ethylbenzothiazoline-6-sulfonic acid (one ABTS tablet diluted in 50 mL ABTS buffer [Roche Diagnostics, Almere, The Netherlands]) and stopped with oxalic acid (Sigma-Aldrich, Zwijndrecht, The Netherlands). Fluorescence at 405 nm was measured on a microtiter plate reader (Biotek Instruments, Winooski, USA) and the amount of HER2 was expressed as a percentage relative to untreated cells.

Figure 10:
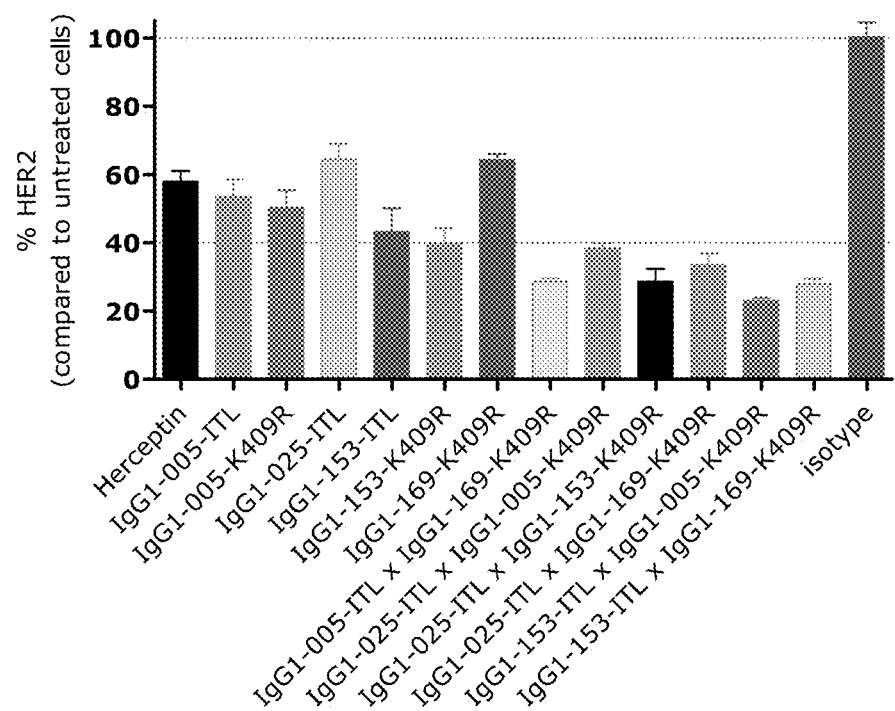
FIG. 10: HER2×HER2 bispecific molecules induced downmodulation of HER2 receptor. Relative percentage of HER2 expression levels in AU565 cell lysates after 3 days incubation with 10 µg/mL mAb. The amount of HER2 was quantified using a HER2-specific capture ELISA and depicted as percentage inhibition compared to untreated cells. Data shown is the mean of two experiments plus standard deviation, except for combinations of monospecific IgG1 antibodies which were tested once.

The results are shown in FIG. 10 and Table 10 which demonstrates that all the tested HER2×HER2 bispecific antibodies induced ≥40% HER2 downmodulation. Interestingly, all HER2×HER2 bispecific antibodies demonstrated increased HER2 downmodulation compared to both of their monospecific counterparts.

TABLE 10

HER2 × HER2 bispecific induced downmodulation of HER2 depicted as percentage HER2 compared to untreated cells

| antibody | % HER2 compared to untreated cells |
|---|---|
| Herceptin | 71 |
| IgG1-005-ITL | 54 |
| IgG1-005-K409R | 50 |
| IgG1-025-ITL | 64 |
| IgG1-153-ITL | 43 |
| IgG1-153-K409R | 40 |
| IgG1-169-K409R | 64 |
| IgG1-005-ITL × IgG1-169-K409R | 29 |
| IgG1-025-ITL × IgG1-005-K409R | 38 |
| IgG1-025-ITL × IgG1-153-K409R | 29 |
| IgG1-025-ITL × IgG1-169-K409R | 34 |
| IgG1-153-ITL × IgG1-005-K409R | 23 |
| IgG1-153-ITL × IgG1-169-K409R | 28 |
| IgG1-005 + IgG1-169 | 28 |
| IgG1-025 + IgG1-005 | 28 |
| IgG1-025 + IgG1-153 | 23 |
| IgG1-025 + IgG1-169 | 25 |
| IgG1-153 + IgG1-005 | 23 |
| IgG1-153 + IgG1-169 | 23 |
| isotype control | 108 |

Example 23

Colocalization of HER2×HER2 Bispecific Antibodies with Lysosomal Marker LAMP1 Analyzed by Confocal Microscopy The HER2 downmodulation assay as described in Example 22 indicated that HER2×HER2 bispecific antibodies were able to increase lysosomal degradation of HER2. To confirm these findings, confocal microscopy technology was applied. AU565 cells were grown on glass coverslips (thickness 1.5 micron, Thermo Fisher Scientific, Braunschweig, Germany) in standard tissue culture medium at 37° C. for 3 days. Cells were pre-incubated for 1 hour with 50 μg/mL leupeptin (Sigma) to block lysosomal activity after which 10 μg/mL HER2 monospecific antibodies or HER2×HER2 bispecific antibodies were added. Also the combination of two monospecific IgG1 antibodies (1:1) was tested at a final concentration of 10 μg/mL. The cells were incubated for an additional 3 or 18 hours at 37° C. Hereafter the cells were washed with PBS and incubated for 30 min. at room temperature with 4% formaldehyde (Klinipath). Slides were washed with blocking buffer (PBS supplemented with 0.1% saponin [Roche] and 2% BSA [Roche]) and incubated for 20 min with blocking buffer containing 20 mM $NH_4Cl$ to quench formaldehyde. Slides were washed again with blocking buffer and incubated for 45 min at room temperature with mouse-anti-human CD107a (LAMP1) (BD Pharmingen) to stain/identify lysosomes. Following washing with blocking buffer, the slides were incubated 30 min at room temperature with a cocktail of secondary antibodies; goat-anti-mouse IgG-Cy5 (Jackson) and goat-anti-human IgG- FITC (Jackson). Slides were washed again with blocking buffer and mounted overnight on microscope slides using 20 µL mounting medium (6 gram Glycerol [Sigma] and 2.4 gram Mowiol 4-88 [Omnilabo] was dissolved in 6 mL distilled water to which 12 mL 0.2M Tris [Sigma] pH8.5 was added followed by incubation for 10 min at 50-60° C. Mounting medium was aliquoted and stored at −20° C.). Slides were imaged with a Leica SPE-II confocal microscope (Leica Microsystems) equipped with a 63× 1.32-0.6 oil immersion objective lens and LAS-AF software. To allow for quantification of overlapping pixel intensities, saturation of pixels should be avoided. Therefore the FITC laser intensity was decreased to 10%, smart gain was set at 830 V and smart offset was set at −9.48%. By using these settings, the bispecific antibodies were clearly visualized without pixel saturation, but the monospecific antibodies were sometimes difficult to detect. To compare lysosomal colocalization between monospecific and bispecific antibodies, these settings were kept the same for all analyzed confocal slides.

12-bit grayscale TIFF images were analyzed for colocalisation using MetaMorph® software (version Meta Series 6.1, Molecular Devices Inc, Sunnyvale Calif., USA). FITC and Cy5 images were imported as stacks and background was subtracted. Identical thresholds settings were used (manually set) for all FITC images and all Cy5 images. Colocalisation was depicted as the pixel intensity of FITC in the region of overlap (ROI), were the ROI is composed of all Cy5 positive regions. To compare different slides stained with several HER2 antibodies, HER2×HER2 bispecific antibodies or the combination of two different monospecific antibodies the images were normalized using the pixel intensity of Cy5. Goat-anti-mouse IgG-Cy5 was used to stain the lysosomal marker LAMP1 (CD107a). The pixel intensity of LAMP1 should not differ between various HER2 antibodies or the HER2×HER2 bispecific antibodies tested (one cell had a pixel intensity of Cy5 of roughly 200.000).

Normalized values for colocalization of FITC and Cy5=[(TPI-FITC×percentage FITC-Cy5 colocalization)/100]×[200.000/TPI-Cy5]

Figure 11A:
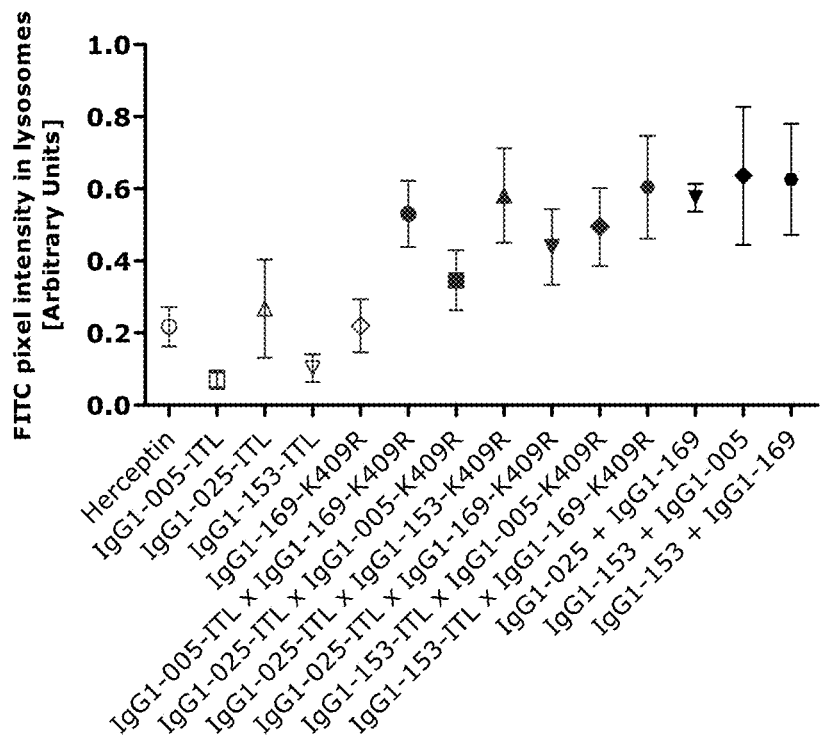
FIGS. 11A and 11B: Colocalization analysis of HER2× HER2 bispecific antibodies (FITC) with lysosomal marker LAMP1 (Cy5). FITC pixel intensity overlapping with Cy5 for various monospecific HER2 antibodies and HER2× HER2 bispecific antibodies (FIG. 11A) FITC pixel intensity in LAMP1/Cy5 positive pixels of three different images is plotted for each antibody tested. Monospecifics show lower FITC pixel intensities in the LAMP1/Cy5 positive pixels compared to bispecifics.
Figure 11B:
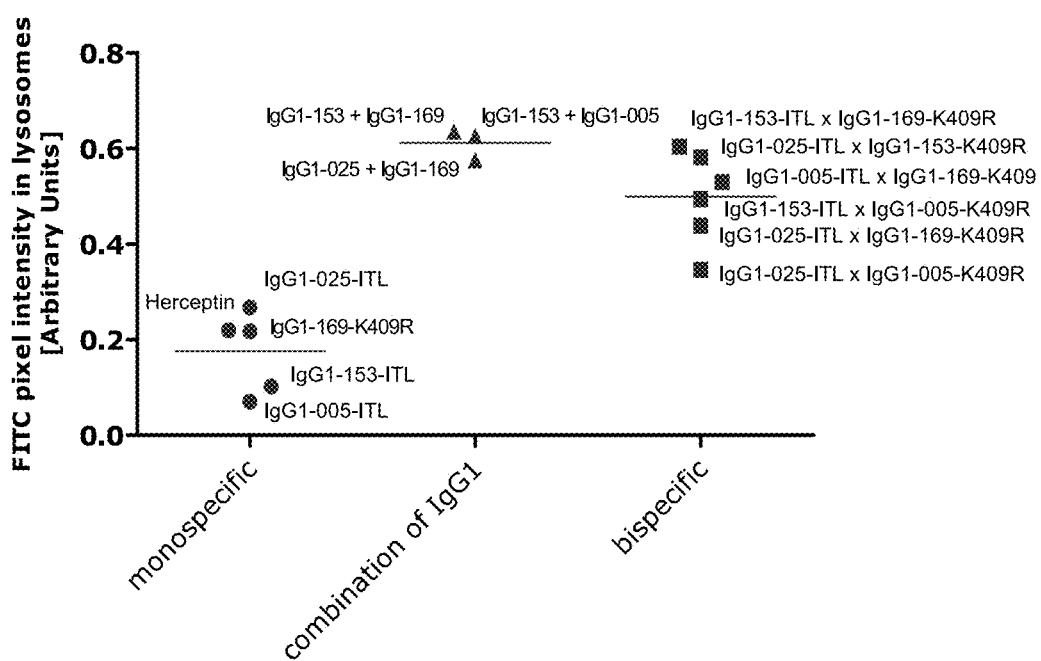

In this formula, TPI stands for Total Pixel Intensity.
FIG. 11 and Table 11 present percentage of viable cells, as measured by the FITC pixel intensity overlapping with Cy5 for various monospecific HER2 antibodies and HER2×HER2 bispecific antibodies. For each antibody or bispecific molecule depicted, three different images were analyzed from one slide containing ~1, 3 or >5 cells. Significant variation was observed between the different images within each slide. However, it was evident that all HER2×HER2 bispecific antibodies demonstrate increased colocalisation with the lysosomal marker LAMP1, when compared with their monospecific counterparts. These results indicate that once internalized, HER2×HER2 bispecific antibodies are efficiently sorted towards lysosomal compartments, making them suitable for a bispecific antibody drug conjugate approach.

TABLE 11

Mean FITC pixel intensities overlapping with Cy5 depicted as arbitrary units

| antibody | FITC pixel intensity in lysosomes [arbitrary units] |
| --- | --- |
| Herceptin | 0.218 |
| IgG1-005-ITL | 0.070 |
| IgG1-025-ITL | 0.268 |
| IgG1-153-ITL | 0.102 |

TABLE 11-continued

Mean FITC pixel intensities overlapping with Cy5 depicted as arbitrary units

| antibody | FITC pixel intensity in lysosomes [arbitrary units] |
| --- | --- |
| IgG1-169-K409R | 0.220 |
| IgG1-005-ITL × IgG1-169-K409R | 0.531 |
| IgG1-025-ITL × IgG1-005-K409R | 0.347 |
| IgG1-025-ITL × IgG1-153-K409R | 0.582 |
| IgG1-025-ITL × IgG1-169-K409R | 0.439 |
| IgG1-153-ITL × IgG1-005-K409R | 0.494 |
| IgG1-153-ITL × IgG1-169-K409R | 0.604 |
| IgG1-025 + IgG1-169 | 0.576 |
| IgG1-153 + IgG1-005 | 0.636 |
| IgG1-153 + IgG1-169 | 0.626 |

Example 24

Inhibition of Proliferation of AU565 Cells Upon Incubation with HER2 Monospecific or HER2×HER2 Bispecific Antibodies The HER2×HER2 bispecific antibodies were tested for their ability to inhibit proliferation of AU565 cells in vitro. Due to the high HER2 expression levels on AU565 cells ~1.000.000 copies per cell as determined with Qifi-kit), HER2 is constitutively active in these cells and thus not dependent on ligand-induced heterodimerization. In a 96-wells tissue culture plate (Greiner bio-one, Frickenhausen, Germany), 9.000 AU565 cells were seeded per well in the presence of 10 µg/mL HER2 antibody or HER2× HER2 bispecific antibodies in serum-free cell culture medium. As a control, cells were seeded in serum-free medium without antibody or bispecific antibodies. After three days, the amount of viable cells was quantified with Alamarblue (BioSource International, San Francisco, US) according to the manufacturer's instructions. Fluorescence was monitored using the EnVision 2101 Multilabel reader (PerkinElmer, Turku, Finland) with standard Alamarblue settings. The Alamarblue signal of antibody-treated cells was plotted as a percentage relative to untreated cells.

Figure 12:
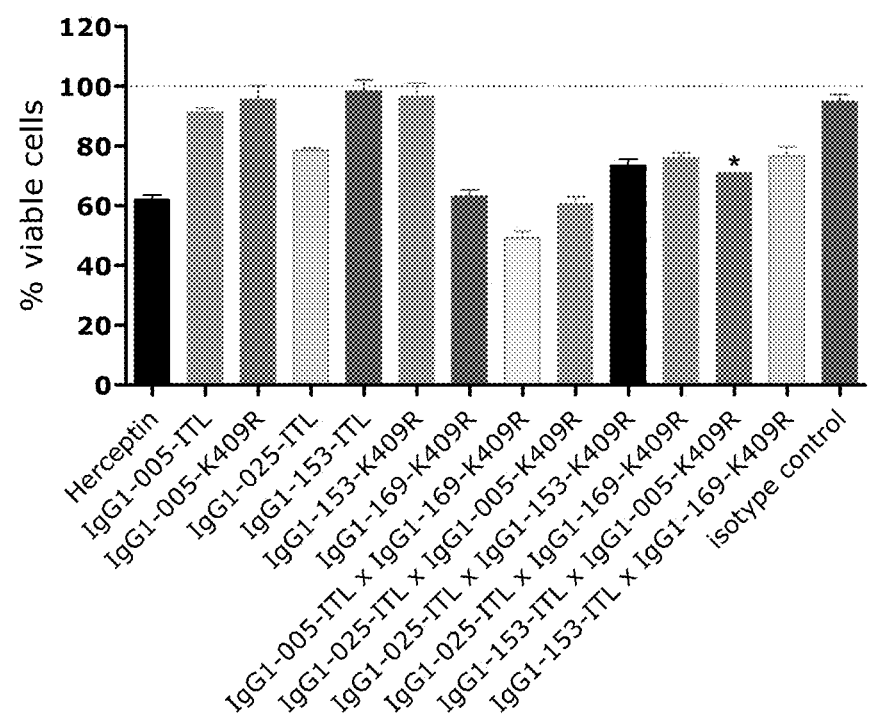
FIG. 12: Inhibition of proliferation by HER-2 mono and bispecific antibodies. AU565 cells were seeded in the presence of 10 µg/mL HER2 antibody or HER2×HER2 bispecific antibody in serum-free cell culture medium. After three days, the amount of viable cells was quantified with Alamarblue and cell viability was presented as a percentage relative to untreated cells. An isotype control antibody was used as negative control. Data shown are percentage viable AU565 cells compared to untreated cells measured in five-fold±the standard deviation. *indicates only one data point was depicted.

FIG. 12 and table 12 depicts the fluorescent intensity of Alamarblue of AU565 cells after incubation with HER2 antibodies and HER2×HER2 bispecific antibodies. Herceptin® (trastuzumab) was included as positive control and demonstrated inhibition of proliferation as described by Juntilla T T. et al., Cancer Cell 2009; 15: 429-440. All HER2×HER2 bispecific antibodies were able to inhibit proliferation of AU565 cells. Bispecific antibodies: IgG1-005-ITL×IgG1-169-K409R and IgG1-025-ITL×IgG1-005-K409R were more effective compared to their monospecific antibody counterparts in this assay.

TABLE 12

Percentage viable AU565 cells after treatment with HER2 × HER2 bispecific antibodies.

| antibody | percentage viable cells |
| --- | --- |
| Herceptin | 62 |
| IgG1-005-ITL | 91 |
| IgG1-005-K409R | 96 |
| IgG1-025-ITL | 79 |

TABLE 12-continued

Percentage viable AU565 cells after treatment
with HER2 x HER2 bispecific antibodies.

| antibody | percentage viable cells |
|---|---|
| IgG1-153-ITL | 98 |
| IgG1-153-K409R | 97 |
| IgG1-169-K409R | 63 |
| IgG1-005-ITL × IgG1-169-K409R | 49 |
| IgG1-025-ITL × IgG1-005-K409R | 61 |
| IgG1-025-ITL × IgG1-153-K409R | 74 |
| IgG1-025-ITL × IgG1-169-K409R | 76 |
| IgG1-153-ITL × IgG1-005-K409R | 71 |
| IgG1-153-ITL × IgG1-169-K409R | 77 |
| isotype control | 95 |

Example 25

Her2×CD3 Bispecific Antibodies Tested in an In Vitro Cytotoxicity Assay

CD3 is a co-receptor in the T cell receptor complex expressed on mature T cells. Combination of a CD3 specific antibody Fab-arm with a tumor antigen specific antibody Fab-arm in a bispecific antibody would result in the specific targeting of T cells to tumor cells, leading to T cell mediated tumor cell lysis. Likewise, CD3 positive T cells could be targeted to other derailed cells in the body, to infected cells or directly to pathogens.

HER2×CD3 bispecific antibodies were generated. Heavy and light chain variable region sequences for the HER2 specific Fab-arm were as indicated for antibody 153 and 169 in Example 21. The following heavy and light chain variable region sequences for the CD3 specific Fab-arm were used: YTH12.5 (Sequence as described by Routledge et al., Eur J Immunol. 1991, 21(11):2717-25)

```
SEQ VH     EVQLLESGGGLVQPGGSLRLSCAASGFTFSSFPMAWVRQAPGKGLEWVSTI
ID YTH12.5 STSGGRTYYRDSVKGRFTISRDNSKNTLYLQMNSLRAEDTAVYYCAKFRQYS
NO:        GGFDYWGQGTLVTVSS
171

SEQ VL     DIQLTQPNSVSTSLGSTVKLSCTLSSGNIENNYVHWYQLYEGRSPTTMIYDD
ID YTH12.5 DKRPDGVPDRFSGSIDRSSNSAFLTIHNVAIEDEAIYFCHSYVSSFNVFGGGT
NO:        KLTVL
172
``` huCLB-T3/4 (Sequence as described by Parren et al., Res Immunol. 1991, 142(9):749-63. Minor amino acid substitutions were introduced to make the sequence resemble the closest human germline)

```
SEQ VH      EVQLVESGGGLVKPGGSLRLSCAASGFTFSSYGMFWVRQAPGKGLEWVAT
ID huCLB-   ISRYSRYIYYPDSVKGRFTISRDNAKNSLYLQMNSLRAEDTAVYYCARRPLY
NO: T3/4    GSSPDYWGQGTLVTVSS
173

SEQ VL      EIVLTQSPATLSLSPGERATLSCSASSSVTYVHWYQQKPGQAPRLLIYDTSK
ID huCLB-   LASGIPARFSGSGSGTDFTLTISSLEPEDFAVYYCFQGSGYPLTFGSGTKLEM
NO: T3/4    R
174
```

All antibodies were expressed as IgG1,κ being modified in their Fc regions as follows: IgG1-HER2-153-K409R and IgG1-HER2-153-N297Q-K409R, IgG1-HER2-169-K409R, IgG1-hu-CLB-T3/4-F405L and IgG1-hu-CLB-T3/4-N297Q-F405L, IgG1-YTH12.5-F405L and IgG1-YTH12.5-N297Q-F405L.

Bispecific antibodies from these HER2 and CD3 specific antibodies were generated as described in Example 20 and tested in an in vitro cytotoxicity assay using AU565 cells. AU565 cells were cultured to near confluency. Cells were washed twice with PBS, and trypsinized for 5 minutes at 37° C. 12 mL culture medium was added to inactivate trypsin and cells were spun down for 5 min, 800 rpm. Cells were resuspended in 10 mL culture medium and a single cell suspension was made by passing the cells through a cell-strainer. 100 µL of a 5×10$^5$ cells/mL suspension was added to each well of a 96-well culture plate, and cells were incubated at least 3 hrs at 37° C., 5% CO2 to allow adherence to the plate. Peripheral blood mononuclear cells (PBMC) were isolated from blood from healthy volunteers using Leucosep 30 mL tubes, according to the manufacturer's protocol (Greiner Bio-one). T cells were isolated from PBMC preparations by negative selection using the Untouched Human T-cells Dynabead kit (Dynal). Isolated cells were resuspended in culture medium to a final concentration op 7×10$^6$ cells/mL.

Culture medium was removed from the adhered AU565 cells, and replaced with 50 µl/well 2× concentrated antibody-dilution and 50 µl/well 7×10$^6$ T cells/mL (ratio effector:target=7:1). Plates were incubated for 3 days at 37° C., 5% CO2. Supernatants were removed and plates were washed twice with PBS. To each well 150 µL culture medium and 15 µL Alamar blue was added. Plates were incubate for 4 hours at 37° C., 5% CO2, and absorbance was measured (Envision, Perkin Elmer).

Figure 13:
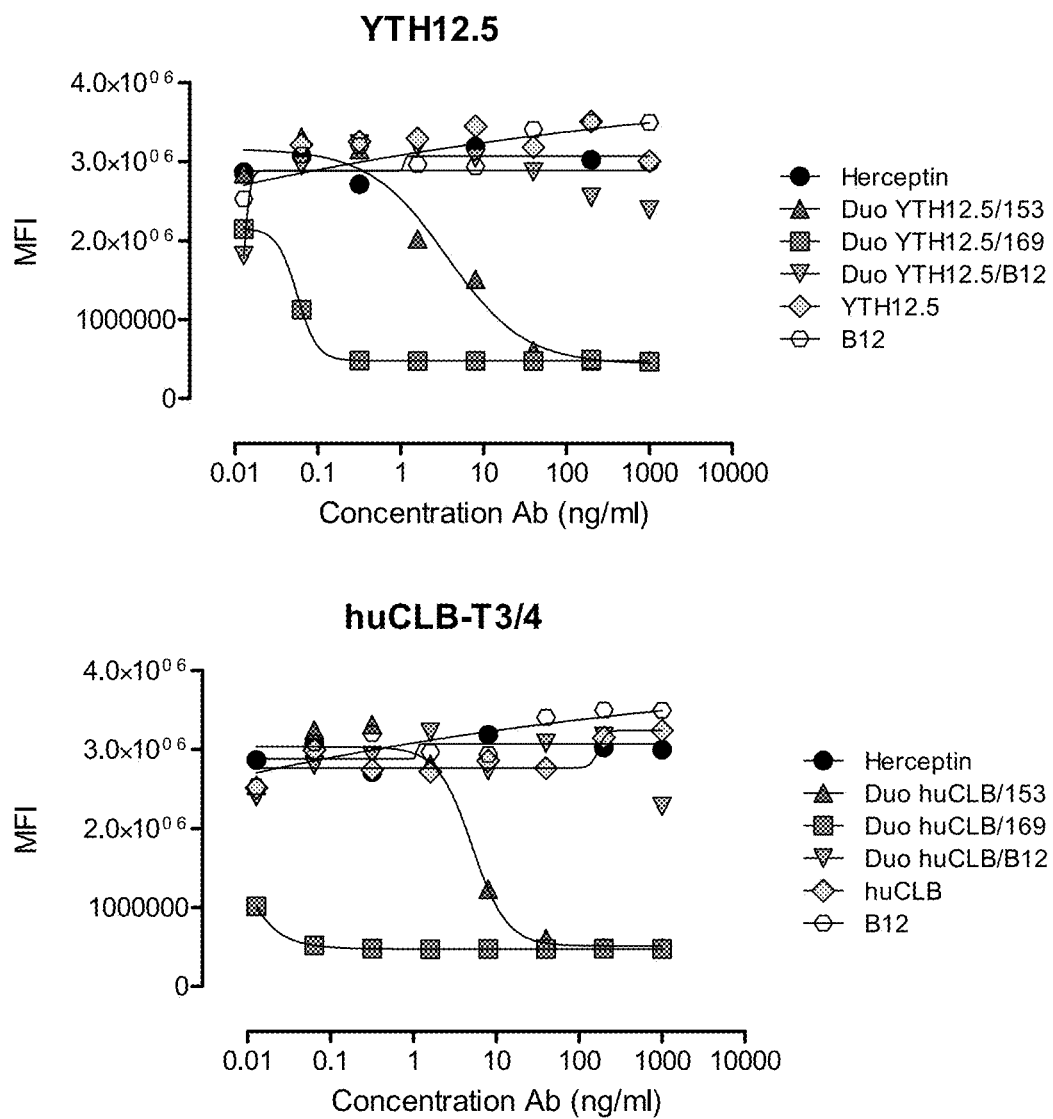
FIG. 13: T cell mediated cytotoxicity of AU565 cells by HER2×CD3 bispecific antibodies as well as by N297Q mutants of HER2×CD3 bispecific antibodies (bispecific indicated as Duo in the figure).
Figure 13:
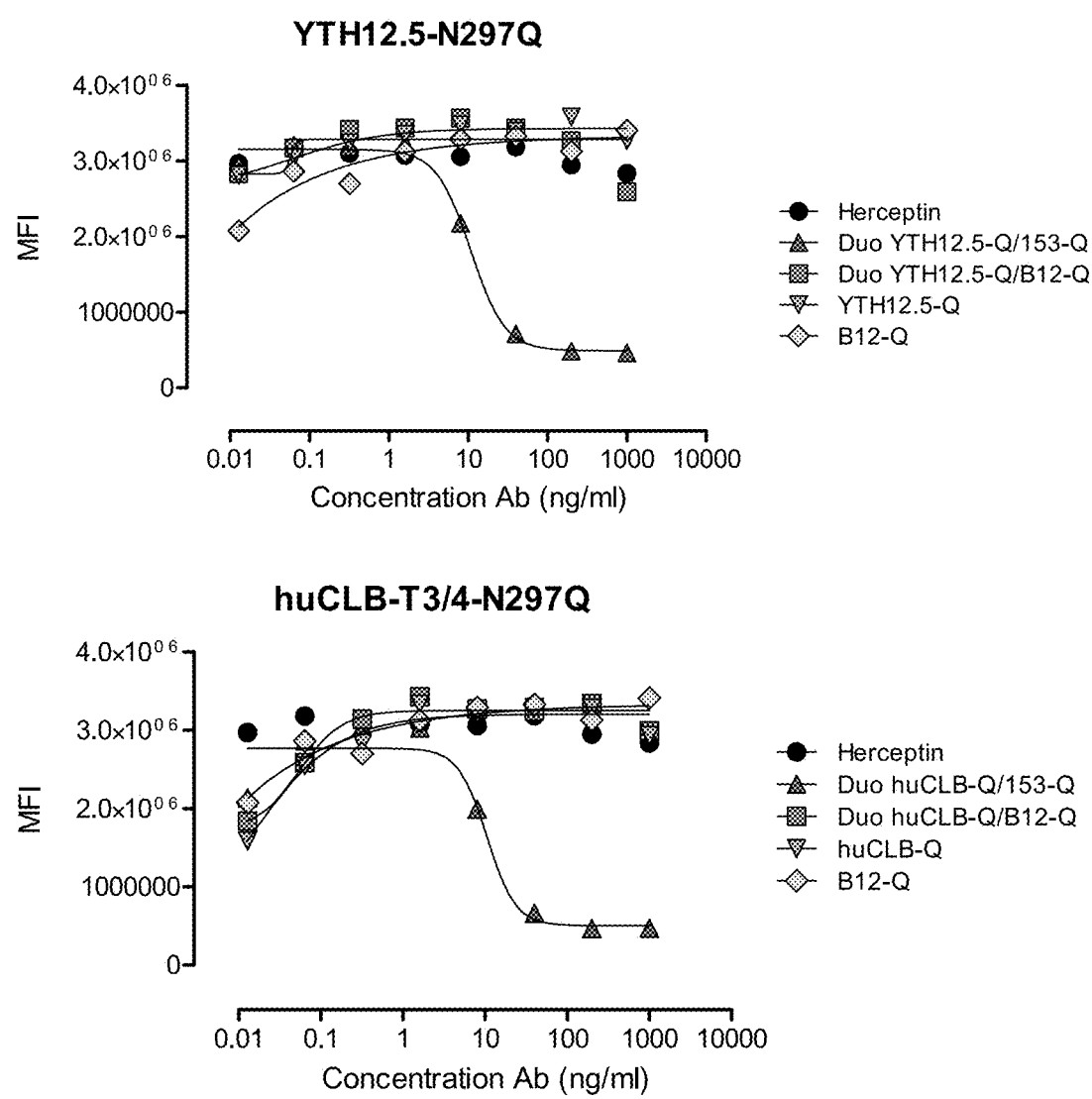

FIG. 13 and table 13 shows that whereas control antibodies (Her2 monospecific IgG1-Herceptin®, CD3 monospecific IgG1-YTH12.5 and monospecific IgG1-huCLB-T3/4, irrelevant antigen monospecific IgG1-b12, and CD3×b12 bispecific antibodies) did not induce T cell mediated cytotoxicity, bispecific (Duo) Her2×CD3 antibodies huCLB/Her2-153, huCLB/Her2-169, YTH12.5/Her2-153 and YTH12.5/Her2-169 induced dose dependent T cell mediated cytotoxicity of AU565 cells. Bispecific antibodies containing Her2-169 were more potent than those containing Her2-153.

Mutants of IgG1-hu-CLB-T3/4, IgG1-YTH12.5 and Her2-153 were made containing a N297Q mutation to remove a glycosylation site; glycosylation at this site is critical for IgG-Fcgamma receptor interactions (Bolt S et al., *Eur J Immunol* 1993, 23:403-411). FIG. 13 shows that N297Q mutation and therefore absence of Fc glycosylation of Her2×CD3 bispecific antibodies YTH12.5/Her2-153 and huCLB/Her2-153 did not impact the potential to induce dose dependent T cell mediated cytotoxicity of AU565 cells.

TABLE 13

$EC_{50}$ values of cell kill induced by HER2 × CD3 bispecific antibodies.

| antibody | EC50 [ng/mL] |
| --- | --- |
| Herceptin | Ndet |
| Duo huCLB-Q/153-Q | 10.55 |
| Duo huCLB-Q/B12-Q | Ndet |
| huCLB-Q | Ndet |
| B12-Q | Ndet |
| Duo YTH12.5-Q/153-Q | 10.73 |
| Duo YTH12.5-Q/B12-Q | Ndet |
| YTH12.5-Q | Ndet |
| B12-Q | Ndet |

"Ndet" means not detected.

Example 26

HER2 Downmodulation

To investigate if enhanced HER2 internalization induced by Group 3 antibodies 098 and 153 also results in enhanced receptor downmodulation, AU565 cells were incubated with HER2 antibodies for 3 days, and analyzed for presence of HER2. AU565 cells were seeded in a 24-wells tissue culture plate (100.000 cells/well) in normal cell culture medium and cultured for 3 days at 37° C. in the presence of 10 μg/mL HER2 antibody. After washing with PBS, cells were lysed by incubating 30 min at room temperature with 25 μL Surefire Lysis buffer (Perkin Elmer, Turku, Finland). Total protein levels were quantified using bicinchoninic acid (BCA) protein assay reagent (Pierce) according to the manufacturer's protocol. HER2 protein levels in the lysates were analyzed using a HER2-specific sandwich ELISA. Rabbit-anti-human HER2 intracellular domain antibody (Cell Signaling) was used to capture HER2 and biotinylated goat-anti-human HER2 polyclonal antibody (R&D), followed by streptavidin-poly-HRP, were used to detect bound HER2. The reaction was visualized using 2,2'-azino-bis 3-ethylbenzothiazoline-6-sulfonic acid (ABTS: dilute one ABTS tablet in 50 mL ABTS buffer [Roche Diagnostics, Almere, The Netherlands]) and stopped with oxalic acid (Sigma-Aldrich, Zwijndrecht, The Netherlands). Fluorescence at 405 nm was measured on a microtiter plate reader (Biotek Instruments, Winooski, USA) and the amount of HER2 was expressed as a percentage relative to untreated cells.

Figure 14:
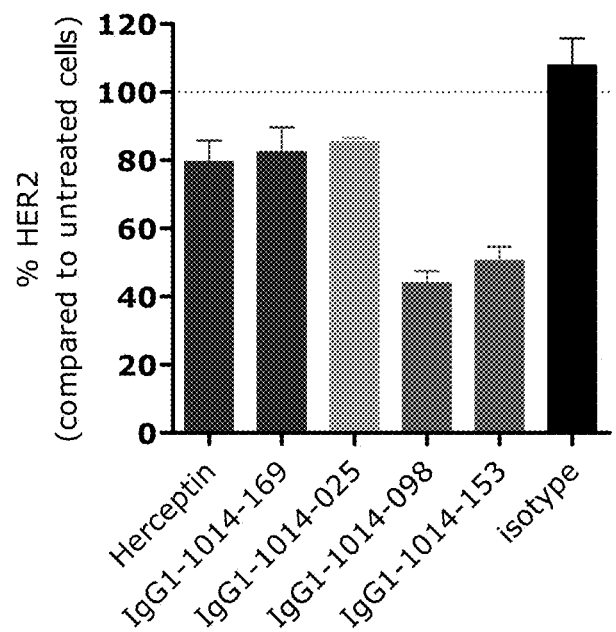
FIG. 14: Antibody induced downmodulation of HER2. Relative percentage of HER2 expressed in AU565 cell lysate after 3 days incubation with 10 µg/mL antibody. The amount of HER2 was quantified using a HER2-specific capture ELISA and plotted as a percentage relative to untreated cells. Data shown are mean of three experiments±standard deviation.

The results shown in FIG. 14 and Table 14 demonstrate that both Group 3 antibodies (098 and 153) induced more than 50% HER2 downmodulation. In contrast, antibodies 025, 169 and Herceptin barely induced downmodulation (approximately 20% of untreated cells). This was in line with enhanced internalization observed by antibodies 098 and 153.

TABLE 14

Antibody induced downmodulation of HER2 depicted as percentage HER2 compared to untreated cells

| antibody | % HER2 compared to untreated cells |
| --- | --- |
| Herceptin | 80 |
| IgG1-1014-169 | 82 |
| IgG1-1014-025 | 85 |
| IgG1-1014-098 | 44 |
| IgG1-1014-153 | 50 |
| isotype control | 108 |

Example 27

Colocalization of HER2 Antibodies with Lysosomal Marker LAMP1 Analyzed by Confocal Microscopy The HER2 downmodulation assay as described in example 26 and the CypHer-5E based internalization assay as described in example 19 indicated that HER2 antibodies from group 3 were more efficiently internalized and targeted towards lysosomes compared to antibodies from Groups 1 and 2. However, in these experiments the confocal imaging was done with settings that allowed discriminating between monospecific and bispecific antibodies but not between different monospecific antibodies, in fact, with these settings monospecific antibodies could hardly be detected. To be able to compare between the different monospecific antibodies, the confocal slides were measured again with increased gain settings, to enhance fluorescence intensity. All other steps of the procedure were the same as described in example 23.

Figure 15:
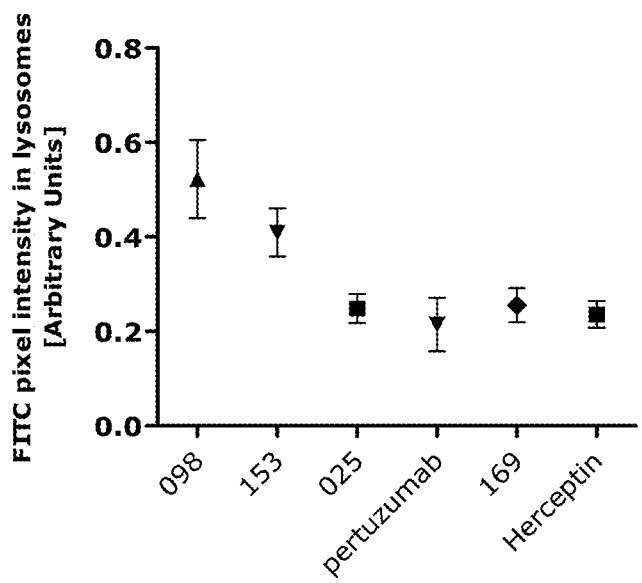
FIG. 15: Colocalization analysis of HER2 antibodies (FITC) with lysosomal marker LAMP1 (Cy5). FITC pixel intensity overlapping with Cy5 for various monospecific HER2 antibodies. FITC pixel intensity in LAMP1/Cy5 positive pixels of three different images is plotted for each antibody. Group 3 antibodies 098 and 153 show higher FITC pixel intensities in the LAMP1/Cy5 positive compartments compared to antibodies 025 and pertuzumab from Group 2 and 169 and Herceptin from Group 1.

The results are depicted in FIG. 15 and Table 15, and show that the FITC pixel intensity overlapping with Cy5 for various monospecific HER2 antibodies. From each slide three different images were analyzed containing ~1, 3 or >5 cells. Significant variation was observed between the different images within each slide. Still, it was evident that antibodies 098 and 153 were more efficiently targeted towards lysosomal compartments, compared to 025, pertuzumab, 169 and Herceptin. This correlated well with the enhanced internalization and receptor degradation induced by these antibodies.

TABLE 15

Mean FITC pixel intensities overlapping with Cy5 depicted as arbitrary units

| antibody | FITC pixel intensity in lysosomes [arbitrary units] |
| --- | --- |
| TH1014-098 | 0.522 |
| TH1014-153 | 0.409 |
| TH1014-025 | 0.248 |
| TH1014-pert | 0.214 |
| TH1014-169 | 0.255 |
| Herceptin | 0.236 |

Example 28

HER2 Extracellular Domain Shuffle Human-To-Chicken

To further define the HER2 binding regions recognized by antibodies from the four different cross-competition groups, a HER2 extracellular domain shuffle experiment was performed. To this end, a small gene-synthesis library with five constructs was generated, swapping the sequences of domain I, II, III or IV of the extracellular domain of human HER2 to the corresponding sequence of chicken HER2 (Gallus gallus isoform B NCBI: NP_001038126.1): 1) fully human HER2 (Uniprot P04626) hereafter named hu-HER2, 2) hu-HER2 with chicken domain I (replacing amino acids (aa) 1-203 of the human Her2 with the corresponding chicken Her2 region) hereafter named hu-HER2-ch(I), 3) hu-HER2 with chicken domain II (replacing amino acids (aa) 204-330 of the human Her2 with the corresponding chicken Her2 region) hereafter named hu-HER2-ch(II), 4) hu-HER2 with chicken domain III (replacing aa 331-507 of the human Her2 with the corresponding chicken Her2 region) hereafter named hu-HER2-ch(III) and 5) hu-HER2 with chicken domain IV (replacing aa 508-651 of the human Her2 with the corresponding chicken Her2 region) hereafter named hu-HER2-ch(IV). The human and chicken HER2 orthologs show 67% homology in their extracellular domain with 62% homology in domain I, 72% homology in domain II, 63% homology in domain III and 68% homology in domain IV. The constructs were transiently transfected in the Freestyle™ CHO—S (Invitrogen) cell line using Freestyle MAX transfection reagent (Invitrogen) according to the instructions of the manufacturer, and transfected cells were cultured for 20 hours. HER2 antibody binding to the transfected cells was analyzed by means of flow cytometry: The transfected CHO—S cells were harvested, washed with FACS buffer and incubated with 10 μg/mL HER2 antibody (30 minutes on ice). Binding of HER2 antibodies was detected using a Phycoerythrin (PE)-conjugated goat-anti-human IgG antibody (Jackson). To check if expression between different batches was the same, cells were fixed and permeabilized using Cytofix/Cytoperm solution (BD) according manufacturer's instruction and stained with a rabbit-anti-human intracellular HER2 antibody (DAKO) in combination with a secondary PE-conjugated goat-anti-rabbit antibody (Jackson). An isotype control antibody was used as negative control. Fluorescence was measured on a FACSCanto-II (BD) and binding curves were made by means of non-linear regression (sigmoidal dose-response with variable slope) using GraphPad Prism V4.03 software (GraphPad Software, San Diego, Calif., USA). Loss of binding was used as read out to identify which HER2 domains were recognized by the different antibodies.

Figure 16:
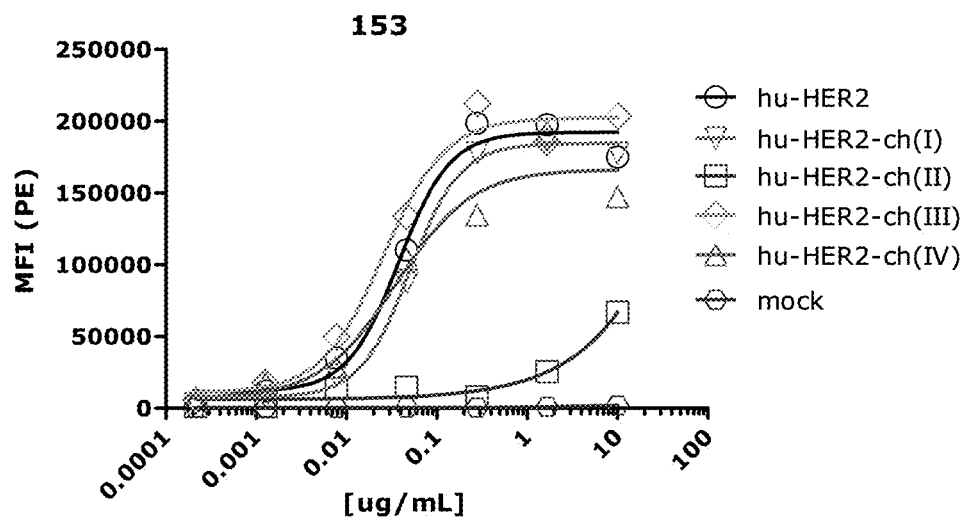
FIG. 16: HER2 antibody binding to CHO—S cells transfected with different HER2 ECD construct analyzed by means of flow cytometry. Hu-HER2=fully human HER2, Hu-HER2-ch(I) CR1=hu-HER2 with chicken domain I, Hu-HER2-ch(II)=hu-HER2 with chicken domain II, hu-HER2-ch(III)=hu-HER2 with chicken domain III and Hu-HER2-ch(IV)=hu-HER2 with chicken domain IV. Data shown are mean fluorescence intensities (MFI) of one representative antibody, TH1014-153. See example 25 for details.

Exemplary binding curves for antibody 153 are shown in FIG. 16. All binding results are shown in Table 16. Group 1 HER2 antibodies 050, 084, 169 and Herceptin showed loss of binding to Hu-HER2-ch(IV), but not to the proteins with one of the remaining domains shuffled, demonstrating that the epitopes of Group 1 mAbs reside in HER2 domain IV. Group 2 antibodies 025, 091, 129 and pertuzumab showed only loss of binding to Hu-HER2-ch(II), indicating that the epitope resides in HER2 domain II. Antibodies 098 and 153 were both defined to Group 3 in the cross-competition assay but showed some variation in the shuffle experiment. Antibody 098 clearly showed loss of binding to Hu-HER2-ch(I) and a minor decrease in binding to Hu-HER2-ch(II), while 153 showed only loss of binding to Hu-HER2-ch(II). These data suggest that Group 3 mAbs 098 and 153 can also bind, at least partially, to the HER2 domain II, with epitopes that possibly extend into HER2 domain I, as is the case for 098.

TABLE 16

Summary of HER2 antibody binding to different HER2ECD receptor constructs. FL; hu-HER2, I; hu-HER2-ch(I), II; hu-HER2-ch(II), III; hu-HER2-ch(III), IV; hu-HER2-ch(IV). +++ indicates normal binding, ++ indicates reduced $EC_{50}$ but the similar maximal binding compared to binding observed to hu-HER2, + indicates reduced $EC_{50}$ and reduced maximal binding detected compared to binding observed to hu-HER2, − indicates no binding.

| Antibody | Group | HER2-domain shuffled | | | | |
| --- | --- | --- | --- | --- | --- | --- |
| | | FL | I | II | III | IV |
| Herceptin | 1 | +++ | +++ | +++ | +++ | − |
| 050 | 1 | +++ | +++ | +++ | +++ | − |
| 084 | 1 | +++ | +++ | +++ | +++ | − |
| 169 | 1 | +++ | +++ | +++ | +++ | + |
| Pertuzumab | 2 | +++ | +++ | + | +++ | +++ |
| 025 | 2 | +++ | +++ | − | +++ | +++ |
| 091 | 2 | +++ | +++ | − | +++ | +++ |
| 129 | 2 | +++ | +++ | − | +++ | +++ |
| 153 | 3 | +++ | +++ | − | +++ | +++ |
| 098 | 3 | +++ | − | ++ | +++ | +++ |

Example 29

In Vivo Efficacy of HER2 HuMabs 091, 084 and 169 in NCI-N87 Human Gastric Carcinoma Xenografts in SCID Mice The in vivo effect of HER2-HuMabs 091 (cross-competition Group 2), 084 and 169 (both cross-competition Group 1) on tumor growth and survival in a NCI-N87 human gastric carcinoma xenograft model in female CB.17 severe combined immunodeficiency (SCID) mice was determined. $10\times10^6$ NCI-N87 tumor cells in 50% matrigel were injected s.c. in female SCID mice, 10 mice per group. Eight days after tumor inoculation, intravenous treatment with HER2-HuMabs 091, 084, and 169 or control antibody HuMab-HepC was started. In FIG. 17 (A) this is indicated as day 1, day of treatment initiation. The first dose was at 40 mg/kg, followed by 10 mg/kg on days 4, 8, 11, 15, 18, 22, and 25 after treatment initiation.

Tumor volume was determined at least 2 times per week. Volumes (mm$^3$) were calculated from caliper (PLEXX) measurements as (width$^2$×length)/2.

Figure 17A:
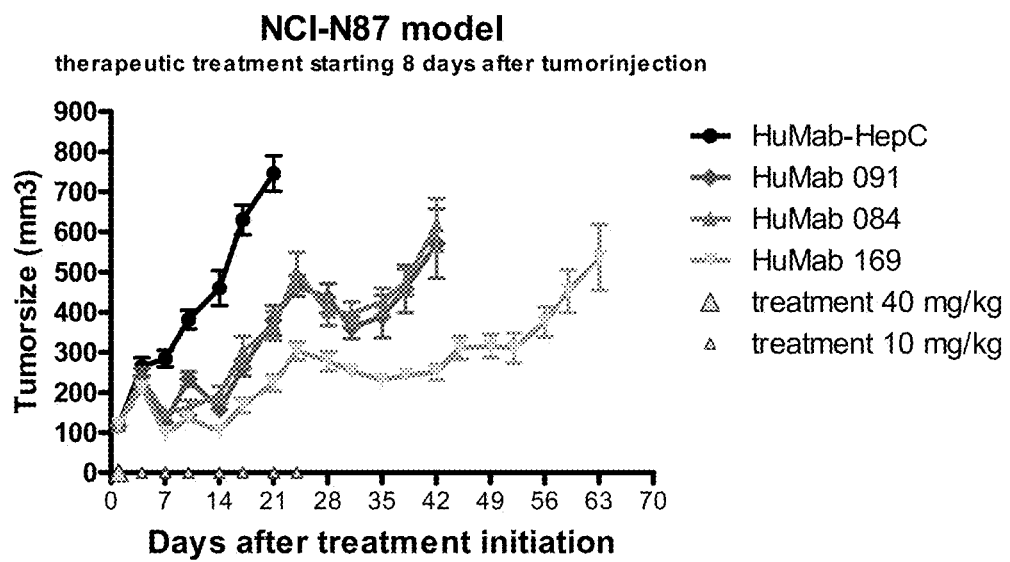
FIGS. 17A and 17B: In vivo effect of HER2-HuMabs in the NCI-N87 human gastric carcinoma xenograft model in female CB.17 severe combined immunodeficiency (SCID) mice. Data shown are mean tumorsize±S.E.M. per group (n=10 mice per group) (FIG. 17A) and survival (FIG. 17B). See example 29 for details.
Figure 17B:
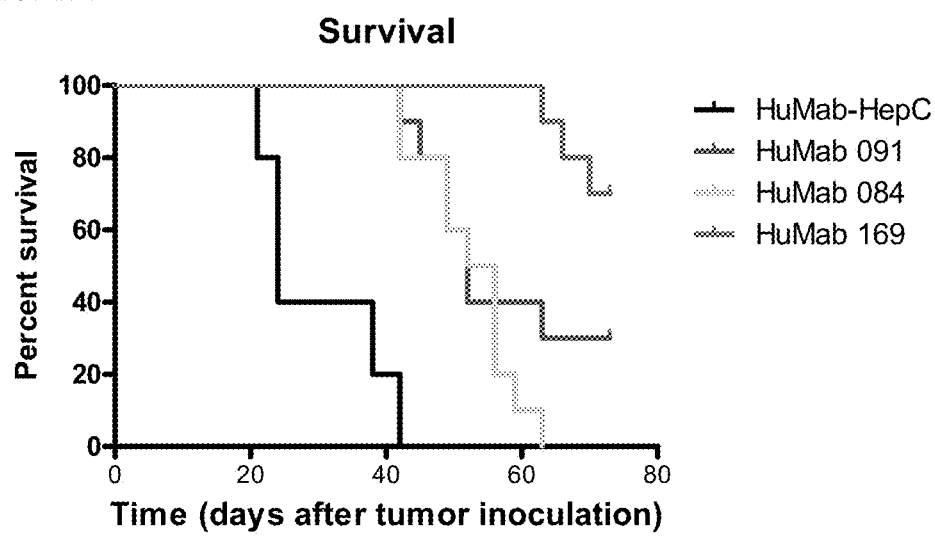

The results are depicted in FIGS. 17A and 17B which shows that the mice administered with HuMab 084, 169 and 091 demonstrated slower tumor growth (A) and better survival (B) than the mice that received negative control antibody HuMab-HepC. All treatments were well-tolerated.

Example 30

Therapeutic Treatment of BT-474 Breast Tumor Xenografts in Balb/C Nude Mice

The effect of therapeutic treatment of five different HER2 HuMabs on human subcutaneous BT-474 breast tumor xenografts in Balb/C nude mice was determined. BT-474 tumor cells were injected 24 to 72 hours after a whole body irradiation with a γ-source (1.8 Gy, Co60, BioMep, France). $2\times10^7$ BT-474 cells in 200 μl of RPMI 1640 containing matrigel (50:50, v:v; BD Biosciences) were injected subcutaneously into the right flank of female Balb/C nude mice. Body weight and tumor volume of the mice was recorded twice a week. Tumor volumes (mm$^3$) were calculated from caliper (PLEXX) measurements as: (width$^2$×length)/2.

Treatment with HER2 HuMabs was started when the tumors reached a mean volume of 100-200 mm³. Tumor bearing mice were randomized into groups of 8 mice. One group received twice weekly intravenous (i.v.) injections of the control mAb HuMab-HepC. Four other groups received twice weekly i.v. injections of HER2 HuMab 025, 129, 153 and 091, with a first dose of 20 mg/kg and following 9 doses of 5 mg/kg.

Figure 18A:
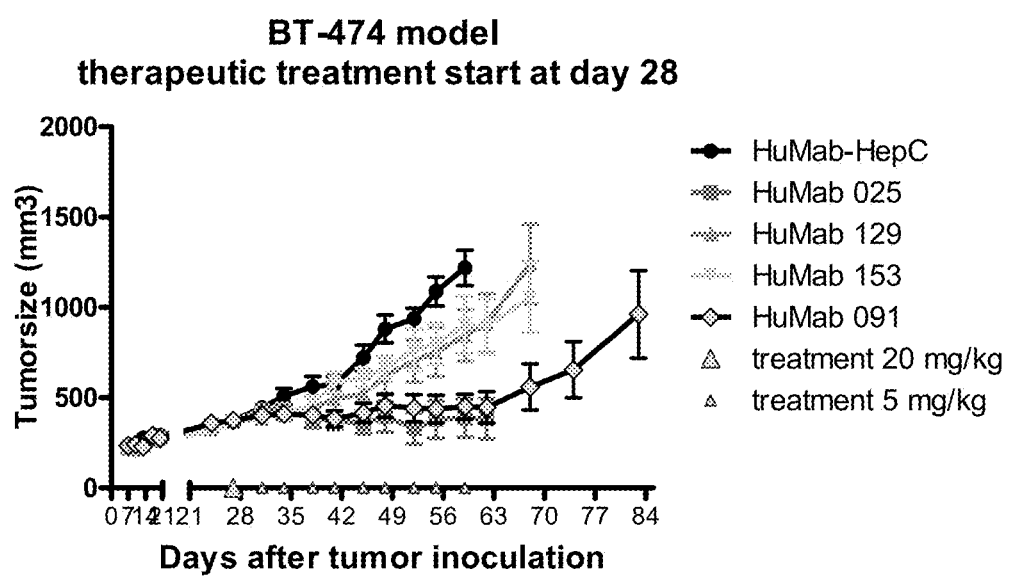
FIGS. 18A and 18B: In vivo effect of HER2 HuMabs in BT-474 breast tumor xenografts in Balb/C nude mice. Data shown are mean tumorsize±S.E.M. per group (n=8 mice per group) (FIG. 18A) and survival (FIG. 18B). See example 30 for details.
Figure 18B:
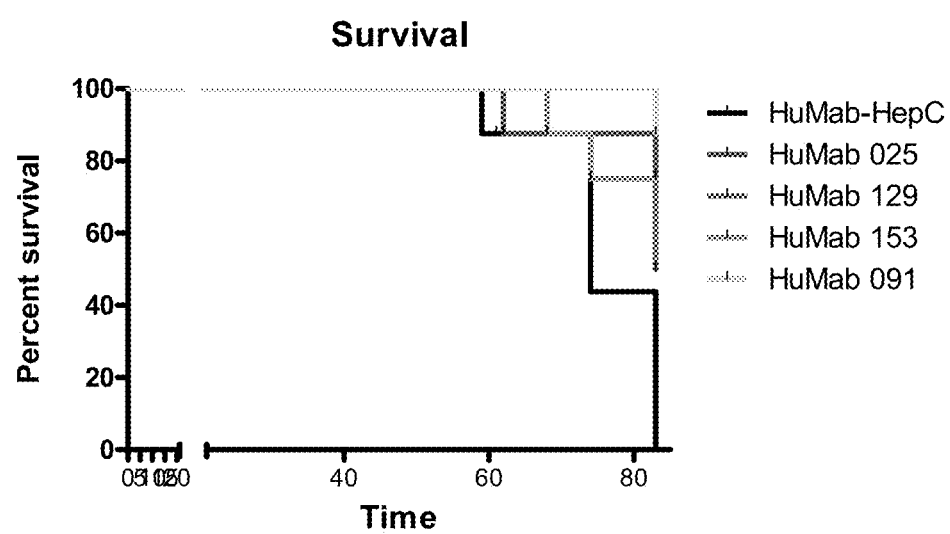

The results are depicted in FIGS. 18A and 18B and show that BT-474 tumor growth was partially inhibited with HuMab 129 and HuMab 153 treatment (about 30 and 50% of inhibition compared to HuMab-HepC control treatment). HuMab-025 and HuMab-091 strongly inhibited the BT-474 tumor growth and the time to reach a tumor volume of 800 mm³ was significantly delayed by these antibodies. Survival was also improved in the HER2 HuMAb receiving mice.

The invention claimed is:

1. A method for inhibiting growth and/or proliferation of one or more tumor cells expressing human epidermal growth factor receptor 2 (HER2), the method comprising administering to an individual in need thereof an antibody which binds HER2 and comprises a VH region and a VL region selected from the group consisting of:
   a) a VH region comprising the CDR1, CDR2 and CDR3 sequences of SEQ ID NOs:2, 3 and 4, respectively; and a VL region comprising the CDR1, CDR2 and CDR3 sequences of SEQ ID NO:6, the amino acid sequence DAS, and SEQ ID NO:7, respectively;
   b) a VH region comprising the CDR1, CDR2 and CDR3 sequences of SEQ ID NOs:9, 10 and 11, respectively; and a VL region comprising the CDR1, CDR2 and CDR3 sequences of SEQ ID NO:13, the amino acid sequence AAS, and SEQ ID NO:14, respectively;
   c) a VH region comprising the CDR1, CDR2 and CDR3 sequences of SEQ ID NOs:16, 17 and 18, respectively; and a VL region comprising the CDR1, CDR2 and CDR3 sequences of SEQ ID NO:20, the amino acid sequence VAS, and SEQ ID NO:21, respectively;
   d) a VH region comprising the CDR1, CDR2 and CDR3 sequences of SEQ ID NOs:23, 24 and 25, respectively; and a VL region comprising the CDR1, CDR2 and CDR3 sequences of SEQ ID NO:27, the amino acid sequence AAS, and SEQ ID NO:28, respectively;
   e) a VH region comprising the CDR1, CDR2 and CDR3 sequences of SEQ ID NOs:30, 163 and 31, respectively; and a VL region comprising the CDR1, CDR2 and CDR3 sequences of SEQ ID NO:33, the amino acid sequence AAS, and SEQ ID NO:34, respectively;
   f) a VH region comprising the CDR1, CDR2 and CDR3 sequences of SEQ ID NOs:36, 37 and 38, respectively; and a VL region comprising the CDR1, CDR2 and CDR3 sequences of SEQ ID NO:40, the amino acid sequence DAS, and SEQ ID NO:41, respectively;
   g) a VH region comprising the CDR1, CDR2 and CDR3 sequences of SEQ ID NOs:43, 44 and 45, respectively; and a VL region comprising the CDR1, CDR2 and CDR3 sequences of SEQ ID NO:47, the amino acid sequence AAS, and SEQ ID NO:48, respectively;
   h) a VH region comprising the CDR1, CDR2 and CDR3 sequences of SEQ ID NOs:50, 51 and 52, respectively; and a VL region comprising the CDR1, CDR2 and CDR3 sequences of SEQ ID NO:54, the amino acid sequence AAS, and SEQ ID NO:55, respectively;
   i) a VH region comprising the CDR1, CDR2 and CDR3 sequences of SEQ ID NOs:57, 58 and 59, respectively; and a VL region comprising the CDR1, CDR2 and CDR3 sequences of SEQ ID NO:61, the amino acid sequence AAS, and SEQ ID NO:62, respectively;
   j) a VH region comprising the CDR1, CDR2 and CDR3 sequences of SEQ ID NOs:64, 65 and 66, respectively; and a VL region comprising the CDR1, CDR2 and CDR3 sequences of SEQ ID NO:68, the amino acid sequence DAS, and SEQ ID NO:69, respectively; and
   k) a VH region comprising the CDR1, CDR2 and CDR3 sequences of SEQ ID NOs:71, 72 and 73, respectively; and a VL region comprising the CDR1, CDR2 and CDR3 sequences of SEQ ID NO:75, the amino acid sequence DAS, and SEQ ID NO:76, respectively.

2. The method of claim 1, wherein the antibody comprises a VH region and a VL region selected from the group consisting of:
   a) a VH region comprising the sequence of SEQ ID NO:1 and a VL region comprising the sequence of SEQ ID NO:5;

b) a VH region comprising the sequence of SEQ ID NO:8 and a VL region comprising the sequence of SEQ ID NO:12;
c) a VH region comprising the sequence of SEQ ID NO:15 and a VL region comprising the sequence of SEQ ID NO:19;
d) a VH region comprising the sequence of SEQ ID NO:77 and a VL region comprising the sequence of SEQ ID NO:78;
e) a VH region comprising the sequence of SEQ ID NO:79 and a VL region comprising the sequence of SEQ ID NO:80;
f) a VH region comprising the sequence of SEQ ID NO:81 and a VL region comprising the sequence of SEQ ID NO:82;
g) a VH region comprising the sequence of SEQ ID NO:83 and a VL region comprising the sequence of SEQ ID NO:84;
h) a VH region comprising the sequence of SEQ ID NO:85 and a VL region comprising the sequence of SEQ ID NO:86;
i) a VH region comprising the sequence of SEQ ID NO:87 and a VL region comprising the sequence of SEQ ID NO:88;
j) a VH region comprising the sequence of SEQ ID NO:22 and a VL region comprising the sequence of SEQ ID NO:26;
k) a VH region comprising the sequence of SEQ ID NO:29 and a VL region comprising the sequence of SEQ ID NO:32;
l) a VH region comprising the sequence of SEQ ID NO:35 and a VL region comprising the sequence of SEQ ID NO:39;
m) a VH region comprising the sequence of SEQ ID NO:89 and a VL region comprising the sequence of SEQ ID NO:90;
n) a VH region comprising the sequence of SEQ ID NO:91 and a VL region comprising the sequence of SEQ ID NO:92;
o) a VH region comprising the sequence of SEQ ID NO:93 and a VL region comprising the sequence of SEQ ID NO:94;
p) a VH region comprising the sequence of SEQ ID NO:95 and a VL region comprising the sequence of SEQ ID NO:96;
q) a VH region comprising the sequence of SEQ ID NO:97 and a VL region comprising the sequence of SEQ ID NO:98;
r) a VH region comprising the sequence of SEQ ID NO:99 and a VL region comprising the sequence of SEQ ID NO:100;
s) a VH region comprising the sequence of SEQ ID NO:101 and a VL region comprising the sequence of SEQ ID NO:102;
t) a VH region comprising the sequence of SEQ ID NO:103 and a VL region comprising the sequence of SEQ ID NO:104;
u) a VH region comprising the sequence of SEQ ID NO:105 and a VL region comprising the sequence of SEQ ID NO:106;
v) a VH region comprising the sequence of SEQ ID NO:107 and a VL region comprising the sequence of SEQ ID NO:108;
w) a VH region comprising the sequence of SEQ ID NO:42 and a VL region comprising the sequence of SEQ ID NO:46;
x) a VH region comprising the sequence of SEQ ID NO:49 and a VL region comprising the sequence of SEQ ID NO:53;
y) a VH region comprising the sequence of SEQ ID NO:56 and a VL region comprising the sequence of SEQ ID NO:60;
z) a VH region comprising the sequence of SEQ ID NO:63 and a VL region comprising the sequence of SEQ ID NO:67;
aa) a VH region comprising the sequence of SEQ ID NO:70 and a VL region comprising the sequence of SEQ ID NO:74;
bb) a VH region comprising the sequence of SEQ ID NO:109 and a VL region comprising the sequence of SEQ ID NO:110;
cc) a VH region comprising the sequence of SEQ ID NO:111 and a VL region comprising the sequence of SEQ ID NO:112;
dd) a VH region comprising the sequence of SEQ ID NO:113 and a VL region comprising the sequence of SEQ ID NO:114;
ee) a VH region comprising the sequence of SEQ ID NO:115 and a VL region comprising the sequence of SEQ ID NO:116;
ff) a VH region comprising the sequence of SEQ ID NO:117 and a VL region comprising the sequence of SEQ ID NO:118;
gg) a VH region comprising the sequence of SEQ ID NO:119 and a VL region comprising the sequence of SEQ ID NO:120;
hh) a VH region comprising the sequence of SEQ ID NO:121 and a VL region comprising the sequence of SEQ ID NO:122;
ii) a VH region comprising the sequence of SEQ ID NO:123 and a VL region comprising the sequence of SEQ ID NO:124;
jj) a VH region comprising the sequence of SEQ ID NO:125 and a VL region comprising the sequence of SEQ ID NO:126; and
kk) a variant of any of said antibodies, wherein said variant has 1-3 amino acid substitutions.

3. The method of claim 1, wherein the antibody has an $EC_{50}$ value for binding to HER2-expressing cells lower than 0.80 µg/ml.

4. The method of claim 1, wherein the antibody induces antibody-dependent cell-mediated cytotoxicity.

5. The method of claim 1, wherein the antibody, when conjugated directly or indirectly to a therapeutic moiety, kills HER2-expressing cells.

6. The method of claim 1, wherein a higher amount of the antibody than trastuzumab is internalized by a HER2-expressing tumor cell-line.

7. The method of claim 1, wherein the antibody is a full-length antibody.

8. The method of claim 1, wherein the antibody is a bispecific antibody.

9. The method of claim 8, wherein the bispecific antibody comprises a second antigen-binding site having a different binding specificity.

10. The method of claim 8, wherein the bispecific antibody comprises (i) a first antibody and a (ii) second antibody, wherein the first antibody is an antibody comprising a VH region and a VL region selected from the group consisting of:
a) a VH region comprising the CDR1, CDR2 and CDR3 sequences of SEQ ID NOs:2, 3 and 4, respectively; and a VL region comprising the CDR1, CDR2 and CDR3 sequences of SEQ ID NO:6, the amino acid sequence DAS, and SEQ ID NO:7, respectively;

b) a VH region comprising the CDR1, CDR2 and CDR3 sequences of SEQ ID NOs:9, 10 and 11, respectively; and a VL region comprising the CDR1, CDR2 and CDR3 sequences of SEQ IDNO:13, the amino acid sequence AAS, and SEQ ID NO:14, respectively;

c) a VH region comprising the CDR1, CDR2 and CDR3 sequences of SEQ ID NOs:16, 17 and 18, respectively; and a VL region comprising the CDR1, CDR2 and CDR3 sequences of SEQ IDNO:20, the amino acid sequence VAS, and SEQ ID NO:21, respectively;

d) a VH region comprising the CDR1, CDR2 and CDR3 sequences of SEQ ID NOs:23, 24 and 25, respectively; and a VL region comprising the CDR1, CDR2 and CDR3 sequences of SEQ IDNO:27, the amino acid sequence AAS, and SEQ ID NO:28, respectively;

e) a VH region comprising the CDR1, CDR2 and CDR3 sequences of SEQ ID NOs:30, 163 and 31, respectively; and a VL region comprising the CDR1, CDR2 and CDR3 sequences of SEQ IDNO:33, the amino acid sequence AAS, and SEQ ID NO:34, respectively;

f) a VH region comprising the CDR1, CDR2 and CDR3 sequences of SEQ ID NOs:36, 37 and 38, respectively; and a VL region comprising the CDR1, CDR2 and CDR3 sequences of SEQ IDNO:40, the amino acid sequence DAS, and SEQ ID NO:41, respectively;

g) a VH region comprising the CDR1, CDR2 and CDR3 sequences of SEQ ID NOs:43, 44 and 45, respectively; and a VL region comprising the CDR1, CDR2 and CDR3 sequences of SEQ IDNO:47, the amino acid sequence AAS, and SEQ ID NO:48, respectively;

h) a VH region comprising the CDR1, CDR2 and CDR3 sequences of SEQ ID NOs:50, 51 and 52, respectively; and a VL region comprising the CDR1, CDR2 and CDR3 sequences of SEQ IDNO:54, the amino acid sequence AAS, and SEQ ID NO:55, respectively;

i) a VH region comprising the CDR1, CDR2 and CDR3 sequences of SEQ ID NOs:57, 58 and 59, respectively; and a VL region comprising the CDR1, CDR2 and CDR3 sequences of SEQ ID NO:61, the amino acid sequence AAS, and SEQ ID NO:62, respectively;

j) a VH region comprising the CDR1, CDR2 and CDR3 sequences of SEQ ID NOs:64, 65 and 66, respectively; and a VL region comprising the CDR1, CDR2 and CDR3 sequences of SEQ IDNO:68, the amino acid sequence DAS, and SEQ ID NO:69, respectively; and k) a VH region comprising the CDR1, CDR2 and CDR3 sequences of SEQ ID NOs:71, 72 and 73, respectively; and a VL region comprising the CDR1, CDR2 and CDR3 sequences of SEQ IDNO:75, the amino acid sequence DAS, and SEQ ID NO:76, respectively, and wherein the second antibody binds to a different epitope than the first antibody.

11. The method of claim 10, wherein the second antibody is a CD3 antibody.

12. The method of claim 11, wherein the CD3 antibody comprises a) a VH region comprising the sequence of SEQ ID NO:171 and a VL region comprising the sequence of SEQ ID NO:172; or b) a VH region comprising the sequence of SEQ ID NO:173 and a VL region comprising the sequence of SEQ ID NO:174.

13. The method of claim 1, wherein the antibody is conjugated to another moiety.

14. The method of claim 13, wherein the moiety is selected from the group consisting of taxol; cytochalasin B; gramicidin D; ethidium bromide; emetine; mitomycin; etoposide; tenoposide; vincristine; vinblastine; colchicin; doxorubicin; daunorubicin; dihydroxy anthracin dione; a tubulin-inhibitor; mitoxantrone; mithramycin; actinomycin D; 1-dehydrotestosterone; a glucocorticoid; procaine; tetracaine; lidocaine; propranolol; puromycin; calicheamicin or an analog or derivative thereof; an antimetabolite; an alkylating agent; an antibiotic; an antimitotic agent; a toxin; ribonuclease (RNase); DNase I, Staphylococcal enterotoxin A; pokeweed antiviral protein; diphtherin toxin; and *Pseudomonas* endotoxin.

15. The method of claim 13, wherein the moiety is selected from the group consisting of maytansine, calicheamicin, duocarmycin, rachelmycin (CC-1065), monomethyl auristatin E, monomethyl auristatin F, and an analog, derivative, or prodrug of any thereof.

16. The method of claim 13, wherein the antibody is conjugated to a cytokine selected from the group consisting of IL-2, IL-4, IL-6, IL-7, IL-10, IL-12, IL-13, IL-15, IL-18, IL-23, IL-24, IL-27, IL-28a, IL-28b, IL-29, KGF, IFNα, IFNβ, IFNγ, GM-CSF, CD40L, Flt3 ligand, stem cell factor, ancestim, and TNFα.

17. The method of claim 13, wherein the antibody is conjugated to a radioisotope.

18. The method of claim 1, wherein the antibody comprises a VH region comprising the CDR1, CDR2 and CDR3 sequences of SEQ ID NOs:2, 3 and 4, respectively; and a VL region comprising the CDR1, CDR2 and CDR3 sequences of SEQ ID NO:6, the amino acid sequence DAS, and SEQ ID NO:7, respectively.

19. The method of claim 1, wherein the antibody comprises a VH region comprising the CDR1, CDR2 and CDR3 sequences of SEQ ID NOs:23, 24 and 25, respectively; and a VL region comprising the CDR1, CDR2 and CDR3 sequences of SEQ ID NO:27, the amino acid sequence AAS, and SEQ ID NO:28, respectively.

20. The method of claim 1, wherein the antibody comprises a VH region comprising the CDR1, CDR2 and CDR3 sequences of SEQ ID NOs:64, 65 and 66, respectively; and a VL region comprising the CDR1, CDR2 and CDR3 sequences of SEQ ID NO:68, the amino acid sequence DAS, and SEQ ID NO:69, respectively.

21. The method of claim 1, wherein the antibody comprises a VH region comprising the sequence of SEQ ID NO:1 and a VL region comprising the sequence of SEQ ID NO:5.

22. The method of claim 1, wherein the antibody comprises a VH region comprising the sequence of SEQ ID NO:22 and a VL region comprising the sequence of SEQ ID NO:26.

23. The method of claim 1, wherein the antibody comprises a VH region comprising the sequence of SEQ ID NO:63 and a VL region comprising the sequence of SEQ ID NO:67.

* * * * *

SEQUENCE LISTING

```
<160> NUMBER OF SEQ ID NOS: 208

<210> SEQ ID NO 1
<211> LENGTH: 121
<212> TYPE: PRT
<213> ORGANISM: Homo sapiens

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Leu Ser Ala Tyr Ser Gly Asn Thr Ile Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ile Val Val Arg Pro Asp Tyr Phe Asp Tyr Trp Gly
            100                 105                 110

Gln Gly Thr Leu Val Thr Val Ser Ser
        115                 120

<210> SEQ ID NO 2
<211> LENGTH: 8
<212> TYPE: PRT
<213> ORGANISM: Homo sapiens

<400> SEQUENCE: 2

Gly Tyr Thr Phe Thr Asn Tyr Gly
1               5

<210> SEQ ID NO 3
<211> LENGTH: 8
<212> TYPE: PRT
<213> ORGANISM: Homo sapiens

<400> SEQUENCE: 3

Leu Ser Ala Tyr Ser Gly Asn Thr
1               5

<210> SEQ ID NO 4
<211> LENGTH: 14
<212> TYPE: PRT
<213> ORGANISM: Homo sapiens

<400> SEQUENCE: 4

Ala Arg Asp Arg Ile Val Val Arg Pro Asp Tyr Phe Asp Tyr
1               5                   10
```

<210> SEQ ID NO 5
<211> LENGTH: 107
<212> TYPE: PRT
<213> ORGANISM: Homo sapiens

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 6
<211> LENGTH: 6
<212> TYPE: PRT
<213> ORGANISM: Homo sapiens

<400> SEQUENCE: 6

Gln Ser Val Ser Ser Tyr
1               5

<210> SEQ ID NO 7
<211> LENGTH: 9
<212> TYPE: PRT
<213> ORGANISM: Homo sapiens

<400> SEQUENCE: 7

Gln Gln Arg Ser Asn Trp Pro Arg Thr
1               5

<210> SEQ ID NO 8
<211> LENGTH: 119
<212> TYPE: PRT
<213> ORGANISM: Homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Arg Gly Gly Thr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Lys Ala Arg Ala Asn Trp Asp Tyr Phe Asp Tyr Trp Gly Gln Gly
            100                 105                 110

```
Thr Leu Val Thr Val Ser Ser
        115

<210> SEQ ID NO 9
<211> LENGTH: 8
<212> TYPE: PRT
<213> ORGANISM: Homo sapiens

<400> SEQUENCE: 9

Gly Phe Thr Phe Ser Ser Tyr Ala
1               5

<210> SEQ ID NO 10
<211> LENGTH: 8
<212> TYPE: PRT
<213> ORGANISM: Homo sapiens

<400> SEQUENCE: 10

Ile Ser Gly Arg Gly Gly Thr Thr
1               5

<210> SEQ ID NO 11
<211> LENGTH: 12
<212> TYPE: PRT
<213> ORGANISM: Homo sapiens

<400> SEQUENCE: 11

Ala Lys Ala Arg Ala Asn Trp Asp Tyr Phe Asp Tyr
1               5                   10

<210> SEQ ID NO 12
<211> LENGTH: 107
<212> TYPE: PRT
<213> ORGANISM: Homo sapiens

<400> SEQUENCE: 12

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 13
<211> LENGTH: 6
<212> TYPE: PRT
<213> ORGANISM: Homo sapiens

<400> SEQUENCE: 13

Gln Gly Ile Ser Ser Trp
1               5

<210> SEQ ID NO 14
<211> LENGTH: 9
```

<212> TYPE: PRT
<213> ORGANISM: Homo sapiens

<400> SEQUENCE: 14

Gln Gln Ala Asn Ser Phe Pro Ile Thr
1               5

<210> SEQ ID NO 15
<211> LENGTH: 121
<212> TYPE: PRT
<213> ORGANISM: Homo sapiens

<400> SEQUENCE: 15

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Thr Tyr
            20                  25                  30

Ala Ile Asn Trp Val Arg Gln Ala Pro Gly Gln Gly Leu Glu Trp Met
        35                  40                  45

Gly Arg Ile Asn Thr Val Leu Gly Ile Val Asn His Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Asn Ser Leu Arg Ser Glu Asp Thr Ala Val Tyr Tyr Cys
                85                  90                  95

Ala Arg Glu Lys Gly Val Asp Tyr Tyr Tyr Gly Ile Glu Val Trp Gly
            100                 105                 110

Gln Gly Thr Thr Val Thr Val Ser Ser
        115                 120

<210> SEQ ID NO 16
<211> LENGTH: 8
<212> TYPE: PRT
<213> ORGANISM: Homo sapiens

<400> SEQUENCE: 16

Gly Gly Thr Phe Arg Thr Tyr Ala
1               5

<210> SEQ ID NO 17
<211> LENGTH: 8
<212> TYPE: PRT
<213> ORGANISM: Homo sapiens

<400> SEQUENCE: 17

Ile Asn Thr Val Leu Gly Ile Val
1               5

<210> SEQ ID NO 18
<211> LENGTH: 14
<212> TYPE: PRT
<213> ORGANISM: Homo sapiens

<400> SEQUENCE: 18

Ala Arg Glu Lys Gly Val Asp Tyr Tyr Tyr Gly Ile Glu Val
1               5                   10

<210> SEQ ID NO 19
<211> LENGTH: 107
<212> TYPE: PRT
<213> ORGANISM: Homo sapiens

<400> SEQUENCE: 19

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Val Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys
            100                 105

<210> SEQ ID NO 20
<211> LENGTH: 6
<212> TYPE: PRT
<213> ORGANISM: Homo sapiens

<400> SEQUENCE: 20

Gln Gly Ile Ser Ser Trp
1               5

<210> SEQ ID NO 21
<211> LENGTH: 9
<212> TYPE: PRT
<213> ORGANISM: Homo sapiens

<400> SEQUENCE: 21

Gln Gln Ala Asn Ser Phe Pro Leu Thr
1               5

<210> SEQ ID NO 22
<211> LENGTH: 120
<212> TYPE: PRT
<213> ORGANISM: Homo sapiens

<400> SEQUENCE: 22

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile His His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Asp Ser Gly Val Tyr Tyr Phe Asp Tyr Trp Ala Gln
            100                 105                 110

Gly Thr Leu Val Thr Val Ser Ser
        115                 120

<210> SEQ ID NO 23

```
<211> LENGTH: 8
<212> TYPE: PRT
<213> ORGANISM: Homo sapiens

<400> SEQUENCE: 23

Gly Gly Ser Phe Ser Asp Tyr Tyr
1               5

<210> SEQ ID NO 24
<211> LENGTH: 7
<212> TYPE: PRT
<213> ORGANISM: Homo sapiens

<400> SEQUENCE: 24

Ile His His Ser Gly Ser Thr
1               5

<210> SEQ ID NO 25
<211> LENGTH: 14
<212> TYPE: PRT
<213> ORGANISM: Homo sapiens

<400> SEQUENCE: 25

Ala Arg Gly Tyr Tyr Asp Ser Gly Val Tyr Tyr Phe Asp Tyr
1               5                   10

<210> SEQ ID NO 26
<211> LENGTH: 107
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 27
<211> LENGTH: 6
<212> TYPE: PRT
<213> ORGANISM: Homo sapiens

<400> SEQUENCE: 27

Gln Gly Ile Ser Arg Trp
1               5

<210> SEQ ID NO 28
<211> LENGTH: 9
<212> TYPE: PRT
<213> ORGANISM: Homo sapiens

<400> SEQUENCE: 28
```

Gln Gln Tyr Asn Ser Tyr Pro Ile Thr
1               5

<210> SEQ ID NO 29
<211> LENGTH: 120
<212> TYPE: PRT
<213> ORGANISM: Homo sapiens

<400> SEQUENCE: 29

Gln Val Gln Leu Gln Gln Trp Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Glu Ile Tyr His Ser Gly Asp Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Tyr Ser Val Thr Ala Ala Asp Thr Ala Val Tyr Tyr Cys Ala
                85                  90                  95

Arg Leu Tyr Phe Gly Ser Gly Ile Tyr Tyr Leu Asp Tyr Trp Gly Gln
            100                 105                 110

Gly Thr Leu Val Thr Val Ser Ser
        115                 120

<210> SEQ ID NO 30
<211> LENGTH: 8
<212> TYPE: PRT
<213> ORGANISM: Homo sapiens

<400> SEQUENCE: 30

Gly Gly Ser Phe Ser Gly Tyr Tyr
1               5

<210> SEQ ID NO 31
<211> LENGTH: 14
<212> TYPE: PRT
<213> ORGANISM: Homo sapiens

<400> SEQUENCE: 31

Ala Arg Leu Tyr Phe Gly Ser Gly Ile Tyr Tyr Leu Asp Tyr
1               5                   10

<210> SEQ ID NO 32
<211> LENGTH: 107
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Val Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
            85                  90                  95

Thr Phe Gly Gln Gly Thr Lys Val Glu Ile Lys
            100                 105

<210> SEQ ID NO 33
<211> LENGTH: 6
<212> TYPE: PRT
<213> ORGANISM: Homo sapiens

<400> SEQUENCE: 33

Gln Gly Ile Ser Ser Trp
1               5

<210> SEQ ID NO 34
<211> LENGTH: 9
<212> TYPE: PRT
<213> ORGANISM: Homo sapiens

<400> SEQUENCE: 34

Gln Gln Tyr Asn Ser Phe Pro Pro Thr
1               5

<210> SEQ ID NO 35
<211> LENGTH: 119
<212> TYPE: PRT
<213> ORGANISM: Homo sapiens

<400> SEQUENCE: 35

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Phe
            20                  25                  30

Ala Ile His Trp Val Arg Gln Ala Pro Gly Lys Gly Leu Glu Trp Val
        35                  40                  45

Ala Val Ile Ser Tyr Asp Gly His Lys Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
            85                  90                  95

Ala Arg Gly Leu Gly Val Trp Gly Ala Phe Asp Tyr Trp Gly Gln Gly
            100                 105                 110

Thr Leu Val Thr Val Ser Ser
        115

<210> SEQ ID NO 36
<211> LENGTH: 8
<212> TYPE: PRT
<213> ORGANISM: Homo sapiens

<400> SEQUENCE: 36

Gly Phe Thr Phe Ser Thr Phe Ala
1               5

<210> SEQ ID NO 37
<211> LENGTH: 8
<212> TYPE: PRT
<213> ORGANISM: Homo sapiens

<400> SEQUENCE: 37

```
Ile Ser Tyr Asp Gly Gly His Lys
1               5

<210> SEQ ID NO 38
<211> LENGTH: 12
<212> TYPE: PRT
<213> ORGANISM: Homo sapiens

<400> SEQUENCE: 38

Ala Arg Gly Leu Gly Val Trp Gly Ala Phe Asp Tyr
1               5                   10

<210> SEQ ID NO 39
<211> LENGTH: 106
<212> TYPE: PRT
<213> ORGANISM: Homo sapiens

<400> SEQUENCE: 39

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Trp Thr
                85                  90                  95

Phe Gly Gln Gly Thr Lys Val Glu Ile Lys
            100                 105

<210> SEQ ID NO 40
<211> LENGTH: 6
<212> TYPE: PRT
<213> ORGANISM: Homo sapiens

<400> SEQUENCE: 40

Gln Ser Val Ser Ser Tyr
1               5

<210> SEQ ID NO 41
<211> LENGTH: 8
<212> TYPE: PRT
<213> ORGANISM: Homo sapiens

<400> SEQUENCE: 41

Gln Gln Arg Ser Asn Trp Trp Thr
1               5

<210> SEQ ID NO 42
<211> LENGTH: 123
<212> TYPE: PRT
<213> ORGANISM: Homo sapiens

<400> SEQUENCE: 42

Glu Val Gln Leu Val Gln Ser Gly Ala Glu Val Lys Lys Pro Gly Glu
1               5                   10                  15

Ser Leu Thr Ile Ser Cys Lys Gly Ser Gly Tyr Ser Phe Ser Ile Tyr
            20                  25                  30
```

Trp Ile Gly Trp Val Arg Gln Met Pro Gly Lys Gly Leu Glu Trp Met
            35                  40                  45

Gly Ile Ile Phe Pro Gly Asp Ser Asp Ile Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Pro Gly Asp Trp Ser Pro Arg His Trp Tyr Phe Asp Leu
            100                 105                 110

Trp Gly Arg Gly Thr Leu Val Thr Val Ser Ser
            115                 120

<210> SEQ ID NO 43
<211> LENGTH: 8
<212> TYPE: PRT
<213> ORGANISM: Homo sapiens

<400> SEQUENCE: 43

Gly Tyr Ser Phe Ser Ile Tyr Trp
1               5

<210> SEQ ID NO 44
<211> LENGTH: 8
<212> TYPE: PRT
<213> ORGANISM: Homo sapiens

<400> SEQUENCE: 44

Ile Phe Pro Gly Asp Ser Asp Ile
1               5

<210> SEQ ID NO 45
<211> LENGTH: 16
<212> TYPE: PRT
<213> ORGANISM: Homo sapiens

<400> SEQUENCE: 45

Ala Arg Gln Pro Gly Asp Trp Ser Pro Arg His Trp Tyr Phe Asp Leu
1               5                   10                  15

<210> SEQ ID NO 46
<211> LENGTH: 107
<212> TYPE: PRT
<213> ORGANISM: Homo sapiens

<400> SEQUENCE: 46

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
            20                  25                  30

Leu Ala Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Tyr Leu Gln Ser
65                  70                  75                  80

Glu Asp Phe Ala Thr Tyr Tyr Cys Gln Gln Tyr Tyr Ser Phe Pro Leu
                85                  90                  95

Thr Phe Gly Gly Gly Thr Lys Val Glu Ile Lys

<210> SEQ ID NO 47
<211> LENGTH: 6
<212> TYPE: PRT
<213> ORGANISM: Homo sapiens

<400> SEQUENCE: 47

Gln Gly Ile Ser Ser Tyr
1               5

<210> SEQ ID NO 48
<211> LENGTH: 9
<212> TYPE: PRT
<213> ORGANISM: Homo sapiens

<400> SEQUENCE: 48

Gln Gln Tyr Tyr Ser Phe Pro Leu Thr
1               5

<210> SEQ ID NO 49
<211> LENGTH: 126
<212> TYPE: PRT
<213> ORGANISM: Homo sapiens

<400> SEQUENCE: 49

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Thr Tyr Tyr Asp Ile Leu Thr Gly Tyr Phe Asn Trp
            100                 105                 110

Phe Asp Pro Trp Gly Gln Gly Thr Leu Val Thr Val Ser Ser
        115                 120                 125

<210> SEQ ID NO 50
<211> LENGTH: 8
<212> TYPE: PRT
<213> ORGANISM: Homo sapiens

<400> SEQUENCE: 50

Gly Tyr Asn Phe Thr Ser Tyr Trp
1               5

<210> SEQ ID NO 51
<211> LENGTH: 8
<212> TYPE: PRT
<213> ORGANISM: Homo sapiens

<400> SEQUENCE: 51

Ile Tyr Pro Gly Asp Ser Asp Thr
1               5

```
<210> SEQ ID NO 52
<211> LENGTH: 15
<212> TYPE: PRT
<213> ORGANISM: Homo sapiens

<400> SEQUENCE: 52

Ala Arg Trp Gly Thr Tyr Tyr Asp Ile Leu Thr Gly Tyr Phe Asn
1               5                   10                  15

<210> SEQ ID NO 53
<211> LENGTH: 107
<212> TYPE: PRT
<213> ORGANISM: Homo sapiens

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Trp
                85                  90                  95

Thr Phe Gly Gln Gly Thr Lys Val Glu Ile Lys
            100                 105

<210> SEQ ID NO 54
<211> LENGTH: 6
<212> TYPE: PRT
<213> ORGANISM: Homo sapiens

<400> SEQUENCE: 54

Gln Gly Ile Ser Ser Trp
1               5

<210> SEQ ID NO 55
<211> LENGTH: 9
<212> TYPE: PRT
<213> ORGANISM: Homo sapiens

<400> SEQUENCE: 55

Gln Gln Tyr Tyr Ile Tyr Pro Trp Thr
1               5

<210> SEQ ID NO 56
<211> LENGTH: 124
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Gly Met Ser Trp Val Arg Gln Ala Pro Gly Lys Gly Leu Glu Trp Val
            35                  40                  45

Ser Ala Ile Ser Gly Ser Ala Tyr Ser Thr Tyr Tyr Ala Asp Ser Val
```

```
            50                  55                  60
Lys Gly Arg Phe Thr Ile Ser Arg Asp Asn Ser Lys Asn Thr Leu Trp
 65                  70                  75                  80

Leu Gln Met Asn Ser Leu Arg Ala Glu Asp Thr Ala Val Tyr Tyr Cys
                 85                  90                  95

Ala Lys Ala His Tyr His Gly Ser Gly Ser Tyr Tyr Thr Leu Phe Asp
            100                 105                 110

Tyr Trp Gly Gln Gly Thr Leu Val Thr Val Ser Ser
            115                 120
```

<210> SEQ ID NO 57
<211> LENGTH: 8
<212> TYPE: PRT
<213> ORGANISM: Homo sapiens

<400> SEQUENCE: 57

```
Gly Phe Thr Phe Ser Asn Tyr Gly
 1               5
```

<210> SEQ ID NO 58
<211> LENGTH: 8
<212> TYPE: PRT
<213> ORGANISM: Homo sapiens

<400> SEQUENCE: 58

```
Ile Ser Gly Ser Ala Tyr Ser Thr
 1               5
```

<210> SEQ ID NO 59
<211> LENGTH: 17
<212> TYPE: PRT
<213> ORGANISM: Homo sapiens

<400> SEQUENCE: 59

```
Ala Lys Ala His Tyr His Gly Ser Gly Ser Tyr Tyr Thr Leu Phe Asp
 1               5                  10                  15

Tyr
```

<210> SEQ ID NO 60
<211> LENGTH: 107
<212> TYPE: PRT
<213> ORGANISM: Homo sapiens

<400> SEQUENCE: 60

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
            100                 105
```

```
<210> SEQ ID NO 61
<211> LENGTH: 6
<212> TYPE: PRT
<213> ORGANISM: Homo sapiens

<400> SEQUENCE: 61

Gln Gly Ile Ser Ser Trp
1               5

<210> SEQ ID NO 62
<211> LENGTH: 9
<212> TYPE: PRT
<213> ORGANISM: Homo sapiens

<400> SEQUENCE: 62

Gln Gln Tyr Asn Ser Tyr Pro Tyr Thr
1               5

<210> SEQ ID NO 63
<211> LENGTH: 121
<212> TYPE: PRT
<213> ORGANISM: Homo sapiens

<400> SEQUENCE: 63

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asp Tyr
            20                  25                  30

Val Ile His Trp Val Arg Gln Ala Pro Gly Lys Gly Leu Glu Trp Val
        35                  40                  45

Thr Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Ser Ala Glu Asp Thr Ala Met Tyr Tyr Cys
                85                  90                  95

Ala Arg Gly Gly Ile Thr Gly Thr Thr Gly Val Phe Asp Tyr Trp Gly
            100                 105                 110

Gln Gly Thr Leu Val Thr Val Ser Ser
        115                 120

<210> SEQ ID NO 64
<211> LENGTH: 8
<212> TYPE: PRT
<213> ORGANISM: Homo sapiens

<400> SEQUENCE: 64

Gly Phe Thr Phe Ser Asp Tyr Val
1               5

<210> SEQ ID NO 65
<211> LENGTH: 8
<212> TYPE: PRT
<213> ORGANISM: Homo sapiens

<400> SEQUENCE: 65

Ile Ser Tyr Asp Gly Ser Asn Lys
1               5

<210> SEQ ID NO 66
<211> LENGTH: 14
<212> TYPE: PRT
```

```
<213> ORGANISM: Homo sapiens

<400> SEQUENCE: 66

Ala Arg Gly Gly Ile Thr Gly Thr Thr Gly Val Phe Asp Tyr
1               5                   10

<210> SEQ ID NO 67
<211> LENGTH: 107
<212> TYPE: PRT
<213> ORGANISM: Homo sapiens

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Asp Ala Ser Ser Leu Gln Ser Gly Val Pro Ser Arg Phe Ser Gly
    50                  55                  60

Ser Gly Tyr Gly Thr Asp Phe Ser Leu Thr Ile Ser Ser Leu Gln Pro
65                  70                  75                  80

Glu Asp Phe Ala Ile Tyr Tyr Cys Gln Gln Tyr Lys Ser Tyr Pro Ile
                85                  90                  95

Thr Phe Gly Gln Gly Thr Arg Leu Glu Ile Lys
            100                 105

<210> SEQ ID NO 68
<211> LENGTH: 6
<212> TYPE: PRT
<213> ORGANISM: Homo sapiens

<400> SEQUENCE: 68

Gln Gly Ile Ser Ser Trp
1               5

<210> SEQ ID NO 69
<211> LENGTH: 9
<212> TYPE: PRT
<213> ORGANISM: Homo sapiens

<400> SEQUENCE: 69

Gln Gln Tyr Lys Ser Tyr Pro Ile Thr
1               5

<210> SEQ ID NO 70
<211> LENGTH: 125
<212> TYPE: PRT
<213> ORGANISM: Homo sapiens

<400> SEQUENCE: 70

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Ser Asn Tyr Val Gln Lys Phe
    50                  55                  60

Gln Gly Arg Val Thr Met Thr Thr Asp Thr Thr Thr Ser Thr Ala Tyr
```

```
              65                  70                  75                  80
Met Glu Leu Arg Ser Leu Thr Ser Asp Asp Thr Ala Val Tyr Tyr Cys
                    85                  90                  95

Ala Arg Glu Tyr Ser Tyr Asp Ser Gly Thr Tyr Phe Tyr Tyr Gly Met
                    100                 105                 110

Asp Val Trp Gly Gln Gly Thr Thr Val Thr Val Ser Ser
                    115                 120                 125

<210> SEQ ID NO 71
<211> LENGTH: 8
<212> TYPE: PRT
<213> ORGANISM: Homo sapiens

<400> SEQUENCE: 71

Gly Tyr Thr Phe Thr Ser Tyr Gly
1               5

<210> SEQ ID NO 72
<211> LENGTH: 8
<212> TYPE: PRT
<213> ORGANISM: Homo sapiens

<400> SEQUENCE: 72

Ile Ser Ala Tyr Asn Gly Asn Ser
1               5

<210> SEQ ID NO 73
<211> LENGTH: 18
<212> TYPE: PRT
<213> ORGANISM: Homo sapiens

<400> SEQUENCE: 73

Ala Arg Glu Tyr Ser Tyr Asp Ser Gly Thr Tyr Phe Tyr Tyr Gly Met
1               5                   10                  15

Asp Val

<210> SEQ ID NO 74
<211> LENGTH: 108
<212> TYPE: PRT
<213> ORGANISM: Homo sapiens

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Met
                85                  90                  95

Tyr Thr Phe Gly Gln Gly Thr Lys Leu Glu Ile Lys
                100                 105

<210> SEQ ID NO 75
<211> LENGTH: 6
<212> TYPE: PRT
```

<213> ORGANISM: Homo sapiens

<400> SEQUENCE: 75

Gln Ser Val Ser Ser Tyr
1               5

<210> SEQ ID NO 76
<211> LENGTH: 10
<212> TYPE: PRT
<213> ORGANISM: Homo sapiens

<400> SEQUENCE: 76

Gln Gln Arg Ser Asn Trp Pro Met Tyr Thr
1               5                   10

<210> SEQ ID NO 77
<211> LENGTH: 119
<212> TYPE: PRT
<213> ORGANISM: Homo sapiens

<400> SEQUENCE: 77

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Thr Thr Tyr Tyr Ala Asp Ser Val
    50                  55                  60

Lys Gly Arg Phe Thr Ile Ser Arg Asp Asn Ser Lys Ser Thr Leu Cys
65                  70                  75                  80

Leu Gln Met Asn Ser Leu Arg Ala Glu Asp Thr Ala Val Tyr Tyr Cys
                85                  90                  95

Ala Lys Ala Arg Ala Asn Trp Asp Tyr Phe Asp Tyr Trp Gly Gln Gly
            100                 105                 110

Thr Leu Val Thr Val Ser Ser
        115

<210> SEQ ID NO 78
<211> LENGTH: 107
<212> TYPE: PRT
<213> ORGANISM: Homo sapiens

<400> SEQUENCE: 78

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Arg Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 79
<211> LENGTH: 119
<212> TYPE: PRT
<213> ORGANISM: Homo sapiens

<400> SEQUENCE: 79

Glu Val Gln Leu Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Thr Thr Tyr Tyr Ala Asp Ser Val
    50                  55                  60

Lys Gly Arg Phe Thr Ile Ser Arg Asp Asn Ser Lys Thr Leu Cys
65                  70                  75                  80

Leu Gln Met Asn Ser Leu Arg Ala Glu Asp Thr Ala Val Tyr Tyr Cys
                85                  90                  95

Ala Lys Ala Arg Ala Asn Trp Asp Tyr Phe Asp Tyr Trp Gly Gln Gly
            100                 105                 110

Thr Leu Val Thr Val Ser Ser
        115

<210> SEQ ID NO 80
<211> LENGTH: 107
<212> TYPE: PRT
<213> ORGANISM: Homo sapiens

<400> SEQUENCE: 80

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Arg Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 81
<211> LENGTH: 119
<212> TYPE: PRT
<213> ORGANISM: Homo sapiens

<400> SEQUENCE: 81

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Arg Gly Gly Thr Thr Tyr Tyr Ala Asp Ser Val

```
            50                  55                  60
Lys Gly Arg Phe Thr Ile Ser Arg Asp Asn Ser Lys Ser Thr Leu Cys
 65                  70                  75                  80

Leu Gln Met Asn Ser Leu Arg Ala Glu Asp Thr Ala Val Tyr Tyr Cys
                 85                  90                  95

Ala Lys Ala Arg Ala Asn Trp Asp Tyr Phe Asp Tyr Trp Gly Gln Gly
                100                 105                 110

Thr Leu Val Thr Val Ser Ser
            115

<210> SEQ ID NO 82
<211> LENGTH: 107
<212> TYPE: PRT
<213> ORGANISM: Homo sapiens

<400> SEQUENCE: 82

Asp Ile Gln Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln His Lys Pro Gly Lys Ala Pro Lys Leu Leu Ile
             35                  40                  45

Tyr Ala Ala Ser Ile Leu Gln Ser Gly Val Pro Ser Arg Phe Ser Gly
         50                  55                  60

Ser Gly Ser Gly Thr Asp Phe Thr Leu Thr Ile Ser Ser Leu Arg Pro
 65                  70                  75                  80

Glu Asp Phe Ala Thr Tyr Tyr Cys Gln Gln Ala Asn Ser Phe Pro Ile
                 85                  90                  95

Thr Phe Gly Gln Gly Thr Arg Leu Glu Ile Lys
                100                 105

<210> SEQ ID NO 83
<211> LENGTH: 121
<212> TYPE: PRT
<213> ORGANISM: Homo sapiens

<400> SEQUENCE: 83

Gln Val Gln Leu Val Gln Ser Gly Ala Glu Val Lys Lys Pro Gly Ala
 1               5                  10                  15

Ser Val Lys Val Ser Cys Lys Ala Ala Gly Tyr Thr Phe Thr Asn Tyr
                 20                  25                  30

Gly Ile Ser Trp Val Arg Gln Ala Pro Gly Gln Ala Leu Glu Trp Met
             35                  40                  45

Gly Trp Ile Thr Thr Tyr Ser Ser Asn Thr Ile Tyr Ala Gln Lys Leu
         50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Arg Val Val Val Arg Pro Asp Tyr Phe Asp Tyr Trp Gly
                100                 105                 110

Gln Gly Thr Leu Val Thr Val Ser Ser
            115                 120

<210> SEQ ID NO 84
<211> LENGTH: 107
<212> TYPE: PRT
```

```
<213> ORGANISM: Homo sapiens

<400> SEQUENCE: 84

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser His Trp Pro Arg
                85                  90                  95

Thr Phe Gly Gln Gly Thr Lys Val Glu Ile Lys
            100                 105

<210> SEQ ID NO 85
<211> LENGTH: 121
<212> TYPE: PRT
<213> ORGANISM: Homo sapiens

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Leu Ser Ala Tyr Ser Gly Asn Thr Ile Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Ile Val Val Arg Pro Asp Tyr Phe Asp Tyr Trp Gly
            100                 105                 110

Gln Gly Thr Leu Val Thr Val Ser Ser
        115                 120

<210> SEQ ID NO 86
<211> LENGTH: 107
<212> TYPE: PRT
<213> ORGANISM: Homo sapiens

<400> SEQUENCE: 86

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 87
<211> LENGTH: 121
<212> TYPE: PRT
<213> ORGANISM: Homo sapiens

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ala Gly Tyr Thr Phe Thr Asn Tyr
                20                  25                  30

Gly Ile Ser Trp Val Arg Gln Ala Pro Gly Gln Gly Leu Glu Trp Met
            35                  40                  45

Gly Trp Ile Ile Thr Tyr Asn Gly Asn Thr Ile Tyr Ala Gln Arg Phe
        50                  55                  60

Gln Asp Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Arg Ile Ile Val Arg Pro Asp Tyr Phe Asp Tyr Trp Gly
                100                 105                 110

Gln Gly Thr Leu Val Thr Val Ser Ser
            115                 120

<210> SEQ ID NO 88
<211> LENGTH: 107
<212> TYPE: PRT
<213> ORGANISM: Homo sapiens

<400> SEQUENCE: 88

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 89
<211> LENGTH: 120
<212> TYPE: PRT
<213> ORGANISM: Homo sapiens

<400> SEQUENCE: 89

Gln Val Gln Leu Gln Gln Trp Gly Ala Gly Leu Leu Lys Pro Ser Glu
1               5                   10                  15

```
Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Asn Tyr Gly Ser Gly Tyr Tyr Tyr Phe Asp Leu Trp Gly Arg
            100                 105                 110

Gly Thr Gln Val Thr Val Ser Ser
        115                 120

<210> SEQ ID NO 90
<211> LENGTH: 107
<212> TYPE: PRT
<213> ORGANISM: Homo sapiens

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Phe Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Ser Phe Pro Ile
                85                  90                  95

Thr Phe Gly Gln Gly Thr Arg Leu Glu Ile Lys
            100                 105

<210> SEQ ID NO 91
<211> LENGTH: 120
<212> TYPE: PRT
<213> ORGANISM: Homo sapiens

<400> SEQUENCE: 91

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile His His Ser Gly Ser Ala Asn Tyr Asn Pro Ser Leu Met
50                  55                  60

Ser Arg Val Thr Ile Ser Val Asp Thr Ser Lys Asn Gln Phe Ser Leu
65                  70                  75                  80

Gln Leu Ser Ser Val Thr Ala Ala Asp Thr Ala Val Tyr Tyr Cys Ala
                85                  90                  95

Arg Gly Tyr Tyr Gly Ser Gly Tyr Tyr Tyr Phe Asp Tyr Trp Gly Gln
            100                 105                 110
```

```
Gly Thr Leu Val Thr Val Ser Ser
        115                 120

<210> SEQ ID NO 92
<211> LENGTH: 107
<212> TYPE: PRT
<213> ORGANISM: Homo sapiens

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 93
<211> LENGTH: 120
<212> TYPE: PRT
<213> ORGANISM: Homo sapiens

<400> SEQUENCE: 93

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Asn Trp Ile Arg Gln Pro Pro Gly Lys Gly Leu Glu Trp Ile
        35                  40                  45

Gly Glu Ile His His Val Gly Ser Thr Asn Tyr Asn Pro Ser Leu Lys
    50                  55                  60

Ser Arg Val Thr Ile Ser Val Asp Thr Ser Lys Ser Gln Phe Ser Leu
65                  70                  75                  80

Lys Leu Ser Ser Val Thr Ala Ala Asp Thr Ala Val Tyr Tyr Cys Ala
                85                  90                  95

Arg Gly Tyr Tyr Asp Ser Gly Val Tyr Tyr Phe Asp Tyr Trp Ala Gln
            100                 105                 110

Gly Thr Leu Val Thr Val Ser Ser
        115                 120

<210> SEQ ID NO 94
<211> LENGTH: 107
<212> TYPE: PRT
<213> ORGANISM: Homo sapiens

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Glu Lys Ala Pro Lys Ser Leu Ile
```

```
            35                  40                  45
Tyr Ala Ala Ser Ser Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Ile
                 85                  90                  95

Thr Phe Gly Gln Gly Thr Arg Leu Glu Ile Lys
            100                 105
```

<210> SEQ ID NO 95
<211> LENGTH: 120
<212> TYPE: PRT
<213> ORGANISM: Homo sapiens

<400> SEQUENCE: 95

```
Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Asp Tyr
             20                  25                  30

Tyr Trp Asn Trp Ile Arg Gln Pro Pro Gly Lys Gly Leu Glu Trp Ile
         35                  40                  45

Gly Glu Ile His His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Tyr Tyr Ala Ser Gly Val Tyr Tyr Phe Asp Tyr Trp Gly Gln
            100                 105                 110

Gly Thr Leu Val Thr Val Ser Ser
            115                 120
```

<210> SEQ ID NO 96
<211> LENGTH: 107
<212> TYPE: PRT
<213> ORGANISM: Homo sapiens

<400> SEQUENCE: 96

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
             20                  25                  30

Leu Ala Trp Tyr Gln Gln Lys Pro Glu Lys Ala Pro Lys Ser Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Ile
                 85                  90                  95

Thr Phe Gly Gln Gly Thr Arg Leu Glu Ile Lys
            100                 105
```

<210> SEQ ID NO 97
<211> LENGTH: 120
<212> TYPE: PRT

<213> ORGANISM: Homo sapiens

<400> SEQUENCE: 97

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Phe Trp Asn Trp Ile Arg Gln Pro Pro Gly Lys Gly Leu Glu Trp Ile
        35                  40                  45

Gly Glu Ile His His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Ser Ser Val Thr Ala Ala Asp Thr Ala Val Tyr Tyr Cys Ala
                85                  90                  95

Arg Gly Leu Ile Gly Ser Gly Tyr Tyr Tyr Phe Asp Tyr Trp Asp Gln
            100                 105                 110

Gly Thr Leu Val Thr Val Ser Ser
            115                 120

<210> SEQ ID NO 98
<211> LENGTH: 107
<212> TYPE: PRT
<213> ORGANISM: Homo sapiens

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 99
<211> LENGTH: 120
<212> TYPE: PRT
<213> ORGANISM: Homo sapiens

<400> SEQUENCE: 99

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asp Thr Asn Tyr Asn Pro Ser Leu Thr
    50                  55                  60

Ser Arg Val Thr Ile Ser Val Asp Thr Ser Lys Asn Gln Phe Ser Leu
65                  70                  75                  80

```
Lys Leu Ser Ser Val Thr Ala Ala Asp Thr Ala Val Tyr Tyr Cys Ala
                85                  90                  95

Arg Leu Phe Tyr Gly Ser Gly Ile Tyr Tyr Phe Asp Tyr Trp Gly Gln
            100                 105                 110

Gly Thr Leu Val Thr Val Ser Ser
        115                 120

<210> SEQ ID NO 100
<211> LENGTH: 107
<212> TYPE: PRT
<213> ORGANISM: Homo sapiens

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Thr Phe Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105

<210> SEQ ID NO 101
<211> LENGTH: 120
<212> TYPE: PRT
<213> ORGANISM: Homo sapiens

<400> SEQUENCE: 101

Gln Val Gln Leu Gln Gln Trp Gly Ala Gly Leu Leu Lys Pro Ser Glu
1               5                   10                  15

Thr Leu Ser Leu Thr Cys Ala Ile Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Asp Thr Asn Tyr Asn Pro Ser Leu Thr
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Phe Tyr Gly Ser Gly Ile Tyr Tyr Phe Asp Tyr Trp Gly Gln
            100                 105                 110

Gly Thr Leu Val Thr Val Ser Ser
        115                 120

<210> SEQ ID NO 102
<211> LENGTH: 107
<212> TYPE: PRT
<213> ORGANISM: Homo sapiens

<400> SEQUENCE: 102
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Thr Phe Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
            85                  90                  95

Thr Phe Gly Gln Gly Thr Lys Val Glu Ile Lys
            100                 105

<210> SEQ ID NO 103
<211> LENGTH: 120
<212> TYPE: PRT
<213> ORGANISM: Homo sapiens

<400> SEQUENCE: 103

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Leu Tyr Tyr Gly Ser Gly Ser Tyr Tyr Phe Asp Tyr Trp Gly Gln
            100                 105                 110

Gly Thr Leu Val Thr Val Ser Ser
        115                 120

<210> SEQ ID NO 104
<211> LENGTH: 107
<212> TYPE: PRT
<213> ORGANISM: Homo sapiens

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Thr Trp Tyr Gln Gln Lys Pro Glu Lys Ala Pro Lys Ser Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
            85                  90                  95

```
Thr Phe Gly Gln Gly Thr Lys Val Glu Ile Lys
            100                 105

<210> SEQ ID NO 105
<211> LENGTH: 120
<212> TYPE: PRT
<213> ORGANISM: Homo sapiens

<400> SEQUENCE: 105

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile His His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Leu Trp Tyr Gly Ser Gly Ser Tyr Tyr Phe Asp Tyr Trp Gly Gln
            100                 105                 110

Gly Thr Leu Val Thr Val Ser Ser
        115                 120

<210> SEQ ID NO 106
<211> LENGTH: 107
<212> TYPE: PRT
<213> ORGANISM: Homo sapiens

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gly Gly Thr Lys Val Glu Ile Lys
            100                 105

<210> SEQ ID NO 107
<211> LENGTH: 120
<212> TYPE: PRT
<213> ORGANISM: Homo sapiens

<400> SEQUENCE: 107

Gln Val Gln Leu Gln Gln Trp Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Thr Trp Ile Arg Gln Pro Pro Gly Lys Gly Leu Glu Trp Ile
```

```
            35                  40                  45
Gly Glu Ile Tyr His Ser Gly Asp Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Tyr Ser Val Thr Ala Ala Asp Thr Ala Val Tyr Tyr Cys Ala
                85                  90                  95

Arg Leu Tyr Phe Gly Ser Gly Ile Tyr Tyr Leu Asp Tyr Trp Gly Gln
            100                 105                 110

Gly Thr Leu Val Thr Val Ser Ser
            115                 120

<210> SEQ ID NO 108
<211> LENGTH: 107
<212> TYPE: PRT
<213> ORGANISM: Homo sapiens

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Val Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105

<210> SEQ ID NO 109
<211> LENGTH: 124
<212> TYPE: PRT
<213> ORGANISM: Homo sapiens

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Ala Ile Ser Gly Ser Ala Tyr Ser Thr Tyr Tyr Ala Asp Ser Val
    50                  55                  60

Lys Gly Arg Phe Thr Ile Ser Arg Asp Asn Ser Lys Asn Thr Leu Trp
65                  70                  75                  80

Leu Gln Met Asn Ser Leu Arg Ala Glu Asp Thr Ala Val Tyr Tyr Cys
                85                  90                  95

Ala Lys Ala His Tyr His Gly Ser Gly Ser Tyr Tyr Thr Leu Phe Asp
            100                 105                 110

Tyr Trp Gly Gln Gly Thr Leu Val Thr Val Ser Ser
            115                 120
```

```
<210> SEQ ID NO 110
<211> LENGTH: 107
<212> TYPE: PRT
<213> ORGANISM: Homo sapiens

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 111
<211> LENGTH: 124
<212> TYPE: PRT
<213> ORGANISM: Homo sapiens

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Gly Met Asn Trp Val Arg Gln Ala Pro Gly Lys Gly Leu Glu Trp Val
        35                  40                  45

Ser Ala Ile Ser Gly Thr Gly Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Tyr Phe Gly Ser Gly Ser Tyr Tyr Thr Leu Phe Asp
            100                 105                 110

Tyr Trp Gly Gln Gly Thr Leu Val Thr Val Ser Ser
        115                 120

<210> SEQ ID NO 112
<211> LENGTH: 107
<212> TYPE: PRT
<213> ORGANISM: Homo sapiens

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
            100                 105
```

<210> SEQ ID NO 113
<211> LENGTH: 124
<212> TYPE: PRT
<213> ORGANISM: Homo sapiens

<400> SEQUENCE: 113

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Ala Met Asn Trp Val Arg Gln Ala Pro Gly Lys Gly Leu Glu Trp Val
             35                  40                  45

Ser Thr Ile Ser Gly Ser Gly Tyr Ala Thr Tyr Tyr Ala Asp Ser Val
 50                  55                  60

Lys Gly Arg Phe Thr Ile Ser Arg Asp Asn Ser Lys Thr Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly His Thr Leu Gly Ser Gly Ser Tyr Tyr Thr Leu Phe Asp
            100                 105                 110

Tyr Trp Gly Gln Gly Thr Leu Val Thr Val Ser Ser
        115                 120
```

<210> SEQ ID NO 114
<211> LENGTH: 107
<212> TYPE: PRT
<213> ORGANISM: Homo sapiens

<400> SEQUENCE: 114

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Asn Ser Trp
             20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Tyr
                 85                  90                  95

Thr Phe Gly Gln Gly Thr Lys Leu Glu Ile Lys
            100                 105
```

<210> SEQ ID NO 115
<211> LENGTH: 124
<212> TYPE: PRT
<213> ORGANISM: Homo sapiens

<400> SEQUENCE: 115

Glu Val Gln Leu Trp Glu Gly Gly Ser Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Gly Ile Ser Gly Ser Gly Tyr Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Tyr Tyr His Gly Ser Gly Ser Tyr Tyr Thr Ser Phe Asp
            100                 105                 110

Tyr Trp Gly Gln Gly Thr Leu Val Thr Val Ser Ser
            115                 120

<210> SEQ ID NO 116
<211> LENGTH: 107
<212> TYPE: PRT
<213> ORGANISM: Homo sapiens

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Leu
                85                  90                  95

Thr Phe Gly Gly Gly Thr Lys Val Glu Ile Lys
            100                 105

<210> SEQ ID NO 117
<211> LENGTH: 121
<212> TYPE: PRT
<213> ORGANISM: Homo sapiens

<400> SEQUENCE: 117

Gln Val Gln Leu Val Glu Ser Gly Gly Gly Val Val Gln Thr Gly Arg
1               5                   10                  15

Ser Leu Arg Leu Ser Cys Ala Ala Ser Gly Phe Thr Phe Ser Ser His
            20                  25                  30

Ala Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Asp Tyr Ile Ser Ser Gly Val Phe Asp Tyr Trp Gly
            100                 105                 110

Gln Gly Thr Leu Val Thr Val Ser Ser
        115                 120

<210> SEQ ID NO 118
<211> LENGTH: 107
<212> TYPE: PRT
<213> ORGANISM: Homo sapiens

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 119
<211> LENGTH: 121
<212> TYPE: PRT
<213> ORGANISM: Homo sapiens

<400> SEQUENCE: 119

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser His
            20                  25                  30

Ala Met His Trp Val Arg Gln Ala Pro Gly Lys Gly Leu Glu Trp Val
        35                  40                  45

Ala Ala Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Met Tyr
65                  70                  75                  80

Leu Gln Met Asn Ser Leu Arg Ala Glu Asp Thr Ala Met Cys Tyr Cys
                85                  90                  95

Ala Arg Gly Ser Ile Thr Gly Ser Thr Gly Val Phe Asp Tyr Trp Gly
            100                 105                 110

Gln Gly Thr Leu Val Thr Val Ser Ser
        115                 120

<210> SEQ ID NO 120
<211> LENGTH: 107
<212> TYPE: PRT
<213> ORGANISM: Homo sapiens

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp

```
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 121
<211> LENGTH: 121
<212> TYPE: PRT
<213> ORGANISM: Homo sapiens

<400> SEQUENCE: 121

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ile Ile Gly Ser Thr Gly Val Phe Asp Tyr Trp Gly
            100                 105                 110

Gln Gly Thr Leu Val Thr Val Ser Ser
        115                 120

<210> SEQ ID NO 122
<211> LENGTH: 107
<212> TYPE: PRT
<213> ORGANISM: Homo sapiens

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105
```

```
<210> SEQ ID NO 123
<211> LENGTH: 121
<212> TYPE: PRT
<213> ORGANISM: Homo sapiens

<400> SEQUENCE: 123

Gln Val Gln Val Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ile Thr Gly Ser Thr Gly Val Phe Asp Tyr Trp Gly
            100                 105                 110

Gln Gly Thr Leu Val Thr Val Ser Ser
        115                 120

<210> SEQ ID NO 124
<211> LENGTH: 107
<212> TYPE: PRT
<213> ORGANISM: Homo sapiens

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Glu Lys Ala Pro Lys Ser Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asn Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 125
<211> LENGTH: 121
<212> TYPE: PRT
<213> ORGANISM: Homo sapiens

<400> SEQUENCE: 125

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Ile His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Ile Thr Gly Ser Thr Gly Val Phe Asp Tyr Trp Gly
            100                 105                 110

Gln Gly Thr Leu Val Thr Val Ser Ser
        115                 120

<210> SEQ ID NO 126
<211> LENGTH: 107
<212> TYPE: PRT
<213> ORGANISM: Homo sapiens

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 127
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Arg or Ser
<220> FEATURE:
<221> NAME/KEY: MISC_FEATURE
<222> LOCATION: (7)..(7)
<223> OTHER INFORMATION: Xaa is Thr or Ser

<400> SEQUENCE: 127

Ile Ser Gly Xaa Gly Gly Xaa Thr
1               5

<210> SEQ ID NO 128
<211> LENGTH: 8
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Arg or Ser
<220> FEATURE:
<221> NAME/KEY: MISC_FEATURE
<222> LOCATION: (6)..(6)
<223> OTHER INFORMATION: Xaa is Thr or Ser

<400> SEQUENCE: 128

Gly Gly Thr Phe Xaa Xaa Tyr Ala
1               5

```
<210> SEQ ID NO 129
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Asn or Ile
<220> FEATURE:
<221> NAME/KEY: MISC_FEATURE
<222> LOCATION: (3)..(3)
<223> OTHER INFORMATION: Xaa is Thr or Pro
<220> FEATURE:
<221> NAME/KEY: MISC_FEATURE
<222> LOCATION: (4)..(4)
<223> OTHER INFORMATION: Xaa is Val or Ile
<220> FEATURE:
<221> NAME/KEY: MISC_FEATURE
<222> LOCATION: (8)..(8)
<223> OTHER INFORMATION: Xaa is Val or Ala

<400> SEQUENCE: 129

Ile Xaa Xaa Xaa Leu Gly Ile Xaa
1               5

<210> SEQ ID NO 130
<211> LENGTH: 13
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: Xaa is Ile or Met
<220> FEATURE:
<221> NAME/KEY: MISC_FEATURE
<222> LOCATION: (13)..(13)
<223> OTHER INFORMATION: Xaa is Glu or Asp

<400> SEQUENCE: 130

Ala Arg Glu Lys Gly Val Asp Tyr Tyr Tyr Gly Xaa Xaa
1               5                   10

<210> SEQ ID NO 131
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Asn or Ser

<400> SEQUENCE: 131

Gly Tyr Thr Phe Thr Xaa Tyr Gly
1               5

<210> SEQ ID NO 132
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Ser, Thr or Ile
<220> FEATURE:
<221> NAME/KEY: MISC_FEATURE
<222> LOCATION: (3)..(3)
<223> OTHER INFORMATION: Xaa is Ala or Thr
<220> FEATURE:
<221> NAME/KEY: MISC_FEATURE
<222> LOCATION: (5)..(5)
<223> OTHER INFORMATION: Xaa is Ser or Asn
```

```
<400> SEQUENCE: 132

Ile Xaa Xaa Tyr Xaa Gly Asn Thr
1               5

<210> SEQ ID NO 133
<211> LENGTH: 14
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Ile or Val
<220> FEATURE:
<221> NAME/KEY: MISC_FEATURE
<222> LOCATION: (6)..(6)
<223> OTHER INFORMATION: Xaa is Ile or Val

<400> SEQUENCE: 133

Ala Arg Asp Arg Xaa Xaa Val Arg Pro Asp Tyr Phe Asp Tyr
1               5                   10

<210> SEQ ID NO 134
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Asp or Gly
<220> FEATURE:
<221> NAME/KEY: MISC_FEATURE
<222> LOCATION: (8)..(8)
<223> OTHER INFORMATION: Xaa isTyr or Phe

<400> SEQUENCE: 134

Gly Gly Ser Phe Ser Xaa Tyr Xaa
1               5

<210> SEQ ID NO 135
<211> LENGTH: 7
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is His or Asn
<220> FEATURE:
<221> NAME/KEY: MISC_FEATURE
<222> LOCATION: (4)..(4)
<223> OTHER INFORMATION: Xaa is Ser or Val
<220> FEATURE:
<221> NAME/KEY: MISC_FEATURE
<222> LOCATION: (7)..(7)
<223> OTHER INFORMATION: Xaa is Thr or Ala

<400> SEQUENCE: 135

Ile Xaa His Xaa Gly Ser Xaa
1               5

<210> SEQ ID NO 136
<211> LENGTH: 14
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Tyr, Asn or Leu
<220> FEATURE:
<221> NAME/KEY: MISC_FEATURE
<222> LOCATION: (5)..(5)
```

```
<223> OTHER INFORMATION: Xaa is Tyr or Ile
<220> FEATURE:
<221> NAME/KEY: MISC_FEATURE
<222> LOCATION: (6)..(6)
<223> OTHER INFORMATION: Xaa is Asp, Gly or Ala
<220> FEATURE:
<221> NAME/KEY: MISC_FEATURE
<222> LOCATION: (9)..(9)
<223> OTHER INFORMATION: Xaa is Val or Tyr
<220> FEATURE:
<221> NAME/KEY: MISC_FEATURE
<222> LOCATION: (14)..(14)
<223> OTHER INFORMATION: Xaa is Tyr or Leu

<400> SEQUENCE: 136

Ala Arg Gly Xaa Xaa Xaa Ser Gly Xaa Tyr Tyr Phe Asp Xaa
1               5                   10

<210> SEQ ID NO 137
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Gly or Asp

<400> SEQUENCE: 137

Gly Gly Ser Phe Ser Xaa Tyr Tyr
1               5

<210> SEQ ID NO 138
<211> LENGTH: 7
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Tyr, Asn or His
<220> FEATURE:
<221> NAME/KEY: MISC_FEATURE
<222> LOCATION: (6)..(6)
<223> OTHER INFORMATION: Xaa is Asp or Ser

<400> SEQUENCE: 138

Ile Xaa His Ser Gly Xaa Thr
1               5

<210> SEQ ID NO 139
<211> LENGTH: 14
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Tyr, Phe or Trp
<220> FEATURE:
<221> NAME/KEY: MISC_FEATURE
<222> LOCATION: (5)..(5)
<223> OTHER INFORMATION: Xaa is Tyr or  Phe
<220> FEATURE:
<221> NAME/KEY: MISC_FEATURE
<222> LOCATION: (9)..(9)
<223> OTHER INFORMATION: Xaa is Ile, Thr or Ser
<220> FEATURE:
<221> NAME/KEY: MISC_FEATURE
<222> LOCATION: (12)..(12)
<223> OTHER INFORMATION: Xaa is Leu or Phe

<400> SEQUENCE: 139

Ala Arg Leu Xaa Xaa Gly Ser Gly Xaa Tyr Tyr Xaa Asp Tyr
1               5                   10
```

<210> SEQ ID NO 140
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Thr or Phe
<220> FEATURE:
<221> NAME/KEY: MISC_FEATURE
<222> LOCATION: (7)..(7)
<223> OTHER INFORMATION: Xaa is Phe or Tyr

<400> SEQUENCE: 140

Gly Phe Thr Phe Ser Xaa Xaa Ala
1               5

<210> SEQ ID NO 141
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa is Gly or Ser
<220> FEATURE:
<221> NAME/KEY: MISC_FEATURE
<222> LOCATION: (7)..(7)
<223> OTHER INFORMATION: Xaa is His or Asn

<400> SEQUENCE: 141

Ile Ser Tyr Asp Gly Xaa Xaa Lys
1               5

<210> SEQ ID NO 142
<211> LENGTH: 12
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: Xaa is Ala or Tyr

<400> SEQUENCE: 142

Ala Arg Gly Leu Gly Val Trp Gly Xaa Phe Asp Tyr
1               5                   10

<210> SEQ ID NO 143
<211> LENGTH: 8
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Ser, Asn or Thr
<220> FEATURE:
<221> NAME/KEY: MISC_FEATURE
<222> LOCATION: (6)..(6)
<223> OTHER INFORMATION: Xaa is Asn, Asp or Ser
<220> FEATURE:
<221> NAME/KEY: MISC_FEATURE
<222> LOCATION: (8)..(8)
<223> OTHER INFORMATION: Xaa is Gly or Ala

<400> SEQUENCE: 143

Gly Phe Thr Phe Xaa Xaa Tyr Xaa
1               5

<210> SEQ ID NO 144

```
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Ser or Thr
<220> FEATURE:
<221> NAME/KEY: MISC_FEATURE
<222> LOCATION: (5)..(5)
<223> OTHER INFORMATION: Xaa is Ala or Gly
<220> FEATURE:
<221> NAME/KEY: MISC_FEATURE
<222> LOCATION: (6)..(6)
<223> OTHER INFORMATION: Xaa is Tyr or Gly
<220> FEATURE:
<221> NAME/KEY: MISC_FEATURE
<222> LOCATION: (7)..(7)
<223> OTHER INFORMATION: Xaa is Ser or Ala

<400> SEQUENCE: 144

Ile Ser Gly Xaa Xaa Xaa Xaa Thr
1               5

<210> SEQ ID NO 145
<211> LENGTH: 17
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Ala or Gly
<220> FEATURE:
<221> NAME/KEY: MISC_FEATURE
<222> LOCATION: (4)..(4)
<223> OTHER INFORMATION: Xaa is His or Tyr
<220> FEATURE:
<221> NAME/KEY: MISC_FEATURE
<222> LOCATION: (5)..(5)
<223> OTHER INFORMATION: Xaa is Tyr or Thr
<220> FEATURE:
<221> NAME/KEY: MISC_FEATURE
<222> LOCATION: (6)..(6)
<223> OTHER INFORMATION: Xaa is His, Phe or Leu
<220> FEATURE:
<221> NAME/KEY: MISC_FEATURE
<222> LOCATION: (14)..(14)
<223> OTHER INFORMATION: Xaa is Leu or Ser

<400> SEQUENCE: 145

Ala Lys Xaa Xaa Xaa Xaa Gly Ser Gly Ser Tyr Tyr Thr Xaa Phe Asp
1               5                   10                  15

Tyr

<210> SEQ ID NO 146
<211> LENGTH: 8
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Ser or Thr
<220> FEATURE:
<221> NAME/KEY: MISC_FEATURE
<222> LOCATION: (6)..(6)
<223> OTHER INFORMATION: Xaa is Ile or Ser

<400> SEQUENCE: 146

Gly Tyr Ser Phe Xaa Xaa Tyr Trp
1               5

<210> SEQ ID NO 147
```

```
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Phe or Tyr
<220> FEATURE:
<221> NAME/KEY: MISC_FEATURE
<222> LOCATION: (8)..(8)
<223> OTHER INFORMATION: Xaa is Ile or Thr

<400> SEQUENCE: 147

Ile Xaa Pro Gly Asp Ser Asp Xaa
1               5

<210> SEQ ID NO 148
<211> LENGTH: 16
<212> TYPE: PRT
<213> ORGANISM: Homo sapiens

<400> SEQUENCE: 148

Ala Arg Gln Pro Gly Asp Trp Ser Pro Arg His Trp Tyr Phe Asp Leu
1               5                   10                  15

<210> SEQ ID NO 149
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Asn or Ser

<400> SEQUENCE: 149

Gly Tyr Xaa Phe Thr Ser Tyr Trp
1               5

<210> SEQ ID NO 150
<211> LENGTH: 8
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ser or Thr

<400> SEQUENCE: 150

Ile Ser Ala Tyr Asn Gly Asn Xaa
1               5

<210> SEQ ID NO 151
<211> LENGTH: 18
<212> TYPE: PRT
<213> ORGANISM: Homo sapiens

<400> SEQUENCE: 151

Ala Arg Glu Tyr Ser Tyr Asp Ser Gly Thr Tyr Phe Tyr Tyr Gly Met
1               5                   10                  15

Asp Val

<210> SEQ ID NO 152
<211> LENGTH: 8
<212> TYPE: PRT
<213> ORGANISM: Homo sapiens
<220> FEATURE:
<221> NAME/KEY: MISC_FEATURE
<222> LOCATION: (6)..(6)
```

```
<223> OTHER INFORMATION: Xaa is Asp or Ser
<220> FEATURE:
<221> NAME/KEY: MISC_FEATURE
<222> LOCATION: (7)..(7)
<223> OTHER INFORMATION: Xaa is Tyr or His
<220> FEATURE:
<221> NAME/KEY: MISC_FEATURE
<222> LOCATION: (8)..(8)
<223> OTHER INFORMATION: Xaa is Val or Ala

<400> SEQUENCE: 152

Gly Phe Thr Phe Ser Xaa Xaa Xaa
1               5

<210> SEQ ID NO 153
<211> LENGTH: 8
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Xaa is Asn or Tyr
<220> FEATURE:
<221> NAME/KEY: MISC_FEATURE
<222> LOCATION: (8)..(8)
<223> OTHER INFORMATION: Xaa is Lys or Glu

<400> SEQUENCE: 153

Ile Ser Tyr Asp Gly Ser Xaa Xaa
1               5

<210> SEQ ID NO 154
<211> LENGTH: 14
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Gly, Asp or Ser
<220> FEATURE:
<221> NAME/KEY: MISC_FEATURE
<222> LOCATION: (5)..(5)
<223> OTHER INFORMATION: Xaa is Ile or Tyr
<220> FEATURE:
<221> NAME/KEY: MISC_FEATURE
<222> LOCATION: (6)..(6)
<223> OTHER INFORMATION: Xaa is Thr or Ile
<220> FEATURE:
<221> NAME/KEY: MISC_FEATURE
<222> LOCATION: (7)..(7)
<223> OTHER INFORMATION: Xaa is Gly or Ser
<220> FEATURE:
<221> NAME/KEY: MISC_FEATURE
<222> LOCATION: (8)..(8)
<223> OTHER INFORMATION: Xaa is Thr or Ser
<220> FEATURE:
<221> NAME/KEY: MISC_FEATURE
<222> LOCATION: (9)..(9)
<223> OTHER INFORMATION: Xaa is Thr or Ser
<220> FEATURE:
<221> NAME/KEY: MISC_FEATURE
<222> LOCATION: (11)..(11)
<223> OTHER INFORMATION: Xaa is Tyr or Val

<400> SEQUENCE: 154

Ala Arg Gly Xaa Xaa Xaa Xaa Xaa Xaa Gly Xaa Phe Asp Tyr
1               5                   10

<210> SEQ ID NO 155
<211> LENGTH: 9
<212> TYPE: PRT
<213> ORGANISM: Homo sapiens
<220> FEATURE:
```

```
<221> NAME/KEY: MISC_FEATURE
<222> LOCATION: (8)..(8)
<223> OTHER INFORMATION: Xaa is Ile or Leu

<400> SEQUENCE: 155

Gln Gln Ala Asn Ser Phe Pro Xaa Thr
1               5

<210> SEQ ID NO 156
<211> LENGTH: 9
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Asn or His

<400> SEQUENCE: 156

Gln Gln Arg Ser Xaa Trp Pro Arg Thr
1               5

<210> SEQ ID NO 157
<211> LENGTH: 6
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Xaa is Arg or Ser

<400> SEQUENCE: 157

Gln Gly Ile Ser Xaa Trp
1               5

<210> SEQ ID NO 158
<211> LENGTH: 9
<212> TYPE: PRT
<213> ORGANISM: Homo sapiens

<400> SEQUENCE: 158

Gln Gln Tyr Asn Ser Phe Pro Pro Thr
1               5

<210> SEQ ID NO 159
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Ser or Asn

<400> SEQUENCE: 159

Gln Gly Ile Xaa Ser Trp
1               5

<210> SEQ ID NO 160
<211> LENGTH: 9
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Tyr or Leu

<400> SEQUENCE: 160

Gln Gln Tyr Asn Ser Tyr Pro Xaa Thr
1               5
```

```
<210> SEQ ID NO 161
<211> LENGTH: 6
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Ser or Asn
<220> FEATURE:
<221> NAME/KEY: MISC_FEATURE
<222> LOCATION: (5)..(5)
<223> OTHER INFORMATION: Xaa is Ser or Asn

<400> SEQUENCE: 161

Gln Gly Ile Xaa Xaa Trp
1               5

<210> SEQ ID NO 162
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Lys or Asn

<400> SEQUENCE: 162

Gln Gln Tyr Xaa Ser Tyr Pro Ile Thr
1               5

<210> SEQ ID NO 163
<211> LENGTH: 7
<212> TYPE: PRT
<213> ORGANISM: Homo sapiens

<400> SEQUENCE: 163

Ile Tyr His Ser Gly Asp Thr
1               5

<210> SEQ ID NO 164
<211> LENGTH: 122
<212> TYPE: PRT
<213> ORGANISM: Homo sapiens

<400> SEQUENCE: 164

Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Ser Phe His Phe Tyr
                20                  25                  30

Trp Ile Gly Trp Val Arg Gln Met Pro Gly Lys Gly Leu Glu Trp Met
            35                  40                  45

Gly Ser Ile Tyr Pro Gly Asp Ser Asp Thr Arg Tyr Arg Pro Ser Phe
        50                  55                  60

Gln Gly Gln Val Thr Ile Ser Ala Asp Lys Ser Ile Ser Thr Ala Tyr
65                  70                  75                  80

Leu Gln Trp Thr Ser Leu Lys Ala Ser Asp Thr Ala Ile Tyr Tyr Cys
                85                  90                  95

Ala Arg Gln Arg Gly Asp Tyr Tyr Phe Tyr Gly Met Asp Val Trp
                100                 105                 110

Gly Gln Gly Thr Thr Val Thr Val Ser Ser
            115                 120
```

```
<210> SEQ ID NO 165
<211> LENGTH: 107
<212> TYPE: PRT
<213> ORGANISM: Homo sapiens

<400> SEQUENCE: 165

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Val Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105

<210> SEQ ID NO 166
<211> LENGTH: 8
<212> TYPE: PRT
<213> ORGANISM: Homo sapiens

<400> SEQUENCE: 166

Gly Tyr Ser Phe His Phe Tyr Trp
1               5

<210> SEQ ID NO 167
<211> LENGTH: 8
<212> TYPE: PRT
<213> ORGANISM: Homo sapiens

<400> SEQUENCE: 167

Ile Tyr Pro Gly Asp Ser Asp Thr
1               5

<210> SEQ ID NO 168
<211> LENGTH: 15
<212> TYPE: PRT
<213> ORGANISM: Homo sapiens

<400> SEQUENCE: 168

Ala Arg Gln Arg Gly Asp Tyr Tyr Tyr Phe Tyr Gly Met Asp Val
1               5                   10                  15

<210> SEQ ID NO 169
<211> LENGTH: 7
<212> TYPE: PRT
<213> ORGANISM: Homo sapiens

<400> SEQUENCE: 169

Gln Ser Val Ser Ser Ser Tyr
1               5

<210> SEQ ID NO 170
<211> LENGTH: 8
<212> TYPE: PRT
<213> ORGANISM: Homo sapiens

<400> SEQUENCE: 170
```

Gln Gln Tyr Gly Ser Ser Leu Thr
1               5

<210> SEQ ID NO 171
<211> LENGTH: 119
<212> TYPE: PRT
<213> ORGANISM: Homo sapiens

<400> SEQUENCE: 171

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
                20                  25                  30

Pro Met Ala Trp Val Arg Gln Ala Pro Gly Lys Gly Leu Glu Trp Val
            35                  40                  45

Ser Thr Ile Ser Thr Ser Gly Gly Arg Thr Tyr Tyr Arg Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Arg Gln Tyr Ser Gly Gly Phe Asp Tyr Trp Gly Gln Gly
            100                 105                 110

Thr Leu Val Thr Val Ser Ser
        115

<210> SEQ ID NO 172
<211> LENGTH: 110
<212> TYPE: PRT
<213> ORGANISM: Homo sapiens

<400> SEQUENCE: 172

Asp Ile Gln Leu Thr Gln Pro Asn Ser Val Ser Thr Ser Leu Gly Ser
1               5                   10                  15

Thr Val Lys Leu Ser Cys Thr Leu Ser Ser Gly Asn Ile Glu Asn Asn
                20                  25                  30

Tyr Val His Trp Tyr Gln Leu Tyr Glu Gly Arg Ser Pro Thr Thr Met
            35                  40                  45

Ile Tyr Asp Asp Asp Lys Arg Pro Asp Gly Val Pro Asp Arg Phe Ser
        50                  55                  60

Gly Ser Ile Asp Arg Ser Ser Asn Ser Ala Phe Leu Thr Ile His Asn
65                  70                  75                  80

Val Ala Ile Glu Asp Glu Ala Ile Tyr Phe Cys His Ser Tyr Val Ser
                85                  90                  95

Ser Phe Asn Val Phe Gly Gly Gly Thr Lys Leu Thr Val Leu
            100                 105                 110

<210> SEQ ID NO 173
<211> LENGTH: 119
<212> TYPE: PRT
<213> ORGANISM: Homo sapiens

<400> SEQUENCE: 173

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

```
Gly Met Phe Trp Val Arg Gln Ala Pro Gly Lys Gly Leu Glu Trp Val
        35                  40                  45

Ala Thr Ile Ser Arg Tyr Ser Arg Tyr Ile Tyr Tyr Pro Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Arg Pro Leu Tyr Gly Ser Ser Pro Asp Tyr Trp Gly Gln Gly
            100                 105                 110

Thr Leu Val Thr Val Ser Ser
        115

<210> SEQ ID NO 174
<211> LENGTH: 106
<212> TYPE: PRT
<213> ORGANISM: Homo sapiens

<400> SEQUENCE: 174

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Thr Tyr Val
             20                  25                  30

His Trp Tyr Gln Gln Lys Pro Gly Gln Ala Pro Arg Leu Leu Ile Tyr
         35                  40                  45

Asp Thr Ser Lys Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Phe Gln Gly Ser Gly Tyr Pro Leu Thr
                 85                  90                  95

Phe Gly Ser Gly Thr Lys Leu Glu Met Arg
            100                 105

<210> SEQ ID NO 175
<211> LENGTH: 113
<212> TYPE: PRT
<213> ORGANISM: Homo sapiens

<400> SEQUENCE: 175

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Phe Asp Tyr Trp Gly Gln Gly Thr Leu Val Thr Val Ser
            100                 105                 110

Ser
```

```
<210> SEQ ID NO 176
<211> LENGTH: 119
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (10)..(10)
<223> OTHER INFORMATION: X can be G or D
<220> FEATURE:
<221> NAME/KEY: misc_feature
<222> LOCATION: (35)..(35)
<223> OTHER INFORMATION: X can be N or S
<220> FEATURE:
<221> NAME/KEY: misc_feature
<222> LOCATION: (54)..(54)
<223> OTHER INFORMATION: X can be R or S
<220> FEATURE:
<221> NAME/KEY: misc_feature
<222> LOCATION: (57)..(57)
<223> OTHER INFORMATION: X can be S or T
<220> FEATURE:
<221> NAME/KEY: misc_feature
<222> LOCATION: (77)..(77)
<223> OTHER INFORMATION: X can be S or N
<220> FEATURE:
<221> NAME/KEY: misc_feature
<222> LOCATION: (80)..(80)
<223> OTHER INFORMATION: X can be C or Y
<220> FEATURE:
<221> NAME/KEY: misc_feature
<222> LOCATION: (84)..(84)
<223> OTHER INFORMATION: X can be N or S

<400> SEQUENCE: 176

Glu Val Gln Leu Leu Glu Ser Gly Gly Xaa Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Xaa Trp Val Arg Gln Ala Pro Gly Lys Gly Leu Glu Trp Val
        35                  40                  45

Ser Ala Ile Ser Gly Xaa Gly Gly Xaa Thr Tyr Tyr Ala Asp Ser Val
    50                  55                  60

Lys Gly Arg Phe Thr Ile Ser Arg Asp Asn Ser Lys Xaa Thr Leu Xaa
65                  70                  75                  80

Leu Gln Met Xaa Ser Leu Arg Ala Glu Asp Thr Ala Val Tyr Tyr Cys
                85                  90                  95

Ala Lys Ala Arg Ala Asn Trp Asp Tyr Phe Asp Tyr Trp Gly Gln Gly
            100                 105                 110

Thr Leu Val Thr Val Ser Ser
        115

<210> SEQ ID NO 177
<211> LENGTH: 113
<212> TYPE: PRT
<213> ORGANISM: Homo sapiens

<400> SEQUENCE: 177

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
```

-continued

```
             50                  55                  60
Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Met Asp Val Trp Gly Gln Gly Thr Thr Val Thr Val Ser
            100                 105                 110

Ser

<210> SEQ ID NO 178
<211> LENGTH: 121
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (30)..(30)
<223> OTHER INFORMATION: X can be S or R
<220> FEATURE:
<221> NAME/KEY: misc_feature
<222> LOCATION: (31)..(31)
<223> OTHER INFORMATION: X can be S or T
<220> FEATURE:
<221> NAME/KEY: misc_feature
<222> LOCATION: (52)..(52)
<223> OTHER INFORMATION: X can be I or N
<220> FEATURE:
<221> NAME/KEY: misc_feature
<222> LOCATION: (53)..(53)
<223> OTHER INFORMATION: X can be P or T
<220> FEATURE:
<221> NAME/KEY: misc_feature
<222> LOCATION: (54)..(54)
<223> OTHER INFORMATION: X can be I or V
<220> FEATURE:
<221> NAME/KEY: misc_feature
<222> LOCATION: (58)..(58)
<223> OTHER INFORMATION: X can be A or V
<220> FEATURE:
<221> NAME/KEY: misc_feature
<222> LOCATION: (60)..(60)
<223> OTHER INFORMATION: X can be Y or H
<220> FEATURE:
<221> NAME/KEY: misc_feature
<222> LOCATION: (77)..(77)
<223> OTHER INFORMATION: X can be S or N
<220> FEATURE:
<221> NAME/KEY: misc_feature
<222> LOCATION: (84)..(84)
<223> OTHER INFORMATION: X can be S or N
<220> FEATURE:
<221> NAME/KEY: misc_feature
<222> LOCATION: (108)..(108)
<223> OTHER INFORMATION: X can be M or I
<220> FEATURE:
<221> NAME/KEY: misc_feature
<222> LOCATION: (109)..(109)
<223> OTHER INFORMATION: X can be D or E

<400> SEQUENCE: 178

Gln Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Xaa Xaa Tyr
                 20                  25                  30

Ala Ile Asn Trp Val Arg Gln Ala Pro Gly Gln Gly Leu Glu Trp Met
             35                  40                  45

Gly Arg Ile Xaa Xaa Xaa Leu Gly Ile Xaa Asn Xaa Ala Gln Lys Phe
         50                  55                  60
```

Gln Gly Arg Val Thr Ile Thr Ala Asp Lys Ser Thr Xaa Thr Ala Tyr
65                  70                  75                  80

Met Glu Leu Xaa Ser Leu Arg Ser Glu Asp Thr Ala Val Tyr Tyr Cys
                85                  90                  95

Ala Arg Glu Lys Gly Val Asp Tyr Tyr Tyr Gly Xaa Xaa Val Trp Gly
            100                 105                 110

Gln Gly Thr Thr Val Thr Val Ser Ser
            115                 120

<210> SEQ ID NO 179
<211> LENGTH: 113
<212> TYPE: PRT
<213> ORGANISM: Homo sapiens

<400> SEQUENCE: 179

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Arg Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser

<210> SEQ ID NO 180
<211> LENGTH: 121
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (31)..(31)
<223> OTHER INFORMATION: X can be S or N
<220> FEATURE:
<221> NAME/KEY: misc_feature
<222> LOCATION: (44)..(44)
<223> OTHER INFORMATION: X can be G or A
<220> FEATURE:
<221> NAME/KEY: misc_feature
<222> LOCATION: (52)..(52)
<223> OTHER INFORMATION: X can be S, T or I
<220> FEATURE:
<221> NAME/KEY: misc_feature
<222> LOCATION: (53)..(53)
<223> OTHER INFORMATION: X can be A or T
<220> FEATURE:
<221> NAME/KEY: misc_feature
<222> LOCATION: (55)..(55)
<223> OTHER INFORMATION: X can be S or N
<220> FEATURE:
<221> NAME/KEY: misc_feature
<222> LOCATION: (59)..(59)
<223> OTHER INFORMATION: X can be N or I
<220> FEATURE:
<221> NAME/KEY: misc_feature
<222> LOCATION: (63)..(63)
<223> OTHER INFORMATION: X can be K or R
<220> FEATURE:

```
<221> NAME/KEY: misc_feature
<222> LOCATION: (64)..(64)
<223> OTHER INFORMATION: X can be L or F
<220> FEATURE:
<221> NAME/KEY: misc_feature
<222> LOCATION: (77)..(77)
<223> OTHER INFORMATION: X can be S or T
<220> FEATURE:
<221> NAME/KEY: misc_feature
<222> LOCATION: (101)..(101)
<223> OTHER INFORMATION: X can be I or V
<220> FEATURE:
<221> NAME/KEY: misc_feature
<222> LOCATION: (102)..(102)
<223> OTHER INFORMATION: X can be I or V

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Tyr
                20                  25                  30

Gly Ile Ser Trp Val Arg Gln Ala Pro Gly Gln Xaa Leu Glu Trp Met
            35                  40                  45

Gly Trp Ile Xaa Xaa Tyr Xaa Gly Asn Thr Xaa Tyr Ala Gln Xaa Xaa
    50                  55                  60

Gln Gly Arg Val Thr Met Thr Thr Asp Thr Ser Thr Xaa Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Xaa Xaa Val Arg Pro Asp Tyr Phe Asp Tyr Trp Gly
            100                 105                 110

Gln Gly Thr Leu Val Thr Val Ser Ser
        115                 120

<210> SEQ ID NO 181
<211> LENGTH: 112
<212> TYPE: PRT
<213> ORGANISM: Homo sapiens

<400> SEQUENCE: 181

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Phe Asp Tyr Trp Gly Gln Gly Thr Leu Val Thr Val Ser Ser
            100                 105                 110

<210> SEQ ID NO 182
<211> LENGTH: 120
<212> TYPE: PRT
<213> ORGANISM: Artificial Sequence
<220> FEATURE:
<223> OTHER INFORMATION: Consensus sequence derived from human sequences
<220> FEATURE:
```

```
<221> NAME/KEY: misc_feature
<222> LOCATION: (31)..(31)
<223> OTHER INFORMATION: X can be G or D
<220> FEATURE:
<221> NAME/KEY: misc_feature
<222> LOCATION: (33)..(33)
<223> OTHER INFORMATION: X can be Y or F
<220> FEATURE:
<221> NAME/KEY: misc_feature
<222> LOCATION: (35)..(35)
<223> OTHER INFORMATION: X can be S or N
<220> FEATURE:
<221> NAME/KEY: misc_feature
<222> LOCATION: (52)..(52)
<223> OTHER INFORMATION: X can be H or N
<220> FEATURE:
<221> NAME/KEY: misc_feature
<222> LOCATION: (54)..(54)
<223> OTHER INFORMATION: X can be S or V
<220> FEATURE:
<221> NAME/KEY: misc_feature
<222> LOCATION: (57)..(57)
<223> OTHER INFORMATION: X can be T or A
<220> FEATURE:
<221> NAME/KEY: misc_feature
<222> LOCATION: (64)..(64)
<223> OTHER INFORMATION: X can be K or M
<220> FEATURE:
<221> NAME/KEY: misc_feature
<222> LOCATION: (76)..(76)
<223> OTHER INFORMATION: X can be N or S
<220> FEATURE:
<221> NAME/KEY: misc_feature
<222> LOCATION: (81)..(81)
<223> OTHER INFORMATION: X can be K, Q or N
<220> FEATURE:
<221> NAME/KEY: misc_feature
<222> LOCATION: (99)..(99)
<223> OTHER INFORMATION: X can be Y, N or L
<220> FEATURE:
<221> NAME/KEY: misc_feature
<222> LOCATION: (100)..(100)
<223> OTHER INFORMATION: X can be Y or I
<220> FEATURE:
<221> NAME/KEY: misc_feature
<222> LOCATION: (101)..(101)
<223> OTHER INFORMATION: X can be D, G or A
<220> FEATURE:
<221> NAME/KEY: misc_feature
<222> LOCATION: (104)..(104)
<223> OTHER INFORMATION: X can be V or Y
<220> FEATURE:
<221> NAME/KEY: misc_feature
<222> LOCATION: (109)..(109)
<223> OTHER INFORMATION: X can be Y or L
<220> FEATURE:
<221> NAME/KEY: misc_feature
<222> LOCATION: (111)..(111)
<223> OTHER INFORMATION: X can be G, A or D
<220> FEATURE:
<221> NAME/KEY: misc_feature
<222> LOCATION: (112)..(112)
<223> OTHER INFORMATION: X can be Q or R
<220> FEATURE:
<221> NAME/KEY: misc_feature
<222> LOCATION: (115)..(115)
<223> OTHER INFORMATION: X can be L or Q

<400> SEQUENCE: 182

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Xaa Tyr
            20                  25                  30

Xaa Trp Xaa Trp Ile Arg Gln Pro Pro Gly Lys Gly Leu Glu Trp Ile
        35                  40                  45
```

-continued

Gly Glu Ile Xaa His Xaa Gly Ser Xaa Asn Tyr Asn Pro Ser Leu Xaa
        50                  55                  60

Ser Arg Val Thr Ile Ser Val Asp Thr Ser Lys Xaa Gln Phe Ser Leu
65                  70                  75                  80

Xaa Leu Ser Ser Val Thr Ala Ala Asp Thr Ala Val Tyr Tyr Cys Ala
                85                  90                  95

Arg Gly Xaa Xaa Xaa Ser Gly Xaa Tyr Tyr Phe Asp Xaa Trp Xaa Xaa
            100                 105                 110

Gly Thr Xaa Val Thr Val Ser Ser
        115                 120

<210> SEQ ID NO 183
<211> LENGTH: 112
<212> TYPE: PRT
<213> ORGANISM: Homo sapiens

<400> SEQUENCE: 183

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Tyr Phe Asp Tyr Trp Gly Gln Gly Thr Leu Val Thr Val Ser Ser
            100                 105                 110

<210> SEQ ID NO 184
<211> LENGTH: 120
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (24)..(24)
<223> OTHER INFORMATION: X can be V or I
<220> FEATURE:
<221> NAME/KEY: misc_feature
<222> LOCATION: (25)..(25)
<223> OTHER INFORMATION: X can be S or Y
<220> FEATURE:
<221> NAME/KEY: misc_feature
<222> LOCATION: (31)..(31)
<223> OTHER INFORMATION: X can be G or D
<220> FEATURE:
<221> NAME/KEY: misc_feature
<222> LOCATION: (35)..(35)
<223> OTHER INFORMATION: X can be S or T
<220> FEATURE:
<221> NAME/KEY: misc_feature
<222> LOCATION: (52)..(52)
<223> OTHER INFORMATION: X can be Y, N, or H
<220> FEATURE:
<221> NAME/KEY: misc_feature
<222> LOCATION: (56)..(56)
<223> OTHER INFORMATION: X can be S or D
<220> FEATURE:
<221> NAME/KEY: misc_feature
<222> LOCATION: (64)..(64)
<223> OTHER INFORMATION: X can be K or T

```
<220> FEATURE:
<221> NAME/KEY: misc_feature
<222> LOCATION: (83)..(83)
<223> OTHER INFORMATION: X can be S or Y
<220> FEATURE:
<221> NAME/KEY: misc_feature
<222> LOCATION: (99)..(99)
<223> OTHER INFORMATION: X can be Y, F or W
<220> FEATURE:
<221> NAME/KEY: misc_feature
<222> LOCATION: (100)..(100)
<223> OTHER INFORMATION: X can be F or Y
<220> FEATURE:
<221> NAME/KEY: misc_feature
<222> LOCATION: (104)..(104)
<223> OTHER INFORMATION: X can be I, T or S
<220> FEATURE:
<221> NAME/KEY: misc_feature
<222> LOCATION: (107)..(107)
<223> OTHER INFORMATION: X can be F or L

<400> SEQUENCE: 184

Gln Val Gln Leu Gln Gln Trp Gly Ala Gly Leu Leu Lys Pro Ser Glu
1               5                   10                  15

Thr Leu Ser Leu Thr Cys Ala Xaa Xaa Gly Gly Ser Phe Ser Xaa Tyr
            20                  25                  30

Tyr Trp Xaa Trp Ile Arg Gln Pro Pro Gly Lys Gly Leu Glu Trp Ile
        35                  40                  45

Gly Glu Ile Xaa His Ser Gly Xaa Thr Asn Tyr Asn Pro Ser Leu Xaa
    50                  55                  60

Ser Arg Val Thr Ile Ser Val Asp Thr Ser Lys Asn Gln Phe Ser Leu
65                  70                  75                  80

Lys Leu Xaa Ser Val Thr Ala Ala Asp Thr Ala Val Tyr Tyr Cys Ala
                85                  90                  95

Arg Leu Xaa Xaa Gly Ser Gly Xaa Tyr Tyr Xaa Asp Tyr Trp Gly Gln
            100                 105                 110

Gly Thr Leu Val Thr Val Ser Ser
        115                 120

<210> SEQ ID NO 185
<211> LENGTH: 113
<212> TYPE: PRT
<213> ORGANISM: Homo sapiens

<400> SEQUENCE: 185

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser
```

```
<210> SEQ ID NO 186
<211> LENGTH: 119
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (31)..(31)
<223> OTHER INFORMATION: X can be S or T
<220> FEATURE:
<221> NAME/KEY: misc_feature
<222> LOCATION: (32)..(32)
<223> OTHER INFORMATION: X can be Y or F
<220> FEATURE:
<221> NAME/KEY: misc_feature
<222> LOCATION: (34)..(34)
<223> OTHER INFORMATION: X can be M or I
<220> FEATURE:
<221> NAME/KEY: misc_feature
<222> LOCATION: (56)..(56)
<223> OTHER INFORMATION: X can be S or G
<220> FEATURE:
<221> NAME/KEY: misc_feature
<222> LOCATION: (57)..(57)
<223> OTHER INFORMATION: X can be N or H
<220> FEATURE:
<221> NAME/KEY: misc_feature
<222> LOCATION: (59)..(59)
<223> OTHER INFORMATION: X can be Y or F
<220> FEATURE:
<221> NAME/KEY: misc_feature
<222> LOCATION: (93)..(93)
<223> OTHER INFORMATION: X can be V or M
<220> FEATURE:
<221> NAME/KEY: misc_feature
<222> LOCATION: (105)..(105)
<223> OTHER INFORMATION: X can be Y or A

<400> SEQUENCE: 186

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Xaa Xaa
            20                  25                  30

Ala Xaa His Trp Val Arg Gln Ala Pro Gly Lys Gly Leu Glu Trp Val
        35                  40                  45

Ala Val Ile Ser Tyr Asp Gly Xaa Xaa Lys Xaa Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Xaa Tyr Tyr Cys
                85                  90                  95

Ala Arg Gly Leu Gly Val Trp Gly Xaa Phe Asp Tyr Trp Gly Gln Gly
            100                 105                 110

Thr Leu Val Thr Val Ser Ser
        115

<210> SEQ ID NO 187
<211> LENGTH: 113
<212> TYPE: PRT
<213> ORGANISM: Homo sapiens

<400> SEQUENCE: 187

Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Phe Ser Ser Tyr
            20                  25                  30
```

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Phe Asp Tyr Trp Gly Gln Gly Thr Leu Val Thr Val Ser
            100                 105                 110

Ser

<210> SEQ ID NO 188
<211> LENGTH: 124
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (5)..(5)
<223> OTHER INFORMATION: X can be L or W
<220> FEATURE:
<221> NAME/KEY: misc_feature
<222> LOCATION: (11)..(11)
<223> OTHER INFORMATION: X can be L or S
<220> FEATURE:
<221> NAME/KEY: misc_feature
<222> LOCATION: (30)..(30)
<223> OTHER INFORMATION: X can be S, N or T
<220> FEATURE:
<221> NAME/KEY: misc_feature
<222> LOCATION: (31)..(31)
<223> OTHER INFORMATION: X can be S, N or D
<220> FEATURE:
<221> NAME/KEY: misc_feature
<222> LOCATION: (33)..(33)
<223> OTHER INFORMATION: X can be A or G
<220> FEATURE:
<221> NAME/KEY: misc_feature
<222> LOCATION: (35)..(35)
<223> OTHER INFORMATION: X can be S or N
<220> FEATURE:
<221> NAME/KEY: misc_feature
<222> LOCATION: (50)..(50)
<223> OTHER INFORMATION: X can be A, T or G
<220> FEATURE:
<221> NAME/KEY: misc_feature
<222> LOCATION: (54)..(54)
<223> OTHER INFORMATION: X can be S or I
<220> FEATURE:
<221> NAME/KEY: misc_feature
<222> LOCATION: (55)..(55)
<223> OTHER INFORMATION: X can be G or A
<220> FEATURE:
<221> NAME/KEY: misc_feature
<222> LOCATION: (56)..(56)
<223> OTHER INFORMATION: X can be G or Y
<220> FEATURE:
<221> NAME/KEY: misc_feature
<222> LOCATION: (57)..(57)
<223> OTHER INFORMATION: X can be S or A
<220> FEATURE:
<221> NAME/KEY: misc_feature
<222> LOCATION: (77)..(77)
<223> OTHER INFORMATION: X can be N or T
<220> FEATURE:
<221> NAME/KEY: misc_feature
<222> LOCATION: (80)..(80)
<223> OTHER INFORMATION: X can be Y or W
<220> FEATURE:
<221> NAME/KEY: misc_feature
<222> LOCATION: (99)..(99)

```
<223> OTHER INFORMATION: X can be A or G
<220> FEATURE:
<221> NAME/KEY: misc_feature
<222> LOCATION: (100)..(100)
<223> OTHER INFORMATION: X can be H or Y
<220> FEATURE:
<221> NAME/KEY: misc_feature
<222> LOCATION: (101)..(101)
<223> OTHER INFORMATION: X can be Y or T
<220> FEATURE:
<221> NAME/KEY: misc_feature
<222> LOCATION: (102)..(102)
<223> OTHER INFORMATION: X can be H, F or L
<220> FEATURE:
<221> NAME/KEY: misc_feature
<222> LOCATION: (110)..(110)
<223> OTHER INFORMATION: X can be Y, L or S

<400> SEQUENCE: 188

Glu Val Gln Leu Xaa Glu Ser Gly Gly Gly Xaa Val Gln Pro Gly Gly
1               5                   10                  15

Ser Leu Arg Leu Ser Cys Ala Ala Ser Gly Phe Thr Phe Xaa Xaa Tyr
            20                  25                  30

Xaa Met Xaa Trp Val Arg Gln Ala Pro Gly Lys Gly Leu Glu Trp Val
        35                  40                  45

Ser Xaa Ile Ser Gly Xaa Xaa Xaa Xaa Thr Tyr Tyr Ala Asp Ser Val
    50                  55                  60

Lys Gly Arg Phe Thr Ile Ser Arg Asp Asn Ser Lys Xaa Thr Leu Xaa
65                  70                  75                  80

Leu Gln Met Asn Ser Leu Arg Ala Glu Asp Thr Ala Val Tyr Tyr Cys
                85                  90                  95

Ala Lys Xaa Xaa Xaa Xaa Gly Ser Gly Ser Tyr Tyr Thr Xaa Phe Asp
            100                 105                 110

Tyr Trp Gly Gln Gly Thr Leu Val Thr Val Ser Ser
        115                 120

<210> SEQ ID NO 189
<211> LENGTH: 113
<212> TYPE: PRT
<213> ORGANISM: Homo sapiens

<400> SEQUENCE: 189

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Phe Asp Leu Trp Gly Arg Gly Thr Leu Val Thr Val Ser
            100                 105                 110

Ser

<210> SEQ ID NO 190
<211> LENGTH: 123
<212> TYPE: PRT
```

<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (19)..(19)
<223> OTHER INFORMATION: X can be K or T
<220> FEATURE:
<221> NAME/KEY: misc_feature
<222> LOCATION: (30)..(30)
<223> OTHER INFORMATION: X can be T or S
<220> FEATURE:
<221> NAME/KEY: misc_feature
<222> LOCATION: (31)..(31)
<223> OTHER INFORMATION: X can be S or I
<220> FEATURE:
<221> NAME/KEY: misc_feature
<222> LOCATION: (52)..(52)
<223> OTHER INFORMATION: X can be Y or F
<220> FEATURE:
<221> NAME/KEY: misc_feature
<222> LOCATION: (58)..(58)
<223> OTHER INFORMATION: X can be T or I

<400> SEQUENCE: 190

Glu Val Gln Leu Val Gln Ser Gly Ala Glu Val Lys Lys Pro Gly Glu
1               5                   10                  15

Ser Leu Xaa Ile Ser Cys Lys Gly Ser Gly Tyr Ser Phe Xaa Xaa Tyr
            20                  25                  30

Trp Ile Gly Trp Val Arg Gln Met Pro Gly Lys Gly Leu Glu Trp Met
        35                  40                  45

Gly Ile Ile Xaa Pro Gly Asp Ser Asp Xaa Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Pro Gly Asp Trp Ser Pro Arg His Trp Tyr Phe Asp Leu
            100                 105                 110

Trp Gly Arg Gly Thr Leu Val Thr Val Ser Ser
        115                 120

<210> SEQ ID NO 191
<211> LENGTH: 126
<212> TYPE: PRT
<213> ORGANISM: Homo sapiens

<400> SEQUENCE: 191

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Thr Tyr Tyr Asp Ile Leu Thr Gly Tyr Phe Asn Trp
            100                 105                 110

Phe Asp Pro Trp Gly Gln Gly Thr Leu Val Thr Val Ser Ser
         115                 120                 125

<210> SEQ ID NO 192
<211> LENGTH: 126
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (28)..(28)
<223> OTHER INFORMATION: X can be S or N

<400> SEQUENCE: 192

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Xaa Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Trp Gly Thr Tyr Tyr Asp Ile Leu Thr Gly Tyr Phe Asn Trp
            100                 105                 110

Phe Asp Pro Trp Gly Gln Gly Thr Leu Val Thr Val Ser Ser
        115                 120                 125

<210> SEQ ID NO 193
<211> LENGTH: 113
<212> TYPE: PRT
<213> ORGANISM: Homo sapiens

<400> SEQUENCE: 193

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Met Asp Val Trp Gly Gln Gly Thr Thr Val Thr Val Ser
            100                 105                 110

Ser

<210> SEQ ID NO 194
<211> LENGTH: 125
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (58)..(58)
<223> OTHER INFORMATION: X can be T or S
<220> FEATURE:
<221> NAME/KEY: misc_feature
<222> LOCATION: (61)..(61)
<223> OTHER INFORMATION: X can be A or V
<220> FEATURE:
<221> NAME/KEY: misc_feature
<222> LOCATION: (64)..(64)
<223> OTHER INFORMATION: X can be L or F

<400> SEQUENCE: 194

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Xaa Asn Tyr Xaa Gln Lys Xaa
    50                  55                  60

Gln Gly Arg Val Thr Met Thr Thr Asp Thr Thr Thr Ser Thr Ala Tyr
65                  70                  75                  80

Met Glu Leu Arg Ser Leu Thr Ser Asp Asp Thr Ala Val Tyr Tyr Cys
                85                  90                  95

Ala Arg Glu Tyr Ser Tyr Asp Ser Gly Tyr Phe Tyr Tyr Gly Met
            100                 105                 110

Asp Val Trp Gly Gln Gly Thr Thr Val Thr Val Ser Ser
        115                 120                 125
```

<210> SEQ ID NO 195
<211> LENGTH: 113
<212> TYPE: PRT
<213> ORGANISM: Homo sapiens

<400> SEQUENCE: 195

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser
```

<210> SEQ ID NO 196
<211> LENGTH: 121
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature

```
<222> LOCATION: (14)..(14)
<223> OTHER INFORMATION: X can be P or T
<220> FEATURE:
<221> NAME/KEY: misc_feature
<222> LOCATION: (31)..(31)
<223> OTHER INFORMATION: X can be S or D
<220> FEATURE:
<221> NAME/KEY: misc_feature
<222> LOCATION: (32)..(32)
<223> OTHER INFORMATION: X can be Y or H
<220> FEATURE:
<221> NAME/KEY: misc_feature
<222> LOCATION: (33)..(33)
<223> OTHER INFORMATION: X can be A or V
<220> FEATURE:
<221> NAME/KEY: misc_feature
<222> LOCATION: (34)..(34)
<223> OTHER INFORMATION: X can be M or I
<220> FEATURE:
<221> NAME/KEY: misc_feature
<222> LOCATION: (49)..(49)
<223> OTHER INFORMATION: X can be A or T
<220> FEATURE:
<221> NAME/KEY: misc_feature
<222> LOCATION: (50)..(50)
<223> OTHER INFORMATION: X can be V or A
<220> FEATURE:
<221> NAME/KEY: misc_feature
<222> LOCATION: (57)..(57)
<223> OTHER INFORMATION: X can be N or Y
<220> FEATURE:
<221> NAME/KEY: misc_feature
<222> LOCATION: (58)..(58)
<223> OTHER INFORMATION: X can be K or E
<220> FEATURE:
<221> NAME/KEY: misc_feature
<222> LOCATION: (79)..(79)
<223> OTHER INFORMATION: X can be L or M
<220> FEATURE:
<221> NAME/KEY: misc_feature
<222> LOCATION: (87)..(87)
<223> OTHER INFORMATION: X can be R or S
<220> FEATURE:
<221> NAME/KEY: misc_feature
<222> LOCATION: (93)..(93)
<223> OTHER INFORMATION: X can be V or M
<220> FEATURE:
<221> NAME/KEY: misc_feature
<222> LOCATION: (94)..(94)
<223> OTHER INFORMATION: X can be Y or C
<220> FEATURE:
<221> NAME/KEY: misc_feature
<222> LOCATION: (100)..(100)
<223> OTHER INFORMATION: X can be G, D or S
<220> FEATURE:
<221> NAME/KEY: misc_feature
<222> LOCATION: (101)..(101)
<223> OTHER INFORMATION: X can be I or Y
<220> FEATURE:
<221> NAME/KEY: misc_feature
<222> LOCATION: (102)..(102)
<223> OTHER INFORMATION: X can be T or I
<220> FEATURE:
<221> NAME/KEY: misc_feature
<222> LOCATION: (103)..(103)
<223> OTHER INFORMATION: X can be G or S
<220> FEATURE:
<221> NAME/KEY: misc_feature
<222> LOCATION: (104)..(104)
<223> OTHER INFORMATION: X can be T or S
<220> FEATURE:
<221> NAME/KEY: misc_feature
<222> LOCATION: (105)..(105)
<223> OTHER INFORMATION: X can be T or S
<220> FEATURE:
<221> NAME/KEY: misc_feature
<222> LOCATION: (107)..(107)
<223> OTHER INFORMATION: X can be Y or V
```

<400> SEQUENCE: 196

Gln Val Gln Leu Val Glu Ser Gly Gly Gly Val Val Gln Xaa Gly Arg
1               5                   10                  15

Ser Leu Arg Leu Ser Cys Ala Ala Ser Gly Phe Thr Phe Ser Xaa Xaa
            20                  25                  30

Xaa Xaa His Trp Val Arg Gln Ala Pro Gly Lys Gly Leu Glu Trp Val
        35                  40                  45

Xaa Xaa Ile Ser Tyr Asp Gly Ser Xaa Xaa Tyr Tyr Ala Asp Ser Val
50                  55                  60

Lys Gly Arg Phe Thr Ile Ser Arg Asp Asn Ser Lys Asn Thr Xaa Tyr
65                  70                  75                  80

Leu Gln Met Asn Ser Leu Xaa Ala Glu Asp Thr Ala Xaa Xaa Tyr Cys
                85                  90                  95

Ala Arg Gly Xaa Xaa Xaa Xaa Xaa Gly Xaa Phe Asp Tyr Trp Gly
            100                 105                 110

Gln Gly Thr Leu Val Thr Val Ser Ser
        115                 120

<210> SEQ ID NO 197
<211> LENGTH: 107
<212> TYPE: PRT
<213> ORGANISM: Homo sapiens

<400> SEQUENCE: 197

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Glu Ile Lys
            100                 105

<210> SEQ ID NO 198
<211> LENGTH: 107
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (38)..(38)
<223> OTHER INFORMATION: X can be Q or H
<220> FEATURE:
<221> NAME/KEY: misc_feature
<222> LOCATION: (50)..(50)
<223> OTHER INFORMATION: X can be A or V
<220> FEATURE:
<221> NAME/KEY: misc_feature
<222> LOCATION: (53)..(53)
<223> OTHER INFORMATION: X can be S, I or T
<220> FEATURE:
<221> NAME/KEY: misc_feature
<222> LOCATION: (79)..(79)
<223> OTHER INFORMATION: X can be Q or R
<220> FEATURE:

```
<221> NAME/KEY: misc_feature
<222> LOCATION: (96)..(96)
<223> OTHER INFORMATION: X can be I or L
<220> FEATURE:
<221> NAME/KEY: misc_feature
<222> LOCATION: (100)..(100)
<223> OTHER INFORMATION: X can be Q or G
<220> FEATURE:
<221> NAME/KEY: misc_feature
<222> LOCATION: (104)..(104)
<223> OTHER INFORMATION: X can be L or V

<400> SEQUENCE: 198

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Xaa Lys Pro Gly Lys Ala Pro Lys Leu Leu Ile
        35                  40                  45

Tyr Xaa Ala Ser Xaa Leu Gln Ser Gly Val Pro Ser Arg Phe Ser Gly
50                  55                  60

Ser Gly Ser Gly Thr Asp Phe Thr Leu Thr Ile Ser Ser Leu Xaa Pro
65                  70                  75                  80

Glu Asp Phe Ala Thr Tyr Tyr Cys Gln Gln Ala Asn Ser Phe Pro Xaa
                85                  90                  95

Thr Phe Gly Xaa Gly Thr Arg Xaa Glu Ile Lys
            100                 105

<210> SEQ ID NO 199
<211> LENGTH: 107
<212> TYPE: PRT
<213> ORGANISM: Homo sapiens

<400> SEQUENCE: 199

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 200
<211> LENGTH: 107
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (51)..(51)
<223> OTHER INFORMATION: X can be A or T
<220> FEATURE:
<221> NAME/KEY: misc_feature
<222> LOCATION: (93)..(93)
<223> OTHER INFORMATION: X can be N or H
```

<400> SEQUENCE: 200

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Xaa Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Xaa Trp Pro Arg
                85                  90                  95

Thr Phe Gly Gln Gly Thr Lys Val Glu Ile Lys
            100                 105

<210> SEQ ID NO 201
<211> LENGTH: 107
<212> TYPE: PRT
<213> ORGANISM: Homo sapiens

<400> SEQUENCE: 201

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 202
<211> LENGTH: 107
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (31)..(31)
<223> OTHER INFORMATION: X can be S or R
<220> FEATURE:
<221> NAME/KEY: misc_feature
<222> LOCATION: (49)..(49)
<223> OTHER INFORMATION: X can be Y or F
<220> FEATURE:
<221> NAME/KEY: misc_feature
<222> LOCATION: (53)..(53)
<223> OTHER INFORMATION: X can be S or R
<220> FEATURE:
<221> NAME/KEY: misc_feature
<222> LOCATION: (55)..(55)
<223> OTHER INFORMATION: X can be Q or R
<220> FEATURE:
<221> NAME/KEY: misc_feature
<222> LOCATION: (94)..(94)

<223> OTHER INFORMATION: X can be Y or F

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Xaa Trp
            20                  25                  30

Leu Ala Trp Tyr Gln Gln Lys Pro Glu Lys Ala Pro Lys Ser Leu Ile
        35                  40                  45

Xaa Ala Ala Ser Xaa Leu Xaa Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Xaa Pro Ile
                85                  90                  95

Thr Phe Gly Gln Gly Thr Arg Leu Glu Ile Lys
            100                 105

<210> SEQ ID NO 203
<211> LENGTH: 107
<212> TYPE: PRT
<213> ORGANISM: Homo sapiens

<400> SEQUENCE: 203

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Gln Gly Thr Lys Val Glu Ile Lys
            100                 105

<210> SEQ ID NO 204
<211> LENGTH: 107
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (34)..(34)
<223> OTHER INFORMATION: X can be A, V or T
<220> FEATURE:
<221> NAME/KEY: misc_feature
<222> LOCATION: (51)..(51)
<223> OTHER INFORMATION: X can be A or T
<220> FEATURE:
<221> NAME/KEY: misc_feature
<222> LOCATION: (52)..(52)
<223> OTHER INFORMATION: X can be S or F
<220> FEATURE:
<221> NAME/KEY: misc_feature
<222> LOCATION: (53)..(53)
<223> OTHER INFORMATION: X can be S or R
<220> FEATURE:
<221> NAME/KEY: misc_feature
<222> LOCATION: (100)..(100)
<223> OTHER INFORMATION: X can be Q or G

<400> SEQUENCE: 204

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Xaa Trp Tyr Gln Gln Lys Pro Glu Lys Ala Pro Lys Ser Leu Ile
        35                  40                  45

Tyr Ala Xaa Xaa Xaa Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Phe Pro Pro
                85                  90                  95

Thr Phe Gly Xaa Gly Thr Lys Val Glu Ile Lys
            100                 105

<210> SEQ ID NO 205
<211> LENGTH: 107
<212> TYPE: PRT
<213> ORGANISM: Homo sapiens

<400> SEQUENCE: 205

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 206
<211> LENGTH: 107
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (30)..(30)
<223> OTHER INFORMATION: X can be S or N
<220> FEATURE:
<221> NAME/KEY: misc_feature
<222> LOCATION: (96)..(96)
<223> OTHER INFORMATION: X can be Y or L
<220> FEATURE:
<221> NAME/KEY: misc_feature
<222> LOCATION: (100)..(100)
<223> OTHER INFORMATION: X can be Q or G
<220> FEATURE:
<221> NAME/KEY: misc_feature
<222> LOCATION: (104)..(104)
<223> OTHER INFORMATION: X can be L or V

<400> SEQUENCE: 206

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Xaa Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Xaa
                85                  90                  95

Thr Phe Gly Xaa Gly Thr Lys Xaa Glu Ile Lys
            100                 105

<210> SEQ ID NO 207
<211> LENGTH: 107
<212> TYPE: PRT
<213> ORGANISM: Homo sapiens

<400> SEQUENCE: 207

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 208
<211> LENGTH: 107
<212> TYPE: PRT
<213> ORGANISM: Artificial Sequence
<220> FEATURE:
<223> OTHER INFORMATION: Consensus sequence derived from human sequences
<220> FEATURE:
<221> NAME/KEY: misc_feature
<222> LOCATION: (30)..(30)
<223> OTHER INFORMATION: X can be S or N
<220> FEATURE:
<221> NAME/KEY: misc_feature
<222> LOCATION: (31)..(31)
<223> OTHER INFORMATION: X can be S or N
<220> FEATURE:
<221> NAME/KEY: misc_feature
<222> LOCATION: (50)..(50)
<223> OTHER INFORMATION: X can be A or D
<220> FEATURE:
<221> NAME/KEY: misc_feature
<222> LOCATION: (67)..(67)
<223> OTHER INFORMATION: X can be S or Y
<220> FEATURE:
<221> NAME/KEY: misc_feature
<222> LOCATION: (72)..(72)
<223> OTHER INFORMATION: X can be T or S

```
<220> FEATURE:
<221> NAME/KEY: misc_feature
<222> LOCATION: (82)..(82)
<223> OTHER INFORMATION: X can be D or N
<220> FEATURE:
<221> NAME/KEY: misc_feature
<222> LOCATION: (85)..(85)
<223> OTHER INFORMATION: X can be T or I
<220> FEATURE:
<221> NAME/KEY: misc_feature
<222> LOCATION: (92)..(92)
<223> OTHER INFORMATION: X can be N or K

<400> SEQUENCE: 208

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Xaa Xaa Trp
            20                  25                  30

Leu Ala Trp Tyr Gln Gln Lys Pro Glu Lys Ala Pro Lys Ser Leu Ile
        35                  40                  45

Tyr Xaa Ala Ser Ser Leu Gln Ser Gly Val Pro Ser Arg Phe Ser Gly
    50                  55                  60

Ser Gly Xaa Gly Thr Asp Phe Xaa Leu Thr Ile Ser Ser Leu Gln Pro
65              70                  75                  80

Glu Xaa Phe Ala Xaa Tyr Tyr Cys Gln Gln Tyr Xaa Ser Tyr Pro Ile
                85                  90                  95

Thr Phe Gly Gln Gly Thr Arg Leu Glu Ile Lys
                100                 105
```